(12) United States Patent
Beresini et al.

(10) Patent No.: US 10,787,484 B2
(45) Date of Patent: Sep. 29, 2020

(54) COMPOSITIONS AND METHODS FOR TREATING CARDIOVASCULAR DISEASE

(71) Applicant: Genentech, Inc., South San Francisco, CA (US)

(72) Inventors: Maureen Beresini, South San Francisco, CA (US); Daniel Burdick, Burlingame, CA (US); Charles Eigenbrot, Jr., Burlingame, CA (US); Daniel Kirchhofer, Los Altos, CA (US); Robert Lazarus, Millbrae, CA (US); Wei Li, Palo Alto, CA (US); John Quinn, South San Francisco, CA (US); Nicholas Skelton, San Mateo, CA (US); Mark Ultsch, Mill Valley, CA (US); Yingnan Zhang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 7 days.

(21) Appl. No.: 16/229,226

(22) Filed: Dec. 21, 2018

(65) Prior Publication Data
US 2019/0177366 A1    Jun. 13, 2019

Related U.S. Application Data

(63) Continuation of application No. PCT/EP2017/065324, filed on Jun. 21, 2017.

(60) Provisional application No. 62/354,631, filed on Jun. 24, 2016.

(51) Int. Cl.

| | | |
|---|---|---|
| C07K 7/06 | (2006.01) | |
| C07K 7/02 | (2006.01) | |
| C12N 9/64 | (2006.01) | |
| C12Q 1/37 | (2006.01) | |
| G01N 33/573 | (2006.01) | |
| G01N 33/92 | (2006.01) | |
| C40B 40/10 | (2006.01) | |
| C07K 14/00 | (2006.01) | |
| A61K 47/62 | (2017.01) | |
| A61P 3/06 | (2006.01) | |
| A61K 38/00 | (2006.01) | |

(52) U.S. Cl.
CPC ............... *C07K 7/02* (2013.01); *A61K 47/62* (2017.08); *A61P 3/06* (2018.01); *C07K 14/00* (2013.01); *C12N 9/64* (2013.01); *C12N 9/6424* (2013.01); *C12Q 1/37* (2013.01); *C40B 40/10* (2013.01); *G01N 33/573* (2013.01); *G01N 33/92* (2013.01); *A61K 38/00* (2013.01); *G01N 2500/00* (2013.01)

(58) Field of Classification Search
None
See application file for complete search history.

(56) References Cited

U.S. PATENT DOCUMENTS

| 8,889,144 B2 * | 11/2014 | Champion ......... A61K 39/0005 424/197.11 |
| 2013/0344085 A1 * | 12/2013 | Wu ........................ C07K 16/40 424/158.1 |

FOREIGN PATENT DOCUMENTS

| WO | 2008/118386 A2 | 10/2008 |
| WO | 2008/125623 A2 | 10/2008 |
| WO | 2012/059573 A1 | 5/2012 |
| WO | 2012/088313 A1 | 6/2012 |
| WO | 2014/127316 A2 | 8/2014 |
| WO | 2014/139008 A1 | 9/2014 |

OTHER PUBLICATIONS

Schulz et al. ('Molecular and cellular function of the proprotein convertase subtilisin/kexin type 9 (PCSK9)' Basic Res Cardiol v110(4) 2015 pp. 1-19) (Year: 2015).*
Tiller et al. ('Advances in antibody design' Annu Rev Biomed Eng v17 2015 pp. 191-216, printed as pp. 1-31) (Year: 2015).*
Alghamdi et al., "LDL-R promoting activity of peptides derived from human PCSK9 catalytic domain (153-421): Design synthesis and biochemical evaluation" European Journal of Med Chem 92:890-907 (Mar. 1, 2015).
Bottomley et al., "Structural and Biochemical Characterization of the Wild Type PCSK9-EGF(AB) Complex and Natural Familial Hypercholesterolemia Mutants" J. Biol. Chem. 284:1313-1323 (Nov. 10, 2008).
Burdick et al., "Design of Organo-Peptides as Bipartite PCSK9 Antagonists" ACS Chem. Biol. 15:425-436 ( 2020).
International Search Report for PCT/EP2017/065324 dated Nov. 21, 2017.
Kwon et al., "Molecular basis for LDL receptor recognition by PCSK9" PNAS 105(6):1820-1825 (Feb. 12, 2008).
Zhang et al., "Discovery of a cryptic petide-binding site on PCSK9 and design of antagonists" Nat. Struct. Mol. Biol. (Aug. 21, 2017).
Zhang et al., "Supplementary Information—Discovery of a cryptic petide-binding site on PCSK9 and design of antagonists" Nat. Struct. Mol. Biol. (Aug. 21, 2017).
Zhang et al., "Identification of a small Peptide that inhibits PCSK9 Protein binding to the low density lipoprotein receptor" J. Biol. Chem. 289(2):942-955 (Nov. 13, 2013).

\* cited by examiner

*Primary Examiner* — Ronald T Niebauer

(57) ABSTRACT

The invention provides PCSK9 inhibitors, compositions comprising the PCSK9 inhibitors, and methods of identifying and using the PCSK9 inhibitors.

73 Claims, 42 Drawing Sheets
Specification includes a Sequence Listing.

Figure 14

| | Anchor peptide | Extension peptide | PCSK9 ELISA | PCSK9 s/n ratio | PCSK9Δhelix ELISA | PCSK9Δhelix s/n ratio |
|---|---|---|---|---|---|---|
| pep2-8 | TVFTSWEEYLDWV | | 2.9825 | 29.9556 | 2.102 | 21.778 |
| Pep2-8V2A | TAFTSWEEYLDWV | | 1.268 | 16.68 | 0.07 | 1.07 |
| N13 | | | N/A | | N/A | |
| | TAFTSWEEYLDWV | | 2.793 | 26.212 | 2.617 | 8.552 |
| | TAFTSWEEYLDWV | | 2.811 | 21.591 | 2.911 | 22.547 |
| | TAFTSWEEYLDWV | | 2.736 | 24.873 | 2.821 | 26.364 |
| | TAFTSWEEYLDWV | | 2.680 | 27.629 | 2.698 | 29.326 |
| | TAFTSWEEYLDWV | | 2.750 | 23.504 | 2.757 | 24.398 |
| | TAFTSWEEYLDWV | | 2.919 | 18.832 | 2.834 | 26.000 |
| | TAFTSWEEYLDWV | | 2.865 | 28.088 | 2.685 | 25.817 |
| | TAFTSWEEYLDWV | | 2.950 | 26.818 | 2.956 | 26.631 |
| | TAFTSWEEYLDWV | | 2.948 | 30.708 | 2.660 | 29.556 |
| | TAFTSWEEYLDWV | | 2.816 | 29.333 | 2.678 | 27.327 |
| | TAFTSWEEYLDWV | | 2.694 | 22.450 | 2.673 | 24.081 |
| | TAFTSWEEYLDWV | | 2.729 | 25.745 | 2.600 | 9.123 |
| | TAFTSWEEYLDWV | | 2.938 | 12.041 | 2.763 | 13.220 |
| | TAFTSWEEYLDWV | | 2.888 | 28.913 | 3.025 | 25.343 |
| | TAFTSWEEYLDWV | | 2.996 | 29.663 | 2.908 | 31.269 |
| | TAFTSWEEYLDWV | | 2.864 | 27.806 | 2.995 | 30.253 |
| | TAFTSWEEYLDWV | | 3.086 | 23.922 | 3.036 | 20.106 |
| | TAFTSWEEYLDWV | | 2.748 | 26.423 | 2.734 | 12.484 |
| | TAFTSWEEYLDWV | | 2.34 | 28.687 | 2.94 | 26.018 |
| | TAFTSWEEYLDWV | | 2.851 | 22.992 | 2.809 | 22.837 |
| | TAFTSWEEYLDWV | | 2.823 | 27.950 | 2.708 | 25.074 |
| | TAFTSWEEYLDWV | | 2.846 | 18.013 | 2.731 | 24.168 |
| | TAFTSWEEYLDWV | | 2.553 | 22.336 | 2.664 | 26.167 |
| | TAFTSWEEYLDWV | | 2.545 | 24.709 | 2.535 | 29.138 |
| | TAFTSWEEYLDWV | | 2.927 | 26.134 | 2.693 | 18.832 |
| | TAFTSWEEYLDWV | | 2.869 | 26.082 | 1.380 | 8.166 |
| | TAFTSWEEYLDWV | | 2.804 | 25.036 | 2.784 | 26.514 |
| | TAFTSWEEYLDWV | | 2.663 | 25.854 | 2.684 | 26.314 |
| | TAFTSWEEYLDWV | | 2.673 | 25.217 | 2.703 | 24.798 |
| | TAFTSWEEYLDWV | | 2.978 | 23.085 | 3.021 | 27.972 |
| | TAFTSWEEYLDWV | | 2.886 | 25.316 | 2.678 | 24.569 |

| Anchor peptide | Extension peptide | | | | | | | | | | | | | | PCSK9 ELISA | PCSK9 s/n ratio | PCSK9Δhelix ELISA | PCSK9Δhelix s/n ratio |
|---|---|---|---|---|---|---|---|---|---|---|---|---|---|---|---|---|---|---|
| TAFTSWEEYLDWV | | | | | D | V | N | L | W | G | D | D | G | K | 2.719 | 23.643 | 2.805 | 22.992 |
| TAFTSWEEYLDWV | | | | | V | C | G | S | W | I | G | D | C | Y | 2.664 | 23.911 | 2.738 | 25.087 |
| TAFTSWEEYLDWV | K | C | V | L | S | P | G | L | W | F | A | W | D | K | R | 1.451 | 12.841 | 2.612 | 24.411 |
| TAFTSWEEYLDWV | G | V | L | | Y | G | G | M | A | V | G | A | G | S | Y | 2.795 | 13.545 | 2.695 | 17.166 |
| TAFTSWEEYLDWV | | | | | C | R | M | E | A | W | S | C | F | L | R | T | 2.729 | 24.586 | 2.756 | 1.485 |
| TAFTSWEEYLDWV | | | | | Q | Q | Y | P | W | Q | C | R | L | | Q | D | 2.708 | 25.074 | 2.655 | 29.176 |
| TAFTSWEEYLDWV | | | | | C | W | T | Y | L | R | G | G | S | V | T | | 3.0725 | 22.1332 | 3.0525 | 20.2424 |
| TAFTSWEEYLDWV | | | | | P | R | T | Y | M | C | R | G | D | V | S | | 2.767 | 25.6204 | 2.735 | 25.0917 |
| TAFTSWEEYLDWV | | | | | Q | Q | T | Y | L | L | R | V | N | S | | | 2.591 | 26.9896 | 2.291 | 24.3723 |
| TAFTSWEEYLDWV | | | | | G | G | L | S | Y | D | K | A | A | G | V | | 2.7 | 22.8814 | 2.308 | 22.6275 |
| TAFTSWEEYLDWV | | | | | E | E | V | Y | | D | I | G | G | | | H | 2.838 | 30.5161 | 2.829 | 30.0957 |
| TAFTSWEEYLDWV | G | R | M | R | S | V | I | Q | M | T | | | | | | | 2.707 | 28.198 | 2.744 | 26.641 |
| TAFTSWFFYLDWV | G | D | G | P | H | Y | M | C | | | | | | | | | 2.752 | 25.018 | 2.630 | 25.534 |
| TAFTSWEEYLDWV | Q | E | L | Y | H | R | R | K | G | | | | | | | | 2.296 | 19.133 | 2.426 | 14.271 |
| TAFTSWEEYLDWV | N | L | C | D | R | G | Y | M | D | K | | | | | | | 2.909 | 30.947 | 2.831 | 28.596 |
| TAFTSWEEYLDWV | V | C | S | Y | Y | V | G | C | U | E | N | | | | | | 2.992 | 27.395 | 2.939 | 15.380 |
| TAFTSWEEYLDWV | C | C | T | R | G | T | P | R | Y | N | V | G | | | | | 2.873 | 28.608 | 2.875 | 27.194 |
| TAFTSWEEYLDWV | W | E | G | U | L | H | Y | Q | T | V | G | | | L | R | | 2.805 | 28.050 | 2.782 | 25.523 |
| TAFTSWEEYLDWV | P | S | N | L | V | T | G | V | M | G | D | R | Y | S | G | | 2.923 | 27.688 | 2.865 | 25.421 |
| TAFTSWEEYLDWV | C | C | U | C | A | G | Y | S | G | V | G | C | Y | | | | 2.662 | 24.422 | 2.637 | 26.109 |
| TAFTSWEEYLDWV | A | L | P | L | D | R | U | L | R | R | V | Y | L | Q | Y | | 3.065 | 29.0145 | 3.049 | 30.3897 |
| TAFTSWEEYLDWV | D | T | S | S | U | F | H | Y | K | G | R | Y | E | V | S | | 2.709 | 24.4054 | 2.882 | 29.7113 |
| TAFTSWEEYLDWV | T | R | Y | C | A | D | P | V | H | C | R | V | A | C | S | | 3.033 | 30.33 | 3.027 | 27.5182 |
| TAFTSWEEYLDWV | C | C | U | P | U | Y | P | G | V | G | V | Y | Y | | H | | 3.06 | 16.1905 | 3.046 | 29.5728 |
| TAFTSWEEYLDWV | E | W | K | Y | K | R | L | Q | R | M | V | A | C | | | | 2.949 | 30.22 | 3.03 | 30.9368 |
| TAFTSWEEYLDWV | D | C | M | A | S | V | Y | R | D | L | D | | | L | | | 2.311 | 22.4369 | 0.106 | 1.07071 |
| TAFTSWEEYLDWV | U | D | T | U | H | R | R | A | G | V | I | N | G | | | | 2.921 | 32.8202 | 3.013 | 30.4343 |
| TAFTSWEEYLDWV | Y | D | V | R | A | P | T | C | V | V | G | L | U | | | | 2.857 | 28.8586 | 2.853 | 28.53 |
| TAFTSWEEYLDWV | A | P | L | U | R | R | G | S | W | A | L | | | | | | 3.03633 | 29.5937 | 2.871 | 28.9428 |
| TAFTSWEEYLDWV | U | C | P | V | T | E | S | L | A | | | | E | | | | 2.664 | 27.4639 | 0.127 | 1.29592 |
| TAFTSWEEYLDWV | P | S | C | R | Y | P | N | Q | V | L | | | | | | | 2.979 | 20.6875 | 2.561 | 15.8086 |
| TAFTSWEEYLDWV | C | P | U | Y | R | T | Q | A | T | C | V | | | | | | 2.456 | 27.9091 | 0.11 | 1.09879 |
| TAFTSWEEYLDWV | R | Y | P | V | U | C | P | L | | L | V | D | Q | | | | 2.861 | 31.0978 | 3.094 | 31.8969 |
| TAFTSWEEYLDWV | U | C | G | R | A | W | V | V | | | | | | | | | 2.618 | 20.7778 | 2.797 | 28.5408 |
| TAFTSWEEYLDWV | R | R | Y | L | E | N | P | R | | | | | | | | | 3.134 | 29.8476 | 2.919 | 25.6053 |

Figure 15

| clone ID | | | | | | | | | | | | | | | PCSK9 ELISA | PCSK9 s/n | PCSK9Δhelix ELISA | PCSK9Δhelix s/n |
|---|---|---|---|---|---|---|---|---|---|---|---|---|---|---|---|---|---|---|
| V2Aext.04 | S | G | P | R | T | Y | L | R | G | L | V | D | | | 6 0.355 | 3.101 | 0.375 | 3.442 |
| V2Aext.09 | S | G | N | C | W | S | S | L | R | G | I | C | E | N L G | 5 0.609 | 1.469 | 0.601 | 5.198 |
| V2Aext.11 | S | G | M | V | Y | Y | D | R | G | V | R | V | F | T | 5 0.893 | 8.498 | 1.006 | 10.230 |
| V2Aext.12 | S | G | G | C | V | K | Y | R | G | S | V | S | C | Q E S K T | 6 0.373 | 3.323 | 0.378 | 3.365 |
| V2Aext.13 | S | G | E | H | Q | F | Y | S | Y | R | G | V | D | V Y R | 7 0.458 | 1.454 | 0.461 | 3.710 |
| V2Aext.15 | S | G | A | C | L | N | H | F | V | S | G | N | M | I R C | 4 0.607 | 5.189 | 0.649 | 5.548 |
| V2Aext.19 | S | G | S | Y | R | G | A | W | S | V | F | G | G | S T D | 5 1.087 | 5.146 | 1.043 | 7.681 |
| V2Adel.6 | S | G | C | W | T | Y | L | R | G | C | S | | | | 3 0.487 | 4.387 | 0.569 | 5.368 |
| V2Adel.7 | S | G | T | P | E | M | P | A | M | L | | | | | 1 3.012 | 5.737 | 2.250 | 8.065 |
| V2Adel.8 | S | G | L | A | P | T | V | S | D | S | H | | | | 1 0.119 | 1.227 | 0.550 | 4.331 |
| V2Adel.9 | S | G | D | T | R | S | Q | L | S | L | G | | | | 1 2.569 | 11.894 | 1.238 | 11.255 |
| V2Adel.10 | S | G | A | G | K | L | D | L | S | | | | | | 1 2.869 | 11.077 | 1.746 | 4.167 |
| V2Adel.1 | S | G | V | C | S | D | H | Y | I | G | G | K | E | V R C | 2 1.116 | 6.188 | 1.211 | 1.855 |
| V2Adel.2 | S | G | N | A | L | W | N | H | D | R | L | T | | | 1 0.591 | 6.424 | 0.665 | 7.074 |
| V2Adel.3 | S | G | R | N | G | S | G | Y | I | N | R | G | I | E I W | 1 0.447 | 3.853 | 0.638 | 5.500 |
| V2Adel.4 | S | G | H | A | S | K | G | M | V | L | S | G | | | 1 2.487 | 15.544 | 1.640 | 7.523 |
| V2Adel.5 | S | G | G | S | I | P | W | N | L | E | R | I | T | P P R | 1 1.410 | 5.321 | 1.640 | 9.011 |

Figure 16

| pepID | | | | | | | | | | | | | | | | PCSK9 ELISA | PCSK9 s/n ratio | PCSK9Δhelix ELISA | PCSK9Δhelix s/n ratio |
|---|---|---|---|---|---|---|---|---|---|---|---|---|---|---|---|---|---|---|---|
| K9gvpep1 | S | G | C | F | I | P | W | N | L | Q | R | I | G | L | L | C | 2.999 | 8.112 | 3.073 | 8.482 |
| K9gvpep2 | S | G | G | A | C | P | W | N | L | E | R | I | G | L | S | C | 1.417 | 9.771 | 1.936 | 12.283 |
| K9gvpep3 | S | G | D | F | I | P | W | N | L | V | R | I | G | L | L | R | 0.472 | 3.420 | 0.657 | 5.015 |
| K9gvpep4 | S | G | C | R | L | P | W | N | L | Q | R | I | G | L | P | C | 3.288 | 28.591 | 3.350 | 26.464 |
| K9gvpep5 | S | G | R | C | V | N | H | L | I | S | G | N | M | N | S | C | 2.625 | 17.500 | 2.884 | 20.748 |
| K9gvpep6 | S | G | A | C | V | K | P | C | L | A | G | N | L | L | R | R | 1.246 | 9.439 | 2.094 | 18.209 |
| K9gvpep7 | S | G | D | L | M | P | W | N | L | V | R | I | G | L | L | L | 3.156 | 16.524 | 3.230 | 14.682 |
| K9gvpep8 | S | G | G | S | M | P | W | N | L | E | R | I | F | A | L | H | 2.736 | 15.815 | 3.192 | 21.280 |
| K9gvpep9 | S | G | C | S | D | L | W | N | L | A | R | I | Y | P | M | C | 0.514 | 3.594 | 2.211 | 15.144 |
| K9gvpep10 | S | G | C | R | L | P | W | N | L | Q | R | I | G | L | P | C | 3.092 | 27.897 | 3.235 | 29.432 |

Figure 17

| target | phage | peptide | IC50 nM | error |
|---|---|---|---|---|
| PCSK9 | Φpep2-8 | pep2-8_K9gvpep4 | 6.1901 | 0.28577 |
| PCSK9 | ΦK9gvpep4 | pep2-8_K9gvpep4 | 3.4363 | 0.13577 |
| PCSK9 | Φpep2-8 | pep2-8_K9gvpep4 | 14.453 | 0.84065 |
| PCSK9 | ΦK9gvpep4 | pep2-8_K9gvpep7 | 2.6881 | 0.31579 |
| PCSK9Δhelix | Φpep2-8 | pep2-8_K9gvpep4 | 2.9185 | 0.21971 |
| PCSK9Δhelix | ΦK9gvpep4 | pep2-8_K9gvpep4 | 5.6497 | 0.52564 |
| PCSK9Δhelix | Φpep2-8 | pep2-8_K9gvpep7 | 1.7518 | 0.14796 |
| PCSK9Δhelix | ΦK9gvpep4 | pep2-8_K9gvpep7 | 5.9867 | 0.48306 |

Figure 19

SEQUENCE LISTING

```
<160> NUMBER OF SEQ ID NOS: 403

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300
```

```
Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
        340                 345                 350

Thr Asn Phe Gly Arg Cys Val Asp Leu Phe Ala Pro Gly Glu Asp Ile
    355                 360                 365

Ile Gly Ala Ser Ser Asp Cys Ser Thr Cys Phe Val Ser Gln Ser Gly
370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690
```

<210> SEQ ID NO 2
<211> LENGTH: 33
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(13)
<223> OTHER INFORMATION: /replace="Thr-Ala-Phe-Thr-Ser-Trp-Glu-Glu-Tyr-
      Leu-Asp-Trp-Val" or " "
<220> FEATURE:
<221> NAME/KEY: VARIANT
<222> LOCATION: (14)..(17)
<223> OTHER INFORMATION: /replace="Ser" or "5-aminopentanoic acid" or
      "6-aminohexanoic acid" "7-aminoheptanoic acid" or "8-aminooctanoic
      acid" or "9-aminononaoic acid" or "10-aminodecanoic acid" or
      "11-aminoundecanoic acid" or " "
<220> FEATURE:
<221> NAME/KEY: MISC_FEATURE
<222> LOCATION: (14)..(17)
<223> OTHER INFORMATION: /note="This region may encompass 1-4 residues"
<220> FEATURE:
<221> NAME/KEY: VARIANT
<222> LOCATION: (18)..(21)
<223> OTHER INFORMATION: /replace="2-aminocyclohexane-1-carboxylic acid"
      or "Arg" or "Asp" or "Cys" or "Gly" or "3-hydroxyproline" or "Ile"
      or "Leu" or "Met" or "Phe" or "Pro" or "Trp"
<220> FEATURE:
<221> NAME/KEY: MISC_FEATURE
<222> LOCATION: (18)..(21)
<223> OTHER INFORMATION: /note="This region may encompass 1-4 residues"
<220> FEATURE:
<221> NAME/KEY: VARIANT
<222> LOCATION: (25)..(25)
<223> OTHER INFORMATION: /replace="2,3-diaminopropionic acid" or "Gln"
      or "Gly" or "Lys" or "Val"
<220> FEATURE:
<221> NAME/KEY: VARIANT
<222> LOCATION: (26)..(26)
<223> OTHER INFORMATION: /replace="homo-Arg"
<220> FEATURE:
<221> NAME/KEY: MOD_RES
<222> LOCATION: (29)..(33)
<223> OTHER INFORMATION: /replace="Arg" or "Cys" or "Glu" or "Gln" or
      "Gly" or "Leu" or "Lys" or "Phe" or "Pro" or "Ser" or "Thr" or
      "Trp" or " "
<220> FEATURE:
<221> NAME/KEY: MISC_FEATURE
<222> LOCATION: (29)..(33)
<223> OTHER INFORMATION: /note="This region may encompass 1-4 residues"
<220> FEATURE:
<221> NAME/KEY: MISC_FEATURE
<222> LOCATION: (1)..(33)
<223> OTHER INFORMATION: /note="Variant residues given in the sequence
      have no preference with respect to those in the annotations
      for variant positions"

<400> SEQUENCE: 2

Thr Val Phe Thr Ser Trp Glu Glu Tyr Leu Asp Trp Val Gly Gly Gly
1               5                   10                  15

Gly Ala Ala Ala Ala Trp Asn Leu Ala Arg Ile Gly Ala Ala Ala Ala
            20                  25                  30

Ala

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3
```

Thr Val Phe Thr Ser Trp Glu Glu Tyr Leu Asp Trp Val
1               5                   10

<210> SEQ ID NO 4
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Thr Ala Phe Thr Ser Trp Glu Glu Tyr Leu Asp Trp Val
1               5                   10

<210> SEQ ID NO 5
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Ile Pro Trp Asn Leu Glu Arg Ile Thr Pro Pro Arg Tyr Arg Ala
1               5                   10                  15

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Cys Trp Asn Leu Lys Arg Ile Gly Ser Gln Gly Cys
1               5                   10

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asp Leu Met Pro Trp Asn Leu Val Arg Ile Gly Leu Leu Arg
1               5                   10

<210> SEQ ID NO 8
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: homo-Arg

<400> SEQUENCE: 8

```
Met Glu Ser Phe Pro Gly Trp Asn Leu Xaa Ile Gly Leu Leu Arg
1               5                   10                  15
```

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: homo-Arg

<400> SEQUENCE: 9

```
Trp Asn Leu Xaa Ile Gly Leu Leu Arg
1               5
```

<210> SEQ ID NO 10
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
Thr Val Ala Thr Ser Ala Glu Glu Tyr Leu Leu Trp Val
1               5                   10
```

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

```
Gly Gly Ser Gly
1
```

<210> SEQ ID NO 12
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

```
Gly Ser Gly Gly
1
```

<210> SEQ ID NO 13
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gly Ser Gly
1

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Leu Met Pro
1

<210> SEQ ID NO 15
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Cys Ala Leu Pro
1

<210> SEQ ID NO 16
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Cys Phe Ile Pro
1

<210> SEQ ID NO 17
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Cys Phe Leu Pro
1

<210> SEQ ID NO 18
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Cys Arg Ala Pro
1

```
<210> SEQ ID NO 19
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Hyp

<400> SEQUENCE: 19

Cys Arg Leu Xaa
1

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Cys Arg Leu Pro
1

<210> SEQ ID NO 21
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Asp Ala Met Pro
1

<210> SEQ ID NO 22
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp Leu Ala Pro
1

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Leu Met Pro
1
```

```
<210> SEQ ID NO 24
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Gln Gly Cys
1

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Gln Cys Glu Tyr
1               5

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Gln Cys Trp Phe
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser Gln Gly Cys Trp
1               5

<210> SEQ ID NO 28
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr Val Phe Thr Ser Trp Glu Glu Tyr Leu Asp Trp Val Gly Ser Gly
1               5                   10                  15

Lys Leu Trp Asn Leu Gly Arg Val
            20

<210> SEQ ID NO 29
```

```
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Thr Val Phe Thr Ser Trp Glu Glu Tyr Leu Asp Trp Val Gly Ser Gly
1               5                   10                  15

Cys Trp Asn Leu Lys Arg Ile Gly Ser Gln Gly Cys
            20                  25

<210> SEQ ID NO 30
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Trp-6fl

<400> SEQUENCE: 30

Thr Val Phe Thr Ser Xaa Glu Glu Tyr Leu Asp Trp Val
1               5                   10

<210> SEQ ID NO 31
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Thr Val Phe Thr Ser Trp Glu Glu Tyr Leu Asp Trp Val Gly Ser Gly
1               5                   10                  15

Lys Leu Trp Asn Leu Gly Arg
            20

<210> SEQ ID NO 32
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Thr Val Phe Thr Ser Trp Glu Glu Tyr Leu Asp Trp Val Gly Ser Gly
1               5                   10                  15

Lys Leu Trp Asn Leu Gly
            20

<210> SEQ ID NO 33
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 33

Thr Val Phe Thr Ser Trp Glu Glu Tyr Leu Asp Trp Val Gly Ser Gly
1               5                   10                  15

Lys Leu Trp Asn Leu
            20

<210> SEQ ID NO 34
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Thr Val Phe Thr Ser Trp Glu Glu Tyr Leu Asp Trp Val Gly Ser Gly
1               5                   10                  15

Lys Leu Trp Asn
            20

<210> SEQ ID NO 35
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Thr Val Phe Thr Ser Trp Glu Glu Tyr Leu Asp Trp Val Gly Gly Ser
1               5                   10                  15

Gly Lys Leu Trp Asn Leu Gly Arg Val
            20                  25

<210> SEQ ID NO 36
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Thr Val Phe Thr Ser Trp Glu Glu Tyr Leu Asp Trp Val Gly Ser Gly
1               5                   10                  15

Gly Lys Leu Trp Asn Leu Gly Arg Val
            20                  25

<210> SEQ ID NO 37
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Aoc

<400> SEQUENCE: 37

```
Thr Val Phe Thr Ser Trp Glu Glu Tyr Leu Asp Trp Val Xaa Lys Leu
1               5                   10                  15

Trp Asn Leu Gly Arg Val
            20
```

<210> SEQ ID NO 38
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Thr Val Phe Thr Ser Trp Glu Glu Tyr Leu Asp Trp Val Gly Ser Gly
1               5                   10                  15

Cys Trp Asn Leu Gly Arg Ile Gly Ser Gln Gly Cys
            20                  25
```

<210> SEQ ID NO 39
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Thr Val Phe Thr Ser Trp Glu Glu Tyr Leu Asp Trp Val Gly Ser Gly
1               5                   10                  15

Cys Trp Asn Leu Lys Arg Val Gly Ser Gln Gly Cys
            20                  25
```

<210> SEQ ID NO 40
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

```
Thr Val Phe Thr Ser Trp Glu Glu Tyr Leu Asp Trp Val Gly Gly Ser
1               5                   10                  15

Gly Cys Trp Asn Leu Lys Arg Ile Gly Ser Gln Gly Cys
            20                  25
```

<210> SEQ ID NO 41
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

```
Thr Val Phe Thr Ser Trp Glu Glu Tyr Leu Asp Trp Val Gly Ser Gly
1               5                   10                  15

Gly Cys Trp Asn Leu Lys Arg Ile Gly Ser Gln Gly Cys
            20                  25
```

<210> SEQ ID NO 42
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Aoc

<400> SEQUENCE: 42

Thr Val Phe Thr Ser Trp Glu Glu Tyr Leu Asp Trp Val Xaa Cys Trp
1               5                   10                  15

Asn Leu Lys Arg Ile Gly Ser Gln Gly Cys
            20                  25

<210> SEQ ID NO 43
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahp

<400> SEQUENCE: 43

Thr Val Phe Thr Ser Trp Glu Glu Tyr Leu Asp Trp Val Xaa Lys Leu
1               5                   10                  15

Trp Asn Leu Gly Arg Val
            20

<210> SEQ ID NO 44
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

<400> SEQUENCE: 44

Thr Val Phe Thr Ser Trp Glu Glu Tyr Leu Asp Trp Val Xaa Cys Trp
1               5                   10                  15

Asn Leu Lys Arg Ile Gly Ser Gln Gly Cys
            20                  25

<210> SEQ ID NO 45
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

```
<400> SEQUENCE: 45

Thr Val Phe Thr Ser Trp Glu Glu Tyr Leu Asp Trp Val Xaa Lys Leu
1               5                   10                  15

Trp Asn Leu Gly Arg Val
            20

<210> SEQ ID NO 46
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Thr Val Phe Thr Ser Trp Glu Glu Tyr Leu Asp Trp Val Gly Ser Gly
1               5                   10                  15

Cys Arg Leu Pro Trp Asn Leu Gln Arg Ile Gly Leu Pro Cys
            20                  25                  30

<210> SEQ ID NO 47
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Thr Val Phe Thr Ser Trp Glu Glu Tyr Leu Asp Trp Val Gly Ser Gly
1               5                   10                  15

Asp Leu Met Pro Trp Asn Leu Val Arg Ile Gly Leu Leu Arg
            20                  25                  30

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Cys Trp Asn Leu Lys Arg Ile Gly Ser Gln Gly Cys
1               5                   10

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Ser Gly Cys Trp Asn Leu Lys Arg Ile Gly Ser Gln Gly Cys
1               5                   10                  15

<210> SEQ ID NO 50
<211> LENGTH: 10
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ser Pro Cys Arg Val Gly Tyr Thr Pro Cys
1               5                   10

<210> SEQ ID NO 51
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahp

<400> SEQUENCE: 51

Thr Val Phe Thr Ser Trp Glu Glu Tyr Leu Asp Trp Val Xaa Cys Trp
1               5                   10                  15

Asn Leu Lys Arg Ile Gly Ser Gln Gly Cys
            20                  25

<210> SEQ ID NO 52
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Thr Val Phe Thr Ser Trp Glu Glu Tyr Leu Asp Trp Val Gly Ser Gly
1               5                   10                  15

Gly Cys Arg Leu Pro Trp Asn Leu Gln Arg Ile Gly Leu Pro Cys
            20                  25                  30

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Gly Cys Phe Ile Pro Trp Asn Leu Gln Arg Ile Gly Leu Leu Cys
1               5                   10                  15

<210> SEQ ID NO 54
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Gly Cys Arg Leu Pro Trp Asn Leu Gln Arg Ile Gly Leu Pro Cys

```
<210> SEQ ID NO 55
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ser Gly Asp Leu Met Pro Trp Asn Leu Val Arg Ile Gly Leu Leu Arg
1               5                   10                  15

<210> SEQ ID NO 56
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser Gly Cys Phe Ile Pro Trp Asn Leu Gln Arg Ile Gly Leu Leu Cys
1               5                   10                  15

<210> SEQ ID NO 57
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Gly Cys Arg Leu Pro Trp Asn Leu Gln Arg Ile Gly Leu Pro Cys
1               5                   10                  15

<210> SEQ ID NO 58
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Cys Phe Ile Pro Trp Asn Leu Gln Arg Ile Gly Leu Leu Cys
1               5                   10

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Cys Arg Leu Pro Trp Asn Leu Gln Arg Ile Gly Leu Pro Cys
1               5                   10

<210> SEQ ID NO 60
```

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ser Gly Ser Gly Cys Phe Ile Pro Trp Asn Leu Gln Arg Ile Gly Leu
1               5                   10                  15

Leu Cys

<210> SEQ ID NO 61
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Gly Ser Gly Cys Arg Leu Pro Trp Asn Leu Gln Arg Ile Gly Leu
1               5                   10                  15

Pro Cys

<210> SEQ ID NO 62
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Asp Leu Met Pro Trp Asn Leu Val Arg Ile Gly Leu Leu Arg
1               5                   10

<210> SEQ ID NO 63
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Cit

<400> SEQUENCE: 63

Ser Gly Cys Phe Ile Pro Trp Asn Leu Gln Xaa Ile Gly Leu Pro Cys
1               5                   10                  15

<210> SEQ ID NO 64
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Hyp
```

<400> SEQUENCE: 64

Ser Gly Cys Arg Leu Xaa Trp Asn Leu Gln Arg Ile Gly Leu Pro Cys
1               5                   10                  15

<210> SEQ ID NO 65
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Thr Val Phe Thr Ser Trp Glu Glu Tyr Leu Asp Trp Val Gly Ser Gly
1               5                   10                  15

Gly Cys Phe Leu Pro Trp Asn Leu Gln Arg Ile Gly Leu Leu Cys
            20                  25                  30

<210> SEQ ID NO 66
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Cys Trp Asn Leu Lys Arg Ile Gly Ser Gln Gly Cys Trp
1               5                   10

<210> SEQ ID NO 67
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Ser Gly Cys Trp Asn Leu Lys Arg Ile Gly Ser Gln Gly Cys Trp
1               5                   10                  15

<210> SEQ ID NO 68
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Leu Met Pro Ala Asn Leu Val Arg Ile Gly Leu Leu Arg
1               5                   10

<210> SEQ ID NO 69
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asp Leu Met Ala Trp Asn Leu Val Arg Ile Gly Leu Leu Arg
1               5                   10

<210> SEQ ID NO 70
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Asp Leu Ala Pro Trp Asn Leu Val Arg Ile Gly Leu Leu Arg
1               5                   10

<210> SEQ ID NO 71
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Asp Ala Met Pro Trp Asn Leu Val Arg Ile Gly Leu Leu Arg
1               5                   10

<210> SEQ ID NO 72
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ala Leu Met Pro Trp Asn Leu Val Arg Ile Gly Leu Leu Arg
1               5                   10

<210> SEQ ID NO 73
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Asp Leu Met Pro Trp Asn Leu Val Arg Ile Gly Leu Leu
1               5                   10

<210> SEQ ID NO 74
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Leu Met Pro Trp Asn Leu Val Arg Ile Gly Leu
1               5                   10

```
<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asp Leu Met Pro Trp Asn Leu Val Arg Ile Gly
1               5                   10

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Asp Leu Met Pro Trp Asn Leu Val Arg Ile
1               5                   10

<210> SEQ ID NO 77
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Leu Met Pro Trp Asn Leu Val Arg Ile Gly Leu Leu Arg
1               5                   10

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Met Pro Trp Asn Leu Val Arg Ile Gly Leu Leu Arg
1               5                   10

<210> SEQ ID NO 79
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Pro Trp Asn Leu Val Arg Ile Gly Leu Leu Arg
1               5                   10

<210> SEQ ID NO 80
<211> LENGTH: 10
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Trp Asn Leu Val Arg Ile Gly Leu Leu Arg
1               5                   10

<210> SEQ ID NO 81
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asp Leu Met Pro Trp Asn Leu Val Arg Ile Gly Leu Leu Ala
1               5                   10

<210> SEQ ID NO 82
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Asp Leu Met Pro Trp Asn Leu Val Arg Ile Gly Leu Ala Arg
1               5                   10

<210> SEQ ID NO 83
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Asp Leu Met Pro Trp Asn Leu Val Arg Ile Gly Ala Leu Arg
1               5                   10

<210> SEQ ID NO 84
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Asp Leu Met Pro Trp Asn Leu Val Arg Ile Ala Leu Leu Arg
1               5                   10

<210> SEQ ID NO 85
<211> LENGTH: 14
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 85

Asp Leu Met Pro Trp Asn Leu Val Arg Ala Gly Leu Leu Arg
1               5                   10

<210> SEQ ID NO 86
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Asp Leu Met Pro Trp Asn Leu Val Ala Ile Gly Leu Leu Arg
1               5                   10

<210> SEQ ID NO 87
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Asp Leu Met Pro Trp Asn Leu Ala Arg Ile Gly Leu Leu Arg
1               5                   10

<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Asp Leu Met Pro Trp Asn Ala Val Arg Ile Gly Leu Leu Arg
1               5                   10

<210> SEQ ID NO 89
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Asp Leu Met Pro Trp Ala Leu Val Arg Ile Gly Leu Leu Arg
1               5                   10

<210> SEQ ID NO 90
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90
```

```
Met Cys Leu Trp Asn Leu Lys Arg Ile Gly Ser Gln Cys Glu Tyr
1               5                   10                  15

<210> SEQ ID NO 91
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Cys Leu Trp Asn Leu Lys Arg Ile Gly Ser Gln Cys Glu Tyr
1               5                   10                  15

<210> SEQ ID NO 92
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Trp Cys Leu Trp Asn Leu Lys Arg Ile Gly Ser Gln Cys Glu Tyr
1               5                   10                  15

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Trp Cys Leu Trp Asn Leu Lys Arg Ile Gly Ser Gln Cys Trp Phe
1               5                   10                  15

<210> SEQ ID NO 94
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Cys Arg Leu Pro Trp Asn Leu Lys Arg Ile Gly Leu Pro Cys
1               5                   10

<210> SEQ ID NO 95
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Cys Arg Leu Pro Trp Asn Leu Gln Arg Ile Gly Leu Ala Cys
1               5                   10
```

```
<210> SEQ ID NO 96
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Cys Arg Leu Pro Trp Asn Leu Gln Arg Ile Gly Ala Pro Cys
1               5                   10

<210> SEQ ID NO 97
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Cys Arg Leu Pro Trp Asn Leu Gln Arg Ile Ala Leu Pro Cys
1               5                   10

<210> SEQ ID NO 98
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Cys Arg Leu Pro Trp Asn Leu Gln Arg Ala Gly Leu Pro Cys
1               5                   10

<210> SEQ ID NO 99
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Cys Arg Leu Pro Trp Asn Leu Gln Ala Ile Gly Leu Pro Cys
1               5                   10

<210> SEQ ID NO 100
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Cys Arg Leu Pro Trp Asn Leu Ala Arg Ile Gly Leu Pro Cys
1               5                   10

<210> SEQ ID NO 101
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Cys Arg Leu Pro Trp Asn Ala Gln Arg Ile Gly Leu Pro Cys
1               5                   10

<210> SEQ ID NO 102
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Cys Arg Leu Pro Trp Ala Leu Gln Arg Ile Gly Leu Pro Cys
1               5                   10

<210> SEQ ID NO 103
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Cys Arg Leu Pro Ala Asn Leu Gln Arg Ile Gly Leu Pro Cys
1               5                   10

<210> SEQ ID NO 104
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Cys Arg Leu Ala Trp Asn Leu Gln Arg Ile Gly Leu Pro Cys
1               5                   10

<210> SEQ ID NO 105
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Cys Arg Ala Pro Trp Asn Leu Gln Arg Ile Gly Leu Pro Cys
1               5                   10

<210> SEQ ID NO 106
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                    Synthetic peptide"

<400> SEQUENCE: 106

Cys Ala Leu Pro Trp Asn Leu Gln Arg Ile Gly Leu Pro Cys
1               5                   10

<210> SEQ ID NO 107
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Cys Arg Leu Pro Trp Asn Leu Gln Arg Ile Gly Leu Gly Cys
1               5                   10

<210> SEQ ID NO 108
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Cys Arg Leu Pro Trp Asn Leu Gln Arg Ile Gly Gly Gly Cys
1               5                   10

<210> SEQ ID NO 109
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Ach

<400> SEQUENCE: 109

Cys Arg Leu Xaa Trp Asn Leu Gln Arg Ile Gly Leu Pro Cys
1               5                   10

<210> SEQ ID NO 110
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Aun

<400> SEQUENCE: 110

Cys Arg Leu Pro Trp Asn Leu Gln Arg Xaa Cys
1               5                   10

<210> SEQ ID NO 111
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Ade

<400> SEQUENCE: 111

Cys Arg Leu Pro Trp Asn Leu Gln Arg Xaa Cys
1               5                   10

<210> SEQ ID NO 112
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Ano

<400> SEQUENCE: 112

Cys Arg Leu Pro Trp Asn Leu Gln Arg Xaa Cys
1               5                   10

<210> SEQ ID NO 113
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Aoc

<400> SEQUENCE: 113

Cys Arg Leu Pro Trp Asn Leu Gln Arg Xaa Cys
1               5                   10

<210> SEQ ID NO 114
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Gly Cys Leu Trp Asn Leu Lys Arg Ile Gly Ser Gln Cys Trp Phe
1               5                   10                  15

<210> SEQ ID NO 115
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115
```

```
Phe Cys Leu Trp Asn Leu Ala Arg Ile Gly Ser Gln Cys Trp Phe
1               5                   10                  15
```

<210> SEQ ID NO 116
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

```
Trp Cys Leu Trp Asn Leu Lys Arg Ile Gly Ser Gln Cys Trp Phe
1               5                   10                  15
```

<210> SEQ ID NO 117
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

```
Trp Cys Leu Trp Asn Leu Lys Arg Ile Gly Ser Gln Cys Trp Phe
1               5                   10                  15
```

<210> SEQ ID NO 118
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

<400> SEQUENCE: 118

```
Thr Val Phe Thr Ser Trp Glu Glu Tyr Leu Asp Trp Val Xaa Ala Trp
1               5                   10                  15

Asn Leu Lys Arg Ile Gly Ser
            20
```

<210> SEQ ID NO 119
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

<400> SEQUENCE: 119

```
Thr Val Phe Thr Ser Trp Glu Glu Tyr Leu Asp Trp Val Xaa Ala Trp
1               5                   10                  15

Asn Leu Lys Arg Ile Gly
            20
```

```
<210> SEQ ID NO 120
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

<400> SEQUENCE: 120

Thr Val Phe Thr Ser Trp Glu Glu Tyr Leu Asp Trp Val Xaa Ala Trp
1               5                   10                  15

Asn Leu Lys Arg Ile
            20

<210> SEQ ID NO 121
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Ahx

<400> SEQUENCE: 121

Thr Val Phe Thr Ser Trp Glu Glu Tyr Leu Asp Trp Val Xaa Ala Trp
1               5                   10                  15

Asn Leu Lys Arg
            20

<210> SEQ ID NO 122
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Phe Cys Leu Trp Asn Leu Lys Arg Ile Gly Ser Gln Cys Glu Tyr
1               5                   10                  15

<210> SEQ ID NO 123
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Phe Cys Leu Trp Asn Leu Lys Arg Ile Gly Ala Gln Cys Trp Phe
1               5                   10                  15

<210> SEQ ID NO 124
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Dpr

<400> SEQUENCE: 124

Gly Ser Gly Cys Trp Asn Leu Xaa Arg Ile Gly Ser Gln Gly Cys
1               5                   10                  15

<210> SEQ ID NO 125
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Ser Gly Cys Trp Asn Leu Lys Arg Ile Gly Ser Gln Gly Cys
1               5                   10                  15

<210> SEQ ID NO 126
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: D-amino acid

<400> SEQUENCE: 126

Cys Arg Leu Pro Trp Asn Leu Gln Arg Ile Gly Leu Pro Cys
1               5                   10

<210> SEQ ID NO 127
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: D-amino acid

<400> SEQUENCE: 127

Cys Arg Leu Pro Trp Asn Leu Gln Arg Ile Gly Leu Pro Cys
1               5                   10

<210> SEQ ID NO 128
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: D-amino acid
```

```
<400> SEQUENCE: 128

Cys Arg Leu Pro Trp Asn Leu Gln Arg Ile Gly Leu Pro Cys
1               5                   10

<210> SEQ ID NO 129
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: D-amino acid

<400> SEQUENCE: 129

Cys Arg Leu Pro Trp Asn Leu Gln Arg Ile Gly Leu Pro Cys
1               5                   10

<210> SEQ ID NO 130
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: D-amino acid

<400> SEQUENCE: 130

Cys Arg Leu Pro Trp Asn Leu Gln Arg Ile Gly Leu Pro Cys
1               5                   10

<210> SEQ ID NO 131
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: D-amino acid

<400> SEQUENCE: 131

Cys Arg Leu Pro Trp Asn Leu Gln Arg Ile Gly Leu Pro Cys
1               5                   10

<210> SEQ ID NO 132
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: D-amino acid

<400> SEQUENCE: 132
```

```
Cys Arg Leu Pro Trp Asn Leu Gln Arg Ile Gly Leu Pro Cys
1               5                   10
```

<210> SEQ ID NO 133
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: D-amino acid

<400> SEQUENCE: 133

```
Cys Arg Leu Pro Trp Asn Leu Gln Arg Ile Gly Leu Pro Cys
1               5                   10
```

<210> SEQ ID NO 134
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: D-amino acid

<400> SEQUENCE: 134

```
Cys Arg Leu Pro Trp Asn Leu Gln Arg Ile Gly Leu Pro Cys
1               5                   10
```

<210> SEQ ID NO 135
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: D-amino acid

<400> SEQUENCE: 135

```
Cys Arg Leu Pro Trp Asn Leu Gln Arg Ile Gly Leu Pro Cys
1               5                   10
```

<210> SEQ ID NO 136
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: D-amino acid

<400> SEQUENCE: 136

```
Cys Arg Leu Pro Trp Asn Leu Gln Arg Ile Gly Leu Pro Cys
1               5                   10
```

```
<210> SEQ ID NO 137
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-amino acid

<400> SEQUENCE: 137

Cys Arg Leu Pro Trp Asn Leu Gln Arg Ile Gly Leu Pro Cys
1               5                   10

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Trp Asn Leu Val Arg Ile Gly Leu Leu Arg
1               5                   10

<210> SEQ ID NO 139
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Trp Asn Leu Val Arg Ile Gly Leu Thr Arg
1               5                   10

<210> SEQ ID NO 140
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Trp Asn Leu Val Arg Ile Gly Thr Thr Arg
1               5                   10

<210> SEQ ID NO 141
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Trp Asn Leu Val Arg Ile Gly Thr Leu Arg
1               5                   10
```

```
<210> SEQ ID NO 142
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Ape

<400> SEQUENCE: 142

Cys Arg Leu Pro Trp Asn Leu Gln Arg Ile Xaa Cys
1               5                   10

<210> SEQ ID NO 143
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Ahx

<400> SEQUENCE: 143

Cys Arg Leu Pro Trp Asn Leu Gln Arg Ile Xaa Cys
1               5                   10

<210> SEQ ID NO 144
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: homo-Arg

<400> SEQUENCE: 144

Cys Arg Leu Pro Trp Asn Leu Gln Xaa Ile Gly Leu Pro Cys
1               5                   10

<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 145

Trp Asn Leu Val Xaa Ile Gly Leu Thr Arg
1               5                   10

<210> SEQ ID NO 146
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Pro Trp Asn Leu Val Arg Ile Gly Leu
1               5

<210> SEQ ID NO 147
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Trp Asn Leu Val Arg Ile Gly Leu
1               5

<210> SEQ ID NO 148
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Ahp

<400> SEQUENCE: 148

Cys Arg Leu Pro Trp Asn Leu Gln Arg Ile Xaa Cys
1               5                   10

<210> SEQ ID NO 149
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Thr Val Phe Thr Ser Trp Glu Glu Tyr Leu Asp Trp Val Ser Gly Gly
1               5                   10                  15

Cys Arg Leu Pro Trp Asn Leu Gln Arg Ile Gly Leu Pro Cys
            20                  25                  30

<210> SEQ ID NO 150
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gly Cys Leu Trp Asn Leu Lys Arg Ile Gly Ser Gln Cys Trp Phe
1               5                   10                  15
```

<210> SEQ ID NO 151
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gly Cys Leu Trp Asn Leu Ala Arg Ile Gly Ser Gln Cys Trp Phe
1               5                   10                  15

<210> SEQ ID NO 152
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Gly Cys Leu Trp Asn Leu Lys Arg Ile Gly Ser Gln Cys Trp Phe
1               5                   10                  15

<210> SEQ ID NO 153
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gly Cys Leu Trp Asn Leu Lys Arg Ile Gly Ser Gln Cys Trp Phe
1               5                   10                  15

<210> SEQ ID NO 154
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(13)
<223> OTHER INFORMATION: /replace="Thr-Val-Phe-Thr-Ser-Trp(6fl)-Glu-Glu-
      Tyr-Leu-Asp-Trp-Val" or "Thr-Ala-Phe-Thr-Ser-Trp-Glu-Glu-Tyr-Leu-
      Asp-Trp-Val" or " "
<220> FEATURE:
<221> NAME/KEY: VARIANT
<222> LOCATION: (14)..(17)
<223> OTHER INFORMATION: /replace="Ser" or "5-aminopentanoic acid" or
      "6-aminohexanoic acid" "7-aminoheptanoic acid" or "8-aminooctanoic
      acid" or "9-aminononanoic acid" or "10-aminodecanoic acid" or
      "11-aminoundecanoic acid" or " "
<220> FEATURE:
<221> NAME/KEY: MISC_FEATURE
<222> LOCATION: (14)..(17)
<223> OTHER INFORMATION: /note="This region may encompass 1-4 residues"
<220> FEATURE:
<221> NAME/KEY: VARIANT
<222> LOCATION: (18)..(23)
<223> OTHER INFORMATION: /replace="2-aminocyclohexane-1-carboxylic acid"
      or "Arg" or "Asp" or "Cys" or "Glu" or "3-hydroxyproline" or "Ile"
      or "Leu" or "Met" or "Phe" or "Pro" or "Trp"
<220> FEATURE:
<221> NAME/KEY: MISC_FEATURE

```
<222> LOCATION: (18)..(23)
<223> OTHER INFORMATION: /note="This region may encompass 1-6 residues"
<220> FEATURE:
<221> NAME/KEY: VARIANT
<222> LOCATION: (24)..(24)
<223> OTHER INFORMATION: /replace="Trp(6fl)" or "Trp(6Cl" or "Trp(6Br)"
      or "Trp(6Me"
<220> FEATURE:
<221> NAME/KEY: VARIANT
<222> LOCATION: (27)..(27)
<223> OTHER INFORMATION: /replace="2,3-diaminopropionic acid" or "Gln"
      or "Gly" or "Lys" or "Val"
<220> FEATURE:
<221> NAME/KEY: VARIANT
<222> LOCATION: (28)..(28)
<223> OTHER INFORMATION: /replace="homo-Arg"
<220> FEATURE:
<221> NAME/KEY: MOD_RES
<222> LOCATION: (31)..(35)
<223> OTHER INFORMATION: /replace="Arg" or "Cys" or "Glu" or "Gln" or
      "Gly" or "Leu" or "Lys" or "Phe" or "Pro" or "Ser" or "Thr" or
      "Trp" or " "
<220> FEATURE:
<221> NAME/KEY: MISC_FEATURE
<222> LOCATION: (31)..(35)
<223> OTHER INFORMATION: /note="This region may encompass 1-5 residues"
<220> FEATURE:
<221> NAME/KEY: MISC_FEATURE
<222> LOCATION: (1)..(35)
<223> OTHER INFORMATION: /note="Variant residues given in the sequence
      have no preference with respect to those in the annotations
      for variant positions"

<400> SEQUENCE: 154

Thr Val Phe Thr Ser Trp Glu Glu Tyr Leu Asp Trp Val Gly Gly
1               5                   10                  15

Gly Ala Ala Ala Ala Ala Ala Trp Asn Leu Ala Arg Ile Gly Ala Ala
            20                  25                  30

Ala Ala Ala
        35

<210> SEQ ID NO 155
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Hyp

<400> SEQUENCE: 155

Cys Phe Ile Xaa
1

<210> SEQ ID NO 156
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Asp Ser Tyr Pro Gly
1               5
```

```
<210> SEQ ID NO 157
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Glu Ser Phe Pro Gly
1               5

<210> SEQ ID NO 158
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Glu Ser Tyr Pro Gly
1               5

<210> SEQ ID NO 159
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Met Asp Ser Phe Pro Gly
1               5

<210> SEQ ID NO 160
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Met Glu Ser Phe Pro Gly
1               5

<210> SEQ ID NO 161
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Ser Phe Ala Phe Pro Gly
1               5

<210> SEQ ID NO 162
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 162

Ser Gly Asp Leu Met Pro Trp Asn Leu Val Arg Ile Gly Leu Leu Arg
1               5                   10                  15

<210> SEQ ID NO 163
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Trp Asn Leu Val Arg Ile Gly Leu Leu Arg
1               5                   10

<210> SEQ ID NO 164
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Gly Leu Met Pro Trp Asn Leu Val Arg Ile Gly Leu Leu Arg
1               5                   10

<210> SEQ ID NO 165
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gly Gly Met Pro Trp Asn Leu Val Arg Ile Gly Leu Leu Arg
1               5                   10

<210> SEQ ID NO 166
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Trp Asn Leu Val Arg Ile Gly Leu Leu Arg
1               5                   10

<210> SEQ ID NO 167
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 167

Trp Asn Leu Val Arg Ile Gly Leu Leu Arg
1               5                   10

<210> SEQ ID NO 168
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Trp Asn Leu Val Arg Ile Gly Leu Leu Arg
1               5                   10

<210> SEQ ID NO 169
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Trp Asn Leu Val Arg Ile Gly Leu Leu Arg
1               5                   10

<210> SEQ ID NO 170
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Trp Asn Leu Val Arg Ile Gly Leu Leu Arg
1               5                   10

<210> SEQ ID NO 171
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Trp Asn Leu Val Arg Ile Gly Leu Leu Arg
1               5                   10

<210> SEQ ID NO 172
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Trp Asn Leu Val Arg Ile Gly Leu Leu Arg
```

<210> SEQ ID NO 173
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Trp Asn Leu Val Arg Ile Gly Leu Leu Arg
1               5                   10

<210> SEQ ID NO 174
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Trp Asn Leu Val Arg Ile Gly Leu Leu Arg
1               5                   10

<210> SEQ ID NO 175
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Trp Asn Leu Val Arg Ile Gly Leu Leu Arg
1               5                   10

<210> SEQ ID NO 176
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Trp Asn Leu Val Arg Ile Gly Leu Leu Arg
1               5                   10

<210> SEQ ID NO 177
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Trp Asn Leu Val Arg Ile Gly Leu Leu Arg
1               5                   10

<210> SEQ ID NO 178

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Trp Asn Leu Val Arg Ile Gly Leu Leu Arg
1               5                   10

<210> SEQ ID NO 179
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Trp Asn Leu Val Arg Ile Gly Leu Leu Arg
1               5                   10

<210> SEQ ID NO 180
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Trp Asn Leu Val Arg Ile Gly Leu Leu Arg
1               5                   10

<210> SEQ ID NO 181
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Trp Asn Leu Val Arg Ile Gly Leu Leu Arg
1               5                   10

<210> SEQ ID NO 182
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Trp Asn Leu Val Arg Ile Gly Leu Leu Arg
1               5                   10

<210> SEQ ID NO 183
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 183

Trp Asn Leu Val Arg Ile Gly Leu Leu Arg
1               5                   10

<210> SEQ ID NO 184
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Trp Asn Leu Val Arg Ile Gly Leu Leu Arg
1               5                   10

<210> SEQ ID NO 185
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Trp Asn Leu Val Arg Ile Gly Leu Leu Arg
1               5                   10

<210> SEQ ID NO 186
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Trp Asn Leu Val Arg Ile Gly Leu Leu Arg
1               5                   10

<210> SEQ ID NO 187
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Trp Asn Leu Val Arg Ile Gly Leu Leu Arg
1               5                   10

<210> SEQ ID NO 188
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 188

Trp Asn Leu Val Arg Ile Gly Leu Leu Arg
1               5                   10

<210> SEQ ID NO 189
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Trp Asn Leu Val Arg Ile Gly Leu Leu Arg
1               5                   10

<210> SEQ ID NO 190
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Trp Asn Leu Val Arg Ile Gly Leu Leu Arg
1               5                   10

<210> SEQ ID NO 191
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Trp Asn Leu Val Arg Ile Gly Leu Leu Arg
1               5                   10

<210> SEQ ID NO 192
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Trp Asn Leu Val Arg Ile Gly Leu Leu Arg
1               5                   10

<210> SEQ ID NO 193
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Met Asp Ser Phe Pro Gly Trp Asn Leu Val Arg Ile Gly Leu Leu Arg
1               5                   10                  15
```

<210> SEQ ID NO 194
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Ser Phe Ala Phe Pro Gly Trp Asn Leu Val Arg Ile Gly Leu Leu Arg
1               5                   10                  15

<210> SEQ ID NO 195
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Asp Ser Tyr Pro Gly Trp Asn Leu Val Arg Ile Gly Leu Leu Arg
1               5                   10                  15

<210> SEQ ID NO 196
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Glu Ser Tyr Pro Gly Trp Asn Leu Val Arg Ile Gly Leu Leu Arg
1               5                   10                  15

<210> SEQ ID NO 197
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Glu Ser Phe Pro Gly Trp Asn Leu Val Arg Ile Gly Leu Leu Arg
1               5                   10                  15

<210> SEQ ID NO 198
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Asp Leu Met Pro Trp Asn Leu Lys Arg Ile Gly Leu Leu Arg
1               5                   10

<210> SEQ ID NO 199
<211> LENGTH: 10

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Trp Asn Leu Lys Arg Ile Gly Leu Leu Arg
1               5                   10

<210> SEQ ID NO 200
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Asp Leu Met Pro Trp Asn Leu Val Arg Ile Gly Leu Pro Arg
1               5                   10

<210> SEQ ID NO 201
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Trp Asn Leu Val Arg Ile Gly Leu Thr Arg
1               5                   10

<210> SEQ ID NO 202
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Trp Asn Leu Val Arg Ile Gly Leu Thr Arg
1               5                   10

<210> SEQ ID NO 203
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Trp Asn Leu Val Arg Ile Gly Leu Thr Arg
1               5                   10

<210> SEQ ID NO 204
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 204

Trp Asn Leu Val Arg Ile Gly Leu Thr Arg
1               5                   10

<210> SEQ ID NO 205
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Trp Asn Leu Val Arg Ile Gly Leu Thr Arg
1               5                   10

<210> SEQ ID NO 206
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Trp Asn Leu Val Arg Ile Gly Leu Thr Arg
1               5                   10

<210> SEQ ID NO 207
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Trp Asn Leu Val Arg Ile Gly Leu Thr Arg
1               5                   10

<210> SEQ ID NO 208
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Trp Asn Leu Val Arg Ile Gly Leu Thr Arg
1               5                   10

<210> SEQ ID NO 209
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209
```

Trp Asn Leu Val Arg Ile Gly Leu Thr Arg
1               5                   10

<210> SEQ ID NO 210
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Trp Asn Leu Val Arg Ile Gly Leu Thr Arg
1               5                   10

<210> SEQ ID NO 211
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Trp Asn Leu Val Arg Ile Gly Leu Thr Arg
1               5                   10

<210> SEQ ID NO 212
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Trp Asn Leu Val Arg Ile Gly Leu Thr Arg
1               5                   10

<210> SEQ ID NO 213
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Trp Asn Leu Val Arg Ile Gly Leu Thr Arg
1               5                   10

<210> SEQ ID NO 214
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Trp-6fl

<400> SEQUENCE: 214

```
Xaa Asn Leu Val Arg Ile Gly Leu Thr Arg
1               5                   10

<210> SEQ ID NO 215
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Trp-6me

<400> SEQUENCE: 215

Xaa Asn Leu Val Arg Ile Gly Leu Thr Arg
1               5                   10

<210> SEQ ID NO 216
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Trp Asn Leu Val Arg Ile Gly Leu Thr Arg
1               5                   10

<210> SEQ ID NO 217
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Trp Asn Leu Val Arg Ile Gly Leu Glu Arg
1               5                   10

<210> SEQ ID NO 218
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Trp Asn Leu Val Arg Ile Gly Leu Asp Arg
1               5                   10

<210> SEQ ID NO 219
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219
```

Trp Asn Leu Val Arg Ile Gly Leu Gly Arg
1               5                   10

<210> SEQ ID NO 220
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Trp Asn Leu Val Arg Ile Gly Leu Ala Arg
1               5                   10

<210> SEQ ID NO 221
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Trp Asn Leu Val Arg Ile Gly Leu Ser Arg
1               5                   10

<210> SEQ ID NO 222
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Trp Asn Leu Val Arg Ile Gly Thr Leu Arg
1               5                   10

<210> SEQ ID NO 223
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Trp Asn Leu Val Arg Ile Gly Thr Leu Arg
1               5                   10

<210> SEQ ID NO 224
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Trp Asn Leu Val Arg Ile Gly Thr Leu Arg
1               5                   10

```
<210> SEQ ID NO 225
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Trp Asn Leu Val Arg Ile Gly Thr Leu Arg
1               5                   10

<210> SEQ ID NO 226
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Trp-6cl

<400> SEQUENCE: 226

Xaa Asn Leu Val Arg Ile Gly Leu Thr Arg
1               5                   10

<210> SEQ ID NO 227
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Trp-6br

<400> SEQUENCE: 227

Xaa Asn Leu Val Arg Ile Gly Leu Thr Arg
1               5                   10

<210> SEQ ID NO 228
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Trp Asn Leu Val Arg Ile Gly Leu Thr Arg
1               5                   10

<210> SEQ ID NO 229
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229
```

Trp Asn Leu Val Arg Ile Gly Leu Thr Arg
1               5                   10

<210> SEQ ID NO 230
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Trp Asn Leu Val Arg Ile Gly Leu Thr Arg
1               5                   10

<210> SEQ ID NO 231
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 231

Trp Asn Leu Val Xaa Ile Gly Leu Leu Arg
1               5                   10

<210> SEQ ID NO 232
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 232

Trp Asn Leu Val Xaa Ile Gly Leu Leu Arg
1               5                   10

<210> SEQ ID NO 233
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 233

Trp Asn Leu Val Xaa Ile Gly Leu Leu Arg
1               5                   10

<210> SEQ ID NO 234
<211> LENGTH: 10

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 234

Trp Asn Leu Val Xaa Ile Gly Leu Leu Arg
1               5                   10

<210> SEQ ID NO 235
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 235

Trp Asn Leu Val Xaa Ile Gly Leu Leu Arg
1               5                   10

<210> SEQ ID NO 236
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 236

Trp Asn Leu Val Xaa Ile Gly Leu Leu Arg
1               5                   10

<210> SEQ ID NO 237
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 237

Trp Asn Leu Val Xaa Ile Gly Leu Leu Arg
1               5                   10

<210> SEQ ID NO 238
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 238

Trp Asn Leu Val Xaa Ile Gly Leu Leu Arg
1               5                   10

<210> SEQ ID NO 239
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 239

Trp Asn Leu Val Xaa Ile Gly Leu Leu Arg
1               5                   10

<210> SEQ ID NO 240
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 240

Trp Asn Leu Val Xaa Ile Gly Leu Leu Arg
1               5                   10

<210> SEQ ID NO 241
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 241

Trp Asn Leu Val Xaa Ile Gly Leu Leu Arg
1               5                   10

<210> SEQ ID NO 242
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (5)..(5)
<223> OTHER INFORMATION: homo-Arg

<400> SEQUENCE: 242

Trp Asn Leu Val Xaa Ile Gly Leu Leu Arg
1               5                   10

<210> SEQ ID NO 243
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 243

Trp Asn Leu Val Xaa Ile Gly Leu Leu Arg
1               5                   10

<210> SEQ ID NO 244
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 244

Trp Asn Leu Val Xaa Ile Gly Leu Leu Arg
1               5                   10

<210> SEQ ID NO 245
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 245

Trp Asn Leu Val Xaa Ile Gly Leu Leu Arg
1               5                   10

<210> SEQ ID NO 246
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
```

<223> OTHER INFORMATION: homo-Arg

<400> SEQUENCE: 246

Trp Asn Leu Val Xaa Ile Gly Leu Leu Arg
1               5                   10

<210> SEQ ID NO 247
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 247

Trp Asn Leu Val Xaa Ile Gly Leu Leu Arg
1               5                   10

<210> SEQ ID NO 248
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 248

Trp Asn Leu Val Xaa Ile Gly Leu Leu Arg
1               5                   10

<210> SEQ ID NO 249
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 249

Trp Asn Leu Val Xaa Ile Gly Leu Leu Arg
1               5                   10

<210> SEQ ID NO 250
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 250

Trp Asn Leu Val Xaa Ile Gly Leu Leu Arg
1               5                   10

<210> SEQ ID NO 251
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 251

Trp Asn Leu Val Xaa Ile Gly Leu Leu Arg
1               5                   10

<210> SEQ ID NO 252
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 252

Trp Asn Leu Val Xaa Ile Gly Leu Leu Arg
1               5                   10

<210> SEQ ID NO 253
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 253

Trp Asn Leu Val Xaa Ile Gly Leu Leu Arg
1               5                   10

<210> SEQ ID NO 254
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 254

Trp Asn Leu Val Xaa Ile Gly Leu Leu Arg
1               5                   10

<210> SEQ ID NO 255
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 255

Trp Asn Leu Val Xaa Ile Gly Leu Leu Arg
1               5                   10

<210> SEQ ID NO 256
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 256

Trp Asn Leu Val Xaa Ile Gly Leu Leu Arg
1               5                   10

<210> SEQ ID NO 257
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 257

Trp Asn Leu Val Xaa Ile Gly Leu Leu Arg
1               5                   10

<210> SEQ ID NO 258
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 258

Trp Asn Leu Val Xaa Ile Gly Leu Leu Arg
1               5                   10

<210> SEQ ID NO 259

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 259

Trp Asn Leu Val Xaa Ile Gly Leu Leu Arg
1               5                   10

<210> SEQ ID NO 260
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 260

Trp Asn Leu Val Xaa Ile Gly Leu Leu Arg
1               5                   10

<210> SEQ ID NO 261
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 261

Trp Asn Leu Val Xaa Ile Gly Leu Leu Arg
1               5                   10

<210> SEQ ID NO 262
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 262

Trp Asn Leu Val Xaa Ile Gly Leu Leu Arg
1               5                   10

<210> SEQ ID NO 263
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 263

Trp Asn Leu Val Xaa Ile Gly Leu Leu Arg
1               5                   10

<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 264

Trp Asn Leu Val Xaa Ile Gly Leu Leu Arg
1               5                   10

<210> SEQ ID NO 265
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 265

Trp Asn Leu Val Xaa Ile Gly Leu Leu Arg
1               5                   10

<210> SEQ ID NO 266
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 266

Trp Asn Leu Val Xaa Ile Gly Leu Leu Arg
1               5                   10

<210> SEQ ID NO 267
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
           Synthetic peptide"
<220> FEATURE:
<221> NAME/KEY: MOD_RES
<222> LOCATION: (10)..(10)
<223> OTHER INFORMATION: homo-Arg

<400> SEQUENCE: 267

Glu Ser Phe Pro Gly Trp Asn Leu Val Xaa Ile Gly Leu Leu Arg
1               5                   10                  15

<210> SEQ ID NO 268
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: homo-Arg

<400> SEQUENCE: 268

Ser Phe Ala Phe Pro Gly Trp Asn Leu Val Xaa Ile Gly Leu Leu Arg
1               5                   10                  15

<210> SEQ ID NO 269
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: homo-Arg

<400> SEQUENCE: 269

Met Glu Ser Phe Pro Gly Trp Asn Leu Val Xaa Ile Gly Leu Leu Arg
1               5                   10                  15

<210> SEQ ID NO 270
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: homo-Arg

<400> SEQUENCE: 270

Asp Ser Tyr Pro Gly Trp Asn Leu Val Xaa Ile Gly Leu Leu Arg
1               5                   10                  15

<210> SEQ ID NO 271
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (10)..(10)
<223> OTHER INFORMATION: homo-Arg

<400> SEQUENCE: 271

Glu Ser Tyr Pro Gly Trp Asn Leu Val Xaa Ile Gly Leu Leu Arg
1               5                   10                  15

<210> SEQ ID NO 272
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: homo-Arg

<400> SEQUENCE: 272

Ser Phe Ala Phe Pro Gly Trp Asn Leu Lys Xaa Ile Gly Leu Leu Arg
1               5                   10                  15

<210> SEQ ID NO 273
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: homo-Arg

<400> SEQUENCE: 273

Met Glu Ser Phe Pro Gly Trp Asn Leu Lys Xaa Ile Gly Leu Leu Arg
1               5                   10                  15

<210> SEQ ID NO 274
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 274

Trp Asn Leu Val Xaa Ile Gly Leu Thr Arg
1               5                   10

<210> SEQ ID NO 275
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg
```

```
<400> SEQUENCE: 275

Trp Asn Leu Val Xaa Ile Gly Leu Thr Arg
1               5                   10

<210> SEQ ID NO 276
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 276

Trp Asn Leu Val Xaa Ile Gly
1               5

<210> SEQ ID NO 277
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 277

Trp Asn Leu Val Xaa Ile Gly Leu Leu Gln
1               5                   10

<210> SEQ ID NO 278
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 278

Trp Asn Leu Val Xaa Ile Gly Leu Leu Asn
1               5                   10

<210> SEQ ID NO 279
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 279

Trp Asn Leu Val Xaa Ile Gly Gln Arg
```

```
1               5
```

```
<210> SEQ ID NO 280
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 280

Trp Asn Leu Val Xaa Ile Gly Asn Arg
1               5

<210> SEQ ID NO 281
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (6)..(6)
<223> OTHER INFORMATION: Trp-6fl

<400> SEQUENCE: 281

Thr Val Phe Thr Ser Xaa Glu Glu Tyr Leu Asp Trp Val Gly Ser Gly
1               5                   10                  15

Cys Arg Leu Pro Trp Asn Leu Gln Arg Ile Gly Leu Pro Cys
            20                  25                  30

<210> SEQ ID NO 282
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Hyp

<400> SEQUENCE: 282

Ser Gly Cys Phe Ile Xaa Trp Asn Leu Gln Arg Ile Gly Leu Leu Cys
1               5                   10                  15

<210> SEQ ID NO 283
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Ser Ile Pro Trp Asn Leu Glu Arg
1               5

<210> SEQ ID NO 284
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Tyr Arg Ala Asp Glu Tyr Gln Pro Pro Asp
1               5                   10

<210> SEQ ID NO 285
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Cys Ser Ile Pro Trp Asn Leu Glu Arg Ile Thr Pro Pro Arg Tyr Arg
1               5                   10                  15

Ala

<210> SEQ ID NO 286
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Thr Val Phe Thr Ser Trp Glu Glu Tyr Leu Asp Trp Val
1               5                   10

<210> SEQ ID NO 287
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Thr Val Ala Thr Ser Ala Glu Glu Tyr Leu Leu Trp Val
1               5                   10

<210> SEQ ID NO 288
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Ser Ile Pro Trp Asn Leu Glu Arg Ile Thr Pro Pro Arg
1               5                   10

<210> SEQ ID NO 289
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Thr Ala Phe Thr Ser Trp Glu Glu Tyr Leu Asp Trp Val Gly Ser Gly
1               5                   10                  15

<210> SEQ ID NO 290
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 290

Pro Trp Asn Leu Xaa Arg Ile Xaa
1               5

<210> SEQ ID NO 291
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Glu Asn Leu Tyr Phe Gln Ser
1               5

<210> SEQ ID NO 292
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Ser Ile Pro Trp Asn Leu Glu Arg Ile Thr Pro Pro Arg Glu Asn Leu
1               5                   10                  15

Tyr Phe Gln

<210> SEQ ID NO 293
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Glu Asn Leu Tyr Phe Gln
```

```
<210> SEQ ID NO 294
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Ser Ile Pro Trp Asn Leu Glu Arg Ile Thr Pro Pro Arg Tyr Arg
1               5                   10                  15

<210> SEQ ID NO 295
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Thr Ala Phe Thr Ser Trp Glu Glu Tyr Leu Asp Trp Val Gly Ser Gly
1               5                   10                  15

<210> SEQ ID NO 296
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any D-amino acid

<400> SEQUENCE: 296

Pro Trp Asn Leu Xaa Arg Ile Gly
1               5

<210> SEQ ID NO 297
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 297

His His His His His His
1               5

<210> SEQ ID NO 298
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 298

Thr Val Phe Thr Ser Trp Glu Glu Tyr Leu Asp Trp Val Gly Ser Gly
```

```
                1               5                  10                  15
Cys Arg Leu Pro Trp Asn Leu Gln Arg Ile Gly Leu Pro Cys
                20                  25                  30
```

<210> SEQ ID NO 299
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 299

```
Thr Val Phe Thr Ser Trp Glu Glu Tyr Leu Asp Trp Val Gly Ser Gly
1               5                   10                  15

Asp Leu Met Pro Trp Asn Leu Val Arg Ile Gly Leu Leu Arg
                20                  25                  30
```

<210> SEQ ID NO 300
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any D-amino acid

<400> SEQUENCE: 300

```
Trp Asn Leu Xaa Arg Ile Gly
1               5
```

<210> SEQ ID NO 301
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 301

```
Trp Asn Leu Val Xaa Ile Gly Leu Leu Arg
1               5                   10
```

<210> SEQ ID NO 302
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 302

```
Trp Asn Leu Val Xaa Ile Gly Leu
1               5
```

<210> SEQ ID NO 303
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 303

Gly Trp Asn Leu Val Arg Leu Gly Leu Leu Arg
1               5                   10

<210> SEQ ID NO 304
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 304

His His His His His His His His
1               5

<210> SEQ ID NO 305
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Ala Arg Ile Ser Pro Ala Asn Gly Asn Thr Asn
1               5                   10

<210> SEQ ID NO 306
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Lys Leu Trp Asn Leu Gly Arg Val
1               5

<210> SEQ ID NO 307
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:

```
                            Synthetic peptide"

<400> SEQUENCE: 307

Asn Cys Trp Ser Ser Leu Arg Gly Ile Cys Glu Asn Leu Gly
1               5                   10

<210> SEQ ID NO 308
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Val Leu Trp Asn His Ser Arg Ile
1               5

<210> SEQ ID NO 309
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Gly Pro Trp Asn Leu Asn Arg Val
1               5

<210> SEQ ID NO 310
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Pro Leu Leu Trp Asn Leu Gln Lys Val His
1               5                   10

<210> SEQ ID NO 311
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ser Cys Ser Trp Asn Val Glu Arg Ile Arg Gly Cys Ser Val
1               5                   10

<210> SEQ ID NO 312
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312
```

```
Lys Leu Trp Asn Leu Thr Arg Ile Ser Ser
1               5                   10

<210> SEQ ID NO 313
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Val Val Leu Trp Asn His Ser Arg Ile Leu
1               5                   10

<210> SEQ ID NO 314
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Val Pro Trp Asn Leu Ala Arg Leu
1               5

<210> SEQ ID NO 315
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Val Pro Trp Asn Leu Ala Lys Ile
1               5

<210> SEQ ID NO 316
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Gly His Pro Leu Trp Asn Leu Ser Arg Ile
1               5                   10

<210> SEQ ID NO 317
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Asn Glu Leu Trp Asn Ile Asn Arg Leu Arg Ser Ser
1               5                   10
```

```
<210> SEQ ID NO 318
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Met Pro Trp Asn Leu Ala Arg Ile Glu Arg
1               5                   10

<210> SEQ ID NO 319
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Ala Leu Trp Asn Met Arg Arg Val Glu Ser Val Ala Phe Arg
1               5                   10

<210> SEQ ID NO 320
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Gly Glu Tyr Leu Trp Asn Leu Lys Arg Leu Glu Ser
1               5                   10

<210> SEQ ID NO 321
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Thr Arg Tyr Ala Asp Arg Gly Val Met Val Tyr Ser Leu Ser
1               5                   10

<210> SEQ ID NO 322
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Met Val Tyr Val Asp Arg Gly Val Arg Val Phe Thr
1               5                   10

<210> SEQ ID NO 323
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 323

Gly Cys Val Lys Tyr Arg Gly Ser Val Ser Cys Gln Glu Ser Lys Thr
1               5                   10                  15

<210> SEQ ID NO 324
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Glu His Gln Phe Tyr Ser Tyr Arg Gly Val Asp Val Tyr Arg
1               5                   10

<210> SEQ ID NO 325
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Lys Asn Asn Tyr Ala Tyr Leu Ile Asn Met Pro Arg Ala Pro Gly Ile
1               5                   10                  15

<210> SEQ ID NO 326
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Arg Gly Gly Tyr Glu Leu Asn Ile Pro Arg
1               5                   10

<210> SEQ ID NO 327
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Ala Cys Leu Asn His Phe Val Ser Gly Asn Met Ile Arg Cys
1               5                   10

<210> SEQ ID NO 328
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 328

Cys Pro Phe Tyr Asp Trp Arg Cys Ser Asp Phe Ser
1               5                   10

<210> SEQ ID NO 329
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Asn Val Arg Cys Tyr Arg Asp Val Pro Ser Cys Ser
1               5                   10

<210> SEQ ID NO 330
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Glu Asp Val Val Cys Tyr Gly Arg Val Asp Tyr Met Pro Leu Cys Val
1               5                   10                  15

<210> SEQ ID NO 331
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Asn Pro Thr Tyr Trp Leu Thr Arg Ile Ser
1               5                   10

<210> SEQ ID NO 332
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Pro His Ser Tyr Trp Leu Asp Arg Val Gln
1               5                   10

<210> SEQ ID NO 333
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Asp Cys Asn Leu Trp Gly Asp Asp Gly Lys Tyr Arg Leu Cys Phe

```
1               5                   10                  15
```

<210> SEQ ID NO 334
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

```
Cys Val Lys Val Gly Leu Ser Trp Ile Gly Asp Cys Asn Ser
1               5                   10
```

<210> SEQ ID NO 335
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

```
Gly Val Leu Gly Val Gly Gly Met Trp Ile Ala
1               5                   10
```

<210> SEQ ID NO 336
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

```
Ser Tyr Arg Gly Ala Trp Ser Val Phe Gly Gly Ser Thr Asp
1               5                   10
```

<210> SEQ ID NO 337
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

```
Cys Met Glu Ala Trp Gln Cys Ser Leu Ala
1               5                   10
```

<210> SEQ ID NO 338
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

```
Gln Cys Tyr Pro Trp Cys Arg Leu
1               5
```

<210> SEQ ID NO 339

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Cys Trp Thr Tyr Leu Arg Gly Gly Cys Ser Val Thr
1               5                   10

<210> SEQ ID NO 340
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Pro Arg Thr Tyr Leu Arg Gly Leu Val Asp
1               5                   10

<210> SEQ ID NO 341
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Gln Thr Thr Tyr Leu Arg Val Ser Ser Ser
1               5                   10

<210> SEQ ID NO 342
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-amino acid

<400> SEQUENCE: 342

Gln Ile Ser Tyr Leu Arg Asn Ala
1               5

<210> SEQ ID NO 343
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Arg Gly Glu Val Tyr Asp Lys Gly Gly Val Ile Val His Leu
1               5                   10

<210> SEQ ID NO 344
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Gly Arg Glu Met Arg Ser Val Ile Gln Met
1               5                   10

<210> SEQ ID NO 345
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Gly Asp Cys Gly Tyr His Tyr Met Cys Ser Met Thr
1               5                   10

<210> SEQ ID NO 346
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Gln Glu Leu Pro Asn His Arg Arg Leu Ser
1               5                   10

<210> SEQ ID NO 347
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Asn Met Cys Tyr Leu Arg Gly Lys Met Asp Cys Asn Ile Val
1               5                   10

<210> SEQ ID NO 348
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Val Cys Ser Asp His Tyr Ile Gly Gly Lys Glu Val Arg Cys
1               5                   10

<210> SEQ ID NO 349
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 349

Cys Cys Ser Tyr Gly Tyr Glu Lys Cys Cys Asn Gly
1               5                   10

<210> SEQ ID NO 350
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Ser Glu Thr Gly Leu Gly Thr Tyr Tyr Gly
1               5                   10

<210> SEQ ID NO 351
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Ser Pro Cys Arg Val Gly Tyr Thr Pro Cys
1               5                   10

<210> SEQ ID NO 352
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Asn Cys Ala Arg Leu Tyr Ser His Gln Arg Asp Tyr Ser Gln Val Cys
1               5                   10                  15

<210> SEQ ID NO 353
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Cys Leu Asp Arg Ser Gly Gly Cys Tyr Thr Arg Glu Gly Tyr Leu Ser
1               5                   10                  15

<210> SEQ ID NO 354
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 354

Ser Ser Thr Trp His Phe Val Gly Gly Val Arg Val
1               5                   10

<210> SEQ ID NO 355
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Cys Tyr Pro Leu Cys Arg Val Gly
1               5

<210> SEQ ID NO 356
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Lys Cys Asp Ser His Tyr Ile Arg Gly Val Val Ala Cys His
1               5                   10

<210> SEQ ID NO 357
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Lys Met Thr His Met Lys Ala Asp
1               5

<210> SEQ ID NO 358
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Gly Cys Gly Tyr Arg Tyr Met Cys Asp Met Ile Asn Gly Leu
1               5                   10

<210> SEQ ID NO 359
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Gly Asp Cys Tyr Pro His Cys Arg Leu Val
1               5                   10
```

<210> SEQ ID NO 360
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Asp Cys Leu Arg Tyr Arg Val Gly Ser Ser Cys Ser
1               5                   10

<210> SEQ ID NO 361
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Pro Thr Ser Gly Leu Thr Pro Ser
1               5

<210> SEQ ID NO 362
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Arg Cys Glu Ser Lys Gly Trp Ala Asn Thr Cys Val Ser Glu
1               5                   10

<210> SEQ ID NO 363
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Gln Val Thr Ser Leu Pro Gln Ala
1               5

<210> SEQ ID NO 364
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Cys Tyr Pro Leu Cys Arg Val Leu
1               5

<210> SEQ ID NO 365
<211> LENGTH: 13

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Arg Cys Gly Leu Ala Trp Cys Val Val Leu Val Asp Gln
1               5                   10

<210> SEQ ID NO 366
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Ser Gly Pro Arg Thr Tyr Leu Arg Gly Leu Val Asp
1               5                   10

<210> SEQ ID NO 367
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Ser Gly Asn Cys Trp Ser Ser Leu Arg Gly Ile Cys Glu Asn Leu Gly
1               5                   10                  15

<210> SEQ ID NO 368
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Ser Gly Met Val Tyr Val Asp Arg Gly Val Arg Val Phe Thr
1               5                   10

<210> SEQ ID NO 369
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ser Gly Gly Cys Val Lys Tyr Arg Gly Ser Val Ser Cys Gln Glu Ser
1               5                   10                  15

Lys Thr

<210> SEQ ID NO 370
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 370

Ser Gly Glu His Gln Phe Tyr Ser Tyr Arg Gly Val Asp Val Tyr Arg
1               5                   10                  15

<210> SEQ ID NO 371
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Ser Gly Ala Cys Leu Asn His Phe Val Ser Gly Asn Met Ile Arg Cys
1               5                   10                  15

<210> SEQ ID NO 372
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Ser Gly Ser Tyr Arg Gly Ala Trp Ser Val Phe Gly Gly Ser Thr Asp
1               5                   10                  15

<210> SEQ ID NO 373
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Ser Gly Cys Trp Thr Tyr Leu Arg Gly Gly Cys Ser Val Thr
1               5                   10

<210> SEQ ID NO 374
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Ser Gly Thr Pro Glu Met Pro Ala Met Leu
1               5                   10

<210> SEQ ID NO 375
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 375

Ser Gly Leu Ala Pro Thr Val Ser Asp Ser
1               5                   10

<210> SEQ ID NO 376
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Ser Gly Asp Thr Arg Ser Gln Leu Ser His
1               5                   10

<210> SEQ ID NO 377
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Ser Gly Ala Gly Lys Leu Asp Leu Ser Gly
1               5                   10

<210> SEQ ID NO 378
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Ser Gly Val Cys Ser Asp His Tyr Ile Gly Gly Lys Glu Val Arg Cys
1               5                   10                  15

<210> SEQ ID NO 379
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Ser Gly Asn Ala Leu Trp Asn His Asp Arg Leu Thr
1               5                   10

<210> SEQ ID NO 380
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Ser Gly Arg Asn Gly Ser Gly Tyr Ile Asn Arg Gly Ile Glu Ile Trp
```

```
1               5                   10                  15

<210> SEQ ID NO 381
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Ser Gly His Ala Ser Lys Gly Met Val Leu Ser Gly
1               5                   10

<210> SEQ ID NO 382
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Ser Gly Gly Ser Ile Pro Trp Asn Leu Glu Arg Ile Thr Pro Pro Arg
1               5                   10                  15

<210> SEQ ID NO 383
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Ser Gly Cys Phe Ile Pro Trp Asn Leu Gln Arg Ile Gly Leu Leu Cys
1               5                   10                  15

<210> SEQ ID NO 384
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Ser Gly Gly Ala Cys Pro Trp Asn Leu Glu Arg Ile Gly Leu Ser Cys
1               5                   10                  15

<210> SEQ ID NO 385
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Ser Gly Asp Phe Ile Pro Trp Asn Leu Val Arg Ile Gly Leu Leu Arg
1               5                   10                  15

<210> SEQ ID NO 386
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Ser Gly Cys Arg Leu Pro Trp Asn Leu Gln Arg Ile Gly Leu Pro Cys
1               5                   10                  15

<210> SEQ ID NO 387
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 387

Ser Gly Arg Cys Leu Asn His Leu Ile Ser Gly Asn Met Asn Ser Cys
1               5                   10                  15

<210> SEQ ID NO 388
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Ser Gly Ala Cys Val Lys Pro Cys Ile Ala Gly Asn Ile Ile Arg
1               5                   10                  15

<210> SEQ ID NO 389
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Ser Gly Asp Leu Met Pro Trp Asn Leu Val Arg Ile Gly Leu Leu Arg
1               5                   10                  15

<210> SEQ ID NO 390
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Ser Gly Gly Ser Met Pro Trp Asn Leu Glu Arg Ile Phe Ala Leu His
1               5                   10                  15

<210> SEQ ID NO 391
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 391

Ser Gly Cys Ser Asp Leu Trp Asn Leu Ala Arg Ile Tyr Pro Met Cys
1               5                   10                  15

<210> SEQ ID NO 392
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Ser Gly Cys Arg Leu Pro Trp Asn Leu Gln Arg Ile Gly Leu Pro Cys
1               5                   10                  15

<210> SEQ ID NO 393
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Ser Gly Cys Phe Ile Pro Trp Asn Leu Gln Arg Ile Gly Leu Leu Cys
1               5                   10                  15

<210> SEQ ID NO 394
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Ser Gly Cys Phe Ile Pro Trp Asn Leu Gln Arg Ile Gly Leu Leu Cys
1               5                   10                  15

<210> SEQ ID NO 395
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Ser Gly Cys Arg Leu Pro Trp Asn Leu Gln Arg Ile Gly Leu Pro Cys
1               5                   10                  15

<210> SEQ ID NO 396
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 396

Ser Gly Asp Leu Met Pro Trp Asn Leu Val Arg Ile Gly Leu Leu Arg
1               5                   10                  15

<210> SEQ ID NO 397
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Ser Gly Gly Ser Met Pro Trp Asn Leu Glu Arg Ile Phe Ala Leu His
1               5                   10                  15

<210> SEQ ID NO 398
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Ser Gly Arg Cys Leu Asn His Leu Ile Ser Gly Asn Met Asn Ser Cys
1               5                   10                  15

<210> SEQ ID NO 399

<400> SEQUENCE: 399

000

<210> SEQ ID NO 400
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Thr Val Phe Thr Ser Trp Glu Glu Tyr Leu Asp Trp Val Gly Ser Gly
1               5                   10                  15

Cys Trp Asn Leu Lys Arg Ile Gly Ser Gln Gly Cys
            20                  25

<210> SEQ ID NO 401
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: homo-Arg

<400> SEQUENCE: 401

Trp Asn Leu Val Xaa Ile Gly Leu Thr Arg
1               5                   10
```

```
<210> SEQ ID NO 402
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Trp Asn Leu Val Arg Ile Gly Leu Thr Arg
1               5                   10

<210> SEQ ID NO 403
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

Phe Pro Gly Trp
1
```

COMPOSITIONS AND METHODS FOR TREATING CARDIOVASCULAR DISEASE

RELATED APPLICATIONS

This application is a continuation of International Application No. PCT/EP2017/065324, filed Jun. 21, 2017, claiming priority under 35 USC 119(e) to provisional application No. 62/354,631 filed Jun. 24, 2016, each of which are incorporated herein by reference in its entirety.

SEQUENCE LISTING

This application contains a Sequence Listing which has been submitted via EFS-Web and is hereby incorporated by reference in its entirety. Said ASCII copy, created on Dec. 6, 2018, is named Sequence Listing and is 128,918 bytes in size.

FIELD OF THE INVENTION

The present invention relates to organic compounds useful for therapy and/or prophylaxis in a mammal, and in particular to compounds that inhibit proprotein convertase subtilisin/kexin type 9 (PCSK9) and assays for identifying them, to complexes comprising PCSK9 and a PCSK9 inhibitor, and to methods of inhibiting PCSK9, which are useful for the treatment of cardiovascular disease.

BACKGROUND OF THE INVENTION

Atherosclerotic cardiovascular disease (CVD) is the leading cause of mortality worldwide (Mendis et al. (2011) World Health Organization, Geneva). Atherosclerosis occurs as a consequence of metabolic and inflammatory changes to the arterial wall, which promote the macrophage-mediated intimal deposition of pro-atherogenic low density lipoprotein cholesterol (LDL-C), contributing to plaque formation, limiting blood flow to vital organs and increasing the risk of atherothrombotic and atheroembolic sequelae. Dyslipidemia has become an important risk factor to target in both the primary and secondary prevention of CVD. With the advent of statins, which inhibit 3-hydroxy-3-methylglutaryl-coenzyme A (HMG-CoA) reductase, sustained reductions in LDL-C have become achievable. Large-scale clinical trials demonstrate that a 40 mg/dL (1 mmol/L) decrease in LDL-C results in a 22% reduction in adverse cardiovascular events (Baigent et al., Lancet, 2010, 376(9753): 1670-1681; Mihaylova et al., Lancet, 2012 380(9841):581-590). The overwhelming evidence of the clinical efficacy and cost-effectiveness of statins has led to their establishment as the first-line treatment of dyslipidemia (Koo, Diabetes Metab J, 2014, 38(1):32-34). However, despite optimal statin therapy, less than half of recurrent cardiovascular events can be prevented. Indeed, satisfactory control of dyslipidemia is not achieved in certain patients, even with combination lipid-lowering therapy.

Impelled by the need for additional lipid management strategies, recent attention has focused on a new class of agent, proprotein convertase subtilisin/kexin type 9 (PCSK9) inhibitors. These demonstrate much promise, particularly for those unable to take statins, e.g. due to adverse effects or drug-drug interactions (Corrao et al., Clin Ther, 2010 32(2):300-310). The discovery of PCSK9-based therapies began in 2003, with an astute clinical observation of a French family, which demonstrated features of familial hypercholesterolemia (FH), without mutations in the genes contemporaneously recognized to cause FH; the LDL receptor gene (LDLR, accounting for 95% of FH defects), or apolipoprotein B gene, encoding the protein that binds to the LDLR (ApoB, accounting for 4% of FH defects) (Abifadel et al., Nat Genet, 2003, 34(2): 154-156; Graham et al., Atherosclerosis, 2005, 182(2):331-340). These findings led to the identification of two novel missense mutations that increased the activity of a serine protease enzyme, originally called neural apoptosis-regulated convertase 1 (NARC-1) and subsequently renamed proprotein convertase subtilisin/kexin type 9 (Seidah et al., Proc Natl Acad Sci, 2003, 100(3):928-933). This discovery has led to novel therapeutic options in lipid management (Lambert et al., J Lipid Res, 2010, 53(12):2515-2524; Vogel, J Am Coll Cardiol, 2012, 59(25):2354-2355).

Recently, monoclonal antibodies that bind circulating PCSK9 were approved for therapeutic use to reduce LDL-C levels to control hypercholesterolemia. Alirocumab (Praluent®, Sanofi/Regeneron) was approved in the USA by the FDA in July 2015, and in Europe by the EMA in September 2015 (Robinson et al., N. Engl. J. Med., 372 (16) (2015 Apr. 16), pp. 1489-1499), whereas evolocumab (Repatha®, Amgen) was approved in Europe in July 2015, and in the USA in August 2015 (M. S. Sabatine et al., N. Engl. J. Med., 372 (16) (2015 Apr. 16), pp. 1500-1509). Another anti-PCSK9 antibody, YW508.20.33b (Ab33), is disclosed in U.S. Pat. No. 9,266,961. Other monoclonal antibodies in development include bococizumab (RN316, Pfizer/Rinat), LGT-209 (Novartis), and 1D05-IgG2 (Merck). Other classes of PCSK9 inhibitors undergoing clinical and pre-clinical evaluation include siRNA oligonucleotides, such as ALN-PCS02 (Alnylam Pharmaceuticals/The Medicines Group); monobodies, such as BMS-962476 (Bristol-Myers Squibb/Adnexus); antisense oligonucleotides (Idera Pharmaceuticals); mimetic peptides, such as LDL-EGF-AB peptide fragment (Schering-Plough); and vaccines such as ATH-04 and ATH-06 (Affiris). Small molecule inhibitors of PCSK9 are also known, such as those disclosed in PCT Patent Publication Nos. WO2016040305, WO2016029037, WO2014170786, WO2014150395, WO 2014150326, WO2014139008, WO2014127316, WO2013177536, and WO2011051961. Compounds that selectively inhibit the translation of PCSK9 mRNA to PCSK9 protein are disclosed in WO2014170786.

There is a need for alternative therapeutics that modulate the activity of PCSK9 and the corresponding role PCSK9 plays in various diseases and disorders. The compounds, compositions, and methods described herein help meet these and other needs.

SUMMARY OF THE INVENTION

The present invention relates to PCSK9 inhibitors that bind an epitope of SEQ ID NO: 1, wherein the epitope comprises at least one residue selected from the group consisting of V241, T339, D343, P364, A442, A443, and L444 of SEQ ID NO: 1.

In one aspect, the invention relates to a PCSK9 inhibitor selected from compounds of Formula I:

Formula I
(SEQ ID NO: 2)
$R^1$-$X^1$-$X^2$-$X^3$-Trp-Asn-Leu-$X^4$-$X^5$-Ile-Gly-$X^6$-$R^2$, and pharmaceutically acceptable salts thereof;
wherein,
$R^1$ is $C_1$-$C_4$ acyl; or $R^1$ is absent;

X¹ is an amino acid sequence selected from: TVFTS-WEEYLDWV (SEQ ID NO: 3) and TAFTSWEEYLDWV (SEQ ID NO: 4); or X¹ is absent;

X² is an amino acid sequence comprising 1 to 4 amino acid residues selected from: glycine and serine; or X² is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid; or X² is absent;

X³ is an amino acid sequence comprising 1 to 4 amino acid residues selected from: alanine, 2-aminocyclohexane-1-carboxylic acid, arginine, aspartic acid, cysteine, glycine, 3-hydroxyproline, isoleucine, leucine, methionine, phenylalanine, proline, and tryptophan;

X⁴ is an amino acid residue selected from: alanine, 2,3-diaminopropionic acid, glutamine, glycine, lysine, and valine;

X⁵ is an amino acid residue selected from: arginine and homo-arginine;

X⁶ is an amino acid sequence comprising 1 to 5 amino acid residues selected from: alanine, arginine, cysteine, glutamic acid, glutamine, glycine, leucine, lysine, phenylalanine, proline, serine, threonine, and tryptophan; or X⁶ is absent; and R² is amino; or R² is absent.

In one aspect, the invention relates to an inhibited PCSK9 comprising a PCSK9 inhibitor described herein bound to PCSK9.

In one aspect, the invention relates to a pharmaceutical composition comprising a PCSK9 inhibitor described herein and a pharmaceutically acceptable carrier.

In one aspect, the invention relates to a method for modulating the activity of PCSK9 comprising contacting PCSK9 with an effective amount of a PCSK9 inhibitor described herein.

In one aspect, the invention relates to a method for inhibiting the binding of PCSK9 to LDLR in an individual in need thereof, comprising administering to the individual a therapeutically effective amount of a PCSK9 inhibitor described herein or a pharmaceutical composition thereof.

In one aspect, the invention relates to a PCSK9 inhibitor described herein or a pharmaceutical composition thereof, for use in a method of treatment of the human or animal body by therapy.

In one aspect, the invention relates to a PCSK9 inhibitor described herein or a pharmaceutical composition thereof, for use in a method of modulating the activity of PCSK9.

In one aspect, the invention relates to a PCSK9 inhibitor described herein or a pharmaceutical composition thereof, for use in a method of inhibiting the binding of PCSK9 to LDLR.

In one aspect, the invention relates to a use of a PCSK9 inhibitor described herein for the manufacture of a medicament for modulating the activity of PCSK9.

In one aspect, the invention relates to a use of a PCSK9 inhibitor described herein for the manufacture of a medicament for inhibiting the binding of PCSK9 to LDLR.

In one aspect, the invention relates to a method for identifying a candidate compound as a PCSK9 inhibitor that binds an epitope of SEQ ID NO: 1, wherein the epitope comprises at least one residue selected from the group consisting of V241, T339, D343, P364, A442, A443, and L444 of SEQ ID NO: 1. of SEQ ID NO: 1; the method comprising the steps of: a) contacting PCSK9 with the candidate compound; b) contacting PCSK9Δhelix with the candidate compound; c) measuring binding affinities of the candidate compound for PCSK9 and PCSK9Δhelix; and d) determining that the binding affinity of the candidate compound for PCSK9Δhelix is stronger than the binding affinity of the candidate compound for PCSK9; wherein said determination is indicative of the candidate compound being a PCSK9 inhibitor that binds the epitope of SEQ ID NO: 1.

BRIEF DESCRIPTION OF THE DRAWINGS

FIG. 14 shows sequences of extension peptides (SEQ ID NOS 288, 306-313, 6, 314-317, 283, 308, 318, 319, 6 and 320-332, respectively, in order of appearance), which as fusion peptides with Pep2-8(V2A) (SEQ ID NO: 4), gave improved binding to PCSK9 and to PCSK9Δhelix in phage spot ELISA assays. The GSG linker is not shown. Figure discloses "pep2-8" as SEQ ID NO: 3.

FIG. 15 shows sequences of additional extension peptides (SEQ ID NOS 333-354, 321, 355-365 and 326, respectively, in order of appearance), which as fusion peptides with Pep2-8(V2A) ("Anchor peptide" disclosed as SEQ ID NO: 4), gave improved binding to PCSK9 and to PCSK9Δhelix in phage spot ELISA assays. The GSG linker is not shown.

FIG. 16 shows sequences of 17 extension peptides (SEQ ID NOS 366-382, respectively, in order of appearance), which retained binding to PCSK9 and to PCSK9Δhelix, after reformatting the fusion peptides shown in FIGS. 14 and 15 by deleting the anchor sequence (Pep2-8V2A) plus the first Gly in the linker. The results from phage spot ELISA assays are shown on the right.

FIG. 17 shows the sequences of 10 positive clones (SEQ ID NOS 383-392, respectively, in order of appearance) with strong binding signals obtained from affinity maturation experiments of the pooled soft-randomized libraries of the 17 extension peptides shown in FIG. 16. The results from phage spot ELISA assays are shown on the right. The two leftmost residues were part of the GSG linker in the fusion peptides.

FIG. 19 shows the $IC_{50}$ values from competition binding experiments of two synthetic 30 amino acid fusion peptides. Two of the peptides shown in FIG. 18, K9gvpep4 and K9gvpep7, were fused to Pep2-8 via a GSG linker (the two N-terminal residues of K9gvpep4 and K9gvpep7 are the "SG" portion of the "GSG" linker) to produce the synthetic peptides Pep2-8_K9gvpep4 and Pep2-8_K9gvpep7. These two fusion peptides inhibited the binding of phage displaying peptide K9gvpep4 and Pep2-8 to PCSK9 and PCSK9Δhelix with $IC_{50}$ values in the single digit nanomolar range.

The conditions were chosen so that minimal cleavage of K9-AAA occurred by FXIa alone (second lane to left). Both peptides strongly accelerated the cleavage of the P' helix as shown by the reduced signal with the polyclonal anti-N-terminal peptide antibody, similar to the result with Fab33. Incubation of K9-AAA with the two peptides in the absence of FXIa had no effect (two lanes on right).

Figure 32:
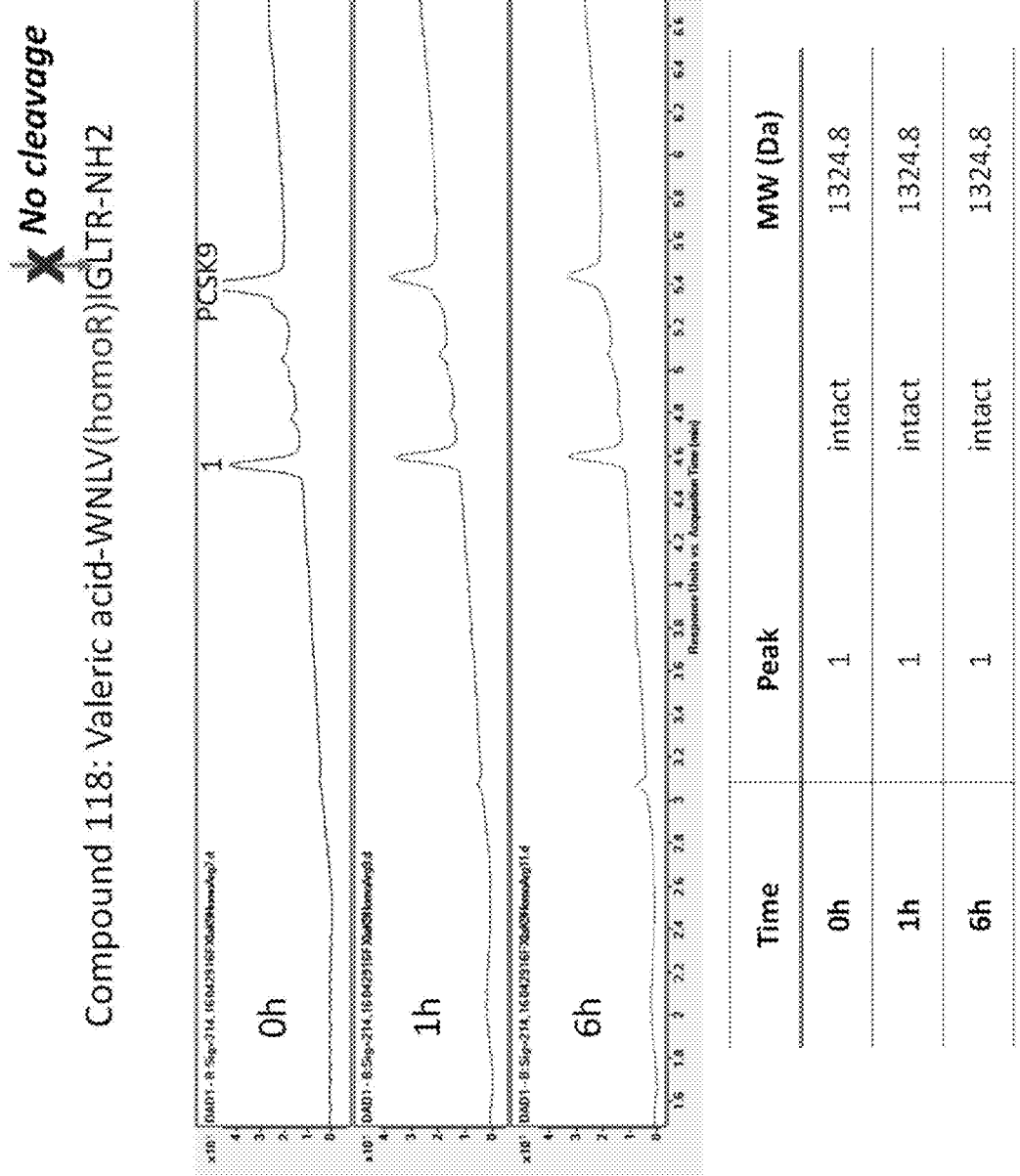

FIG. 32 shows LC-MS results to demonstrate that substitution of the Arginine residue in peptide Compound 112 with a homo-arginine (Compound 118) (SEQ ID NO: 401) prevents peptide cleavage by FXIa. PCSK9-R167A:R215A: R218A (K9-AAA) was incubated together with Compound 118 and treated with FXIa for 1 h and 6 h. The samples were analyzed by LC-MS and peptide cleavage quantified by the disappearance of the intact peptide peak. No cleavage of Compound 118 was detected up to 6 h.

Figure 33:
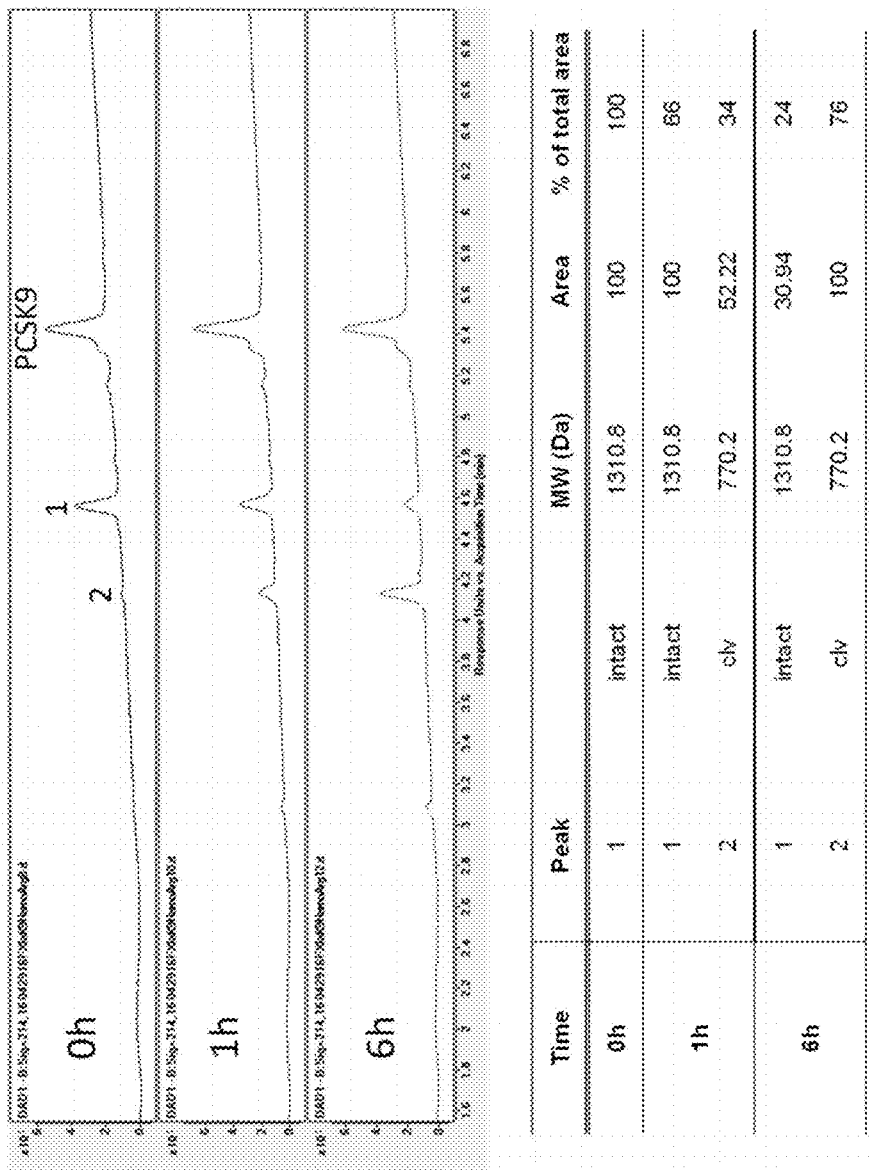

FIG. 33 shows liquid chromatography-mass spectrometry (LC-MS) results to demonstrate that Compound 112 (SEQ ID NO: 402) is cleaved by FXIa. PCSK9-R167A:R215A: R218A (K9-AAA) was incubated together with Compound 112 and treated with FXIa for 1 h and 6 h. The samples were analyzed by LC-MS and peptide cleavage quantified by the disappearance of the intact peptide peak. Compound 112 was cleaved by 34% at 1 h and by 76% at 6 h.

Figure 34:
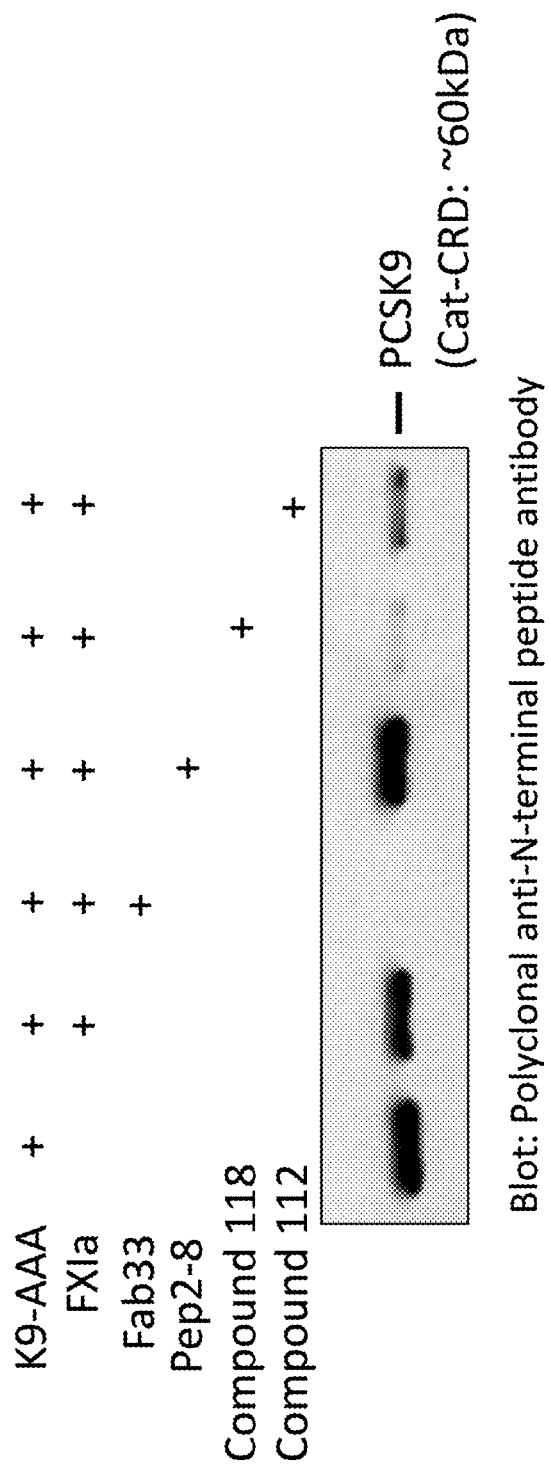

FIG. 34 shows that the homo-arginine containing peptide Compound 118 had a stronger effect on FXIa-mediated cleavage of the P' helix of K9-AAA compared to peptide Compound 112. Fab33 and Pep2-8 were used as positive and negative controls.

Figure 35:
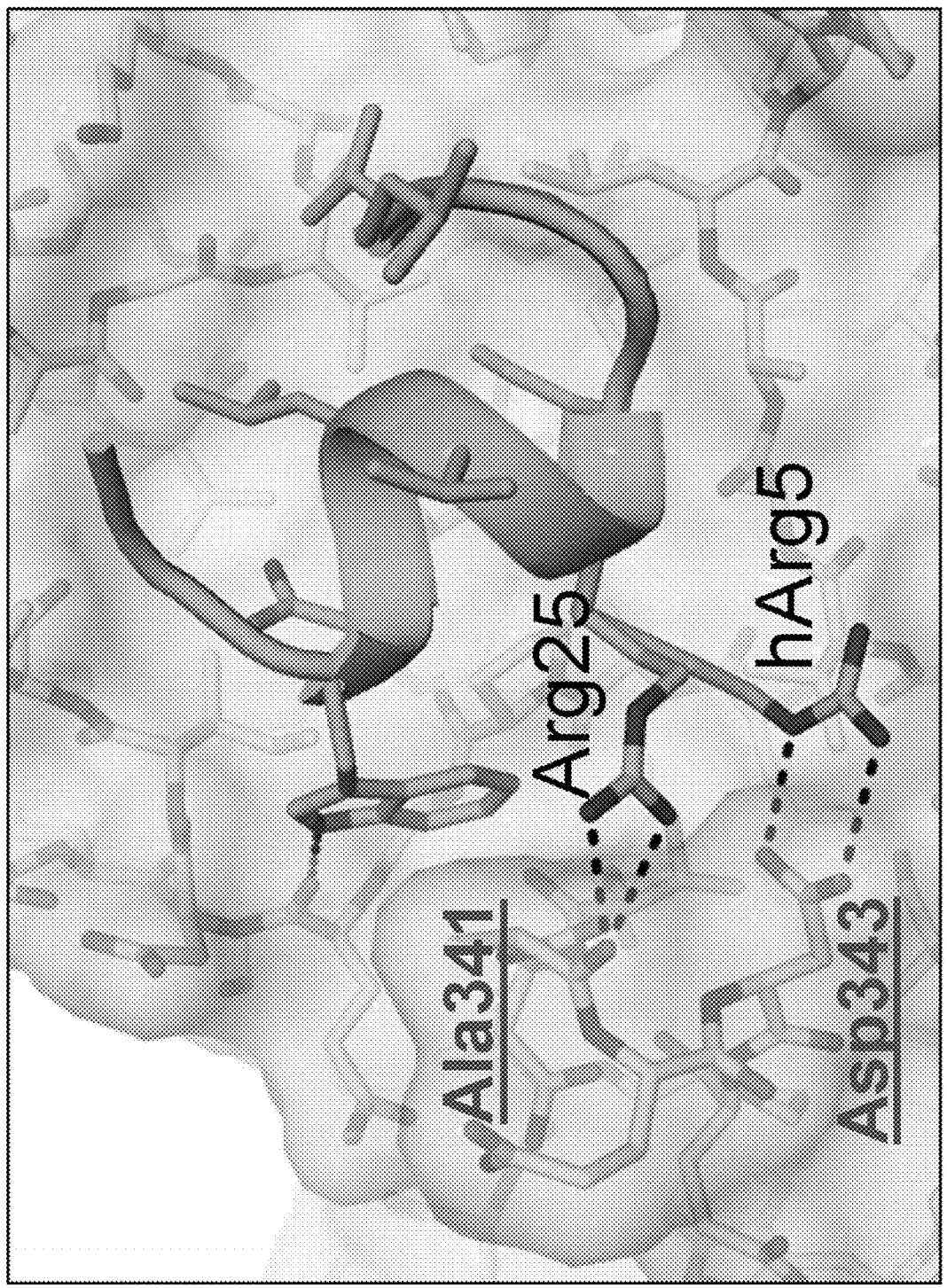

FIG. 35 shows the crystal structure of Compound 192 and Compound 20 bound to PCSK9ΔCRDΔhelix at 2.20 Å resolution. The Arg25 of Compound 20 and its structural analogues in other extension peptides and in the native P'-helix contact the carbonyl oxygen atom of PCSK9 Ala341 with a non-optimal geometry. Homo-Arg5 in Compound 192 has a side chain one carbon atom longer. As a result, this side chain forms a salt-bridge with PCSK9 Asp343 with close-to-optimal geometry.

Figure 36:
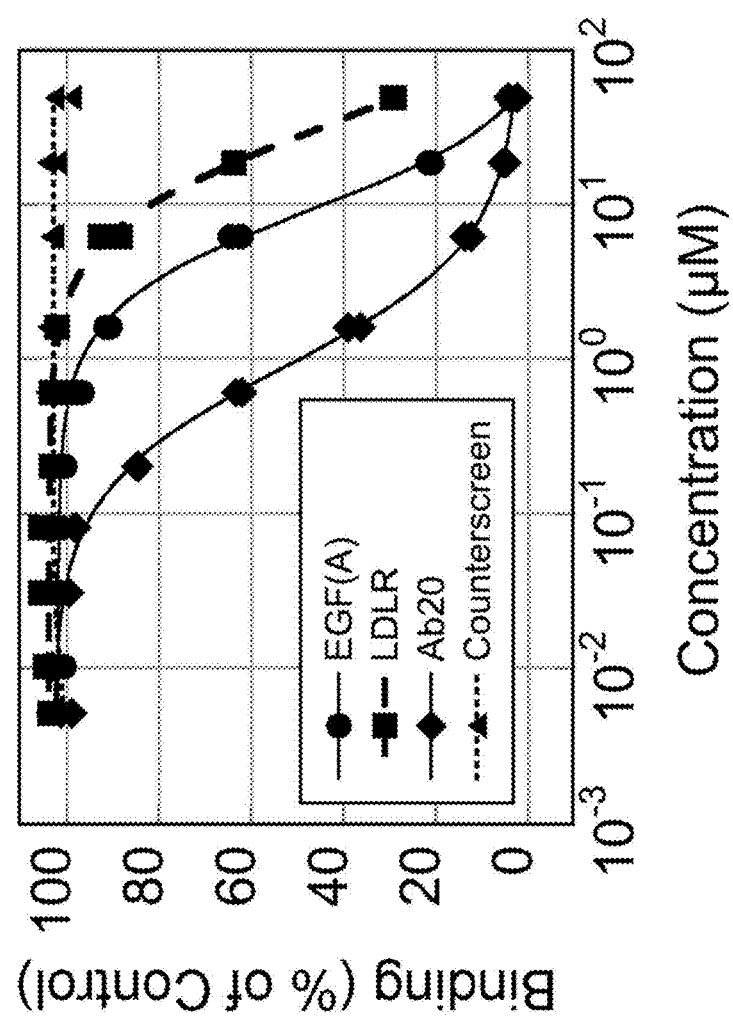

FIG. 36 shows the results of TR-FRET assays showing inhibition by Compound 229 of EGF(A)-Fc and LDLR-Fc binding to PCSK9 and of Ab20 binding to "open groove" PCSK9Δhelix, without interference in the counterscreen.

Figure 37:
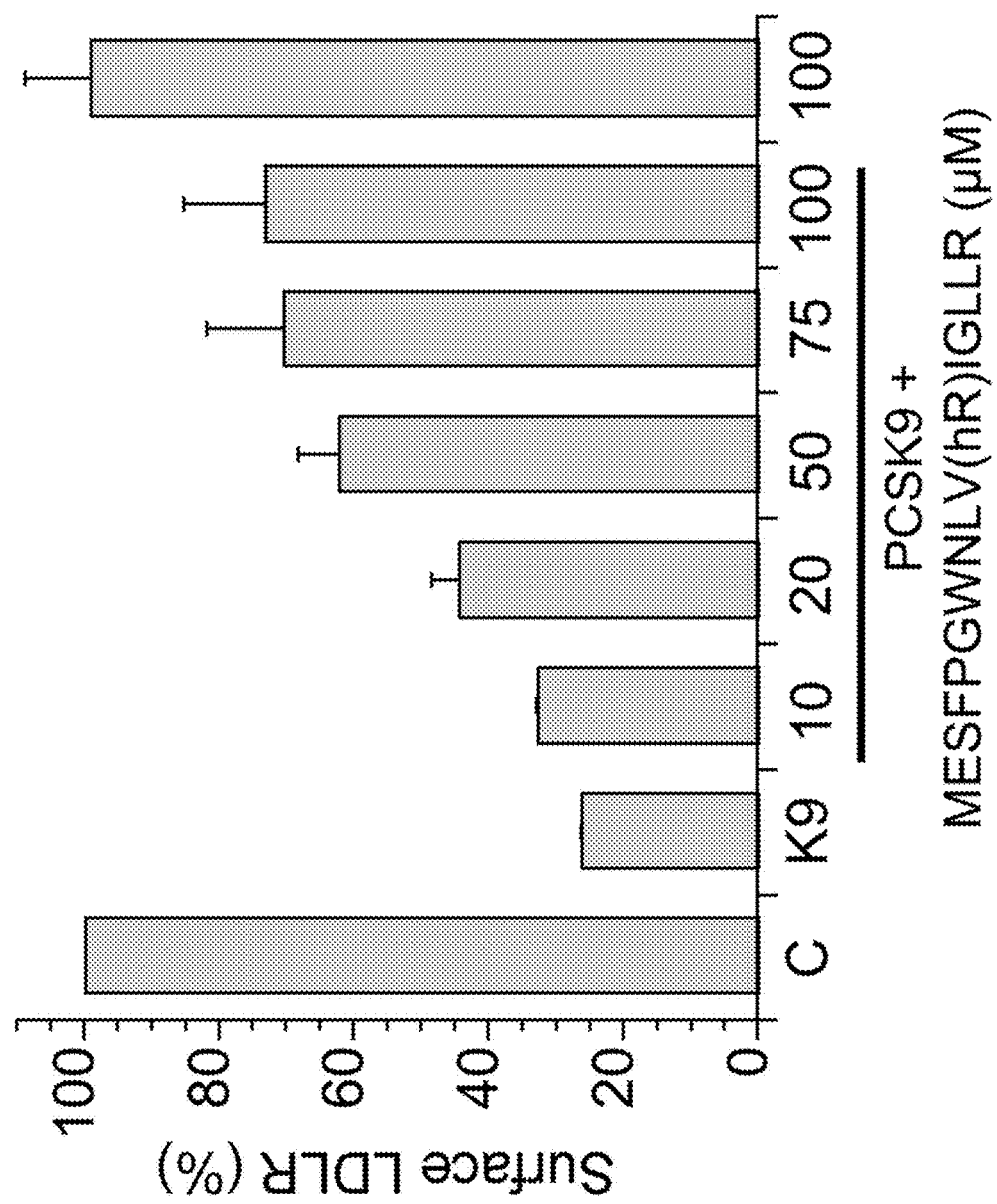

FIG. 37 shows the concentration-dependent inhibition by Compound 229 (SEQ ID NO: 8) of LDLR degradation in a HepG2 cell assay.

Figure 38:
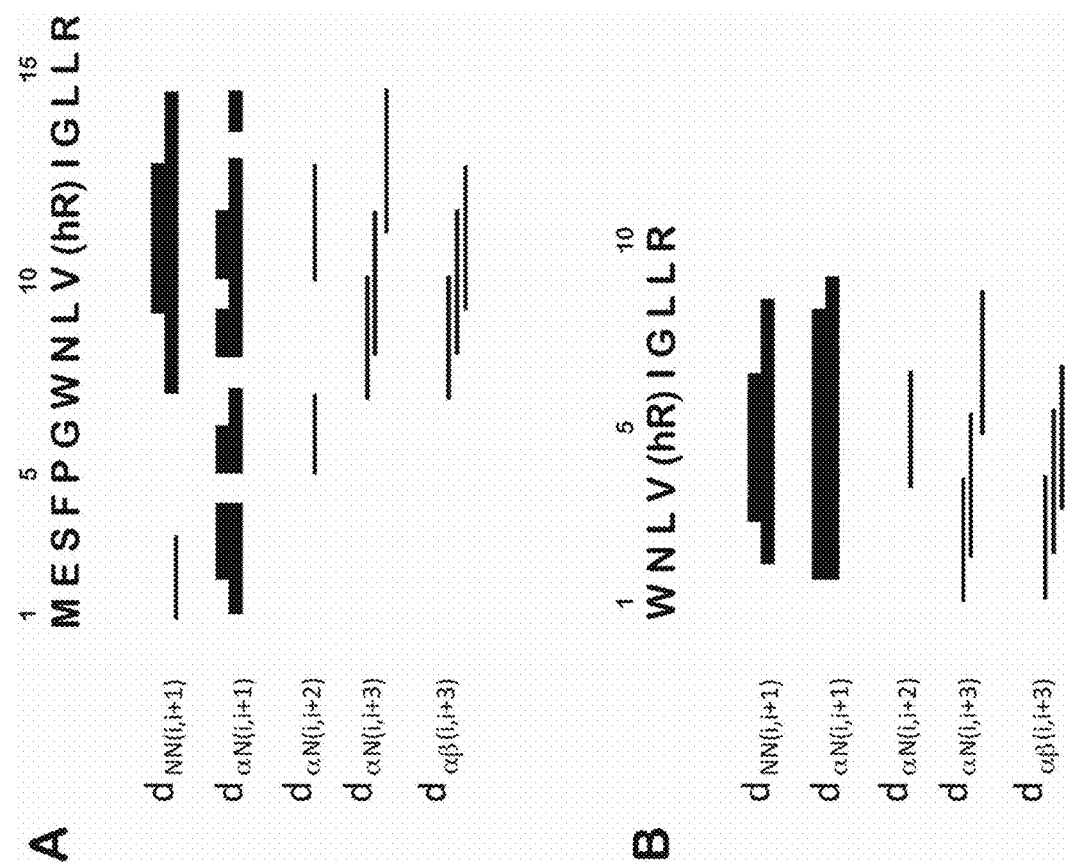

FIG. 38 shows sequential and medium-range NOEs observed for the Compounds 192 and 229 in $H_2O/CD_3CN$ (70:30), at 284K. The thickness of the bars is proportional to the intensities of the NOE signals. The detection of weak, medium-range NOEs indicate a helical propensity for residues W7-L14 of the MESFPGWNL(hR)IGLLR peptide (SEQ ID NO: 8) and for residues W1-L8 of the WNL(hR) IGLLR peptide (SEQ ID NO: 9). Figure discloses SEQ ID NOS 269 and 232, respectively, in order of appearance.

Figure 39:
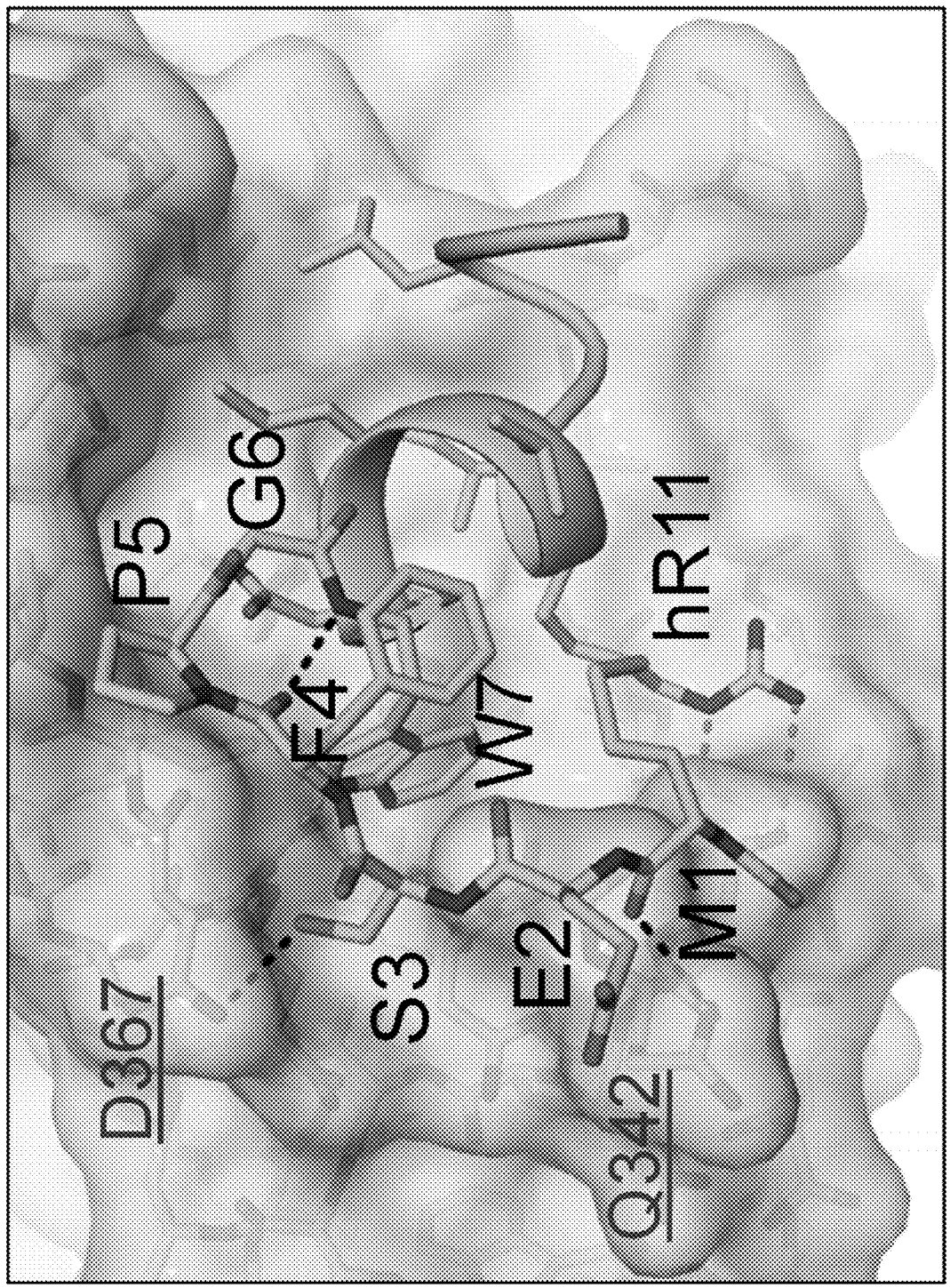

FIG. 39 shows the structure of Compound 229 bound to PCSK9Δhelix. H-bonds to PCSK9 are shown dots. Residues FPGW (SEQ ID NO: 403) form a Type I b-turn with main chain H-bond between F4 and W7.

Figure 40:
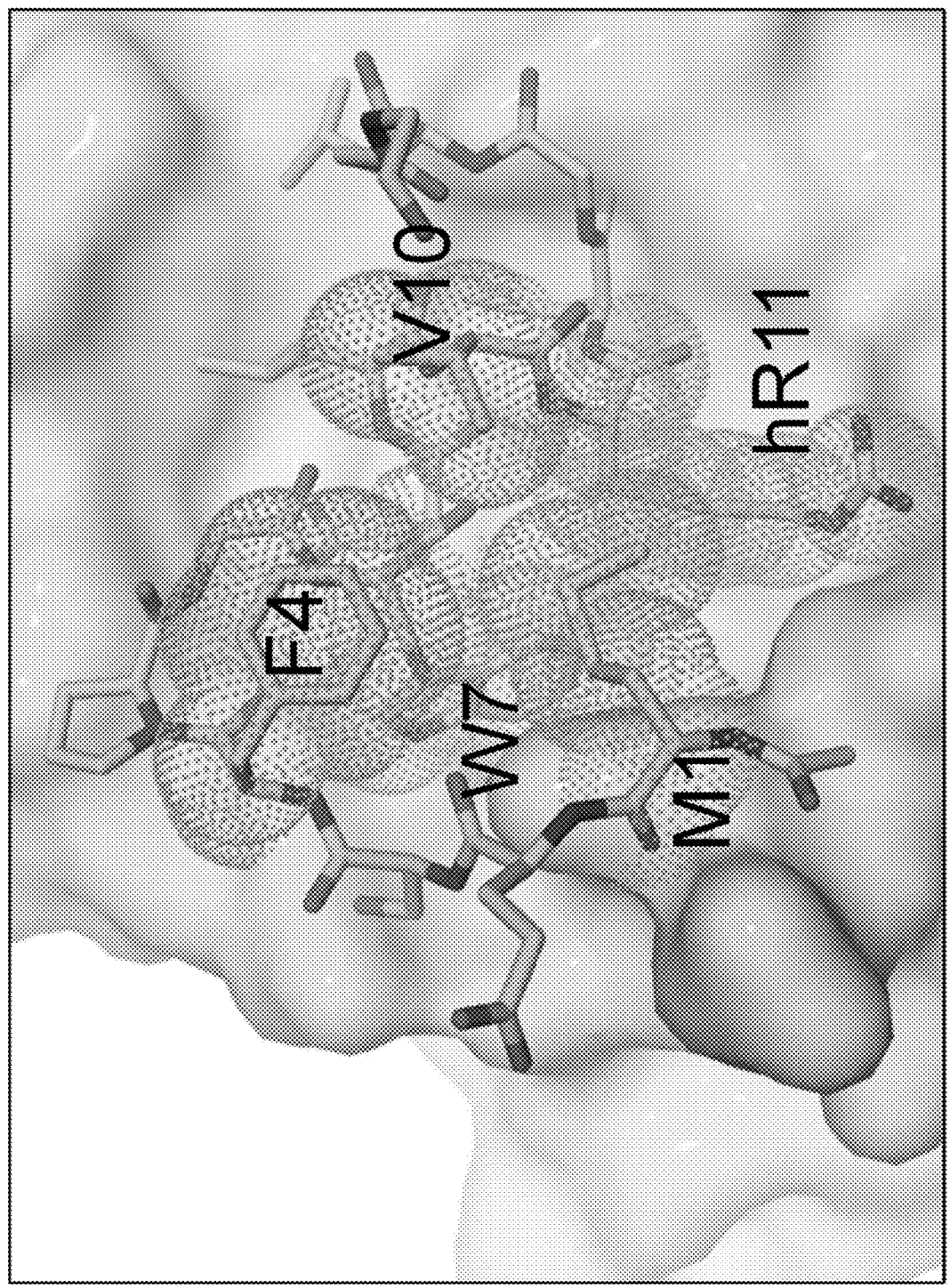

FIG. 40 shows the structure of Compound 229 bound to PCSK9Δhelix. Hydrophobic contacts involving side chains from new residues M1 and F4 and residues W7, V10, and hR11 help determine the conformation of the N-terminal extension. Carbon (and sulfur) atoms from these side chains are shown with dotted surfaces.

Figure 41:
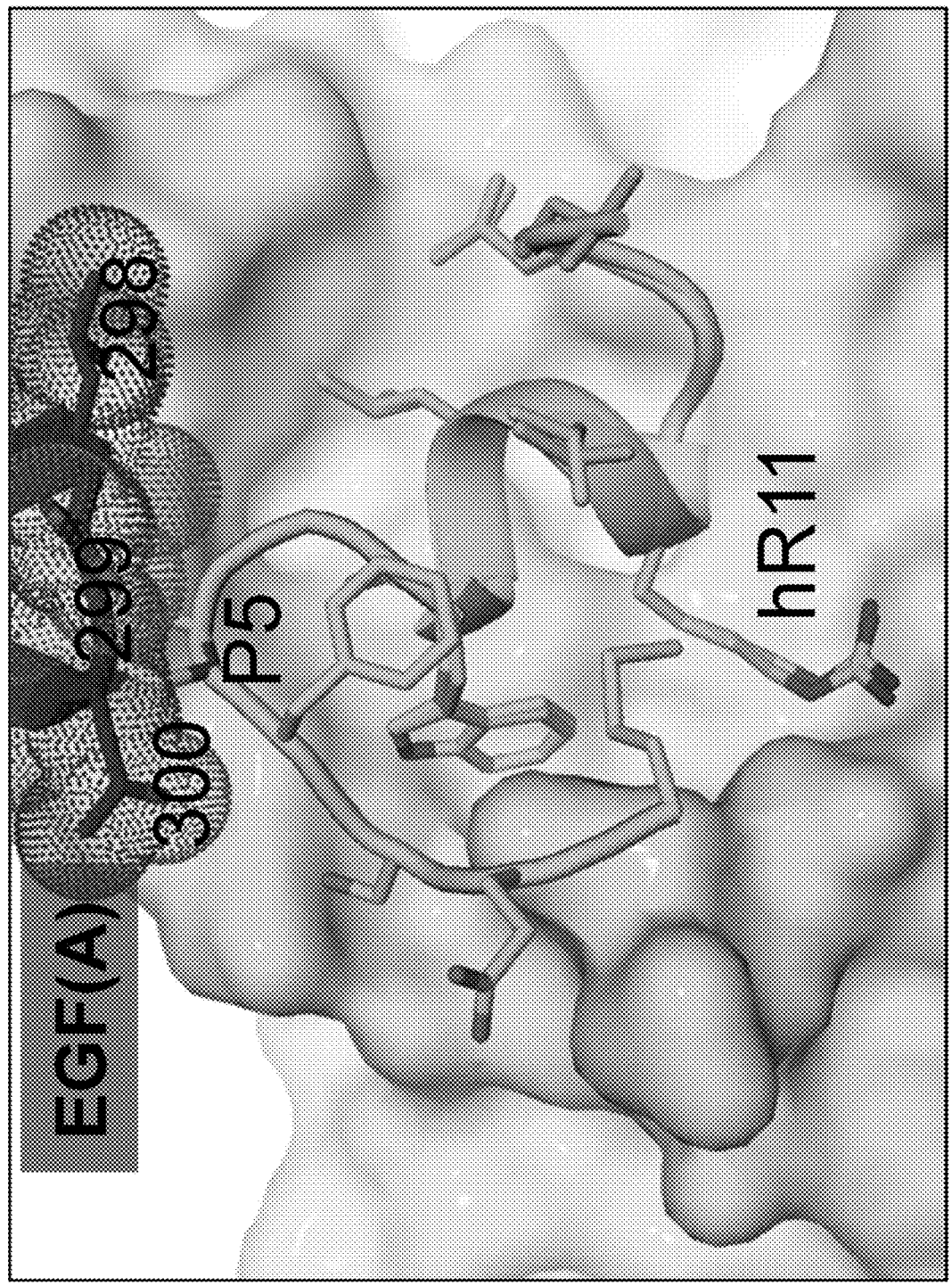

FIG. 41 shows the structure of Compounds 192 and 229 bound to PCSK9Δhelix. Antagonism of Compound 229 arises from a predicted steric conflict between the P5 residue and the L298-D299-N300 segment of EGF(A). The helical segment of Compound 229 binds essentially unchanged versus Compound 192.

Figure 42:
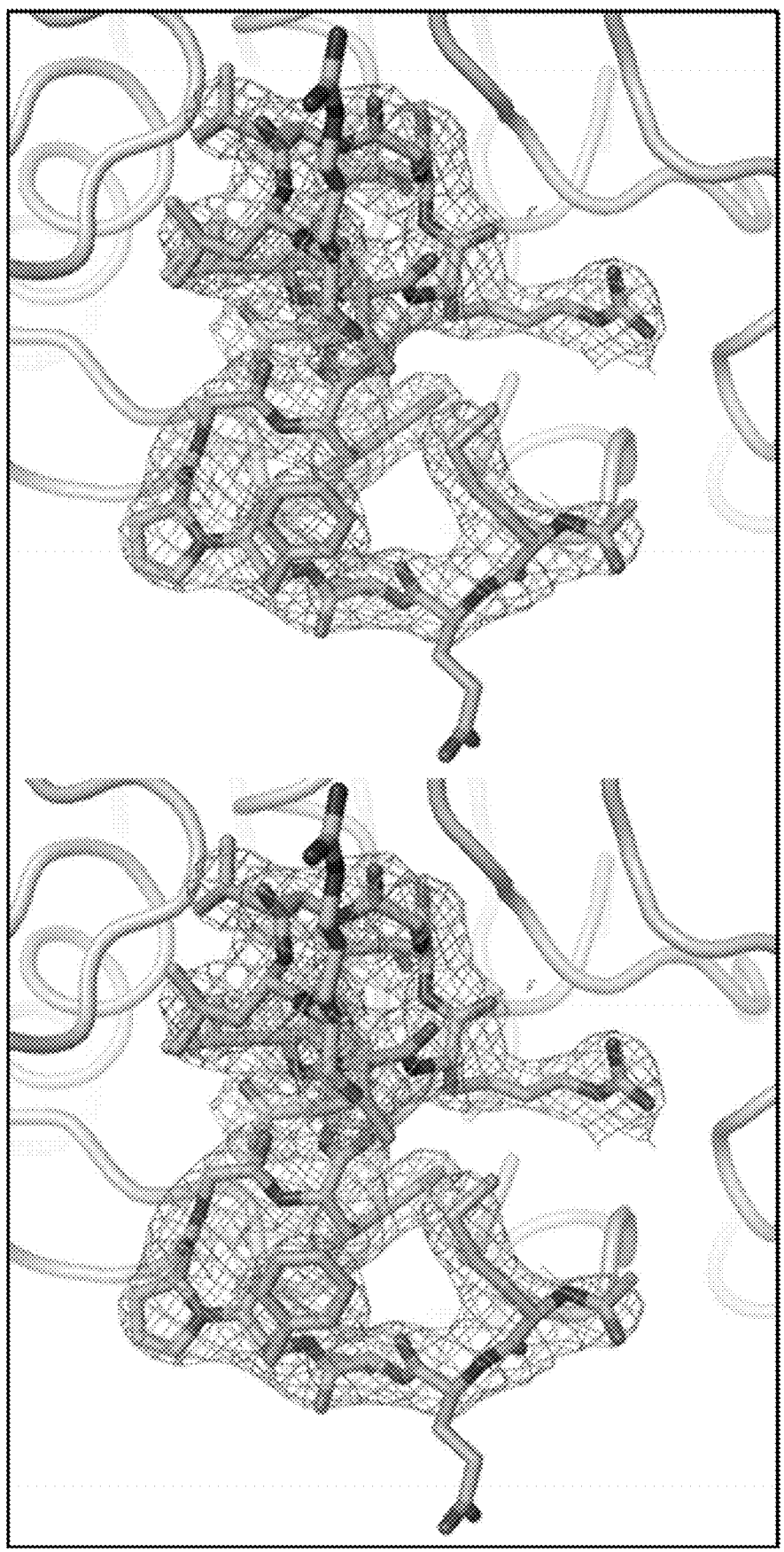

FIG. 42 shows an electron density 2mFo-DFc maps contoured at 1 times rmsd shown for a subset of atoms of Compound 229 bound to PCSK9Δhelix.

DETAILED DESCRIPTION

It should be appreciated that certain features of the invention, which are, for clarity, described in the context of separate embodiments, can also be provided in a single embodiment. Conversely, various features of the invention, which are, for brevity, described in the context of a single embodiment, can also be provided separately or in any suitable subcombination.

Definitions

Unless defined otherwise, technical and scientific terms used herein have the same meaning as commonly understood by one of ordinary skill in the art to which this invention belongs. For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting.

The term "$C_1$-$C_4$ acyl", as used herein, refers to the group $C_1$-$C_4$ alkyl-C(O)—.

The term "affinity", as used herein, refers to the strength of the sum total of noncovalent interactions between a single binding site of a molecule and its binding partner. Unless indicated otherwise, as used herein, "binding affinity" refers to intrinsic binding affinity which reflects a 1:1 interaction between members of a binding pair. The affinity of a molecule X for its partner Y can generally be represented by the dissociation constant ($K_d$). Affinity can be measured by common methods known in the art, including those described herein.

The term "$C_1$-$C_4$ alkoxy", as used herein, refers to the group $C_1$-$C_4$ alkyl-O—, wherein $C_1$-$C_4$ alkyl is as defined herein.

The term "$C_1$-$C_4$ alkyl", as used herein, refers to a straight or branched hydrocarbon radical containing 1 to 4 carbon atoms.

The term "$C_1$-$C_4$ alkylsulfonyl", as used herein, refers to $C_1$-$C_4$ alkyl-S(O)$_2$—.

The term "amino", as used herein, refers to the group —$NH_2$.

The term "anchor peptide", as used herein, refers to a peptide that binds to PCSK9 and to which peptide extension libraries or "extension peptides" may be C-terminally attached. In some embodiments an extension peptide may be attached to the anchor peptide via a linker. In some embodiments the linker is a GSG linker. In some embodiments the anchor peptide is Pep2-8. In some embodiments the anchor peptide is Pep2-8V2A.

The term "aryl", as used herein, refers to a monocyclic, bicyclic, or tricyclic carbon ring system, including systems containing fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracenyl, biphenylyl, phenanthrenyl, 1,2,3,4-tetrahydronaphthyl, 1H-indenyl, 2,3-dihydro-1H-indenyl (indanyl), and the like. In some embodiments, aryl is phenyl. In some embodiments, aryl is indanyl.

The term "arylcarbonyl", as used herein, refers to aryl-C(O)—.

The term "aryl-$C_1$-$C_4$ alkyl", as used herein, refers to "aryl-$C_1$-$C_4$ alkyl-".

The term "aryloxy", as used herein, refers to aryl-O—.

The term "baseline" level (such as baseline level for LDL-C level) in an individual, as used herein, refers to the level before an administration of a PCSK9 inhibitor described herein to the individual. In certain embodiments, the baseline may be a mean or average of two or more measurements obtained before administration of a PCSK9 inhibitor.

The term "contacting", as used herein, refers to an interaction between a PCSK9 inhibitor and PCSK9. In some embodiments the interaction comprises one or more hydrogen bonds, covalent bonds, ionic bonds, hydrophobic contacts, and/or van der Waals contacts. In some embodiments the one or more hydrogen bonds, covalent bonds, ionic bonds, hydrophobic contacts, and/or van der Waals contacts occur at a distance between the PCSK9 inhibitor and PCSK9 of 10 Å or less, 9 Å or less, 8 Å or less, 7 Å or less, 6 Å or less, 5 Å or less, 4 Å or less, 3 Å or less, or 2 Å or less.

The term "carboxamide", as used herein, refers to —C(O)NH$_2$.

The term "carboxyamino", as used herein, refers to —NHCO$_2$H.

The term "$C_3$-$C_7$ cycloalkyl", as used herein, refers to a saturated ring radical containing 3 to 7 carbons. Some embodiments contain 3 to 6 carbons. Some embodiments contain 3 to 5 carbons Some embodiments contain 5 to 7 carbons. Some embodiments contain 3 to 4 carbons. Examples include cyclopropyl, cyclobutyl, cyclopentyl, cyclohexyl, cycloheptyl and the like.

The term "$C_3$-$C_7$ cycloalkylcarbonyl", as used herein, refers to $C_3$-$C_7$ cycloalkyl-C(O)—.

The term "Cys-rich domain" (CRD), as used herein, refers to the cysteine-rich C-terminal domain of PCSK9 consisting of residues 455-692 of SEQ ID NO: 1 (Holla et al., J Lipid Res. 2011 October; 52(10): 1787-1794).

The term "dyslipidemia", as used herein, refers to a condition (or a group of conditions) wherein a patient has an abnormal amount of lipids in the blood. Most dyslipidemias are hyperlipidemias, including hypercholesterolemia, hyperglyceridemia, hyperlipoproteinemia and combined hyperlipidemia. Dyslipidemia may be manifested by increases in total cholesterol, LDL-C, and triglycerides, and a decrease in high-density lipoprotein (HDL) cholesterol in the blood.

The term "effective amount" of an agent, e.g., a pharmaceutical formulation, as used herein, refers to an amount effective, at dosages and for periods of time necessary, to achieve the desired therapeutic or prophylactic result.

The term "extension peptide", as used herein, refers to a peptide that is C-terminally attached to an anchor peptide and that binds to the N-terminal groove of PCSK9 which normally harbors the N-terminal P' helix.

The term "Fab33", as used herein, refers to the antigen-binding fragment of the anti-PCSK9 antibody, YW508.20.33b, disclosed in U.S. Pat. No. 9,266,961.

The term "FAM", as used herein, refers to 5-carboxyfluorescein.

The term "Fmoc", as used herein, refers to fluorenylmethyloxycarbonyl.

The term "fusion peptide", as used herein, refers to a peptide that binds to PCSK9 and that comprises an "extension peptide" C-terminally attached to an "anchor peptide". In some embodiments an extension peptide may be attached to the anchor peptide via a linker. In some embodiments the linker is a GSG linker. In some embodiments the anchor peptide is Pep2-8. In some embodiments the anchor peptide is Pep2-8V2A.

The terms "halo" and "halogen", as used herein, refer to an atom selected from fluorine (fluoro, —F), chlorine (chloro, —Cl), bromine (bromo, —Br), and iodine (iodo, —I).

The term "heteroaryl", as used herein, refers to a monocyclic, bicyclic or tricyclic ring system, including systems containing fused rings, having 5 to 14 ring atoms, wherein at least one ring is aromatic and wherein at least one ring atom is a heteroatom. Examples of heteroatoms include nitrogen, oxygen, and sulfur. In some embodiments, heteroaryl includes 5-6 membered monocyclic aromatic groups where one or more ring atoms is nitrogen, oxygen, or sulfur. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Any nitrogen atom may optionally be oxidized (e.g. NO). Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridinyl, pyridinyl N-oxide, pyrimidinyl, pyrazinyl, pyridazinyl, triazinyl, tetrazinyl, tetrazolo[1,5-b]pyridazinyl, imidazol[1,2-a]pyrimidinyl, purinyl, benzoxazolyl, 2-oxo-2,3-dihydrobenzo[d]oxazolyl, benzofuryl, benzothiazolyl, benzothiadiazolyl, benzotriazolyl, benzoimidazolyl, indolyl, indolinyl, 1,3-thiazolyl, 1,2,3-triazolyl, 1,3,4-triazolyl, 1,3-oxazolyl, 1,3,4-oxadiazolyl, 1,2,4-oxadiazolyl, 1,3,4-thiadiazolyl, 1H-tetrazolyl, pyrazolo[4,3-c]pyridinyl, isoindolyl, isoindolinyl, 1-oxo-isoindolinyl, benzothienyl, benzofuranyl, dibenzofuranyl, indazolyl, benzimidazolyl, benzthiazolyl, quinolyl, isoquinolyl, 1-oxo-isoquinolinyl, 1-oxo-3,4-dihydro-isoquinolinyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl.

The term "heteroaryl-$C_1$-$C_4$ alkyl", as used herein, refers to heteroaryl-$C_1$-$C_4$ alkyl-.

The term "heteroarylcarbonyl", as used herein, refers to heteroaryl-C(O)—.

The term "heterocyclyl", as used herein, refers to a monocyclic, bicyclic or tricyclic, saturated or partially unsaturated, non-aromatic ring system, including systems containing fused rings, having 3 to 20 ring atoms, wherein at least one ring atom is a heteroatom. Examples of heteroatoms include nitrogen, oxygen, and sulfur. In some embodiments, a heterocyclyl refers to a saturated ring system, such as a 3 to 12 membered saturated heterocyclyl ring system, or a 3 to 8 membered saturated heterocyclyl ring system. In some embodiments, a heterocyclyl refers to a 5 to 8 membered saturated heterocyclyl ring system. In some embodiments, a heterocyclyl refers to a 5 to 6 membered saturated heterocyclyl ring system. In some embodiments, a heterocyclyl includes 1 to 4 heteroatoms. In some embodiments, a heterocyclyl includes 3- to 7-membered monocycles having one or more heteroatoms selected from nitrogen, oxygen, and sulfur. In some embodiments, a heterocyclyl includes 4- to 6-membered monocycles having one or more heteroatoms selected from nitrogen, oxygen, and sulfur. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothiophenyl, tetrahydrothiophenyl, imidazolidinyl, piperidinyl, piperazinyl, morpholinyl, thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, oxazolidinonyl, tetrahydrobenzoimidazolyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidinyl, tetrahydropyrimidinyl, pyrrolinyl, pyrrolinyl, thiapyranyl, pyranyl, dioxanyl, 1,3-dioxolanyl, pyrazolinyl, pyrazolidinyl, dithianyl, 1,3-dithiolanyl, 3-azabicyclo[3.1.0] hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, azaspiro[5.5]undecanyl, tetrahydroindolyl, octahydroindolyl, tetrahydroisoindolyl, tetrahydroindazolyl, and the like.

The term "heterocyclylcarbonyl", as used herein, refers to heterocyclyl-C(O)—.

The term "hydroxy", as used herein, refers to —OH.

The term "hydroxy-$C_1$-$C_4$ alkyl", as used herein, refers to —$C_1$-$C_4$ alkyl-OH.

The term "hypercholesterolemia", as used herein, refers to a condition in which cholesterol levels are elevated above a desired level. In certain embodiments, the LDL cholesterol level is elevated above the desired level. In certain embodiments, the serum LDL cholesterol levels are elevated above the desired level.

The term "individual" or "subject", as used herein, refers to a mammal. Mammals include, but are not limited to, domesticated animals (e.g., cows, sheep, cats, dogs, and horses), primates (e.g., humans and nonhuman primates such as monkeys), rabbits, and rodents (e.g., mice and rats). In certain embodiments, the individual or subject is a human.

The term "N-terminal groove", as used herein, refers to the N-terminal groove of the PCSK9 catalytic domain which normally harbors the N-terminal P' helix.

The term "oxo", as used herein, refers to =O.

The term "P' helix" or "N-terminal P' helix", as used herein, refers to the N-terminal alpha helix of the PCSK9 catalytic domain as defined in Bottomley et al., J Biol Chem. 2009 Jan. 9; 284(2): 1313-23. In some embodiments, the P' helix consists of residues S153-T162 of PCSK9.

The term "package insert", as used herein, refers to instructions customarily included in commercial packages of therapeutic products, that contain information about the indications, usage, dosage, administration, combination therapy, contraindications and/or warnings concerning the use of such therapeutic products.

The term "PCSK9 inhibitor", as used herein, refers to an organic compound that is capable of binding PCSK9 with sufficient affinity such that the compound is useful as a diagnostic and/or therapeutic agent in targeting PCSK9. In one embodiment, the extent of binding of a PCSK9 inhibitor to an unrelated, non-PCSK9 protein is less than about 10% of the binding of the PCSK9 inhibitor to PCSK9 as measured by common methods known in the art, including those described herein. In certain embodiments, a PCSK9 inhibitor that binds to PCSK9 has a dissociation constant ($K_d$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "PCSK9Δhelix", as used herein refers to PCSK9 that is lacking the P' helix as that term is defined herein.

The term "PCSK9ΔCRDΔhelix", as used herein refers to PCSK9 that is lacking the Cys-rich domain and the P' helix as those terms are defined herein.

The term "Pep2-8", as used herein, refers to a peptide having the following sequence: Ac-TVFTSWEEYLDWV-NH$_2$ (SEQ ID NO: 3).

The term "Pep2-8-ctrl", as used herein, refers to a peptide having the following sequence: Ac-TVATSAEEYLLWV-NH$_2$ (SEQ ID NO: 10).

The term "Pep2-8V2A", as used herein, refers to a peptide having the following sequence: Ac-TAFTSWEEYLDWV-NH$_2$ (SEQ ID NO: 4).

The term "pharmaceutical formulation" or "pharmaceutical composition", as used herein, refers to a preparation which is in such form as to permit the biological activity of an active ingredient contained therein to be effective, and which contains no additional components which are unacceptably toxic to a subject to which the formulation would be administered.

The term "pharmaceutically acceptable carrier", as used herein, refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "proprotein convertase subtilisin kexin type 9," "PCSK9," or "NARC-1", as used herein, refers to any native PCSK9 from any vertebrate source, including mammals such as primates (e.g. humans) and rodents (e.g., mice and rats), unless otherwise indicated. The term encompasses "full-length," unprocessed PCSK9 as well as any form of PCSK9 that results from processing in the cell or any fragment thereof. The term also encompasses naturally occurring variants of PCSK9, e.g., splice variants or allelic variants. In some embodiments PCSK9 is human PCSK9 having the sequence shown in SEQ ID NO: 1.

The term "PCSK9 activity" or "biological activity" of PCSK9, as used herein, refers to any biological effect of PCSK9. In certain embodiments, PCSK9 activity includes the ability of PCSK9 to interact or bind to a substrate or receptor. In certain embodiments, the biological activity of PCSK9 is the ability of PCSK9 to bind to a LDL-receptor (LDLR). In certain embodiments, PCSK9 binds to and catalyzes a reaction involving LDLR. In certain embodiments, PCSK9 activity includes the ability of PCSK9 to decrease or reduce the availability of LDLR. In certain embodiments, the biological activity of PCSK9 includes the ability of PCSK9 to increase the amount of LDL in a subject. In certain embodiments, the biological activity of PCSK9 includes the ability of PCSK9 to decrease the amount of LDLR that is available to bind to LDL in a subject. In certain embodiments, the biological activity of PCSK9 includes the ability of PCSK9 to decrease the amount of LDLR that is available to bind to LDL. In certain embodiments, biological activity of PCSK9 includes any biological activity resulting from PCSK9 signaling.

The term "ureido", as used herein, refers to —NHC(O)NH$_2$.

The term "treatment" (and grammatical variations thereof such as "treat" or "treating"), as used herein, refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, PCSK9 inhibitors of the invention are used to delay development of a disease or to slow the progression of a disease.

As used herein, the singular form "a", "an", and "the" includes plural references unless indicated otherwise. The term "about" as used herein refers to the usual error range for the respective value readily known to the skilled person in this technical field. Reference to "about" a value or parameter herein includes (and describes) embodiments that are directed to that value or parameter per se. It is understood that aspect and embodiments of the invention described herein include "comprising," "consisting," and "consisting essentially of" aspects and embodiments.

Amino Acid Abbreviations

Unless otherwise indicated, amino acid sequences are written left to right in amino to carboxy orientation.

| Amino Acid | Abbreviations |
| --- | --- |
| Glycine | Gly (G/g)* |
| Alanine | Ala (A/a)* |
| Serine | Ser (S/s)* |
| Threonine | Thr (T/t)* |
| Cysteine | Cys (C/c)* |
| Valine | Val (V/v)* |
| Leucine | Leu (L/l)* |
| Isoleucine | Ile (I/i)* |
| Methionine | Met (M/m)* |
| Proline | Pro (P/p)* |
| Phenylalanine | Phe (F/f)* |
| Tyrosine | Tyr (Y/y)* |
| Tryptophan | Trp (W/w)* |
| Aspartic Acid | Asp (D/d)* |
| Glutamic Acid | Glu (E/e)* |
| Asparagine | Asn (N/n)* |
| Glutamine | Gln (Q/q)* |
| 6-Methyltryptophan | W6me |
| 6-Bromotryptophan | W6br |
| Histidine | His (H/h)* |
| Lysine | Lys (K/k)* |
| Arginine | Arg (R/r)* |
| Homo-arginine | homo-Arg (homoR or hR) |
| 6-Fluorotryptophan | W6fl |
| 2,3-Diaminopropionic acid | Dpr |
| 5-Aminopentanoic acid | Ape |
| 6-Aminohexanoic acid | Ahx |
| 2-Aminocyclohexane-1-carboxylic acid | Ach |
| 7-Aminoheptanoic acid | Ahp |
| 8-Aminooctanoic acid | Aoc |
| 9-Aminononanoic acid | Ano |
| 10-Aminodecanoic acid | Ade |
| 11-Aminoundecanoic acid | Aun |
| 3-Hydroxyproline | Hyp |
| Citruline | Cit |
| 6-Chlorotryptophan | W6cl |

*Upper case = L-amino acid; Lower case = D-amino acid

Structure and Function of PCSK9

PCSK9, found at chromosome 1p32, is 22 kb in length, with 12 exons that encode a 692-amino acid protein (Artenstein and Opal, N Engl J Med, 2011, 365(26):2507-2518). It is a proteinase K-like enzyme, belongs to the secretory subtilase family and is primarily synthesized and secreted by hepatocytes (Maxwell and Breslow, Proc Natl Acad Sci USA, 2004, 101(18):7100-7105; Seidah and Prat, Nat Rev Drug Discovery, 2012, 11(5): 367-383). The synthesis of PCSK9 is upregulated by sterol-regulatory-element-binding protein-2 (SREBP-2), a transcription factor that regulates PCSK9 expression by binding to the sterol-regulatory element in the promoter region of the gene (Jeong et al., J Lipid Res 49(2):399-409). SREBP-2 also increases LDLR and cholesterol synthesis, via the activation of genes encoding key enzymes involved in cholesterol homeostasis, including HMG-CoA reductase (Goldstein and Brown (2009) Arterioscler Thromb Vasc Biol 29(4):431-438). It is activated by low intracellular cholesterol concentrations. SREBP-2 and PCSK9 expression is suppressed in fasting mice fed a cholesterol-rich diet (Kosenko et al. (2013) J Biol Chem 288(12):8279-8288). Prolonged fasting in animals and humans, however, also causes a decrease in PCSK9 and SREBP-2 activity (Browning and Horton (2010) J Lipid Res 51(11):3359-3363). In addition, in vivo evidence suggests a possible role for insulin in increasing the expression of PCSK9 (Costet et al. (2006) J Biol Chem 281(10):6211-6218).

The PCSK9 protein product is comprised of an N-terminal signal peptide, prodomain, catalytic domain, hinge region, and cysteine-rich C-terminal domain (Seidah and Prat (2012) Nat Rev Drug Discovery 11(5): 367-383; Benjannet et al. (2004) J Biol Chem 279(47):48865-48875). Following the removal of the signal peptide domain, PCSK9 is synthesized as a ~74 kDa zymogen, which undergoes autocatalytic cleavage in the endoplasmic reticulum, to generate a prodomain fragment and ~62 kDa mature protein, which remain strongly associated to one another (Park et al. (2004) J Biol Chem 279(48):50630-50638; Nassoury et al. (2007) Traffic 8(6):718-732; Lambert (2007) Current opinion in lipidology 18(3):304-309).

The first 8 members of the PCSK family, PCSK 1-8, are serine proteases involved in the processing of inactive precursor proteins to generate functional and bioactive peptides, polypeptides and hormones, which play important roles in regulating growth and metabolism (Turpeinen et al. (2013) Current genomics 14(7):453; Desai et al. (2013) Circulation 128(9):962-969; Couture et al. (2011) Biomol Concepts 2(5):421-438). In contrast, PCSK9 plays a crucial role in the regulation of LDLR recycling (Cariou et al. (2011) Atherosclerosis 216(2):258-265). PCSK9 binds to the epidermal growth factor A (EGF-A) domain of the LDLR. Upon endocytosis, the PCSK9:LDLR complex is directed to lysosomes for degradation, resulting in reduced LDLR levels and reduced clearance of circulating LDL-C. Extrahepatic actions of PCSK9 include enhancement of chylomicron secretion and regulation of enterocyte cholesterol balance (Seidah and Prat, Nat Rev Drug Discovery, 2012, 11(5): 367-383). Moreover, data from experimental models suggest that the role of PCSK9 extends beyond lipid homeostasis; it is implicated as a regulator of glucose metabolism, liver regeneration and susceptibility to hepatitis C virus infection (Levy et al. (2013) Atherosclerosis 227 (2):297-306 28; Farnier (2014) Archives of cardiovascular diseases 107(1):58-66 29; Farnier (2013) Curr Opin Lipidol 24(3): 251-258 30; and Bridge et al. (2015) J Hepatol 62(4):763-770).

In mouse models, the accumulation of cholesteryl esters in aortic atherosclerotic lesions was markedly reduced by PCSK9 inactivation (Denis et al. (2012) Circulation 125(7):

894-901). Conversely, overexpression of PCSK9 induced an excess burden of atherosclerosis. In LDLR-deficient mice, knockdown or overexpression of PCSK9 had no significant effects on cholesteryl ester accumulation or atheromatous plaque size. This study strongly suggested that the process by which PCSK9 enhances atherosclerosis is primarily mediated by its action on the LDLR (Denis et al. (2012) Circulation 125(7):894-901).

In human studies, PCSK9 loss-of-function mutations have been associated with reductions in LDL-C and cardiovascular events (Cohen et al. (2006) N Engl J Med 354(12): 1264-1272). Conversely, gain-of-function mutations on PCSK9 are associated with a severe form of autosomal dominant hypercholesterolemia, phenotypically indistinguishable from FH due to LDLR mutations (Cohen et al. (2006) N Engl J Med 354(12):1264-1272).

PCSK9 concentrations demonstrate a diurnal rhythm synchronous to cholesterol synthesis, with changes of ±15% from the mean value (Persson et al. (2010) Arterioscler Thromb Vasc Biol 30(12):2666-2672). PCSK9 synthesis is also induced by insulin and repressed by glucagon in rodents (Costet et al. (2006) J Biol Chem 281(10):6211-6218). In healthy humans, PCSK9 levels are demonstrably reduced with fasting (decreasing 60% over 36 h), and increase in the post-prandial period, suggesting a similar effect (Persson et al. (2010) Arterioscler Thromb Vasc Biol 30(12):2666-2672; Browning and Horton (2010) J Lipid Res 51(11):3359-3363). In addition, PCSK9 is positively controlled by the oxysterol-activated liver X receptor (LXR) (Costet et al. (2006) J Biol Chem 281(10):6211-6218; Maxwell et al. (2003) J Lipid Res 44(11):2109-2119).

PCSK9 circulates in plasma in three main forms (Tavori et al. (2013) Circ Res 113(12): 1290-1295). When secreted, PCSK9 exists as a monomer, but can self-associate into di- and trimeric complexes, facilitated by the catalytic domain. It is present in free and protein-bound forms in human plasma, with 40% of circulating PCSK9 exclusively associated with LDL (Kosenko et al. (2013) J Biol Chem 288(12):8279-8288). LDL-bound PCSK9 has diminished LDLR-binding activity. It has been proposed that this is a regulatory mechanism, by which higher plasma concentrations of LDL results in a greater proportion of LDL-bound PCSK9, thereby inhibiting PCSK9-mediated degradation of the LDLR (Kosenko et al. (2013) J Biol Chem 288(12): 8279-8288). In vitro evidence suggests that self-associated di-/trimers have enhanced LDLR-binding and degrading activity, compared with the monomer form (Fan et al. (2008) Biochemistry 47(6): 1631-1639). PCSK9 also circulates as a 55 kDa furin-cleaved inactive fragment, resulting from the cleavage of the 62 kDa protein: mutations in the mature PCSK9 protein have been associated with increased or decreased susceptibility to furin cleavage, leading to PCSK9 loss-of-function and gain-of-function phenotypes (Lambert (2007) Current opinion in lipidology 18(3):304-309).

PCSK9 acts primarily as a soluble protein, targeting degradation of the membrane-bound LDLR by extracellular binding via rerouting to the lysosomal pathway (Horton et al. (2007) Trends Biochem Sci 32(2):71-77). At the molecular level, PCSK9 blocks the LDLR in an extended (open) conformation. This is achieved when the catalytic domain of PCSK9 (aa153-421) and the EGF-A domain of LDLR (aa314-355) bind (Leren (2014) Atherosclerosis 237(1):76-81). This failure of the receptor to adopt a closed conformation results in a slowed recycling to the plasma membrane and subsequent degradation. LDLRs—like PCSK9—are particularly abundant in the liver, the primary organ responsible for clearance of plasma LDL. As the number of LDLRs on the surface of liver cells determines the rate of LDL removal from the bloodstream, PCSK9 presented an appealing target to beneficially modulate lipid homeostasis.

Two separate routes of LDLR degradation are induced by PCSK9, as indicated by several mechanistic studies. In the "Intracellular-route of LDLR degradation", newly formed PCSK9 binds to the LDLR, and then directs it from the trans-Golgi network to lysosomes for degradation. The existence of this route has been shown through studies in HepG2 cells, where, clathrin light chain small interfering RNAs, which ablate intracellular trafficking from the trans-Golgi network to lysosomes, rapidly increase LDLR levels in a PCSK9-dependent fashion without affecting the ability of exogenous PCSK9 to enhance LDLR degradation (Poirier et al., J. Biol. Chem. 284 (42) (2009 Oct. 16) 28856-28864).

In the second route of LDLR degradation, secreted PCSK9 binds to the first epidermal growth factor-like repeat (EGFA) of LDLR at the cell surface to direct internalization of the PCSK9-LDLR complex. Following internalization, the endocytic recycling of LDLRs is inhibited by bound PCSK9, which promotes the lysosomal degradation of both proteins (Lo et al., EMBO Rep. 12 (12) (2011 December) 1300-1305). Monoclonal antibodies (mAB) to PCSK9 ablate the PCSK9-LDLR interaction at the EGFA domain, indicating that the second or the cell-surface route exerts the principal effect on hepatic LDLR levels in humans (Stein et al., Curr. Atheroscler. Rep. 15 (3) (2013 March) 310).

Studies by Tavori et al. (Circulation 127 (24) (2013 Jun. 18) 2403-2413) indicate that the LDLR acts as the principal route of elimination of PCSK9, and a reciprocal control mechanism between these two proteins regulates serum PCSK9 levels, LDLR expression in the liver, and serum LDL-C levels.

PCSK9 inhibition may also reduce lipoprotein(a) levels. High levels of lipoprotein(a) are an independent predictor of cardiovascular mortality, even in statin-treated patients with low LDL-C (Khera et al. (2014) Circulation 129(6): 635-642). PCSK9 inhibitors reduce lipoprotein(a) by approximately 30%. Such an effect is not observed with statin- or ezetimibe-mediated upregulation of LDLR activity (Rader et al. (1994) J Clin Invest 93(6):2758-2763). Thus, PCSK9 inhibition as a therapeutic strategy has theoretical advantages beyond LDL-C lowering, raising the possibility that cardiovascular outcomes may be additionally favorable.

Compositions and Methods

In one aspect, the invention is based, in part, on experimental results obtained with PCSK9 inhibitors. Results obtained indicate that blocking biological activity of PCSK9 with a PCSK9 inhibitor leads to a prevention of reduction in LDLR. In addition, the results demonstrate that administration of a PCSK9 inhibitor reduces total LDL-C level in a subject. Accordingly, PCSK9 inhibitors of the invention, as described herein, provide important therapeutic and diagnostic agents for use in targeting pathological conditions associated with PCSK9, e.g., cholesterol related disorders.

In certain embodiments, a "cholesterol related disorder" includes any one or more of the following: hypercholesterolemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using a PCSK9 inhibitor, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apoplipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. PCSK9 inhibitors described herein can also be useful in preventing or treating atherosclerotic diseases, such as, for example, coronary heart disease, coronary artery disease, peripheral arterial disease, stroke (ischemic and hemorrhagic), angina pectoris, or cerebrovascular disease and acute coronary syndrome, myocardial infarction. In certain embodiments, the PCSK9 inhibitors described herein are useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In certain embodiments, the PCSK9 inhibitors and methods described herein can be used to reduce the risk of recurrent cardiovascular events.

PCSK9 Inhibitors

In certain embodiments, a PCSK9 inhibitor that binds to PCSK9 or a fragment thereof is provided, wherein the PCSK9 inhibitor binds to an epitope within a fragment of PCSK9. In certain embodiments, a PCSK9 inhibitor that binds to PCSK9 or a fragment thereof is provided, wherein the PCSK9 inhibitor binds in a pocket lined by the following portions of PCSK9ΔCRDΔhelix: A239-V241, T339-D343, P364-I368, H391 and V441-L444. In some embodiments, the PCSK9 inhibitor binds an epitope of SEQ ID NO: 1 comprising at least one residue selected from the group consisting of V241, T339, D343, P364, A442, A443, and L444 of SEQ ID NO: 1. In some embodiments, the epitope comprises at least two residues selected from the group consisting of V241, T339, D343, P364, A442, A443, and L444 of SEQ ID NO: 1. In some embodiments, the epitope comprises at least three residues selected from the group consisting of V241, T339, D343, P364, A442, A443, and L444 of SEQ ID NO: 1. In some embodiments, the epitope comprises at least four residues selected from the group consisting of V241, T339, D343, P364, A442, A443, and L444 of SEQ ID NO: 1. In some embodiments, the epitope comprises at least five residues selected from the group consisting of V241, T339, D343, P364, A442, A443, and L444 of SEQ ID NO: 1. In some embodiments, the epitope comprises at least six residues selected from the group consisting of V241, T339, D343, P364, A442, A443, and L444 of SEQ ID NO: 1. In some embodiments, the epitope comprises the residues V241, T339, D343, P364, A442, A443, and L444 of SEQ ID NO: 1. In some embodiments, the epitope comprises at least eleven residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises at least twelve residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises at least thirteen residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises at least fourteen residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises at least fifteen residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises at least sixteen residues selected from the group consisting of A239, G240, V241, T339, N340, A341, D343, P364, E366, D367, I368, I369, G370, H391, A442, A443, and L444 of SEQ ID NO: 1. In some embodiments, the epitope comprises the residues A239, G240, V241, T339, N340, A341, D343, P364, E366, D367, I368, I369, G370, H391, A442, A443, and L444 of SEQ ID NO: 1. In some embodiments, the epitope comprises at least eleven residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least twelve residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least thirteen residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least fourteen residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least fifteen residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least sixteen residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises at least seventeen residues selected from the group consisting of A239, G240, V241, T339, N340, A341, Q342, D343, P364, E366, D367, I368, I369, G370, H391, A442, A443, and L444 of SEQ ID NO: 1. In some embodiments, the epitope comprises the residues A239, G240, V241, T339, N340, A341, Q342, D343, P364, E366, D367, I368, I369, G370, H391, A442, A443, and L444 of SEQ ID NO: 1. In some embodiments, the epitope comprises V241 of SEQ ID NO: 1. In some embodiments, the epitope comprises T339 of SEQ ID NO: 1. In some embodiments, the epitope comprises D343 of SEQ ID NO: 1. In some embodiments, the epitope comprises P364 of SEQ ID NO: 1. In some embodiments, the epitope comprises A442 of SEQ ID NO: 1. In some embodiments, the epitope comprises A443 of SEQ ID NO: 1. In some embodiments, the epitope comprises L444 of SEQ ID NO: 1. In some embodiments, the epitope comprises V241 of SEQ ID NO: 1 and at least one residue selected from the group consisting of A239, G240, T339, N340, A341, D343, P364, E366, D367, I368, I369, G370, H391, A442, A443, and L444 of SEQ ID NO: 1. In some embodiments, the epitope comprises T339 of SEQ ID NO: 1 and at least one residue selected from the group consisting of A239, G240, V241, N340, A341, D343, P364, E366, D367, I368, I369, G370, H391, A442, A443, and L444 of SEQ ID NO: 1. In some embodiments, the epitope comprises D343 of SEQ ID NO: 1 and at least one residue selected from the group consisting of A239, G240, V241, T339, N340, A341, P364, E366, D367, I368, I369, G370, H391, A442, A443, and L444 of SEQ ID NO: 1. In some embodiments, the epitope comprises P364 of SEQ ID NO: 1 and at least one residue selected from the group consisting of A239, G240, V241, T339, N340, A341, D343, E366, D367, I368, I369, G370, H391, A442, A443, and L444 of SEQ ID NO: 1. In some embodiments, the epitope comprises A442 of SEQ ID NO: 1 and at least one residue selected from the group consisting of A239, G240, V241, T339, N340, A341, D343, P364, E366, D367, I368, I369, G370, H391, A443, and L444 of SEQ ID NO: 1. In some embodiments, the epitope comprises A443 of SEQ ID NO: 1 and at least one residue selected from the group consisting of A239, G240, V241, T339, N340, A341, D343, P364, E366, D367, I368, I369, G370, H391, A442, and L444 of SEQ ID NO: 1. In some embodiments, the epitope comprises L444 of SEQ ID NO: 1 and at least one residue selected from the group consisting of A239, G240, V241, T339, N340, A341, D343, P364, E366, D367, I368, I369, G370, H391, A442, and A443 of SEQ ID NO: 1. In some embodiments, the epitope comprises V241 of SEQ ID NO: 1 and at least one residue selected from the group consisting of A239, G240, T339, N340, A341, Q342, D343, P364, E366, D367, I368, I369, G370, H391, A442, A443, and L444 of SEQ ID NO: 1. In some embodiments, the epitope comprises T339 of SEQ ID NO: 1 and at least one residue selected from the group consisting of A239, G240, V241, N340, A341, Q342, D343, P364, E366, D367, I368, I369, G370, H391, A442, A443, and L444 of SEQ ID NO: 1. In some embodiments, the epitope comprises D343 of SEQ ID NO: 1 and at least one residue selected from the group consisting of A239, G240, V241, T339, N340, A341, Q342, P364, E366, D367, I368, I369, G370, H391, A442, A443, and L444 of SEQ ID NO: 1. In some embodiments, the epitope comprises P364 of SEQ ID NO: 1 and at least one residue selected from the group consisting of A239, G240, V241, T339, N340, A341, Q342, D343, E366, D367, I368, I369, G370, H391, A442, A443, and L444 of SEQ ID NO: 1. In some embodiments, the epitope comprises A442 of SEQ ID NO: 1 and at least one residue selected from the group consisting of A239, G240, V241, T339, N340, A341, Q342, D343, P364, E366, D367, I368, I369, G370, H391, A443, and L444 of SEQ ID NO: 1. In some embodiments, the epitope comprises A443 of SEQ ID NO: 1 and at least one residue selected from the group consisting of A239, G240, V241, T339, N340, A341, Q342, D343, P364, E366, D367, I368, I369, G370, H391, A442, and L444 of SEQ ID NO: 1. In some embodiments, the epitope comprises L444 of SEQ ID NO: 1 and at least one residue selected from the group consisting of A239, G240, V241, T339, N340, A341, Q342, D343, P364, E366, D367, I368, I369, G370, H391, A442, and A443 of SEQ ID NO: 1. In some embodiments, the epitope comprises A239 of SEQ ID NO: 1 and at least one residue selected from the group consisting of V241, T339, D343, P364, A442, A443, and L444 of SEQ ID NO: 1. In some embodiments, the epitope comprises G240 of SEQ ID NO: 1 and at least one residue selected from the group consisting of V241, T339, D343, P364, A442, A443, and L444 of SEQ ID NO: 1. In some embodiments, the epitope comprises N340 of SEQ ID NO: 1 and at least one residue selected from the group consisting of V241, T339, D343, P364, A442, A443, and L444 of SEQ ID NO: 1. In some embodiments, the epitope comprises A341 of SEQ ID NO: 1 and at least one residue selected from the group consisting of V241, T339, D343, P364, A442, A443, and L444 of SEQ ID NO: 1. In some embodiments, the epitope comprises E366 of SEQ ID NO: 1 and at least one residue selected from the group consisting of V241, T339, D343, P364, A442, A443, and L444 of SEQ ID NO: 1. In some embodiments, the epitope comprises D367 of SEQ ID NO: 1 and at least one residue selected from the group consisting of V241, T339, D343, P364, A442, A443, and L444 of SEQ ID NO: 1. In some embodiments, the epitope comprises I368 of SEQ ID NO: 1 and at least one residue selected from the group consisting of V241, T339, D343, P364, A442, A443, and L444 of SEQ ID NO: 1. In some embodiments, the epitope comprises I369 of SEQ ID NO: 1 and at least one residue selected from the group consisting of V241, T339, D343, P364, A442, A443, and L444 of SEQ ID NO: 1. In some embodiments, the epitope comprises G370 of SEQ ID NO: 1 and at least one residue selected from the group consisting of V241, T339, D343, P364, A442, A443, and L444 of SEQ ID NO: 1. In some embodiments, the epitope comprises H391 of SEQ ID NO: 1 and at least one residue selected from the group consisting of V241, T339, D343, P364, A442, A443, and L444 of SEQ ID NO: 1. In some embodiments, the epitope comprises one, two, three, four, five, six, or all of the following residues: V241, T339, D343, P364, A442, A443, and L444 of SEQ ID NO: 1. In some embodiments, the epitope comprises eleven, twelve, thirteen, fourteen, fifteen, sixteen, or all of the following residues: A239, G240, V241, T339, N340, A341, D343, P364, E366, D367, I368, I369, G370, H391, A442, A443, and L444 of SEQ ID NO: 1. In some embodiments, the epitope comprises eleven, twelve, thirteen, fourteen, fifteen, sixteen, seventeen, or all of the following residues: A239, G240, V241, T339, N340, A341, Q342, D343, P364, E366, D367, I368, I369, G370, H391, A442, A443, and L444 of SEQ ID NO: 1. In some embodiments the distance between the PCSK9 inhibitor and a SEQ ID NO: 1 residue in the epitope is 10 Å or less, 9 Å or less, 8 Å or less, 7 Å or less, 6 Å or less, 5 Å or less, 4 Å or less, 3 Å or less, or 2 Å or less.

In some embodiments, the PCSK9 inhibitor is selected from compounds of Formula I:

Formula I
(SEQ ID NO: 2)
$R^1-X^1-X^2-X^3-Trp-Asn-Leu-X^4-X^5-Ile-Gly-X^6-R^2$, and pharmaceutically acceptable salts thereof;
wherein,
$R^1$ is $C_1-C_4$ acyl; or $R^1$ is absent;
$X^1$ is an amino acid sequence selected from: TVFTSWEEYLDWV (SEQ ID NO: 3) and TAFTSWEEYLDWV (SEQ ID NO: 4); or $X^1$ is absent;
$X^2$ is an amino acid sequence comprising 1 to 4 amino acid residues selected from: glycine and serine; or $X^2$ is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid; or $X^2$ is absent;
$X^3$ is an amino acid sequence comprising 1 to 4 amino acid residues selected from: alanine, 2-aminocyclohexane-1-carboxylic acid, arginine, aspartic acid, cysteine, glycine, 3-hydroxyproline, isoleucine, leucine, methionine, phenylalanine, proline, and tryptophan;
$X^4$ is an amino acid residue selected from: alanine, 2,3-diaminopropionic acid, glutamine, glycine, lysine, and valine;

X⁵ is an amino acid residue selected from: arginine and homo-arginine;

X⁶ is an amino acid sequence comprising 1 to 5 amino acid residues selected from: alanine, arginine, cysteine, glutamic acid, glutamine, glycine, leucine, lysine, phenylalanine, proline, serine, threonine, and tryptophan; or X⁶ is absent; and R² is amino; or R² is absent.

In some embodiments, R¹ is $C_1$-$C_4$ acyl.
In some embodiments, R¹ is acetyl.
In some embodiments, R¹ is valeryl.
In some embodiments, R¹ is absent.
In some embodiments, X¹ is an amino acid sequence selected from: TVFTSWEEYLDWV (SEQ ID NO: 3) and TAFTSWEEYLDWV (SEQ ID NO: 4).
In some embodiments, X¹ is the amino acid sequence TVFTSWEEYLDWV (SEQ ID NO: 3).
In some embodiments, X¹ is the amino acid sequence TAFTSWEEYLDWV (SEQ ID NO: 4).
In some embodiments, X¹ is absent.
In some embodiments, X² is an amino acid sequence comprising 1 to 4 amino acid residues selected from: glycine and serine.
In some embodiments, X² is an amino acid sequence selected from: SG, GSG, GGSG (SEQ ID NO: 11), GSGG (SEQ ID NO: 12), and SGSG (SEQ ID NO: 13).
In some embodiments, X² is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid.
In some embodiments, X² is the amino acid residue 6-aminohexanoic acid.
In some embodiments, X² is the amino acid residue 7-aminoheptanoic acid.
In some embodiments, X² is the amino acid residue 8-aminooctanoic acid.
In some embodiments, X² is absent.
In some embodiments, X³ is an amino acid sequence selected from: P, MP, LMP, ALMP (SEQ ID NO: 14), CALP (SEQ ID NO: 15), CFIP (SEQ ID NO: 16), CFLP (SEQ ID NO: 17), CRAP (SEQ ID NO: 18), CRL(Hyp) (SEQ ID NO: 19), CRLP (SEQ ID NO: 20), DAMP (SEQ ID NO: 21), DLAP (SEQ ID NO: 22), and DLMP (SEQ ID NO: 23).
In some embodiments, X³ is absent.
In some embodiments, X⁴ is the amino acid residue alanine.
In some embodiments, X⁴ is the amino acid residue 2,3-diaminopropionic acid.
In some embodiments, X⁴ is the amino acid residue glutamine.
In some embodiments, X⁴ is the amino acid residue glycine.
In some embodiments, X⁴ is the amino acid residue lysine.
In some embodiments, X⁴ is the amino acid residue lysine modified with a detection reagent. In some embodiments, the detection reagent is biotin.
In some embodiments, X⁴ is the amino acid residue valine.
In some embodiments, X⁵ is the amino acid residue arginine.
In some embodiments, X⁵ is the amino acid residue homo-arginine.
In some embodiments, X⁶ is an amino acid sequence selected from: L, S, LL, LAR, LGC, LLA, LLC, LLR, LPC, LTR, SQGC (SEQ ID NO: 24), SQCEY (SEQ ID NO: 25), SQCWF (SEQ ID NO: 26), and SQGCW (SEQ ID NO: 27).
In some embodiments, X⁶ is absent
In some embodiments, R² is amino.

In some embodiments, the PCSK9 inhibitor is a compound selected from the following peptides shown in Table 1.

TABLE 1

| SEQ ID NO: | Compound No. | Peptide |
|---|---|---|
| 28 | 1 | Ac-TVFTSWEEYLDWV-GSG-KLWNLGRV-NH₂ |
| 29 | 2 | Ac-TVFTSWEEYLDWV-GSG-CWNLKRIGSQGC-NH₂ |
| 30 | 3 | Ac-TVFTS(W6f1)EEYLDWV-NH₂ |
| 31 | 4 | Ac-TVFTSWEEYLDWV-GSG-KLWNLGR-NH₂ |
| 32 | 5 | Ac-TVFTSWEEYLDWV-GSG-KLWNLG-NH₂ |
| 33 | 6 | Ac-TVFTSWEEYLDWV-GSG-KLWNL-NH₂ |
| 34 | 7 | Ac-TVFTSWEEYLDWV-GSG-KLWN-NH₂ |
| 35 | 8 | Ac-TVFTSWEEYLDWV-GGSG-KLWNLGRV-NH₂ |
| 36 | 9 | Ac-TVFTSWEEYLDWV-GSGG-KLWNLGRV-NH₂ |
| 37 | 10 | Ac-TVFTSWEEYLDWV-(Aoc)-KLWNLGRV-NH₂ |
| 38 | 11 | Ac-TVFTSWEEYLDWV-GSG-CWNLGRIGSQGC-NH₂ |
| 39 | 12 | Ac-TVFTSWEEYLDWV-GSG-CWNLKRVGSQGC-NH₂ |
| 40 | 13 | Ac-TVFTSWEEYLDWV-GGSG-CWNLKRIGSQGC-NH₂ |
| 41 | 14 | Ac-TVFTSWEEYLDWV-GSGG-CWNLKRIGSQGC-NH₂ |
| 42 | 15 | Ac-TVFTSWEEYLDWV-(Aoc)-CWNLKRIGSQGC-NH₂ |

TABLE 1-continued

| SEQ ID NO: | Compound No. | Peptide |
|---|---|---|
| 43 | 16 | Ac-TVFTSWEEYLDWV-(Ahp)-KLWNLGRV-NH$_2$ |
| 44 | 17 | Ac-TVFTSWEEYLDWV-(Ahx)-CWNLKRIGSQGC-NH$_2$ |
| 45 | 18 | Ac-TVFTSWEEYLDWV-(Ahx)-KLWNLGRV-NH$_2$ |
| 46 | 19 | Ac-TVFTSWEEYLDWV-GSG-CRLPWNLQRIGLPC-NH$_2$ |
| 47 | 20 | Ac-TVFTSWEEYLDWV-GSG-DLMPWNLVRIGLLR-NH$_2$ |
| 48 | 21 | Ac-CWNLKRIGSQGC-NH$_2$ |
| 49 | 22 | Ac-GSG-CWNLKRIGSQGC-NH$_2$ |
| 50 | 23 | Ac-SPCRVGYTPC-NH$_2$ |
| 51 | 24 | Ac-TVFTSWEEYLDWV-(Ahp)-CWNLKRIGSQGC-NH$_2$ |
| 52 | 25 | Ac-TVFTSWEEYLDWV-GSGG-CRLPWNLQRIGLPC-NH$_2$ |
| 53 | 26 | SG-CFIPWNLQRIGLLC-NH$_2$ |
| 54 | 27 | SG-CRLPWNLQRIGLPC-NH$_2$ |
| 55 | 28 | SG-DLMPWNLVRIGLLR |
| 56 | 29 | Ac-SG-CFIPWNLQRIGLLC-NH$_2$ |
| 57 | 30 | Ac-SG-CRLPWNLQRIGLPC-NH$_2$ |
| 58 | 31 | Ac-CFIPWNLQRIGLLC-NH$_2$ |
| 59 | 32 | Ac-CRLPWNLQRIGLPC-NH$_2$ |
| 60 | 33 | FAM-SGSG-CFIPWNLQRIGLLC-NH$_2$ |
| 61 | 34 | FAM-SGSG-CRLPWNLQRIGLPC-NH$_2$ |
| 62 | 35 | Ac-DLMPWNLVRIGLLR-NH$_2$ |
| 63 | 36 | Ac-SG-CFIPWNLQ(Cit)IGLPC-NH$_2$ |
| 64 | 37 | Ac-SG-CRL(Hyp)WNLQRIGLPC-NH$_2$ |
| 65 | 38 | Ac-TVFTSWEEYLDWV-GSGG-CFLPWNLQRIGLLC-NH$_2$ |
| 66 | 39 | Ac-CWNLKRIGSQGCW-NH$_2$ |
| 67 | 40 | Ac-GSG-CWNLKRIGSQGCW-NH$_2$ |
| 68 | 41 | Ac-DLMPANLVRIGLLR-NH$_2$ |
| 69 | 42 | Ac-DLMAWNLVRIGLLR-NH$_2$ |
| 70 | 43 | Ac-DLAPWNLVRIGLLR-NH$_2$ |
| 71 | 44 | Ac-DAMPWNLVRIGLLR-NH$_2$ |
| 72 | 45 | Ac-ALMPWNLVRIGLLR-NH$_2$ |
| 73 | 46 | Ac-DLMPWNLVRIGLL-NH$_2$ |
| 74 | 47 | Ac-DLMPWNLVRIGL-NH$_2$ |
| 75 | 48 | Ac-DLMPWNLVRIG-NH$_2$ |
| 76 | 49 | Ac-DLMPWNLVRI-NH$_2$ |
| 77 | 50 | Ac-LMPWNLVRIGLLR-NH$_2$ |
| 78 | 51 | Ac-MPWNLVRIGLLR-NH$_2$ |
| 79 | 52 | Ac-PWNLVRIGLLR-NH$_2$ |
| 80 | 53 | Ac-WNLVRIGLLR-NH$_2$ |
| 81 | 54 | Ac-DLMPWNLVRIGLLA-NH$_2$ |

TABLE 1-continued

| SEQ ID NO: | Compound No. | Peptide |
|---|---|---|
| 82 | 55 | Ac-DLMPWNLVRIGLAR-NH$_2$ |
| 83 | 56 | Ac-DLMPWNLVRIGALR-NH$_2$ |
| 84 | 57 | Ac-DLMPWNLVRIALLR-NH$_2$ |
| 85 | 58 | Ac-DLMPWNLVRAGLLR-NH$_2$ |
| 86 | 59 | Ac-DLMPWNLVAIGLLR-NH$_2$ |
| 87 | 60 | Ac-DLMPWNLARIGLLR-NH$_2$ |
| 88 | 61 | Ac-DLMPWNAVRIGLLR-NH$_2$ |
| 89 | 62 | Ac-DLMPWALVRIGLLR-NH$_2$ |
| 90 | 63 | Ac-MCLWNLKRIGSQCEY-NH$_2$ |
| 91 | 64 | Ac-DCLWNLKRIGSQCEY-NH$_2$ |
| 92 | 65 | Ac-WCLWNLKRIGSQCEY-NH$_2$ |
| 93 | 66 | WCLWNLKRIGSQCWF |
| 94 | 67 | Ac-CRLPWNLKRIGLPC-NH$_2$ |
| 95 | 68 | Ac-CRLPWNLQRIGLAC-NH$_2$ |
| 96 | 69 | Ac-CRLPWNLQRIGAPC-NH$_2$ |
| 97 | 70 | Ac-CRLPWNLQRIALPC-NH$_2$ |
| 98 | 71 | Ac-CRLPWNLQRAGLPC-NH$_2$ |
| 99 | 72 | Ac-CRLPWNLQAIGLPC-NH$_2$ |
| 100 | 73 | Ac-CRLPWNLARIGLPC-NH$_2$ |
| 101 | 74 | Ac-CRLPWNAQRIGLPC-NH$_2$ |
| 102 | 75 | Ac-CRLPWALQRIGLPC-NH$_2$ |
| 103 | 76 | Ac-CRLPANLQRIGLPC-NH$_2$ |
| 104 | 77 | Ac-CRLAWNLQRIGLPC-NH$_2$ |
| 105 | 78 | Ac-CRAPWNLQRIGLPC-NH$_2$ |
| 106 | 79 | Ac-CALPWNLQRIGLPC-NH$_2$ |
| 107 | 80 | Ac-CRLPWNLQRIGLGC-NH$_2$ |
| 108 | 81 | Ac-CRLPWNLQRIGGGC-NH$_2$ |
| 109 | 82 | Ac-CRL(Ach)WNLQRIGLPC-NH$_2$ |
| 110 | 83 | Ac-CRLPWNLQR-(Aun)-C-NH$_2$ |
| 111 | 84 | Ac-CRLPWNLQR-(Ade)-C-NH$_2$ |
| 112 | 85 | Ac-CRLPWNLQR-(Ano)-C-NH$_2$ |
| 113 | 86 | Ac-CRLPWNLQR-(Aoc)-C-NH$_2$ |
| 114 | 87 | Ac-GCLWNLKRIGSQCWF-NH$_2$ |
| 115 | 88 | Ac-FCLWNLARIGSQCWF-NH$_2$ |
| 116 | 89 | WCLWNLKRIGSQCWF-NH$_2$ |
| 117 | 90 | Ac-WCLWNLKRIGSQCWF |
| 118 | 91 | Ac-TVFTSWEEYLDWV-(Ahx)-AWNLKRIGS-NH$_2$ |
| 119 | 92 | Ac-TVFTSWEEYLDWV-(Ahx)-AWNLKRIG-NH$_2$ |

TABLE 1-continued

| SEQ ID NO: | Compound No. | Peptide |
|---|---|---|
| 120 | 93 | Ac-TVFTSWEEYLDWV-(Ahx)-AWNLKRI-NH$_2$ |
| 121 | 94 | Ac-TVFTSWEEYLDWV-(Ahx)-AWNLKR-NH$_2$ |
| 122 | 95 | Ac-FCLWNLKRIGSQCEY-NH$_2$ |
| 123 | 96 | Ac-FCLWNLKRIGAQCWF-NH$_2$ |
| 124 | 97 | Ac-GSG-CWNL(Dpr)RIGSQGC-NH$_2$ |
| 125 | 98 | Fmoc-GSG-CWNLKRIGSQGC-NH$_2$ |
| 126 | 99 | Ac-CRLPWNLQRIGLpC-NH$_2$ |
| 127 | 100 | Ac-CRLPWNLQRIGlPC-NH$_2$ |
| 128 | 101 | Ac-CRLPWNLQRiGLPC-NH$_2$ |
| 129 | 102 | Ac-CRLPWNLQrIGLPC-NH$_2$ |
| 130 | 103 | Ac-CRLPWNLqRIGLPC-NH$_2$ |
| 131 | 104 | Ac-CRLPWNlQRIGLPC-NH$_2$ |
| 132 | 105 | Ac-CRLPWnLQRIGLPC-NH$_2$ |
| 133 | 106 | Ac-CRLPwNLQRIGLPC-NH$_2$ |
| 134 | 107 | Ac-CRLpWNLQRIGLPC-NH$_2$ |
| 135 | 108 | Ac-CRlPWNLQRIGLPC-NH$_2$ |
| 136 | 109 | Ac-CrLPWNLQRIGLPC-NH$_2$ |
| 137 | 110 | Ac-cRLPWNLQRIGLPC-NH$_2$ |
| 138 | 111 | n-BuC(O)-WNLVRIGLLR-NH$_2$ |
| 139 | 112 | n-BuC(O)-WNLVRIGLTR-NH$_2$ |
| 140 | 113 | n-BuC(O)-WNLVRIGTTR-NH$_2$ |
| 141 | 114 | n-BuC(O)-WNLVRIGTLR-NH$_2$ |
| 142 | 115 | Ac-CRLPWNLQRI-(Ape)-C-NH$_2$ |
| 143 | 116 | Ac-CRLPWNLQRI-(Ahx)-C-NH$_2$ |
| 144 | 117 | Ac-CRLPWNLQ(homoR)IGLPC-NH$_2$ |
| 145 | 118 | n-BuC(O)-WNLV(homoR)IGLTR-NH$_2$ |
| 146 | 119 | Ac-PWNLVRIGL-NH$_2$ |
| 147 | 120 | Ac-WNLVRIGL-NH$_2$ |
| 148 | 121 | Ac-CRLPWNLQRI-(Ahp)-C-NH$_2$ |

In some embodiments, the PCSK9 inhibitor is selected from the following compounds and pharmaceutically acceptable salts thereof: Ac-TVFTSWEEYLDWV-GSG-CWNLKRIGSQGC-NH$_2$ (SEQ ID NO: 29); Ac-TVFTSWEEYLDWV-GSG-CWNLGRIGSQGC-NH$_2$ (SEQ ID NO: 38); Ac-TVFTSWEEYLDWV-GGSG-CWNLKRIGSQGC-NH$_2$ (SEQ ID NO: 40); Ac-TVFTSWEEYLDWV-GSGG-CWNLKRIGSQGC-NH$_2$ (SEQ ID NO: 41); Ac-TVFTSWEEYLDWV-(Aoc)-CWNLKRIGSQGC-NH$_2$ (SEQ ID NO: 42); Ac-TVFTSWEEYLDWV-(Ahp)-KLWNLGRV-NH$_2$ (SEQ ID NO: 43); Ac-TVFTSWEEYLDWV-(Ahx)-CWNLKRIGSQGC-NH$_2$ (SEQ ID NO: 44); Ac-TVFTSWEEYLDWV-GSG-CRLPWNLQRIGLPC-NH$_2$ (SEQ ID NO: 46); Ac-TVFTSWEEYLDWV-GSG-DLMPWNLVRIGLLR-NH$_2$ (SEQ ID NO: 47); Ac-CWNLKRIGSQGC-NH$_2$ (SEQ ID NO: 48); Ac-GSG-CWNLKRIGSQGC-NH$_2$ (SEQ ID NO: 49); Ac-TVFTSWEEYLDWV-(Ahp)-CWNLKRIGSQGC-NH$_2$ (SEQ ID NO: 51); Ac-TVFTSWEEYLDWV-SGG-CRLPWNLQRIGLPC-NH$_2$ (SEQ ID NO: 149); Ac-TVFTSWEEYLDWV-GSGG-CRLPWNLQRIGLPC-NH$_2$ (SEQ ID NO: 52); SG-CFIPWNLQRIGLLC-NH$_2$ (SEQ ID NO: 53); SG-CRLPWNLQRIGLPC-NH$_2$ (SEQ ID NO: 54); SG-DLMPWNLVRIGLLR (SEQ ID NO: 55); Ac-SG-CFIPWNLQRIGLLC-NH$_2$ (SEQ ID NO: 56); Ac-SG-CRLPWNLQRIGLPC-NH$_2$ (SEQ ID NO: 57); Ac-CFIPWNLQRIGLLC-NH$_2$ (SEQ ID NO: 58); Ac-CRLPWNLQRIGLPC-NH$_2$ (SEQ ID NO: 59); Ac-DLMPWNLVRIGLLR-NH$_2$ (SEQ ID NO: 62); Ac-SG-CRL(Hyp)WNLQRIGLPC-NH$_2$ (SEQ ID NO: 64);

Ac-TVFTSWEEYLDWV-GSGG-CFLPWNLQRIGLLC-NH$_2$ (SEQ ID NO: 65); Ac-CWNLKRIGSQGCW-NH$_2$ (SEQ ID NO: 66); Ac-GSG-CWNLKRIGSQGCW-NH$_2$ (SEQ ID NO: 67); Ac-DLMAWNLVRIGLLR-NH$_2$ (SEQ ID NO: 69); Ac-DLAPWNLVRIGLLR-NH$_2$ (SEQ ID NO: 70); Ac-DAMPWNLVRIGLLR-NH$_2$ (SEQ ID NO: 71); Ac-ALMPWNLVRIGLLR-NH$_2$ (SEQ ID NO: 72); Ac-DLMPWNLVRIGLL-NH$_2$ (SEQ ID NO: 73); Ac-DLMPWNLVRIGL-NH$_2$ (SEQ ID NO: 74); Ac-DLMP-WNLVRIG-NH$_2$ (SEQ ID NO: 75); Ac-LMPWNLVRIGLLR-NH$_2$ (SEQ ID NO: 77); Ac-MPWNLVRIGLLR-NH$_2$ (SEQ ID NO: 78); Ac-PWNLVRIGLLR-NH$_2$ (SEQ ID NO: 79); Ac-WNLVRIGLLR-NH$_2$ (SEQ ID NO: 80); Ac-DLMPWNLVRIGLLA-NH$_2$ (SEQ ID NO: 81); Ac-DLMPWNLVRIGLAR-NH$_2$ (SEQ ID NO: 82); Ac-DLMPWNLVRIGALR-NH$_2$ (SEQ ID NO: 83); Ac-DLMPWNLARIGLLR-NH$_2$ (SEQ ID NO: 87); Ac-MCLWNLKRIGSQCEY-NH$_2$ (SEQ ID NO: 90); Ac-DCLWNLKRIGSQCEY-NH$_2$ (SEQ ID NO: 91); Ac-WCL-WNLKRIGSQCEY-NH$_2$ (SEQ ID NO: 92); GCLWN-LKRIGSQCWF (SEQ ID NO: 150); Ac-CRLPWNLKRIGLPC-NH$_2$ (SEQ ID NO: 94); Ac-CR-LPWNLQRIGLAC-NH$_2$ (SEQ ID NO: 95); Ac-CRLPWN-LQRIGAPC-NH$_2$ (SEQ ID NO: 96); Ac-CRLPWNLARI-GLPC-NH$_2$ (SEQ ID NO: 100); Ac-CRLAWNLQRIGLPC-NH$_2$ (SEQ ID NO: 104); Ac-CRAPWNLQRIGLPC-NH$_2$ (SEQ ID NO: 105); Ac-CALPWNLQRIGLPC-NH$_2$ (SEQ ID NO: 106); Ac-CRLPWNLQRIGLGC-NH$_2$ (SEQ ID NO: 107); Ac-CRLPWNLQRIGGGC-NH$_2$ (SEQ ID NO: 108); Ac-CRL(Ach)WNLQRIGLPC-NH$_2$ (SEQ ID NO: 109); Ac-GCLWNLKRIGSQCWF-NH$_2$ (SEQ ID NO: 114); Ac-GCLWNLARIGSQCWF-NH$_2$ (SEQ ID NO: 151); Ac-FCLWNLARIGSQCWF-NH$_2$ (SEQ ID NO: 115); GCL-WNLKRIGSQCWF-NH$_2$ (SEQ ID NO: 152); WCLWN-LKRIGSQCWF-NH$_2$ (SEQ ID NO: 116); Ac-GCLWNLKRIGSQCWF (SEQ ID NO: 153); Ac-WCL-WNLKRIGSQCWF (SEQ ID NO: 117); Ac-TVFTSWEEY-LDWV-(Ahx)-AWNLKRIGS-NH$_2$ (SEQ ID NO: 118); Ac-TVFTSWEEYLDWV-(Ahx)-AWNLKRIG-NH$_2$ (SEQ ID NO: 119); Ac-FCLWNLKRIGSQCEY-NH$_2$ (SEQ ID NO: 122); Ac-FCLWNLKRIGAQCWF-NH$_2$ (SEQ ID NO: 123); Ac-GSG-CWNL(Dpr)RIGSQGC-NH$_2$ (SEQ ID NO: 124); Ac-CRLPWNLQRIGLpC-NH$_2$ (SEQ ID NO: 126); Ac-CRLPWNLQRIGlPC-NH$_2$ (SEQ ID NO: 127); Ac-CRLP-WNLQRIGLPC-NH$_2$ (SEQ ID NO: 59); Ac-CRLPWN-LQRIGLPC-NH$_2$ (SEQ ID NO: 59); Ac-CRLPWNLqRIGLPC-NH$_2$ (SEQ ID NO: 130); Ac-CR-LPWNLQRIGLPC-NH$_2$ (SEQ ID NO: 59); Ac-CRLPWN-LQRIGLPC-NH$_2$ (SEQ ID NO: 59); Ac-CRLPWNLQRI-GLPC-NH$_2$ (SEQ ID NO: 59); Ac-CRLpWNLQRIGLPC-NH$_2$ (SEQ ID NO: 134); Ac-CRlPWNLQRIGLPC-NH$_2$ (SEQ ID NO: 135); Ac-CrLPWNLQRIGLPC-NH$_2$ (SEQ ID NO: 136); Ac-cRLPWNLQRIGLPC-NH$_2$ (SEQ ID NO: 137); n-BuC(O)-WNLVRIGLLR-NH$_2$ (SEQ ID NO: 138); n-BuC(O)-WNLVRIGLTR-NH$_2$ (SEQ ID NO: 139); n-BuC(O)-WNLVRIGTTR-NH$_2$ (SEQ ID NO: 140); n-BuC(O)-WNLVRIGTLR-NH$_2$ (SEQ ID NO: 141); Ac-CRLPWNLQ(homoR)IGLPC-NH$_2$ (SEQ ID NO: 144); n-BuC(O)-WNLV(homoR)IGLTR-NH$_2$ (SEQ ID NO: 145); and Ac-PWNLVRIGL-NH$_2$ (SEQ ID NO: 146).

In some embodiments, the PCSK9 inhibitor is selected from compounds of Formula II:

```
Formula II
                                         (SEQ ID NO: 154)
R¹-X¹-X²-X³-X⁷-Asn-Leu-X⁴-X⁵-Ile-Gly-X⁶-R²,
``` and pharmaceutically acceptable salts thereof, wherein, $R^1$ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:

$C_1$-$C_4$ alkyl;

amino;

aryl, optionally substituted with one or two substituents each independently selected from: $C_1$-$C_4$ alkoxy, amino, halo, and hydroxy;

aryl-$C_1$-$C_4$ alkyl;

arylcarbonyl, optionally substituted with one substituent selected from: $C_1$-$C_4$ alkyl and $C_1$-$C_4$ alkylsulfonyl;

aryloxy, optionally substituted with one or two substituents each independently selected from: $C_1$-$C_4$ acyl, $C_1$-$C_4$ alkoxy, $C_1$-$C_4$ alkyl, halo, and hydroxy-$C_1$-$C_4$ alkyl;

carboxyamino, optionally substituted with one substituent selected from: aryl-$C_1$-$C_4$ alkyl;

$C_3$-$C_7$ cycloalkyl;

heteroaryl, optionally substituted with one or two substituents each independently selected from: $C_1$-$C_4$ alkyl and amino;

heterocyclyl, optionally substituted with one or two substituents each independently selected from: $C_1$-$C_4$ alkyl, $C_1$-$C_4$ alkylsulfonyl, carboxamide, heteroaryl-$C_1$-$C_4$ alkyl, and oxo;

heterocyclylcarbonyl; and ureido;

or $R^1$ is absent;

$X^1$ is an amino acid sequence selected from: TVFTS-WEEYLDWV (SEQ ID NO: 3), TVFTS(W6fl)EEYLDWV (SEQ ID NO: 30), and TAFTSWEEYLDWV (SEQ ID NO: 4); or $X^1$ is absent;

$X^2$ is an amino acid sequence comprising 1 to 4 amino acid residues selected from: glycine and serine; or $X^2$ is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid; or $X^2$ is absent;

$X^3$ is an amino acid sequence comprising 1 to 6 amino acid residues selected from: alanine, 2-aminocyclohexane-1-carboxylic acid, arginine, aspartic acid, cysteine, glutamic acid, glycine, 3-hydroxyproline, isoleucine, leucine, methionine, phenylalanine, proline, serine, tryptophan, and tyrosine;

$X^4$ is an amino acid residue selected from: alanine, 2,3-diaminopropionic acid, glutamine, glycine, lysine, and valine;

$X^5$ is an amino acid residue selected from: arginine and homo-arginine;

$X^6$ is an amino acid sequence comprising 1 to 5 amino acid residues selected from: alanine, arginine, aspartic acid, cysteine, glutamic acid, glutamine, glycine, leucine, lysine, phenylalanine, proline, serine, threonine, and tryptophan; or $X^6$ is absent;

$X^7$ is an amino acid residue selected from: tryptophan, 6-fluorotryptophan, 6-chlorotryptophan, 6-bromotryptophan, and 6-methyltryptophan; and $R^2$ is amino; or $R^2$ is absent.

In some embodiments, $R^1$ is $C_1$-$C_4$ acyl.
In some embodiments, $R^1$ is acetyl.
In some embodiments, $R^1$ is valeryl.
In some embodiments, $R^1$ is absent.
In some embodiments, $R^1$ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:
 $C_1$-$C_4$ alkyl;
 amino;
 aryl, optionally substituted with one or two substituents each independently selected from: methoxy, amino, fluoro, chloro, and hydroxy;
 aryl-$C_1$-$C_4$ alkyl;
 arylcarbonyl, optionally substituted with one substituent selected from: methyl and methylsulfonyl;
 aryloxy, optionally substituted with one or two substituents each independently selected from: acetyl, methoxy, methyl, ethyl, bromo, and hydroxymethyl;
 carboxyamino, optionally substituted with one substituent selected from: phenylmethyl;
 $C_3$-$C_7$ cycloalkyl;
 heteroaryl, optionally substituted with one or two substituents each independently selected from: methyl and amino;
 heterocyclyl, optionally substituted with one or two substituents each independently selected from: methyl, methylsulfonyl, carboxamide, pyridinylmethyl, and oxo;
 heterocyclylcarbonyl; and
 ureido.

In some embodiments, $R^1$ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:
 $C_1$-$C_4$ alkyl selected from: methyl and t-butyl;
 amino;
 phenyl, optionally substituted with one or two substituents each independently selected from: methoxy, amino, fluoro, chloro, and hydroxy;
 phenylmethyl;
 benzoyl, optionally substituted with one substituent selected from: methyl and methylsulfonyl;
 phenoxy, optionally substituted with one or two substituents each independently selected from: acetyl, methoxy, methyl, ethyl, bromo, and hydroxymethyl;
 carboxyamino, optionally substituted with one substituent selected from: phenylmethyl;
 cyclohexyl;
 heteroaryl selected from: imidazolyl, indolyl, pyrazolyl, pyridinyl, and triazolyl, each optionally substituted with one or two substituents each independently selected from: methyl and amino;
 heterocyclyl selected from: morpholinyl, piperidinyl, piperazinyl, pyrrolidinyl, tetrahydrothiophenyl, tetrahydropyrimidinyl, thiomorpholinyl, each optionally substituted with one or two substituents each independently selected from: methyl, methylsulfonyl, carboxamide, pyridinylmethyl, and oxo;
 morpholinylcarbonyl; and
 ureido.

In some embodiments, $R^1$ is selected from: acetyl, n-propionyl, n-butanoyl, isovaleryl, valeryl, benzoyl, cyclopropylcarbonyl, cyclobutylcarbonyl, cyclohexylcarbonyl, indolylcarbonyl, pyrazolylcarbonyl, and pyridinylcarbonyl; each optionally substituted with one or two substituents each independently selected from:
 $C_1$-$C_4$ alkyl selected from: methyl and t-butyl;
 amino;
 phenyl, optionally substituted with one or two substituents each independently selected from: methoxy, amino, fluoro, chloro, and hydroxy;
 phenylmethyl;
 benzoyl, optionally substituted with one substituent selected from: methyl and methylsulfonyl;
 phenoxy, optionally substituted with one or two substituents each independently selected from: acetyl, methoxy, methyl, ethyl, bromo, and hydroxymethyl;
 carboxyamino, optionally substituted with one substituent selected from: phenylmethyl; cyclohexyl;
 heteroaryl selected from: imidazolyl, indolyl, pyrazolyl, pyridinyl, and triazolyl, each optionally substituted with one or two substituents each independently selected from: methyl and amino;
 heterocyclyl selected from: morpholinyl, piperidinyl, piperazinyl, pyrrolidinyl, tetrahydrothiophenyl, tetrahydropyrimidinyl, thiomorpholinyl, each optionally substituted with one or two substituents each independently selected from: methyl, methylsulfonyl, carboxamide, pyridinylmethyl, and oxo;
 morpholinylcarbonyl; and
 ureido.

In some embodiments, $R^1$ is selected from: acetyl, n-butanoyl, 3-(1,1-dioxidothiomorpholino)propanoyl, 2-(1-methyl-1H-pyrazol-4-yl)cyclopropane-1-carbonyl, 3-(2-oxopyrrolidin-1-yl)propanoyl, 1-(1-methylpyrrolidin-3-yl)-1H-pyrazole-4-carbonyl, 2-(1-(pyridin-2-ylmethyl)piperidin-4-yl)acetyl, 3-(4-carbamoylpiperazin-1-yl)propanoyl, 3-(1H-imidazol-4-yl)propanoyl, 2-(1-(methylsulfonyl)piperidin-4-yl)acetyl, 6-morpholinonicotinoyl, 3-(3,5-dimethyl-1H-pyrazol-1-yl)propanoyl, 3-morpholinopropanoyl, 3-(pyridin-3-yl)propanoyl, 2-(1,1-dioxidotetrahydrothiophen-3-yl)acetyl, 3-(4-methylpiperazin-1-yl)propanoyl, 3-ureidopropanoyl, 3-(1H-1,2,4-triazol-1-yl)propanoyl, 2-(2,4-dioxo-3,4-dihydropyrimidin-1(2H)-yl)acetyl, 3-benzylcyclobutane-1-carbonyl, [1,1'-biphenyl]-4-carbonyl, 5-phenylpentanoyl, 4-phenylcyclohexane-1-carbonyl, 5,5-dimethylhexanoyl, 3,5,5-trimethylhexanoyl, 5-(pyridin-4-yl)-1H-pyrazole-3-carbonyl, 3-cyclohexylpropanoyl, 3-(4-aminophenyl)propanoyl, 4-morpholinobutanoyl, 4-(4-(methylsulfonyl)phenyl)-4-oxobutanoyl, 3-(3-aminophenyl)propanoyl, 4-oxo-4-(p-tolyl)butanoyl, 3-(4-methoxyphenyl)propanoyl, 4-morpholino-4-oxobutanoyl, 3-(3-hydroxyphenyl)propanoyl, 4-(((benzyloxy)carbonyl)amino)butanoyl, 3-(4-hydroxyphenyl)propanoyl, 3-(6-aminopyridin-3-yl)propanoyl, 4-(4-bromophenoxy)butanoyl, 4-(4-acetylphenoxy)butanoyl, 3-(pyridin-4-yl)-1H-pyrazole-5-carbonyl, 3-(1H-indol-3-yl)propanoyl, 4-(1H-indol-3-yl)butanoyl, 4-(4-fluorophenyl)butanoyl, 3-(4-fluorophenyl)propanoyl, 3-(4-chlorophenyl)propanoyl, 3-(3-methoxyphenyl)propanoyl, 3-(4-methoxyphenoxy)propanoyl, 4-(4-(hydroxymethyl)-3-methoxyphenoxy)butanoyl, 3-(4-acetylphenoxy)propanoyl, 4-(p-tolyloxy)butanoyl, 4-phenoxybutanoyl, 4-(4-ethylphenoxy)butanoyl, 3-(p-tolyloxy)propanoyl, 4-phenylbutanoyl, 3-(4-hydroxy-3-methoxyphenyl)propanoyl, 4-(4-hydroxyphenyl)butanoyl, 2-(pyridin-3-yl)cyclopropane-1-carbonyl, 1H-indole-6-carbonyl, 2-amino-3-(4-hydroxyphenyl)propanoyl, and 3-(3,4-dihydroxyphenyl)propanoyl.

In some embodiments, $X^1$ is an amino acid sequence selected from: TVFTSWEEYLDWV (SEQ ID NO: 3), TVFTS(W6fl)EEYLDWV (SEQ ID NO: 30), and TAFTSWEEYLDWV (SEQ ID NO: 4).

In some embodiments, $X^1$ is the amino acid sequence TVFTSWEEYLDWV (SEQ ID NO: 3).

In some embodiments, $X^1$ is the amino acid sequence TVFTS(W6fl)EEYLDWV (SEQ ID NO: 30).

In some embodiments, $X^1$ is the amino acid sequence TAFTSWEEYLDWV (SEQ ID NO: 4).

In some embodiments, $X^1$ is absent.

In some embodiments, $X^2$ is an amino acid sequence comprising 1 to 4 amino acid residues selected from: glycine and serine.

In some embodiments, $X^2$ is an amino acid sequence selected from: G, GG, SG, GSG, GGSG (SEQ ID NO: 11), GSGG (SEQ ID NO: 12), and SGSG (SEQ ID NO: 13).

In some embodiments, $X^2$ is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid.

In some embodiments, $X^2$ is the amino acid residue 6-aminohexanoic acid.

In some embodiments, $X^2$ is the amino acid residue 7-aminoheptanoic acid.

In some embodiments, $X^2$ is the amino acid residue 8-aminooctanoic acid.

In some embodiments, $X^2$ is absent.

In some embodiments, $X^3$ is an amino acid sequence selected from: P, MP, LMP, ALMP (SEQ ID NO: 14), CALP (SEQ ID NO: 15), CFI(Hyp) (SEQ ID NO: 155), CFIP (SEQ ID NO: 16), CFLP (SEQ ID NO: 17), CRAP (SEQ ID NO: 18), CRL(Hyp) (SEQ ID NO: 19), CRLP (SEQ ID NO: 20), DAMP (SEQ ID NO: 21), DLAP (SEQ ID NO: 22), DLMP (SEQ ID NO: 23), DSYPG (SEQ ID NO: 156), ESFPG (SEQ ID NO: 157), ESYPG (SEQ ID NO: 158), MDSFPG (SEQ ID NO: 159), MESFPG (SEQ ID NO: 160), and SFAFPG (SEQ ID NO: 161).

In some embodiments, $X^3$ is absent.

In some embodiments, $X^4$ is the amino acid residue alanine.

In some embodiments, $X^4$ is the amino acid residue 2,3-diaminopropionic acid.

In some embodiments, $X^4$ is the amino acid residue glutamine.

In some embodiments, $X^4$ is the amino acid residue glycine.

In some embodiments, $X^4$ is the amino acid residue lysine.

In some embodiments, $X^4$ is the amino acid residue valine.

In some embodiments, $X^5$ is the amino acid residue arginine.

In some embodiments, $X^5$ is the amino acid residue homo-arginine.

In some embodiments, $X^6$ is an amino acid sequence selected from: L, S, LL, LAR, LDR, LER, LGC, LGR, LLA, LLC, LLQ, LLR, LPC, LPR, LSR, LTR, SQGC (SEQ ID NO: 24), SQCEY (SEQ ID NO: 25), SQCWF (SEQ ID NO: 26), and SQGCW (SEQ ID NO: 27).

In some embodiments, $X^6$ is absent

In some embodiments, $X^7$ is tryptophan.

In some embodiments, $X^7$ is 6-fluorotryptophan.

In some embodiments, $X^7$ is 6-chlorotryptophan.

In some embodiments, $X^7$ is 6-bromotryptophan.

In some embodiments, $X^7$ is 6-methyltryptophan.

In some embodiments, $R^2$ is amino.

In some embodiments, $R^2$ is absent.

In some embodiments, the PCSK9 inhibitor is selected from the compounds shown in Table 1 Å and pharmaceutically acceptable salts thereof.

TABLE 1A

| SEQ ID NO: | Compound No. | Peptide |
|---|---|---|
| 162 | 122 | Ac-SG-DLMPWNLVRIGLLR-NH$_2$ |
| 163 | 123 | n-PrC(O)-WNLVRIGLLR-NH$_2$ |
| 164 | 124 | Ac-G-LMPWNLVRIGLLR-NH$_2$ |
| 165 | 125 | Ac-GG-MPWNLVRIGLLR-NH$_2$ |
| 166 | 126 | 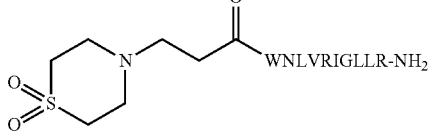 |
| 167 | 127 | 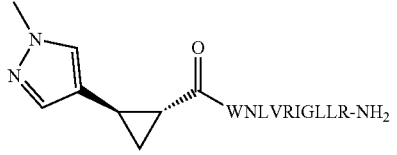 |
| 168 | 128 | 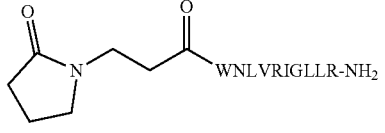 |
| 169 | 129 | 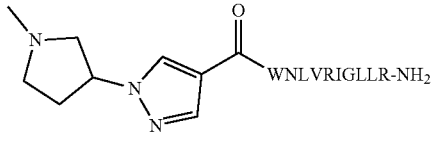 |

TABLE 1A-continued

| SEQ ID NO: | Compound No. | Peptide |
|---|---|---|
| 170 | 130 | [(pyridin-2-ylmethyl)piperidin-4-yl]acetyl-WNLVRIGLLR-NH$_2$ |
| 171 | 131 | 3-(4-carbamoylpiperazin-1-yl)propanoyl-WNLVRIGLLR-NH$_2$ |
| 172 | 132 | 3-(1H-imidazol-4-yl)propanoyl-WNLVRIGLLR-NH$_2$ |
| 173 | 133 | [1-(methylsulfonyl)piperidin-4-yl]acetyl-WNLVRIGLLR-NH$_2$ |
| 174 | 134 | 6-(morpholin-4-yl)pyridine-3-carbonyl-WNLVRIGLLR-NH$_2$ |
| 175 | 135 | (1R,2R)-2-(1-methyl-1H-pyrazol-4-yl)cyclopropanecarbonyl-WNLVRIGLLR-NH$_2$ |
| 176 | 136 | 3-(3,5-dimethyl-1H-pyrazol-1-yl)propanoyl-WNLVRIGLLR-NH$_2$ |
| 177 | 137 | 3-(morpholin-4-yl)propanoyl-WNLVRIGLLR-NH$_2$ |
| 178 | 138 | 3-(pyridin-3-yl)propanoyl-WNLVRIGLLR-NH$_2$ |

TABLE 1A-continued

| SEQ ID NO: | Compound No. | Peptide |
|---|---|---|
| 179 | 139 | (1,1-dioxo-tetrahydrothiophen-3-yl)-CH₂-C(O)-WNLVRIGLLR-NH₂ |
| 180 | 140 | (4-methylpiperazin-1-yl)-CH₂CH₂-C(O)-WNLVRIGLLR-NH₂ |
| 181 | 141 | H₂N-C(O)-NH-CH₂CH₂-C(O)-WNLVRIGLLR-NH₂ |
| 182 | 142 | (1,2,4-triazol-1-yl)-CH₂CH₂-C(O)-WNLVRIGLLR-NH₂ |
| 183 | 143 | (uracil-1-yl)-CH₂-C(O)-WNLVRIGLLR-NH₂ |
| 184 | 144 | (3-benzylcyclobutyl)-C(O)-WNLVRIGLLR-NH₂ |
| 185 | 145 | (biphenyl-4-yl)-C(O)-WNLVRIGLLR-NH₂ |
| 186 | 146 | Ph-CH₂CH₂CH₂CH₂-C(O)-WNLVRIGLLR-NH₂ |
| 187 | 147 | (4-phenylcyclohexyl)-C(O)-WNLVRIGLLR-NH₂ |
| 188 | 148 | (CH₃)₃C-CH₂CH₂CH₂-C(O)-WNLVRIGLLR-NH₂ |

TABLE 1A-continued

| SEQ ID NO: | Compound No. | Peptide |
|---|---|---|
| 189 | 149 | 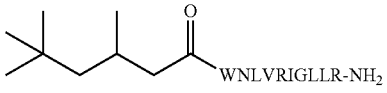WNLVRIGLLR-NH$_2$ |
| 190 | 150 | 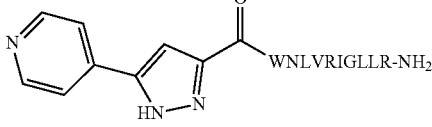WNLVRIGLLR-NH$_2$ |
| 191 | 151 | 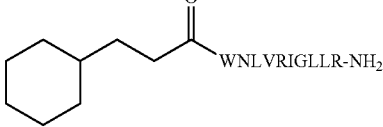WNLVRIGLLR-NH$_2$ |
| 192 | 152 | n-BuC(O)-WNLVRIGLLR |
| 193 | 153 | Ac-MDSFPGWNLVRIGLLR-NH$_2$ |
| 194 | 154 | Ac-SFAFPGWNLVRIGLLR-NH$_2$ |
| 195 | 155 | Ac-DSYPGWNLVRIGLLR-NH$_2$ |
| 196 | 156 | Ac-ESYPGWNLVRIGLLR-NH$_2$ |
| 197 | 157 | Ac-ESFPGWNLVRIGLLR-NH$_2$ |
| 198 | 158 | Ac-DLMPWNLKRIGLLR-NH$_2$ |
| 199 | 159 | n-BuC(O)-WNLKRIGLLR-NH$_2$ |
| 200 | 160 | Ac-DLMPWNLVRIGLPR-NH$_2$ |
| 201 | 161 | 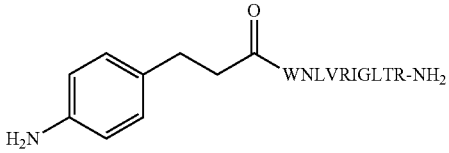WNLVRIGLTR-NH$_2$ |
| 202 | 162 | 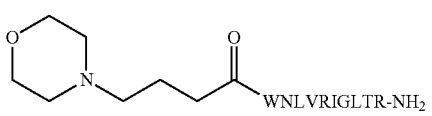WNLVRIGLTR-NH$_2$ |
| 203 | 163 | 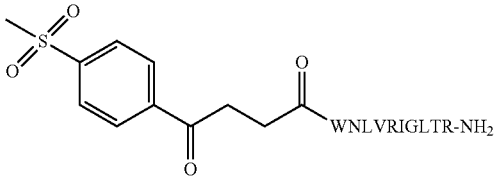WNLVRIGLTR-NH$_2$ |
| 204 | 164 | 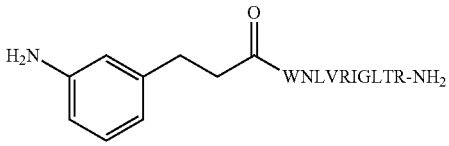WNLVRIGLTR-NH$_2$ |
| 205 | 165 | 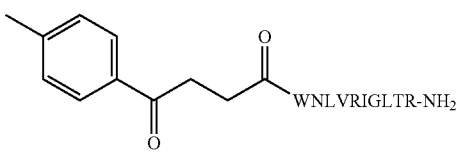WNLVRIGLTR-NH$_2$ |

TABLE 1A-continued

| SEQ ID NO: | Compound No. | Peptide |
|---|---|---|
| 206 | 166 | 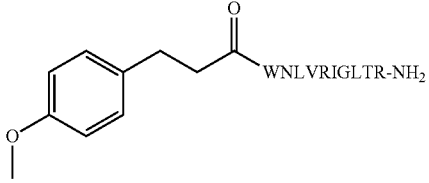 WNLVRIGLTR-NH$_2$ |
| 207 | 167 | 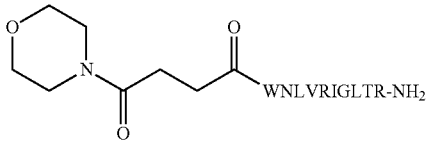 WNLVRIGLTR-NH$_2$ |
| 208 | 168 | 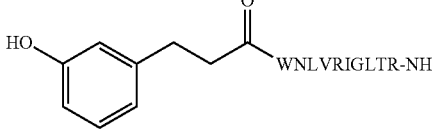 WNLVRIGLTR-NH$_2$ |
| 209 | 169 | 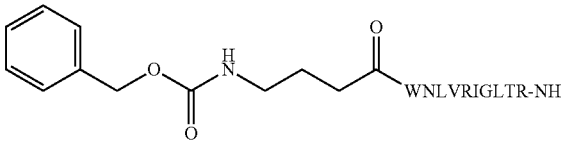 WNLVRIGLTR-NH$_2$ |
| 210 | 170 | 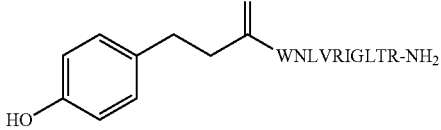 WNLVRIGLTR-NH$_2$ |
| 211 | 171 | 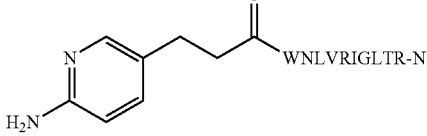 WNLVRIGLTR-NH$_2$ |
| 212 | 172 | 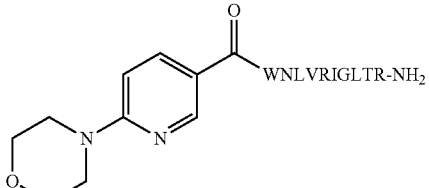 WNLVRIGLTR-NH$_2$ |
| 213 | 173 | 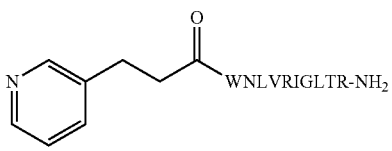 WNLVRIGLTR-NH$_2$ |
| 214 | 174 | n-BuC(O)-(W6fl)NLVRIGLTR-NH$_2$ |
| 215 | 175 | n-BuC(O)-(W6me)NLVRIGLTR-NH$_2$ |
| 216 | 176 | n-BuC(O)-WNLVRIGLTR |
| 217 | 177 | n-BuC(O)-WNLVRIGLER-NH$_2$ |
| 218 | 178 | n-BuC(O)-WNLVRIGLDR-NH$_2$ |
| 219 | 179 | n-BuC(O)-WNLVRIGLGR-NH$_2$ |
| 220 | 180 | n-BuC(O)-WNLVRIGLAR-NH$_2$ |
| 221 | 181 | n-BuC(O)-WNLVRIGLSR-NH$_2$ |

TABLE 1A-continued

| SEQ ID NO: | Compound No. | Peptide |
|---|---|---|
| 222 | 182 | 4-(4-bromophenoxy)butanoyl-WNLVRIGLTR-NH₂ |
| 223 | 183 | 4-(4-acetylphenoxy)butanoyl-WNLVRIGLTR-NH₂ |
| 224 | 184 | (3-benzylcyclobutyl)carbonyl-WNLVRIGLTR-NH₂ |
| 225 | 185 | (4-phenylcyclohexyl)carbonyl-WNLVRIGLTR-NH₂ |
| 226 | 186 | n-BuC(O)-(W6cl)NLVRIGLTR-NH₂ |
| 227 | 187 | n-BuC(O)-(W6br)NLVRIGLTR-NH₂ |
| 228 | 188 | [3-(pyridin-4-yl)-1H-pyrazol-5-yl]carbonyl-WNLVRIGLTR-NH₂ |
| 229 | 189 | 3-(1H-indol-3-yl)propanoyl-WNLVRIGLTR-NH₂ |
| 230 | 190 | 4-(1H-indol-3-yl)butanoyl-WNLVRIGLTR-NH₂ |
| 231 | 191 | n-BuC(O)-WNLV(homoR)IGLLR-NH₂ |
| 232 | 192 | Ac-WNLV(homoR)IGLLR-NH₂ |
| 233 | 193 | 4-(morpholin-4-yl)butanoyl-WNLV(homoR)IGLLR-NH₂ |
| 234 | 194 | 4-(morpholin-4-yl)-4-oxobutanoyl-WNLV(homoR)IGLLR-NH₂ |

TABLE 1A-continued
| SEQ ID NO: | Compound No. | Peptide |
|---|---|---|
| 235 | 195 | n-BuC(O)-WNLV(homoR)IGLLR |
| 236 | 196 | 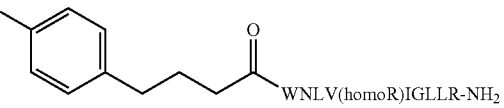 4-F-C6H4-(CH2)3-C(O)-WNLV(homoR)IGLLR-NH2 |
| 237 | 197 | 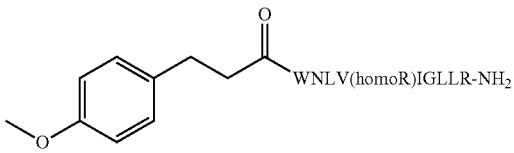 4-MeO-C6H4-(CH2)2-C(O)-WNLV(homoR)IGLLR-NH2 |
| 238 | 198 | 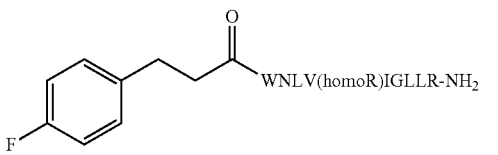 4-F-C6H4-(CH2)2-C(O)-WNLV(homoR)IGLLR-NH2 |
| 239 | 199 | 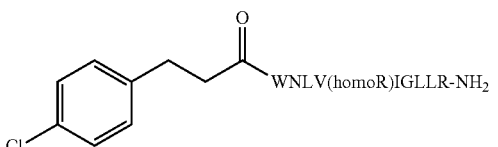 4-Cl-C6H4-(CH2)2-C(O)-WNLV(homoR)IGLLR-NH2 |
| 240 | 200 | 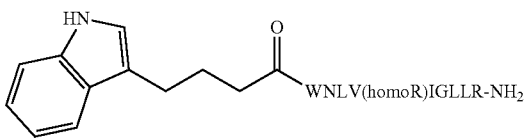 indol-3-yl-(CH2)3-C(O)-WNLV(homoR)IGLLR-NH2 |
| 241 | 201 | 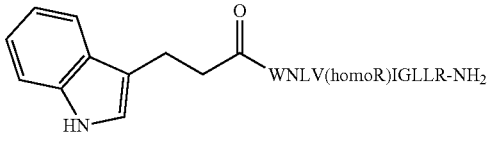 indol-3-yl-(CH2)2-C(O)-WNLV(homoR)IGLLR-NH2 |
| 242 | 202 | 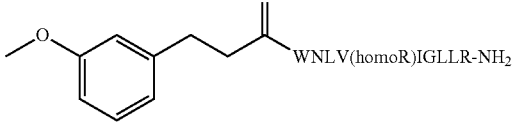 3-MeO-C6H4-(CH2)2-C(O)-WNLV(homoR)IGLLR-NH2 |
| 243 | 203 | 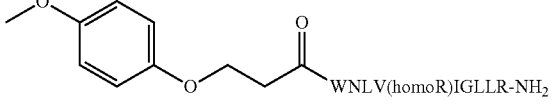 4-MeO-C6H4-O-(CH2)2-C(O)-WNLV(homoR)IGLLR-NH2 |
| 244 | 204 | 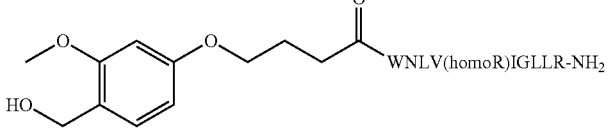 |
| 245 | 205 | 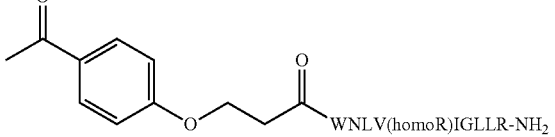 |

TABLE 1A-continued

| SEQ ID NO: | Compound No. | Peptide |
|---|---|---|
| 246 | 206 | 4-(4-bromophenoxy)butanoyl-WNLV(homoR)IGLLR-NH$_2$ |
| 247 | 207 | 4-(4-methylphenoxy)butanoyl-WNLV(homoR)IGLLR-NH$_2$ |
| 248 | 208 | (4-phenylcyclohexyl)carbonyl-WNLV(homoR)IGLLR-NH$_2$ |
| 249 | 209 | 4-phenoxybutanoyl-WNLV(homoR)IGLLR-NH$_2$ |
| 250 | 210 | 4-(4-ethylphenoxy)butanoyl-WNLV(homoR)IGLLR-NH$_2$ |
| 251 | 211 | 3-(4-methylphenoxy)propanoyl-WNLV(homoR)IGLLR-NH$_2$ |
| 252 | 212 | 4-phenylbutanoyl-WNLV(homoR)IGLLR-NH$_2$ |
| 253 | 213 | 3-(4-hydroxy-3-methoxyphenyl)propanoyl-WNLV(homoR)IGLLR-NH$_2$ |
| 254 | 214 | 3-(4-hydroxyphenyl)propanoyl-WNLV(homoR)IGLLR-NH$_2$ |

TABLE 1A-continued

| SEQ ID NO: | Compound No. | Peptide |
|---|---|---|
| 255 | 215 | H₂N-C₆H₄-CH₂CH₂-C(O)-WNLV(homoR)IGLLR-NH₂ (3-aminophenyl) |
| 256 | 216 | 6-amino-pyridin-3-yl-CH₂CH₂-C(O)-WNLV(homoR)IGLLR-NH₂ |
| 257 | 217 | HO-C₆H₄-CH₂CH₂-C(O)-WNLV(homoR)IGLLR-NH₂ (3-hydroxyphenyl) |
| 258 | 218 | H₂N-C₆H₄-CH₂CH₂-C(O)-WNLV(homoR)IGLLR-NH₂ (4-aminophenyl) |
| 259 | 219 | 6-morpholino-pyridin-3-yl-C(O)-WNLV(homoR)IGLLR-NH₂ |
| 260 | 220 | HO-C₆H₄-CH₂CH₂CH₂-C(O)-WNLV(homoR)IGLLR-NH₂ (4-hydroxyphenyl) |
| 261 | 221 | (pyridin-3-yl)-trans-cyclopropyl-C(O)-WNLV(homoR)IGLLR-NH₂ |
| 262 | 222 | 1H-indol-6-yl-C(O)-WNLV(homoR)IGLLR-NH₂ |
| 263 | 223 | D-Tyr-WNLV(homoR)IGLLR-NH₂ |

TABLE 1A-continued

| SEQ ID NO: | Compound No. | Peptide |
|---|---|---|
| 264 | 224 | (3,4-dihydroxyphenyl)propanoyl-WNLV(homoR)IGLLR-NH₂ |
| 265 | 225 | (2-(pyridin-3-yl)cyclopropanecarbonyl)-WNLV(homoR)IGLLR-NH₂ |
| 266 | 226 | (L-tyrosyl)-WNLV(homoR)IGLLR-NH₂ |
| 267 | 227 | Ac-ESFPGWNLV(homoR)IGLLR-NH₂ |
| 268 | 228 | Ac-SFAFPGWNLV(homoR)IGLLR-NH₂ |
| 269 | 229 | Ac-MESFPGWNLV(homoR)IGLLR-NH₂ |
| 270 | 230 | Ac-DSYPGWNLV(homoR)IGLLR-NH₂ |
| 271 | 231 | Ac-ESYPGWNLV(homoR)IGLLR-NH₂ |
| 272 | 232 | Ac-SFAFPGWNLK(homoR)IGLLR-NH₂ |
| 273 | 233 | Ac-MESFPGWNLK(homoR)IGLLR-NH₂ |
| 274 | 234 | n-BuC(O)-WNLV(homoR)IGLTR-NH₂ |
| 275 | 235 | n-BuC(O)-WNLV(homoR)IGLTR |
| 276 | 236 | WNLV(homoR)IG-NH₂ |
| 277 | 237 | WNLV(homoR)IGLLQ-NH₂ |
| 278 | 238 | (3-methoxy-4-hydroxyphenyl)propanoyl-WNLV(homoR)IGLLN-NH₂ |
| 279 | 239 | (3-methoxy-4-hydroxyphenyl)propanoyl-WNLV(homoR)IGQR-NH₂ |
| 280 | 240 | (3-methoxy-4-hydroxyphenyl)propanoyl-WNLV(homoR)IGNR-NH₂ |
| 281 | 241 | Ac-TVFTS(W6fl)EEYLDWV-GSG-CRLPWNLQRIGLPC-NH₂ |
| 282 | 242 | Ac-SG-CFI(Hyp)WNLQRIGLLC-NH₂ |

In certain embodiments, the invention provides an inhibited PCSK9 comprising a PCSK9 inhibitor of as described herein bound to PCSK9.

In one aspect, the invention relates to a method for identifying a candidate compound as a PCSK9 inhibitor that binds an epitope of SEQ ID NO: 1, wherein the epitope comprises at least one residue selected from the group consisting of V241, T339, D343, P364, A442, A443, and L444 of SEQ ID NO: 1. of SEQ ID NO: 1; the method comprising the steps of: a) contacting PCSK9 with the candidate compound; b) contacting PCSK9Δhelix with the candidate compound; c) measuring binding affinities of the candidate compound for PCSK9 and PCSK9Δhelix; and d) determining that the binding affinity of the candidate compound for PCSK9Δhelix is stronger than the binding affinity of the candidate compound for PCSK9; wherein said determination is indicative of the candidate compound being a PCSK9 inhibitor that binds the epitope of SEQ ID NO: 1.

A method for identifying a candidate compound as a PCSK9 inhibitor that binds an epitope of SEQ ID NO: 1, wherein the epitope comprises at least one residue selected from the group consisting of V241, T339, D343, P364, A442, A443, and L444 of SEQ ID NO: 1. of SEQ ID NO: 1; the method comprising the steps of: a) contacting PCSK9 with the candidate compound; b) measuring the binding affinity of the candidate compound for PCSK9; c) contacting PCSK9Δhelix with the candidate compound; d)measuring the binding affinity of the candidate compound for PCSK9Δhelix; and e) determining that the binding affinity of the candidate compound for PCSK9Δhelix is stronger than the binding affinity of the candidate compound for PCSK9; wherein said determination is indicative of the candidate compound being a PCSK9 inhibitor that binds the epitope of SEQ ID NO: 1.

In some embodiments, the epitope comprises at least two residues selected from the group consisting of V241, T339, D343, P364, A442, A443, and L444 of SEQ ID NO: 1.

In some embodiments, the epitope comprises at least three residues selected from the group consisting of V241, T339, D343, P364, A442, A443, and L444 of SEQ ID NO: 1.

In some embodiments, the epitope comprises at least four residues selected from the group consisting of V241, T339, D343, P364, A442, A443, and L444 of SEQ ID NO: 1.

In some embodiments, the epitope comprises at least five residues selected from the group consisting of V241, T339, D343, P364, A442, A443, and L444 of SEQ ID NO: 1.

In some embodiments, the epitope comprises at least six residues selected from the group consisting of V241, T339, D343, P364, A442, A443, and L444 of SEQ ID NO: 1.

In some embodiments, the epitope comprises at least eleven residues selected from the group consisting of A239, G240, V241, T339, N340, A341, D343, P364, E366, D367, I368, I369, G370, H391, A442, A443, and L444 of SEQ ID NO: 1.

In some embodiments, the PCSK9 and PCSK9Δhelix are provided on a sensor chip.

In some embodiments, the binding affinities are determined using surface plasmon resonance.

Pharmaceutical Compositions

Another embodiment provides pharmaceutical compositions or medicaments containing the compounds of the invention and a therapeutically inert carrier, diluent or excipient, as well as methods of using the compounds of the invention to prepare such compositions and medicaments. In one example, PCSK9 inhibitors described herein may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a PCSK9 inhibitor described herein is formulated in an acetate buffer, at pH 5. In another embodiment, the PCSK9 inhibitors described herein are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" or "therapeutically effective amount" of the compound to be administered will be governed by such considerations, and is the minimum amount necessary to alter the conformation of PCSK9, and thereby decrease the affinity of the PCSK9 LDLR binding site for LDLRs such that internalization of LDL by hepatocytes is increased and levels of circulating LDL-C are reduced. For example, such amount may be below the amount that is toxic to normal cells, or the mammal as a whole.

In one example, the pharmaceutically effective amount of the compound of the invention administered parenterally per dose will be in the range of about 0.001 to 1,000 (e.g., 0.01-100) mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 1 to about 1,000 (e.g., 25-100) mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 1 to about 1,000 (e.g., 25 mg, 50 mg, 100 mg, 250 mg, or 500 mg) of the compound of the invention compounded with about 10 to 1,000 (e.g., 90-300) mg anhydrous lactose, about 1 to 100 (e.g., 5-40) mg sodium croscarmellose, about 1 to 100 (e.g., 5-30 mg) polyvinylpyrrolidone (PVP) K30, and about 0.1 to 100 (e.g., 1-10 mg) magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 1 to 1,000 (e.g., 5-400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a PCSK9 inhibitor described herein, or a pharmaceutically acceptable salt thereof. In a further embodiment includes a pharmaceutical composition comprising a PCSK9 inhibitor described herein, or a pharmaceutically acceptable salt thereof, together with a pharmaceutically acceptable carrier or excipient.

Another embodiment includes a pharmaceutical composition comprising a PCSK9 inhibitor described herein for use in a method of treatment of the human or animal body by therapy. In certain embodiments, the invention provides a pharmaceutical composition comprising a PCSK9 inhibitor described herein, for use in a method of inhibiting the binding of PCSK9 to LDLR. In certain embodiments, the invention provides a pharmaceutical composition comprising a PCSK9 inhibitor described herein, for use in a method of increasing the availability of LDLR. In certain embodiments, the invention provides a pharmaceutical composition comprising a PCSK9 inhibitor described herein, for use in a method of reducing an LDL-C level. In certain embodiments, the invention provides a pharmaceutical composition comprising a PCSK9 inhibitor described herein, for use in a method of reducing serum LDL-C level. In certain embodiments, the invention provides a pharmaceutical composition comprising a PCSK9 inhibitor described herein, for use in a method of treatment of a cholesterol related disorder. In certain embodiments, the invention provides a pharmaceutical composition comprising a PCSK9 inhibitor described herein, for use in a method of treatment of a disorder associated with an abnormal level of LDL-C. In certain embodiments, the invention provides a pharmaceutical composition comprising a PCSK9 inhibitor described herein, for use in a method of treatment of a condition associated with an elevated level of LDL-C. In certain embodiments, the invention provides a pharmaceutical composition comprising a PCSK9 inhibitor described herein, for use in a method of treatment of dyslipidemia. In certain embodiments, the invention provides a pharmaceutical composition comprising a PCSK9 inhibitor described herein, for use in a method of treatment of hypercholesterolemia.

Indications and Methods of Treatment

The compounds of the invention are PCSK9 inhibitors that bind to PCSK9. In some embodiments the PCSK9 inhibitors decrease the affinity of the PCSK9 LDLR binding site for LDLRs such that internalization of LDL by, e.g., hepatocytes is increased. Accordingly, in some embodiments, the compounds, compositions, and methods of the invention are useful for reducing levels of circulating LDL-C, and for treating diseases and disorders associated with high levels of circulating LDL-C, e.g., hypercholesterolemia and cardiovascular disease.

Any of the PCSK9 inhibitors provided herein may be used in therapeutic methods.

In one aspect, a PCSK9 inhibitor for use as a medicament is provided. In another aspect, a PCSK9 inhibitor for use in treating conditions associated with a cholesterol related disorder is provided. In certain embodiments, a PCSK9 inhibitor for use in treating conditions associated with elevated level of LDL-C is provided. In certain embodiments, a PCSK9 inhibitor for use in a method of treatment is provided. In certain embodiments, the invention provides a PCSK9 inhibitor for use in a method of treating an individual having conditions associated with elevated level of LDL-C comprising administering to the individual an effective amount of the PCSK9 inhibitor. In certain embodiments, the methods and uses described herein further comprise administering to the individual an effective amount of at least one additional therapeutic agent, e.g., a statin. In certain embodiments, the invention provides a PCSK9 inhibitor for use in reducing LDL-C level in a subject. In further embodiments, the invention provides a PCSK9 inhibitor for use in lowering serum LDL-C level in a subject. In certain embodiments, the invention provides a PCSK9 inhibitor for use in increasing availability of LDLR in a subject. In certain embodiments, the invention provides a PCSK9 inhibitor for use in inhibiting binding of PCSK9 to LDLR in a subject. In certain embodiments, the invention provides a PCSK9 inhibitor for use in a method of reducing LDL-C level in an individual comprising administering to the individual an effective amount of the PCSK9 inhibitor to reduce the LDL-C level. In certain embodiments, the invention provides a PCSK9 inhibitor for use in a method of lowering serum LDL-C level in an individual comprising administering to the individual an effective amount of the PCSK9 inhibitor to lower the serum LDL-C level. In certain embodiments, the invention provides a PCSK9 inhibitor for use in a method of increasing availability of LDLR in an individual comprising administering to the individual an effective amount of the PCSK9 inhibitor to increase availability of LDLR. In certain embodiments, the invention provides a PCSK9 inhibitor for use in a method of inhibiting binding of PCSK9 to LDLR in an individual comprising administering to the individual an effective amount of the PCSK9 inhibitor to inhibit the binding of PCSK9 to LDLR.

An "individual" or "subject" according to any of the embodiments described herein is preferably a human.

In a further aspect, the invention provides for the use of a PCSK9 inhibitor in the manufacture or preparation of a medicament. In one embodiment, the medicament is for treatment of a cholesterol related disorder. In certain embodiments, the cholesterol related disorder is hypercholesterolemia. In another embodiment, the medicament is for use in a method of treating hypercholesterolemia comprising administering to an individual having hypercholesterolemia an effective amount of the medicament.

In certain embodiments, the invention provides a pharmaceutical composition comprising a PCSK9 inhibitor described herein and a pharmaceutically acceptable carrier. In certain embodiments, the invention provides a method for modulating the activity of PCSK9 comprising contacting PCSK9 with an effective amount of a PCSK9 inhibitor described herein. In certain embodiments, the invention provides a method for inhibiting the binding of PCSK9 to LDLR in an individual in need thereof, comprising administering to the individual a therapeutically effective amount of a PCSK9 inhibitor described herein or a pharmaceutical composition thereof. In certain embodiments, the invention provides a method for increasing the availability of LDLR in an individual in need thereof, comprising administering to the individual a therapeutically effective amount of a PCSK9 inhibitor described herein or a pharmaceutical composition thereof. In certain embodiments, the invention provides a method for reducing an LDL-C level in an individual in need thereof, comprising administering to the individual a therapeutically effective amount of a PCSK9 inhibitor described herein or a pharmaceutical composition thereof. In certain embodiments, the invention provides a method for reducing serum LDL-C level in an individual in need thereof, comprising administering to the individual a therapeutically effective amount of a PCSK9 inhibitor described herein or a pharmaceutical composition thereof. In certain embodiments, the invention provides a method for the treatment of a cholesterol related disorder in an individual in need thereof, comprising administering to the individual a therapeutically effective amount of a PCSK9 inhibitor described herein or a pharmaceutical composition thereof. In certain embodiments, the invention provides a method for the treatment of a disorder associated with an abnormal level of LDL-C in an individual in need thereof, comprising administering to the individual a therapeutically effective amount of a PCSK9 inhibitor described herein or a pharmaceutical composition thereof. In certain embodiments, the invention provides a method for the treatment of a condition associated with an elevated level of LDL-C in an individual in need thereof, comprising administering to the individual a therapeutically effective amount of a PCSK9 inhibitor described herein or a pharmaceutical composition thereof. In certain embodiments, the invention provides a method for the treatment of dyslipidemia in an individual in need thereof, comprising administering to the individual a therapeutically effective amount of a PCSK9 inhibitor described herein or a pharmaceutical composition thereof. In certain embodiments, the invention provides a method for the treatment of hypercholesterolemia in an individual in need thereof, comprising administering to the individual a therapeutically effective amount of a PCSK9 inhibitor described herein or a pharmaceutical composition thereof. In certain embodiments, the invention provides a PCSK9 inhibitor described herein, for use in a method of treatment of the human or animal body by therapy. In certain embodiments, the invention provides a PCSK9 inhibitor described herein, for use in a method of modulating the activity of PCSK9. In certain embodiments, the invention provides a PCSK9 inhibitor described herein, for use in a method of inhibiting the binding of PCSK9 to LDLR. In certain embodiments, the invention provides a PCSK9 inhibitor described herein, for use in a method of increasing the availability of LDLR. In certain embodiments, the invention provides a PCSK9 inhibitor described herein, for use in a method of reducing an LDL-C level. In certain embodiments, the invention provides a PCSK9 inhibitor described herein, for use in a method of reducing serum LDL-C level. In certain embodiments, the invention provides a PCSK9 inhibitor described herein, for use in a method of treatment of a cholesterol related disorder. In certain embodiments, the invention provides a PCSK9 inhibitor described herein, for use in a method of treatment of a disorder associated with an abnormal level of LDL-C. In certain embodiments, the invention provides a PCSK9 inhibitor described herein, for use in a method of treatment of a condition associated with an elevated level of LDL-C. In certain embodiments, the invention provides a PCSK9 inhibitor described herein, for use in a method of treatment of dyslipidemia. In certain embodiments, the invention provides a PCSK9 inhibitor described herein, for use in a method of treatment of hypercholesterolemia. In certain embodiments, the invention provides a use of a PCSK9 inhibitor described herein for the manufacture of a medicament for modulating the activity of PCSK9. In certain embodiments, the invention provides a use of a PCSK9 inhibitor described herein for the manufacture of a medicament for inhibiting the binding of PCSK9 to LDLR. In certain embodiments, the invention provides a use of a PCSK9 inhibitor described herein for the manufacture of a medicament for increasing the availability of LDLR. In certain embodiments, the invention provides a use of a PCSK9 inhibitor described herein for the manufacture of a medicament for reducing an LDL-C level. In certain embodiments, the invention provides a use of a PCSK9 inhibitor described herein for the manufacture of a medicament for reducing serum LDL-C level. In certain embodiments, the invention provides a use of a PCSK9 inhibitor described herein for the manufacture of a medicament for the treatment of a cholesterol related disorder. In certain embodiments, the invention provides a use of a PCSK9 inhibitor described herein for the manufacture of a medicament for the treatment of a disorder associated with an abnormal level of LDL-C. In certain embodiments, the invention provides a use of a PCSK9 inhibitor described herein for the manufacture of a medicament for the treatment of a condition associated with an elevated level of LDL-C. In certain embodiments, the invention provides a use of a PCSK9 inhibitor described herein for the manufacture of a medicament for the treatment of dyslipidemia. In certain embodiments, the invention provides a use of a PCSK9 inhibitor described herein for the manufacture of a medicament for the treatment of hypercholesterolemia.

In certain embodiments, the disorder treated is any disease or condition which is improved, ameliorated, inhibited or prevented by removal, inhibition or reduction of PCSK9 activity. In certain embodiments, diseases or disorders that are generally addressable (either treatable or preventable) through the use of statins can also be treated. In certain embodiments, disorders or disease that can benefit from the prevention of cholesterol synthesis or increased LDLR expression can also be treated by PCSK9 inhibitors of the present invention. In certain embodiments, individuals treatable by the PCSK9 inhibitors and therapeutic methods of the invention include individuals indicated for LDL apheresis, individuals with PCSK9-activating mutations (gain of function mutations, "GOF"), individuals with heterozygous Familial Hypercholesterolemia (heFH), individuals with primary hypercholesterolemia who are statin intolerant or statin uncontrolled, and individuals at risk for developing hypercholesterolemia who may be preventably treated. Other indications include dyslipidemia associated with secondary causes such as type 2 diabetes mellitus, cholestatic liver diseases (primary biliary cirrhosis), nephrotic syndrome, hypothyroidism, obesity, and the prevention and treatment of atherosclerosis and cardiovascular diseases. In certain embodiments, the individuals treatable by the PCSK9 inhibitors and therapeutic methods described herein include individuals with LDL-C levels of 90-250 mg/dL and with coronary heart disease (CHD) or a CHD risk equivalent.

In certain embodiments, the methods described herein comprise administering a PCSK9 inhibitor to an individual suffering from coronary heart disease. In certain embodiments, an individual with coronary heart disease has a history of documented myocardial infarction. In certain embodiments, an individual with coronary heart disease refers to an individual who has had a prior coronary revascularization procedure (e.g., percutaneous coronary intervention or coronary artery bypass graft). In certain embodiments, an individual with coronary heart disease refers to an individual having at least one coronary atherosclerotic lesion with 50% diameter stenosis (e.g., as determined by coronary angiography including invasive coronary angiography or cardiac computed tomography coronary angiography).

In certain embodiments, the methods described herein comprise administering a PCSK9 inhibitor to an individual having at least one CHD risk equivalent. In certain embodiments, an individual with a CHD risk equivalent is an individual having one or more forms of clinical atherosclerotic disease, such as, for example, peripheral arterial disease (e.g., ankle/brachial blood pressure index of <0.85, prior percutaneous or surgical peripheral arterial revascularization procedure, prior non-traumatic amputation of a lower extremity due to peripheral artery disease, or ≥50% diameter stenosis on prior vascular imaging), carotid artery disease (e.g., carotid atherosclerotic lesion with ≥50% diameter stenosis or prior cutaneous or surgical carotid revascularization procedure), prior ischemic stroke, or abdominal aortic aneurysm. In certain embodiments, an individual with a CHD risk equivalent is an individual having type II diabetes. In certain embodiments, an individual with a CHD risk equivalent is an individual having type I diabetes coupled with organ damage (e.g., retinopathy, neuropathy, or nephropathy including microalbuminuria). In certain embodiments, an individual with a CHD risk equivalent is an individual having moderate to severe chronic kidney disease.

In certain embodiments, the methods described herein comprise administering a PCSK9 inhibitor to an individual having one or more of the following risk factors: age (≥45 years for men or ≥55 years for women), smoking (within 1 month), hypertension (systolic blood pressure ≥140 mmHg, diastolic blood pressure ≥90 mmHg, or taking an antihypertensive medication), low HDL cholesterol (<40 mg/dL), or a family history of premature CHD.

In certain embodiments, the methods and uses described herein further comprise administering to the individual an effective amount of at least one additional therapeutic agent, e.g., a statin. In certain embodiments, the additional therapeutic agent is for preventing and/or treating atherosclerosis and/or cardiovascular diseases. In certain embodiment, the additional therapeutic agent is for use in a method of reducing the risk of recurrent cardiovascular events. In certain embodiments, the additional therapeutic agent is for elevating the level of HDL-cholesterol in a subject.

In a further aspect, the invention provides pharmaceutical formulations comprising any of the PCSK9 inhibitors provided herein, e.g., for use in any of the above therapeutic methods. In one embodiment, a pharmaceutical formulation comprises any of the PCSK9 inhibitors provided herein and a pharmaceutically acceptable carrier. In another embodiment, a pharmaceutical formulation comprises any of the PCSK9 inhibitors provided herein and at least one additional therapeutic agent, e.g., a statin.

PCSK9 inhibitors of the invention can be used either alone or in combination with other agents in a therapy. For instance, a PCSK9 inhibitor of the invention may be co-administered with at least one additional therapeutic agent. In certain embodiments, such additional therapeutic agent elevates the level of LDLR. In certain embodiments, an additional therapeutic agent is a LDL-C lowering drug such as a statin, e.g., atorvastatin, fluvastatin, lovastatin, mevastatin, pitavastatin, pravastatin, rosuvastatin, simvastatin, or any combination thereof, e.g., VYTORIN®, ADVICOR® or SIMCOR®. In certain embodiments, an additional therapeutic agent is a HDL-cholesterol raising drug.

Such combination therapies noted above encompass combined administration (where two or more therapeutic agents are included in the same or separate formulations), and separate administration, in which case, administration of the PCSK9 inhibitor of the invention can occur prior to, simultaneously, and/or following, administration of the additional therapeutic agent and/or adjuvant.

In certain embodiments, the LDL-C level in the individual treated by the methods described herein is reduced by at least about 45%, at least about 50%, at least about 55%, or at least about 60% from baseline. In some embodiments, the LDL-C level in the individual treated by the methods described herein is reduced by at least about 45%, at least about 50%, at least about 55%, or at least about 60% from baseline, and maintains at the reduced level for at least two weeks, at least one month, at least two months, or three months after last dosing. In some embodiments, the LDL-C level in the individual treated by the methods described herein is reduced by at least about 45%, at least about 50%, at least about 55%, or at least about 60% from baseline within about 1 week, about 10 days, or about 2 weeks of the initial dose. In some embodiments, the LDL-C level in the individual treated by the methods described herein is reduced by at least about 45%, at least about 50%, at least about 55%, or at least about 60% from baseline within about 1 week, about 10 days, or about 2 weeks of the initial dose, and maintains at the reduced level for at least two weeks, at least one month, at least two months, or three months after last dosing. In certain embodiments, the LDL-C level in the individual treated by the methods described herein is reduced by at least about 45% and maintains at the reduced level for at least about six weeks, at least about 7 weeks or at least about 1.5 months. In certain embodiments, the LDL-C level in the individual treated by the methods described herein is reduced by at least about 45% within about 1 week from the initial dose and maintains at the reduced level for at least about six weeks, at least about 7 weeks or at least about 1.5 months. In certain embodiments, the LDL-C level in the individual treated by the methods described herein is reduced by at least about 50% and maintains at the reduced level for at least about four weeks or at least about 1 month. In certain embodiments, the LDL-C level in the individual treated by the methods described herein is reduced by at least about 50% within about 10 days from the initial dose and maintains at the reduced level for at least about four weeks or at least about 1 month. In certain embodiments, the LDL-C level in the individual treated by the methods described herein is reduced by at least about 50% and maintains at the reduced level for at least about eight weeks or at least about 2 months. In certain embodiments, the LDL-C level in the individual treated by the methods described herein is reduced by at least about 50% within about 10 days from the initial dose and maintains at the reduced level for at least about eight weeks or at least about 2 months. In certain embodiments, the LDL-C level in the individual treated by the methods described herein is reduced by at least about 55% and maintains at the reduced level for at least about two weeks. In certain embodiments, the LDL-C level in the individual treated by the methods described herein is reduced by at least about 55% within about 2 weeks of the initial dose and maintains at the reduced level for at least about two weeks.

In certain embodiments, the LDL-C level in the individual treated by the methods described herein is reduced by at least about 60 mg/dL, at least about 70 mg/dL, at least about 75 mg/dL, at least about 80 mg/dL, or at least about 90 mg/dL from baseline. In some embodiments, the LDL-C level in the individual treated by the methods described herein is reduced by at least about 60 mg/dL, at least about 70 mg/dL, at least about 75 mg/dL, at least about 80 mg/dL, or at least about 90 mg/dL from baseline, and maintains at the reduced level for at least two weeks, at least one month, at least two months, or three months after last dosing. In some embodiments, the LDL-C level in the individual treated by the methods described herein is reduced by at least about 60 mg/dL, at least about 70 mg/dL, at least about 75 mg/dL, at least about 80 mg/dL, or at least about 90 mg/dL from baseline within about 1 week, about 10 days, or about 2 weeks of the initial dose. In some embodiments, the LDL-C level in the individual treated by the methods described herein is reduced by at least about 60 mg/dL, at least about 70 mg/dL, at least about 75 mg/dL, at least about 80 mg/dL, or at least about 90 mg/dL from baseline within about 1 week, about 10 days, or about 2 weeks of the initial dose, and maintains at the reduced level for at least two weeks, at least one month, at least two months, or three months after last dosing. In certain embodiments, the LDL-C level in the individual treated by the methods described herein is reduced by at least about 60 mg/dL or 70 mg/dL and maintains at the reduced level for at least about six weeks, at least about 7 weeks or at least about 1.5 months. In certain embodiments, the LDL-C level in the individual treated by the methods described herein is reduced by at least about 60 mg/dL or 70 mg/dL within about 1 week from the initial dose and maintains at the reduced level for at least about six weeks, at least about 7 weeks or at least about 1.5 months. In certain embodiments, the LDL-C level in the individual treated by the methods described herein is reduced by at least about 80 mg/dL and maintains at the reduced level for at least about four weeks or at least about 1 month. In certain embodiments, the LDL-C level in the individual treated by the methods described herein is reduced by at least about 80 mg/dL within about 10 days from the initial dose and maintains at the reduced level for at least about four weeks or at least about 1 month. In certain embodiments, the LDL-C level in the individual treated by the methods described herein is reduced by at least about 90 mg/dL and maintains at the reduced level for at least about two weeks. In certain embodiments, the LDL-C level in the individual treated by the methods described herein is reduced by at least about 90 mg/dL within about 2 weeks of the initial dose and maintains at the reduced level for at least about two weeks.

In certain embodiments, the reduction in LDL-C levels is maintained within a certain range between dosings. In certain embodiments, upon administration of a dose of a PCSK9 inhibitor, LDL-C levels are reduced to a nadir of at least about 45%, at least about 50%, at least about 55%, or at least about 60% from baseline and do not increase beyond about 40%, 45%, 50%, 55%, or 60% below baseline before the next dosing of the PCSK9 inhibitor. In certain embodiments, upon administration of a dose of a PCSK9 inhibitor, LDL-C levels are reduced to a nadir of at least about 45% from baseline and do not increase beyond about 40% or 45% below baseline before the next dosing of the PCSK9 inhibitor. In certain embodiments, upon administration of a dose of a PCSK9 inhibitor, LDL-C levels are reduced to a nadir of at least about 50% from baseline and do not increase beyond about 40%, 45%, or 50% below baseline before the next dosing of the PCSK9 inhibitor. In certain embodiments, upon administration of a dose of a PCSK9 inhibitor, LDL-C levels are reduced to a nadir of at least about 55% from baseline and do not increase beyond about 40%, 45%, 50%, or 55% below baseline before the next dosing of the PCSK9 inhibitor. In certain embodiments, upon administration of a dose of a PCSK9 inhibitor, LDL-C levels are reduced to a nadir of at least about 60% from baseline and do not increase beyond about 40%, 45%, 50%, 55%, or 60% below baseline before the next dosing of the PCSK9 inhibitor.

In certain embodiments, the reduction in LDL-C levels is maintained within a certain range between dosings. In certain embodiments, upon administration of a dose of a PCSK9 inhibitor, LDL-C levels are reduced to a nadir of at least about 60 mg/dL, at least about 70 mg/dL, at least about 75 mg/dL, at least about 80 mg/dL, or at least about 90 mg/dL below baseline and do not increase beyond about 55 mg/dL, 60 mg/dL, 65 mg/dL, 70 mg/dL, 75 mg/dL, 80 mg/dL or 90 mg/dL below baseline before the next dosing of the PCSK9 inhibitor. In certain embodiments, upon administration of a dose of a PCSK9 inhibitor, LDL-C levels are reduced to a nadir of at least about 60 mg/dL below baseline and do not increase beyond about 55 mg/dL or 60 mg/dL below baseline before the next dosing of the PCSK9 inhibitor. In certain embodiments, upon administration of a dose of a PCSK9 inhibitor, LDL-C levels are reduced to a nadir of at least about 70 mg/dL below baseline and do not increase beyond about 55 mg/dL, 60 mg/dL, 65 mg/dL, or 70 mg/dL below baseline before the next dosing of the PCSK9 inhibitor. In certain embodiments, upon administration of a dose of a PCSK9 inhibitor, LDL-C levels are reduced to a nadir of at least about 75 mg/dL below baseline and do not increase beyond about 55 mg/dL, 60 mg/dL, 65 mg/dL, 70 mg/dL, or 75 mg/dL below baseline before the next dosing of the PCSK9 inhibitor. In certain embodiments, upon administration of a dose of a PCSK9 inhibitor, LDL-C levels are reduced to a nadir of at least about 80 mg/dL below baseline and do not increase beyond about 55 mg/dL, 60 mg/dL, 65 mg/dL, 70 mg/dL, 75 mg/dL, or 80 mg/dL below baseline before the next dosing of the PCSK9 inhibitor. In certain embodiments, upon administration of a dose of a PCSK9 inhibitor, LDL-C levels are reduced to a nadir of at least about 90 mg/dL below baseline and do not increase beyond about 55 mg/dL, 60 mg/dL, 65 mg/dL, 70 mg/dL, 75 mg/dL, 80 mg/dL or 90 mg/dL below baseline before the next dosing of the PCSK9 inhibitor.

Articles of Manufacture and Kits

In another aspect of the invention, an article of manufacture or kit containing materials useful for the treatment, prevention and/or diagnosis of the disorders described above is provided. In certain embodiments, the article of manufacture or kit comprises a container containing one or more of the PCSK9 inhibitors or the compositions described herein. In certain embodiments, the article of manufacture or kit comprises a container and a label or package insert on or associated with the container. The containers may be formed from a variety of materials such as glass or plastic. The container holds a composition which is by itself or combined with another composition effective for treating, preventing and/or diagnosing the condition. At least one active agent in the composition is a PCSK9 inhibitor of the invention. The label or package insert indicates that the composition is used for treating the condition of choice. Moreover, the article of manufacture or kit may comprise (a) a first container with a composition contained therein, wherein the composition comprises a PCSK9 inhibitor of the invention; and (b) a second container with a composition contained therein, wherein the composition comprises a further therapeutic agent. In certain embodiments, the second container comprises a second therapeutic agent, wherein the second therapeutic agent is a cholesterol-lowering drug of the "statin" class. In certain embodiments, the statin is and/or comprises atorvastatin (e.g., LIPITOR® or Torvast), fluvastatin (e.g., LESCOL), lovastatin (e.g., MEVACOR®, ALTOCOR™, or ALTOPREV®), mevastatin (pitavastatin (e.g., LIVALO® or PITAVA®), pravastatin (e.g., PRAVACHOL®, SELEKTINE®, LIPOSTAT®), rosuvastatin (e.g., CRESTOR®), simvastatin (e.g., ZOCOR®, LIPEX®), or any combination thereof, e.g., VYTORIN®, ADVICOR® or SIMCOR®.

The article of manufacture or kit in this embodiment of the invention may further comprise a package insert indicating that the compositions can be used to treat a particular condition.

EXAMPLES

The invention will be more fully understood by reference to the following examples. They should not, however, be construed as limiting the scope of the invention.

Figure 1:
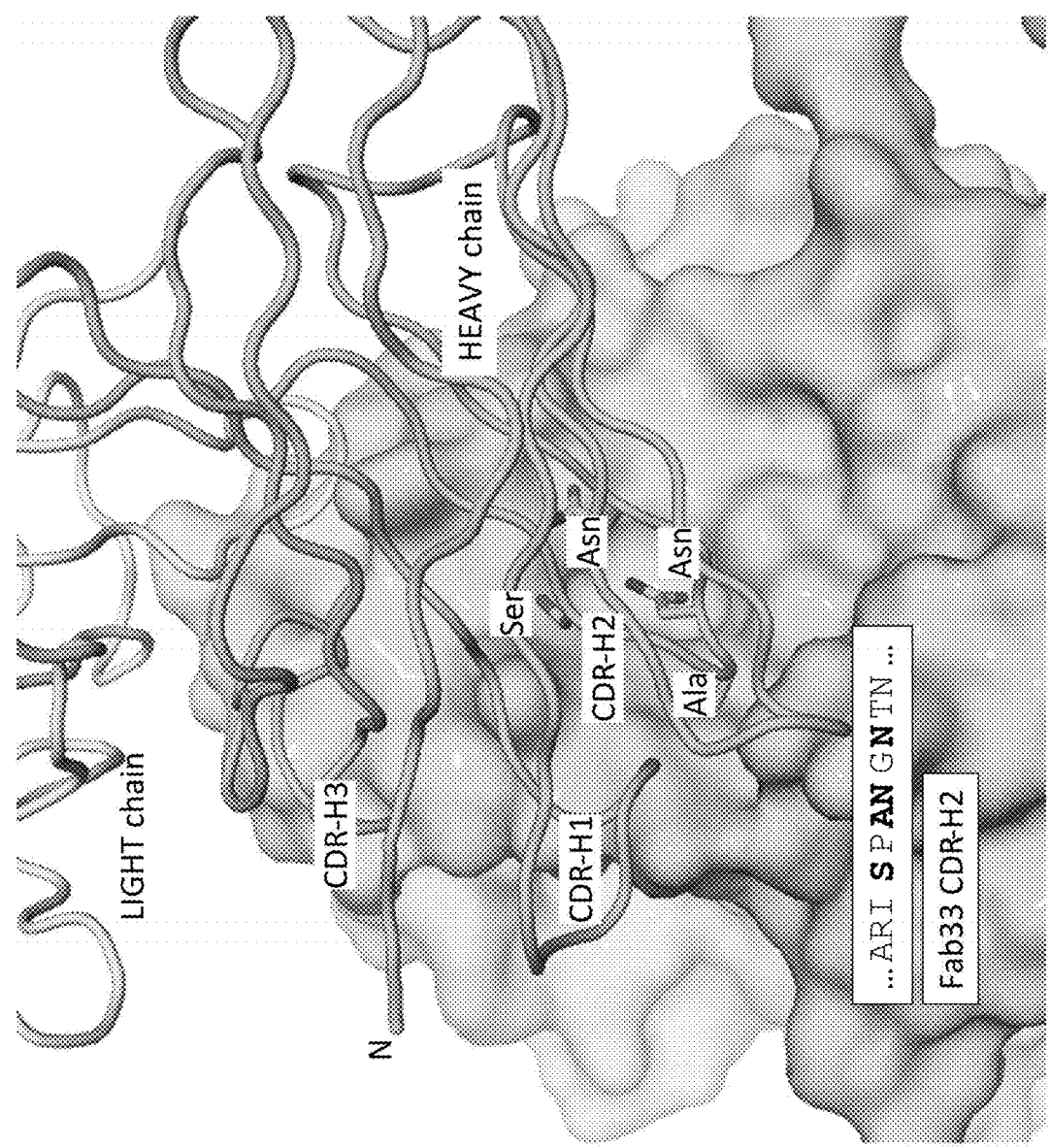
FIG. 1 shows the crystal structure of the Fab33:PCSK9 complex. Figure discloses SEQ ID NO: 305.
Figure 2:
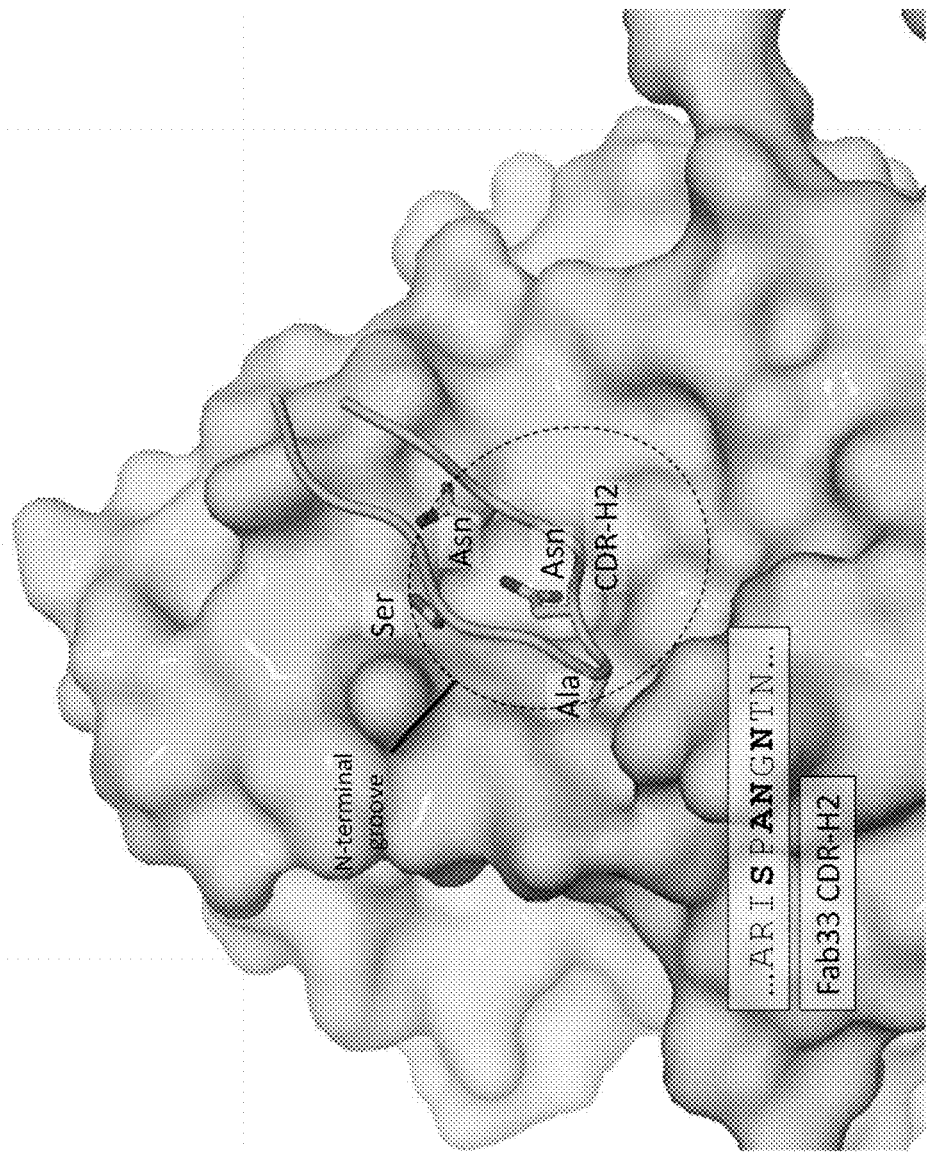
FIG. 2 shows that in the Fab33:PCSK9 complex, the Fab33 CDR-H2 loop projects into the N-terminal groove of PCSK9 indicating that the P' helix of PCSK9 had moved out of the N-terminal groove. Figure discloses SEQ ID NO: 305.
Figure 3:
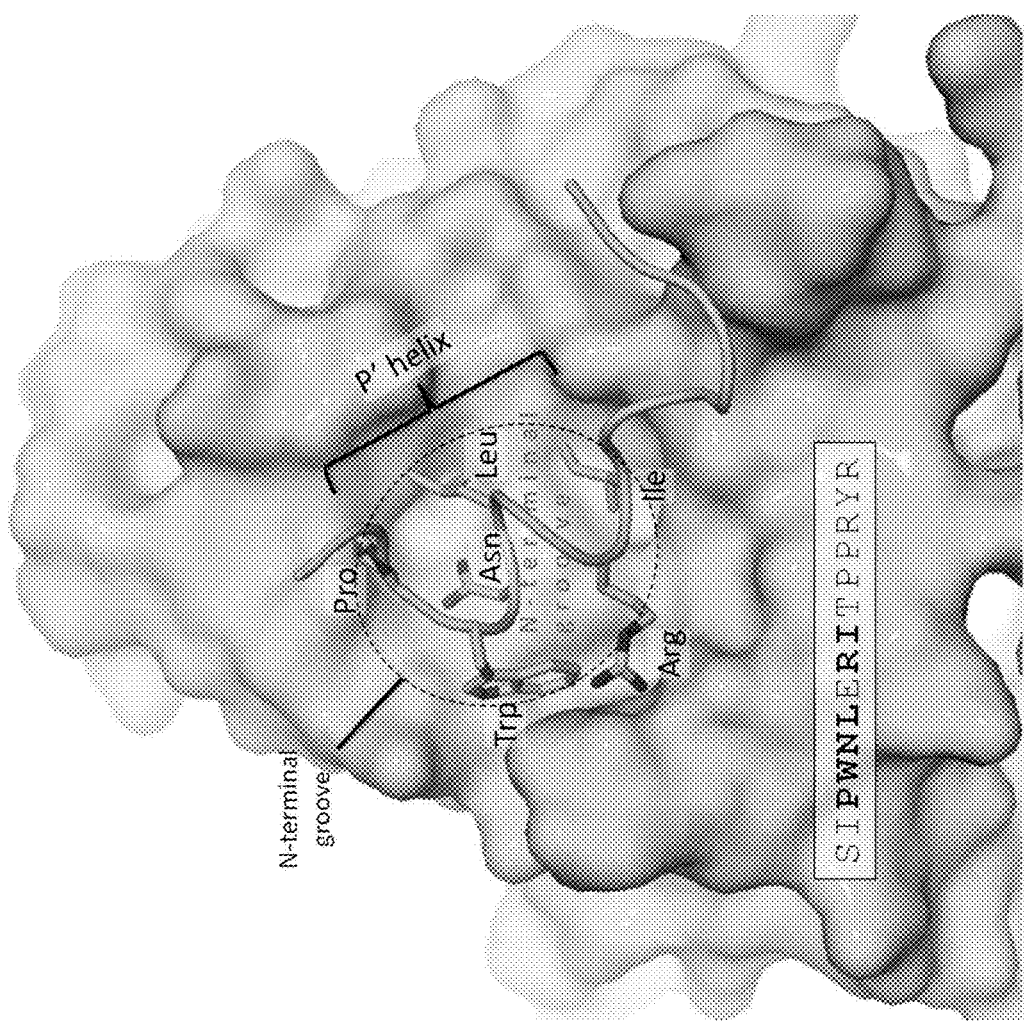
FIG. 3 shows the crystal structure of PCSK9 (Protein Data Bank ID: 2QTW) in which the N-terminal groove harbors the P' helix of PCSK9. Figure discloses SEQ ID NO: 294.

Example 1: Identification of an Accessible Groove (the "N-Terminal Groove") on the PCSK9 Catalytic Domain Adjacent to the LDLR Binding Site Crystal Structure of Fab33:PCSK9 Complex The crystal structure of the Fab33:PCSK9 complex was reported by Wu et al. (U.S. Pat. No. 9,266,961). It shows that the Fab33 binds to the LDLR binding site through its heavy and light chains (FIG. 1). Specifically, one or more amino acid residues from CDR-H1, -H2, -H3, -L1 and -L3 are within 4 Å of an atom of PCSK9. In addition, heavy chain residue Thr73 also is found within 4 Å of PCSK9. The set of PCSK9 amino acid residues within 4 Å of any atom of Fab33 includes residues which are also within 4 Å of the EGFA domain of LDLR (Kwon et al., Proc Natl Acad Sci USA. 2008 Feb. 12; 105(6): 1820-1825). The Fab33 CDR-H2 loop does not interact with the EGFA binding site of PCSK9 (Kwon et al., Proc Natl Acad Sci USA. 2008 Feb. 12; 105(6): 1820-1825) (except for heavy chain residue Arg50), but extends into the N-terminal groove of PCSK9 (FIG. 2), which normally harbors the N-terminal helix of the PCSK9 catalytic domain, the "P' helix" (roughly the residues S153-T162) as shown in FIG. 3. Structures of PCSK9 deposited in the Protein Data Bank (PDB) unanimously show the P' helix being accommodated in the N-terminal groove in the same conformation (e.g. PDB 2P4E, 2PMW, 2QTW, 3BPS, 3GCW, 3GCX, 3H42, 3SQO, 4K8R). In the Fab33:PCSK9 structure no electron density was found for the P' helix. However, there was clear electron density for the Fab33 CDR-H2 loop, which takes up some of the space where the P' helix is normally located. This observation clearly indicated that once the Fab33 is bound to PCSK9, the P' helix cannot possibly bind to the N-terminal groove any longer due to a major steric conflict. It further suggested that the P' helix is not firmly bound to the N-terminal groove, since Fab33 was able to displace the P' helix and bind to PCSK9 with high binding affinity. The antibody 33/PCSK9 disassociation constant ($K_d$) value was 0.4 nM (U.S. Pat. No. 9,266,961). The CDR-H2 loop, which points into the N-terminal groove, did not appear to contribute to the binding energy. The nearest PCSK9 groove residue is H391, 3.8 Å away from CDR-H2 residue N54, a distance that is too great to be considered a hydrogen bond. A 4 Å criterion was applied using the molecular analysis program PYMOL™. PCSK9 residues within 4 Å of any part of Fab33 were determined as an epitope. Based on the analysis, the epitope comprises one or more of the following residues: R194, E195, D238, A239, G240, A341, Q342, E366, D367, I369, S376, T377, C378, F379, and H391 of human PCSK9.

Cleavage of the P' Helix by Contaminating Protease

Figure 4:
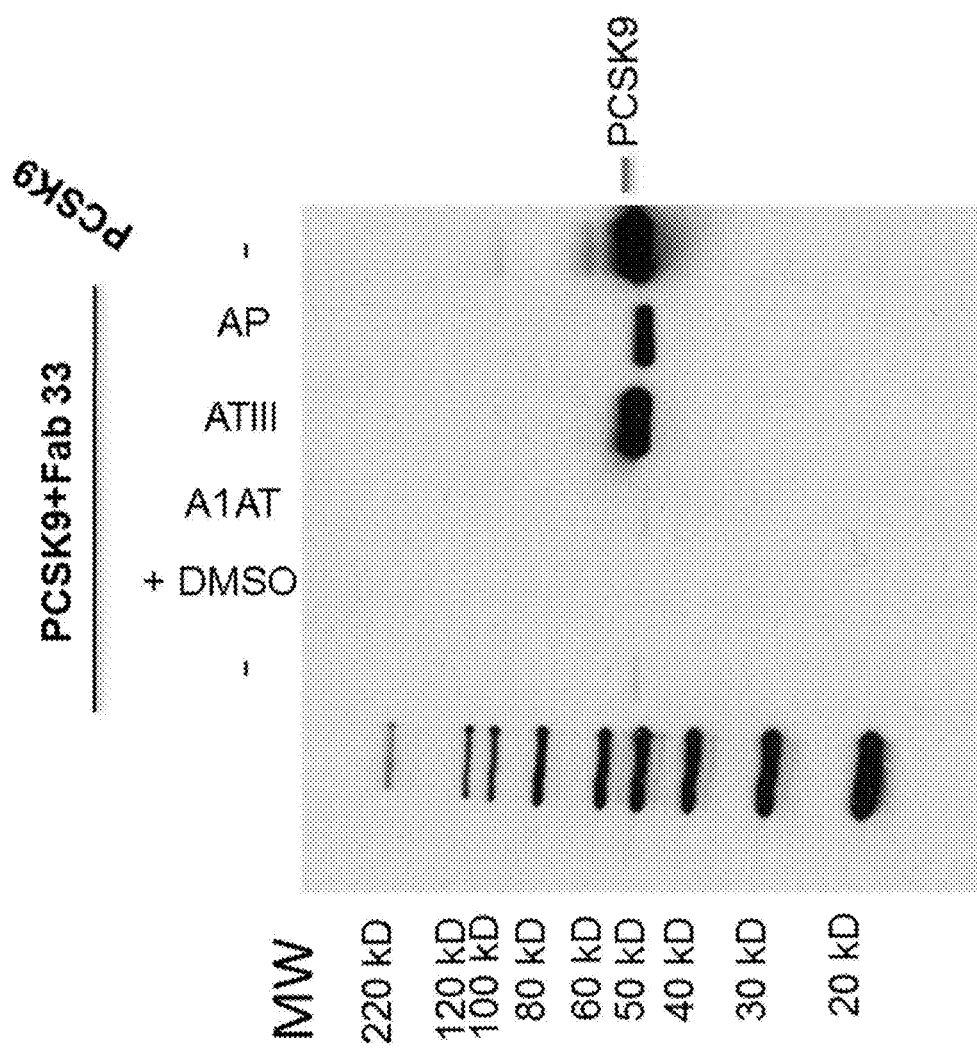
FIG. 4 shows that the serpin antithrombin III (ATIII) and to a lesser degree the Kunitz domain inhibitor Aprotinin (AP) were able to prevent proteolytic cleavage of the P' helix of the Fab33:PCSK9 complex (13.2 mg/mL PCSK9, 19.8 mg/mL Fab33). The serpin alpha1-antitrypsin (A1AT) did not inhibit cleavage. Cleavage was detected by immunoblotting using a polyclonal rabbit antibody raised against the PCSK9 N-terminal peptide (¹⁵³SIPWNLERITPPRYRA¹⁶⁸ (SEQ ID NO: 5)).
Figure 5:
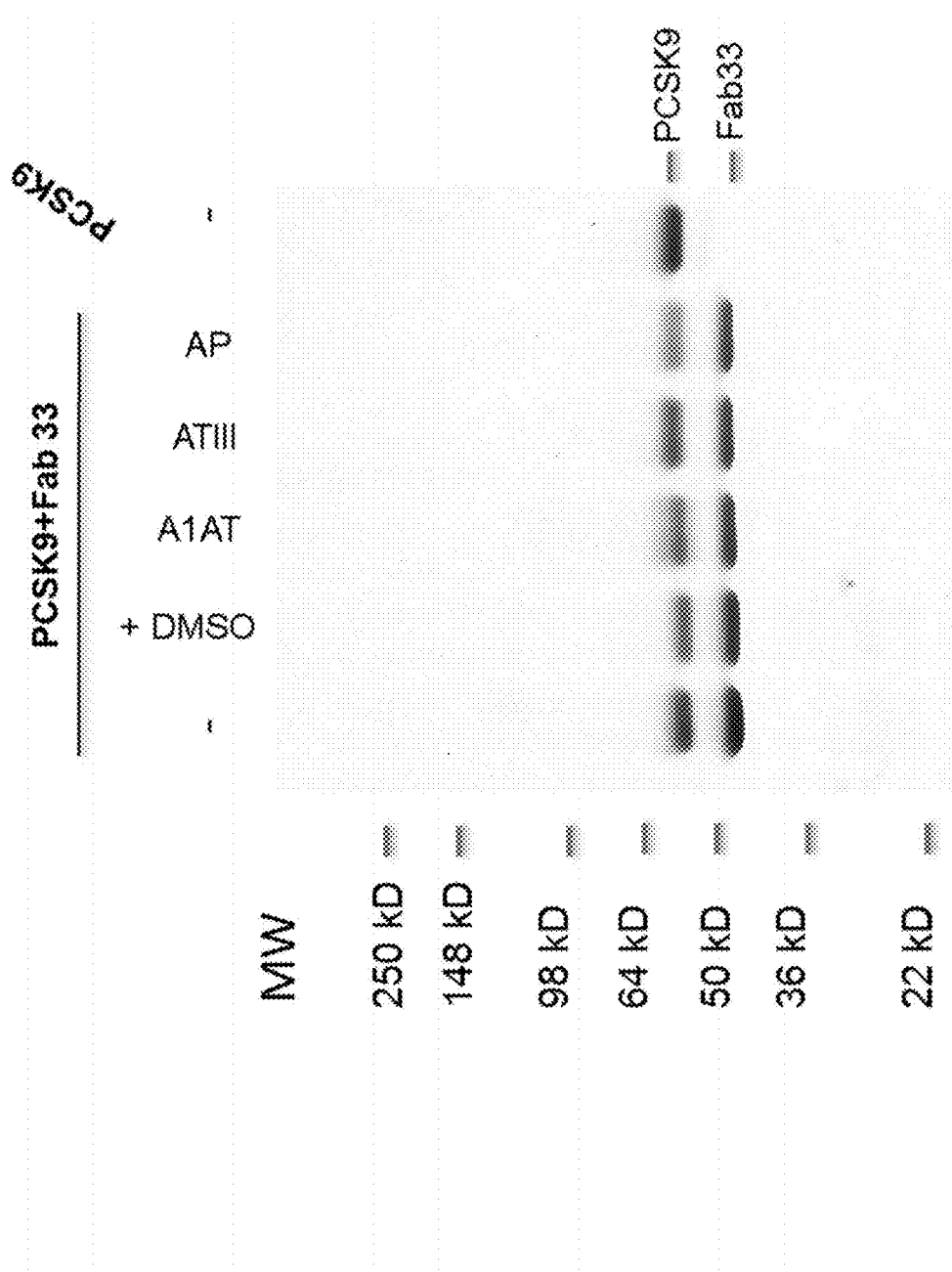
FIG. 5 shows the Coomassie-stained SDS-PAGE corresponding to the immunoblot in FIG. 4. The 2 left lanes are controls without and with DMSO present.

In biochemical assays in which the crystallization conditions were replicated, it was found that a contaminating protease cleaves off the P' helix in the Fab33:PCSK9 complex. This cleavage only occurred at high concentrations of the Fab33:PCSK9 complex over a 48 h incubation period and was dependent on the presence of Fab33, since PCSK9 by itself was not cleaved. The cleavage site was identified as R165-Y166 by N-terminal sequencing, suggesting that the contaminating protease has Arg-specificity, such as members of the trypsin-fold serine protease family. Therefore, serine protease inhibitors were tested under cleavage conditions. To easily determine cleavage, Western blotting was carried out using a polyclonal rabbit antibody that was raised against the synthetic N-terminal peptide [153]SIPWNLERIT-PPRYRA[168] (SEQ ID NO: 5). This antibody only detected the intact N-terminal peptide sequence but not the cleaved forms. It was found that cleavage was prevented by the serpin antithrombin III (Serpin C1) and to a lesser degree by the Kunitz domain inhibitor Aprotinin (FIGS. 4 and 5). The more elastase-specific alpha1-antitrypsin (Serpin A1) did not inhibit cleavage (FIGS. 4 and 5).

Ab33 binds to PCSK9 at concentrations ($K_d$ of 0.4 nM; U.S. Pat. No. 9,266,961), which were much below the concentrations at which cleavage of the P' helix was observed (>14.5 mg/mL Fab33=290 μM in Table 2). Therefore, it was concluded that the binding of Fab33 is not dependent on, or subsequent to, the cleavage of the P' helix. Rather, the results suggested that the cleavage of the P' helix was the result of Fab33 binding and not its prerequisite. The findings further implied that the P' helix was intrinsically labile and could transition between the groove-bound ("in") and the ejected ("out") conformations.

FXIa Cleavage Assays

Figure 6:
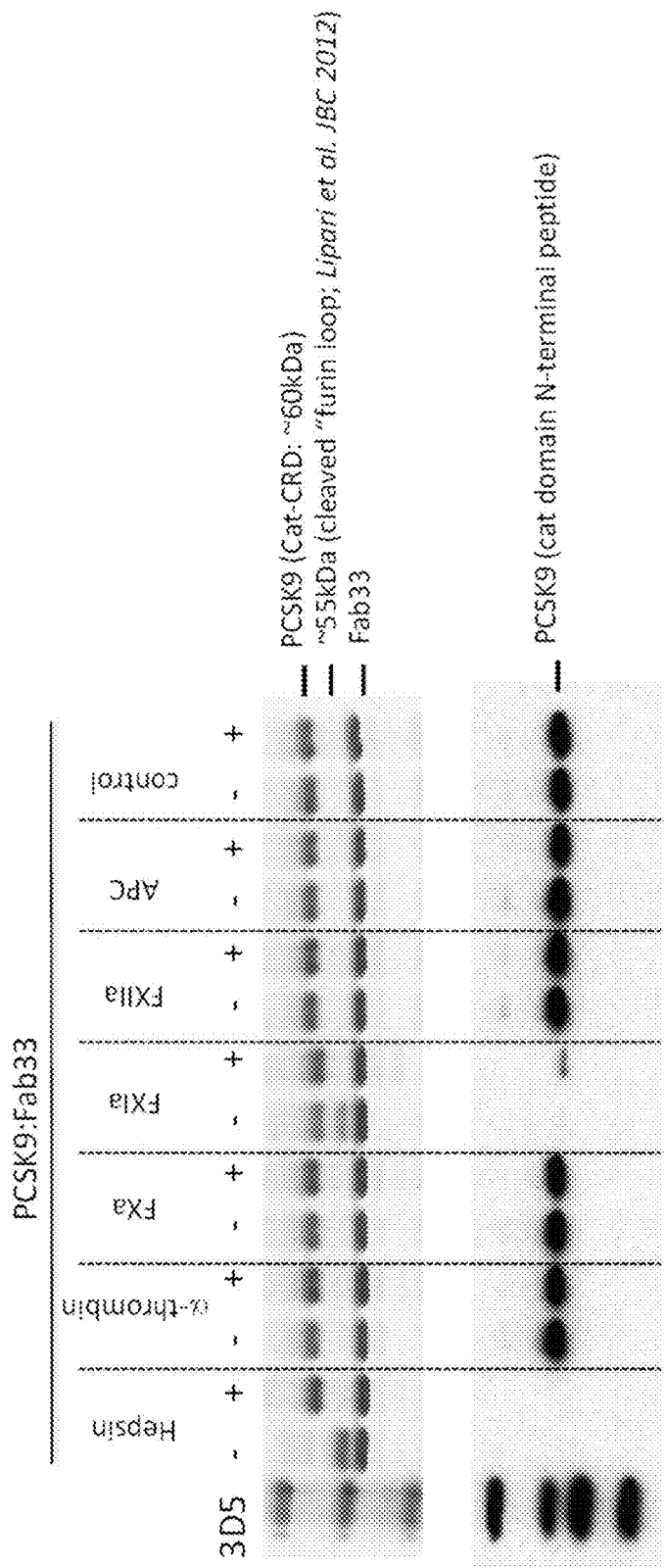
FIG. 6 shows that the serine proteases FXIa and hepsin cleave the P' helix when incubated with the Fab33:PCSK9 complex. The panel of proteases tested included Hepsin, α-thrombin, FXa, FXIa, FXIIa and activated protein C (APC). Only FXIa and hepsin were able to cleave PCSK9 at the P' helix. They also cleaved at the "furin cleavage loop" containing the protease-susceptible residues R215 and R218, as indicated by the appearance of a ~55 kDa band. Addition of the blocking antibody 3D5 (Lipari et al. J Biol Chem. 2012 Dec. 21; 287(52):43482-91) prevented this latter cleavage.

A biochemical assay was set up to provide further evidence for the intrinsic lability of the P' helix. A panel of trypsin-like serine proteases was tested to identify a protease that could cleave off the P' helix similar to what was observed under the crystallization conditions. The proteases were incubated with low concentrations of the Fab33:PCSK9 complex in the presence or absence of antibody 3D5. The 3D5 Ab binds to the "furin cleavage loop" of PCSK9 and prevents cleavage at two Arginine residues, R215 and R218, which are highly susceptible to protease cleavage (Lipari et al. J Biol Chem. 2012 Dec. 21; 287(52): 43482-91). It was found that the proteases hepsin and FXIa cleave the "furin cleavage loop" as shown by the appearance of a ~55 kDa band; this cleavage was prevented by 3D5 (FIG. 6). In addition, in the presence of 3D5, both FXIa and hepsin cleaved at, or close to, the P' helix as shown on the immunoblot (FIG. 6).

Figure 7:
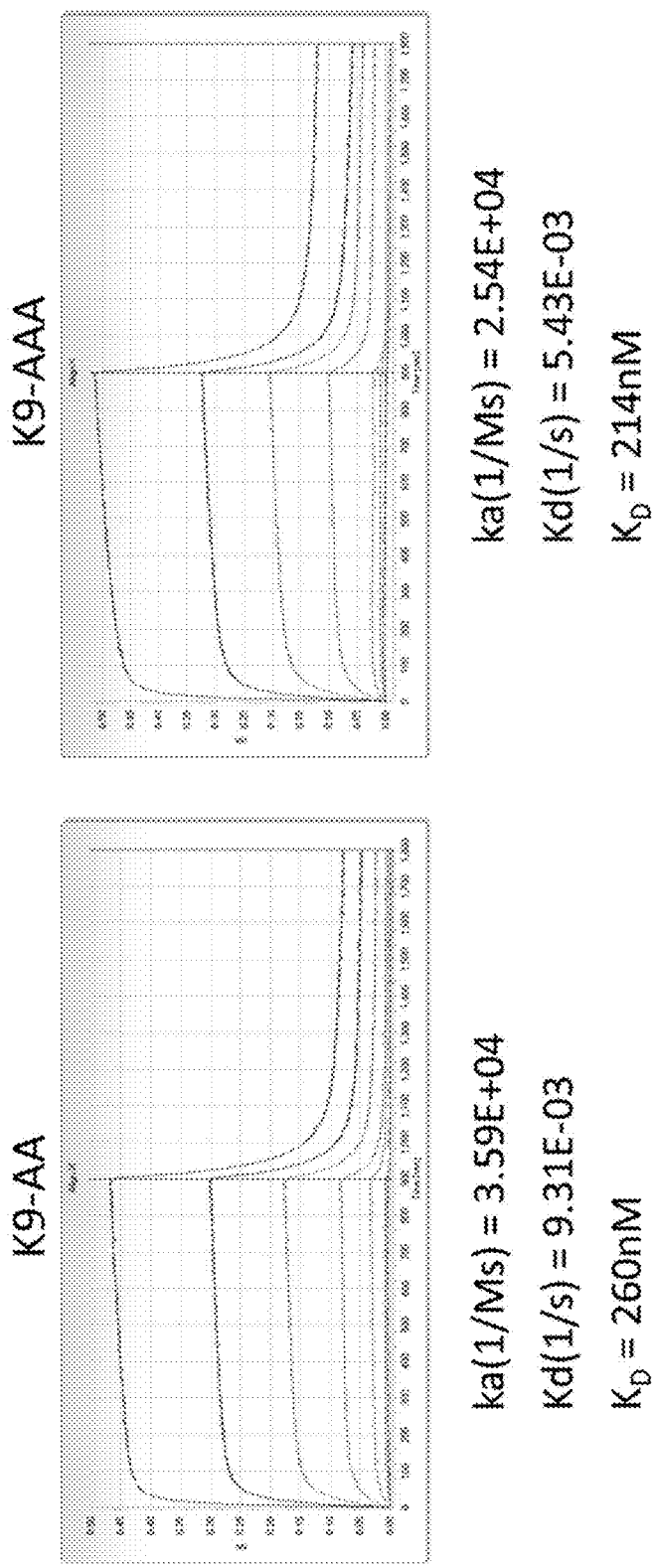
FIG. 7 shows biolayer interferometry experiments to determine the binding affinities of the PCSK9 mutants PCSK9-R215A:R218A (K9-AA) and PCSK9-R167A:R215A:R218A (K9-AAA) to LDLR. The sensorgrams show the association and dissociation phase of the analytes (PCSK9 mutants) to immobilized LDLR ectodomain. The determined $K_d$ values for PCSK9-AA and PCSK9-AAA were 260 nM and 214 nM, respectively.

In further experiments the previously described PCSK9 mutant PCSK9-R215A:R218 Å (=PCSK9-AA) (Lipari et al. J Biol Chem. 2012 Dec. 21; 287(52):43482-91), in which the "furin cleavage loop" residues had been changed to Alanine, was used in order to prevent protease cleavage at the susceptible residues R215 and R218. It was found that FXIa indeed no longer cleaved the "furin cleavage loop" when incubated with the Fab33:PCSK9-AA complex. N-terminal sequencing revealed that FXIa cleaved within the P' helix at R160-I161 and downstream of the P' helix at R167-Ala168. Therefore, to direct the FXIa cleavage specifically to the P' alpha helix residue R160 the triple mutant PCSK9-R167A:R215A:R218 Å (=PCSK9-AAA) was produced. The binding affinities of PCSK9-AAA and PCSK9-AA to the LDLR ectodomain (R & D Systems) were determined by biolayer interferometry as described (Lipari et al. J Biol Chem. 2012 Dec. 21; 287(52):43482-91). PCSK9-AAA bound with a $K_d$ value of 214 nM, similar to the $K_d$ of 260 nM determined for PCSK9-AA (FIG. 7). These values were close to the previously reported $K_d$ values of 130 nM and 170 nM for the wildtype PCSK9 (Lipari et al. J Biol Chem. 2012 Dec. 21; 287(52):43482-91) using the same biolayer interferometry method. Therefore, the introduction of the three mutations did not significantly impair LDLR binding.

Figure 8:
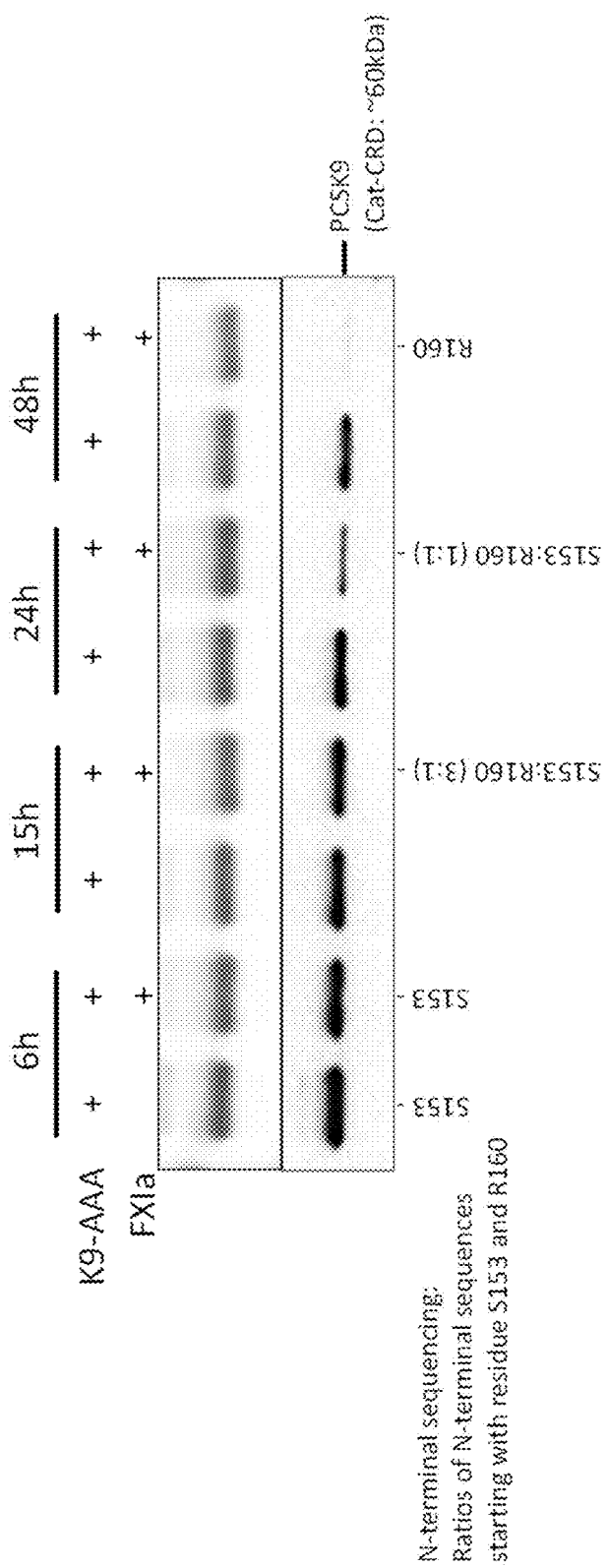
FIG. 8 shows the time-dependent cleavage by FXIa of PCSK9-R167A:R215A:R218A (K9-AAA). K9-AAA was slowly cleaved during the experimental time period, complete cleavage being achieved at 48 h. N-terminal sequencing at each time point confirmed cleavage at the R160-I161 amide bond.

In FXIa assays with PCSK9-AAA, the P' helix was cleaved in a time-dependent manner and complete cleavage was achieved after 48 h (FIG. 8). N-terminal sequencing confirmed that cleavage occurred at R160-I161. Moreover, PCSK9-AAA was not cleaved by FXIa that had been inactivated by treatment with FPR-chloromethyl ketone, indicating that the observed cleavage at R160-I161 with the active FXIa form was specific. The recognition of R160 as the P1 residue (nomenclature according to Schechter and Berger, Biochem Biophys Res Commun. 1968 Sep. 6; 32(5):898-902) was consistent with the known FXIa specificity as a trypsin-fold serine protease. The PCSK9 crystal structures (e.g. PDB 2QTW) show that R160 is in the P' helix and partially buried and, therefore, not accessible to the active site of FXIa. Thus, for FXIa to catalyze R160-I161 cleavage, the P' helix has to move out of the groove and adopt an entirely different conformation. According to the established substrate recognition paradigm of trypsin-fold serine proteases, the substrate P4-P1 residues, i.e. 157NLER160 in case of PCSK9, is presented to the active site in an extended beta-strand conformation, with the P1-P4 residues engaging in beta strand H-bond interactions with the protease S1-S4 subsites (Perona and Craik, Protein Sci. 1995 March; 4(3):337-60). This interaction serves to properly position the scissile bond, i.e. R160-I161 in PCSK9, for catalytic cleavage. This implies that the P' helix, once outside the groove, can adopt an extended non-helical conformation when interacting with the active site of FXIa.

Figure 9:
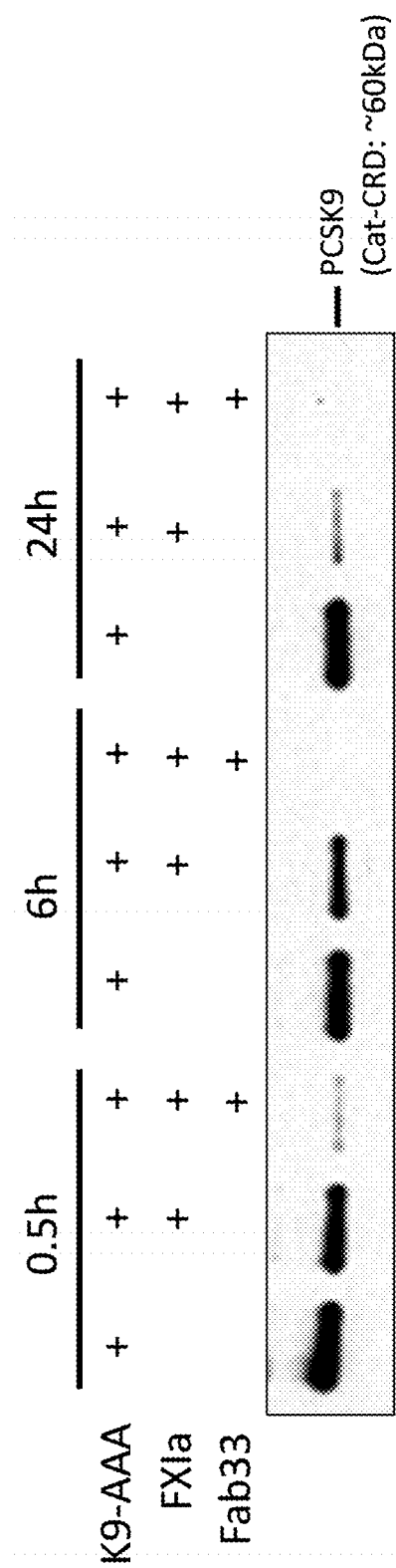
FIG. 9 shows the time-dependent cleavage by FXIa of K9-AAA in complex with Fab33. The presence of Fab33 accelerated the cleavage reaction.
Figure 10:
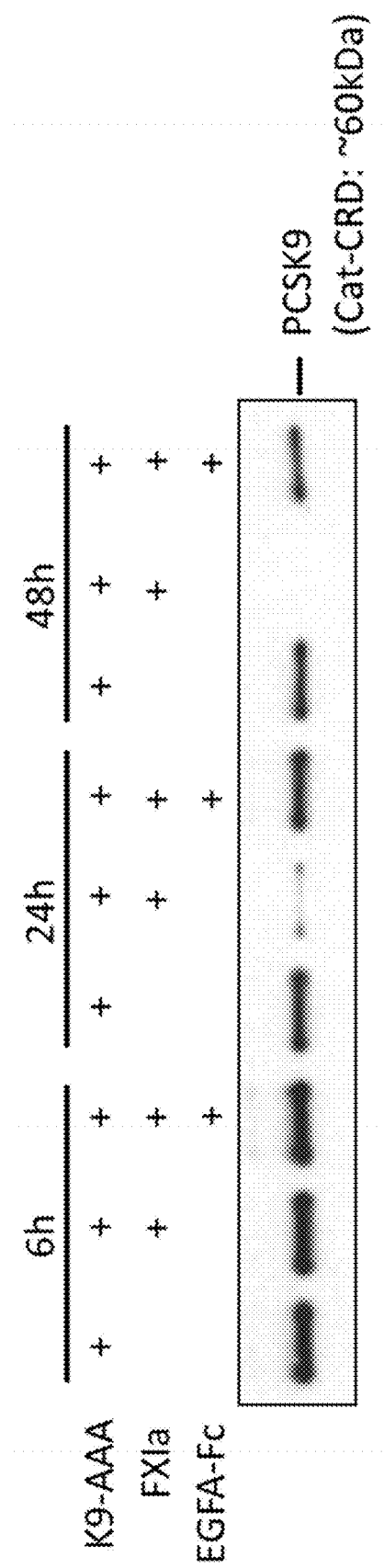
FIG. 10 shows the time-dependent cleavage by FXIa of K9-AAA in complex with EGFA-Fc. Stabilization of the P' helix in the N-terminal groove by EGFA-Fc prevented cleavage.
Figure 11:
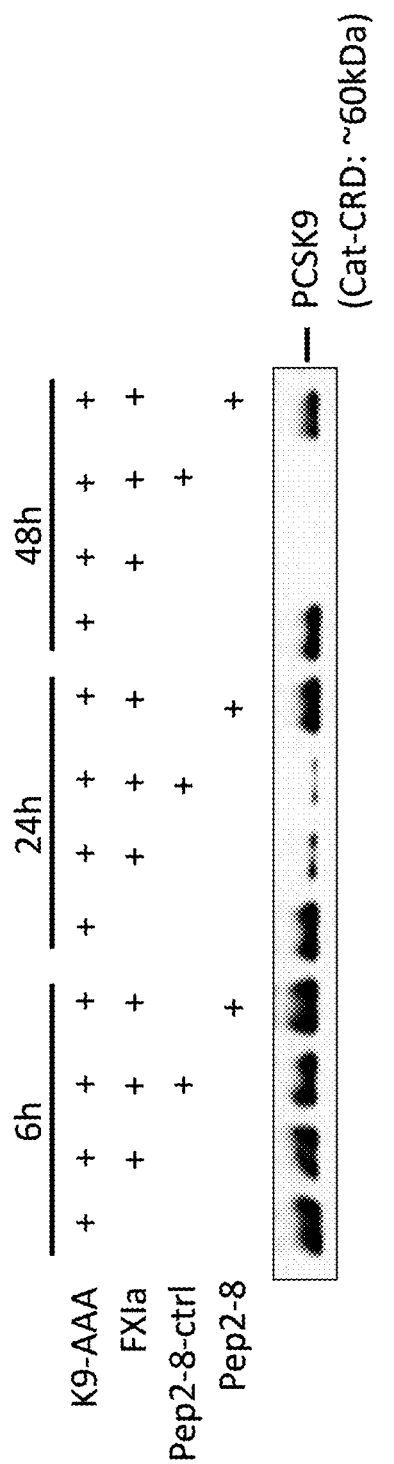
FIG. 11 shows the time-dependent cleavage by FXIa of K9-AAA in complex with Pep2-8. Stabilization of the P' helix in the N-terminal groove by Pep2-8 prevented cleavage. A control peptide (Pep2-8-ctrl) did not prevent cleavage.

Furthermore, addition of Fab33 to PCSK9-AAA dramatically accelerated the cleavage reaction by FXIa. Cleavage was nearly complete at 0.5 h and complete at 6 h (FIG. 9). The structure of Fab33:PCSK9 complex provides a basis to explain this result: in occupying the N-terminal groove site with the CDR-H2 loop, the bound Fab33 thus keeps the P' helix in the proteolytically susceptible "out" conformation. In an orthogonal approach PCSK9-AAA was incubated with EGFA-Fc or with Pep2-8 before exposure to FXIa. Both EGFA domain and Pep2-8 engage in binding interactions with the P' helix, resulting in its stabilization. The PCSK9-Ser153 makes a 2.9 Å salt bridge interaction with the EGFA-Asp299 side chain and PCSK9-Pro155 makes a van der Waals contact with EGFA-Leu298 (Bottomley et al., J Biol Chem. 2009 Jan. 9; 284(2): 1313-23; Kwon et al., Proc Natl Acad Sci USA. 2008 Feb. 12; 105(6): 1820-1825). Similarly, Pep2-8 residue W6 makes a van der Waals contact with PCSK9-Pro155 (Zhang et al., J Biol Chem. 2014 Jan. 10; 289(2):942-55). Therefore, by stabilizing the P' helix in the groove-bound "in" conformation as seen in deposited crystal structures (e.g. PDB 2P4E, 2PMW, 2QTW, 3BPS, 3GCW, 3GCX, 3H42, 3SQO, 4K8R) the helix residue R160 will be resistant to FXIa cleavage, since it remains partially buried. Indeed, both reagents largely prevented cleavage of the P' helix by FXIa (FIGS. 10 and 11). Even at 48 h incubation, most of the PCSK9 still remained intact (FIGS. 10 and 11). The control peptide did not inhibit cleavage and gave similar results as the buffer control, i.e. FXIa alone without reagent addition (FIG. 11).

Figure 12:
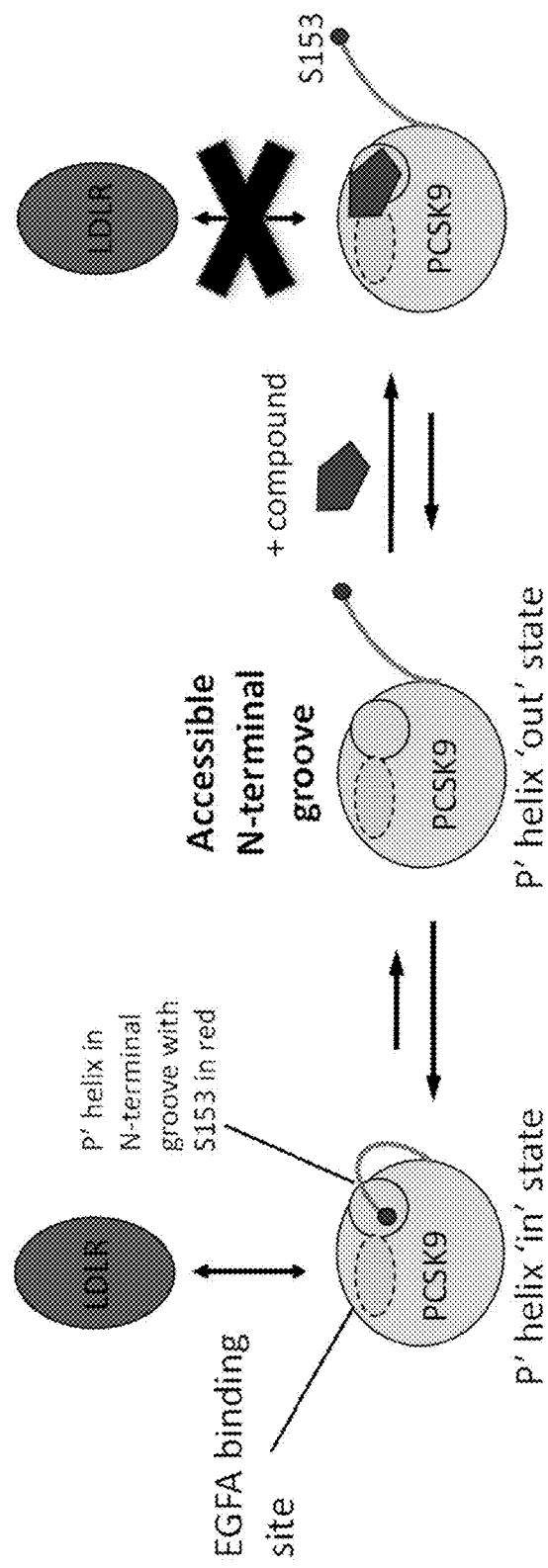
FIG. 12 shows the "equilibrium model" of the intrinsically labile P' helix, which can transition between the "in" and "out" conformational states. In the "out" state, the P' helix adopts a non-helical conformation that becomes susceptible to proteolytic cleavage, e.g. by FXIa. The model implies that the N-terminal groove could be accessible for compounds, such as peptides or organic molecules. Once bound to the groove, such compounds may keep the P' helix in the "ejected" conformation. Because the N-terminal groove is proximal to the LDLR binding site, groove-binding compounds could become competitive inhibitors by directly antagonizing LDLR binding to PCSK9 due to steric clashes between compound and the LDLR-EGFA domain.

The findings support the view that the P' helix is intrinsically labile and is in an equilibrium between the "in" and "out" state as depicted in the model in FIG. 12. It is the "out" conformation that becomes susceptible to cleavage by FXIa. FXIa by itself was able to cleave the P' helix at the R160-I161 peptide bond, albeit at a slow rate, suggesting that the equilibrium is mainly in the "in" state. However, shifting the equilibrium to the "out" state by adding Fab33, dramatically increased the rate of the cleavage reaction. Importantly, the model implies that the N-terminal groove could be accessible to compounds, such as peptides or organic molecules. Once bound to the groove, such compounds may keep the P' helix in the "ejected" conformation, as observed for Fab33. This could result in destabilizing the LDLR binding, as was demonstrated by the reduced LDLR binding of PCSK9 variants bearing mutations in the P' helix region (Bottomley et al., J Biol Chem. 2009 Jan. 9; 284(2): 1313-23). Importantly, because the N-terminal groove is proximal to the LDLR binding site, groove-binding compounds could become competitive inhibitors by directly antagonizing LDLR binding to PCSK9 due to steric clashes between compound and the LDLR-EGFA domain (FIG. 12).

Methods

PCSK9 Cleavage Under Crystallization Conditions and Inhibition by Antithrombin III Three different concentrations of Fab33:PCSK9 complex or of PCSK9 alone (as indicated in Table 2) were incubated in 50 mM Tris, pH 8.0, 150 mM NaCl, 10% glycerol for 48 h at room temperature. After SDS-PAGE of the samples, the 60 kDa band comprising the PCSK9 catalytic domain and Cys-rich domain (CRD) was analyzed by N-terminal sequencing and the results reported in Table 2.

TABLE 2

| Protein concentrations | SEQ ID NO: | N-terminal sequence | Comments |
| --- | --- | --- | --- |
| 87 mg/mL PCSK9 | 283 | 153SIPWNLER | Intact N-terminus |
| 88 mg/mL PCSK9 + 132 mg/mL Fab33 | 284 | 166YRADEYQPPD | Cleavage at R165-Y166 |
| 9.9 mg/mL PCSK9 | 283 | 153SIPWNLER | Intact N-terminus |
| 9.7 mg/mL PCSK9 + 14.5 mg/mL Fab33 | 283 | 153SIPWNLER | Intact N-terminus |
| 1.1 mg/mL PCSK9 | 283 | 153SIPWNLER | Intact N-terminus |
| 0.88 mg/mL PCSK9 + 1.32 mg/mL Fab33 | 283 | 153SIPWNLER | Intact N-terminus |

For inhibition experiments, the Fab33:PCSK9 complex (19.8 mg/mL Fab33, 13.2 mg/mL PCSK9) was incubated with the serpins antithrombin III and alpha1-antitrypsin (150 µM each) (Calbiochem) or with the Kunitz domain inhibitor Aprotinin (1.5 mM) (Roche) in 50 mM Tris, pH 8.0, 150 mM NaCl, 10% glycerol for 9 days at room temperature. Samples were analyzed by SDS-PAGE and transferred to a nitrocellulose membrane using iBlot (Invitrogen). Proteins were then probed with a polyclonal rabbit antibody (1:3000) raised against the PCSK9 N-terminal peptide ($^{153}$SIPWN-LERITPPRYRA$^{168}$ (SEQ ID NO: 5)), followed with HRP-conjugated donkey anti-rabbit antibody (1:5000, GE Healthcare) using iBind (Invitrogen). PCSK9 signals were detected by ECL (GE Healthcare) and visualized by autoradiography. The polyclonal rabbit antibody against the PCSK9 N-terminal peptide $^{153}$SIPWNLERITPPRYRA$^{68}$ (SEQ ID NO: 5) was generated by immunizing rabbits with the synthesized peptide CSIPWNLERITPPRYRA (SEQ ID NO: 285), which contained an extra Cys residue at the N-terminus for conjugation to KLH. The polyclonal antibody IgG was purified from rabbit serum using affinity chromatography with resin-immobilized peptide CSIPWNLERITPPRYRA (SEQ ID NO: 285) (YenZym Antibodies, LLC, San Francisco, Calif.).

PCSK9 Cleavage by Panel of Serine Proteases

The proteases Hepsin (Lipari et al. J Biol Chem. 2012 Dec. 21; 287(52):43482-91), alpha-thrombin, FXa, FXIa, activated Protein C (Haematologic Technologies, Vermont) and FXIIa (Enzyme Research Laboratories) were incubated at a concentration of 50 nM for 6 h at room temperature in 50 mM Tris, pH 8.0, 150 mM NaCl, 4 mM $CaCl_2$ with 3 µM PCSK9 in complex with Fab33 (4 µM) and with or without antibody 3D5 (4 μM). The 3D5 antibody was described by Lipari et al. (J Biol Chem. 2012 Dec. 21; 287(52):43482-91) and binds to the surface exposed "furin cleavage loop" of PCSK9, which contains the two Arg residues R215 and R218. These two residues are susceptible to cleavage by Arg-specific proteases, such as furin and hepsin (Lipari et al. J Biol Chem. 2012 Dec. 21; 287(52):43482-91). To prevent any cleavage at this site, the 3D5 antibody was included in this experiment. After SDS-PAGE of the samples, the 60 kDa PCSK9 band was analyzed by N-terminal sequencing and Western blotting was performed using the PCSK9 N-terminal peptide antibody as described above.

FXIa Cleavage Assay

The PCSK9-R167A:R215A:R218A (=PCSK9-AAA) was constructed based on the mutant PCSK9-R215A:R218A (Lipari et al. J Biol Chem. 2012 Dec. 21; 287(52):43482-91) by adding the mutation R167 Å using site directed mutagenesis. The construct was transiently expressed in CHO cells and purified according to published procedures (Zhang et al. J. Mol. Biol. 422: 685-96, 2012; Zhang et al. J. Biol. Chem. 289:942-55, 2014). The expression and purification of EGFA-Fc was described in Zhang et al. J. Mol. Biol. 422: 685-96, 2012. The peptide Pep2-8 (Ac-TVFTSWEEY-LDWV-NH$_2$ (SEQ ID NO: 286)) and the control peptide Pep2-8-ctrl (Ac-TVATSAEEYLLWV-NH$_2$ (SEQ ID NO: 287)) have been described by Zhang et al. J. Biol. Chem. 289:942-55, 2014.

The PCSK9-AAA mutant (2.6 μM) was incubated with 50 nM FXIa (Haematologic Technologies) in Tris buffer (50 mM Tris, 150 mM NaCl, 4 mM CaCl$_2$, pH 8.0) at room temperature for the indicated time periods. In experiment with Fab33, EGFA-Fc and Pep2-8, 5.2 μM of PCSK9-AAA was incubated with 100 nM FXIa in the presence of either Fab33 (8 μM), or EGFA-Fc (8 μM) or Pep2-8 (8 μM), or the control peptide Pep2-8-ctrl (8 μM) in Tris buffer for the indicated time periods. After SDS-PAGE of the samples, proteins were transferred to a nitrocellulose membrane using iBlot (Invitrogen). Proteins were then probed with a polyclonal rabbit antibody (1:3000) raised against the PCSK9 N-terminal peptide ($^{153}$SIPWNLERITPPRYRA$^{168}$ (SEQ ID NO: 5)), followed with HRP-conjugated donkey anti-rabbit antibody (1:5000, GE Healthcare) using iBind (Invitrogen). PCSK9 signals were detected by ECL (GE Healthcare) and visualized by autoradiography.

Example 2: Engineering of PCSK9 Groove-Binding Peptides by Phage Display

Results

Previously, attempts were made to pan against PCSK9Δhelix with either naïve phage peptide libraries or a soft randomization phage peptide library of SIPWNLERIT-PPR (SEQ ID NO: 288) (referred to as N13), which are the first 13 residues of the PCSK9 catalytic domain and comprise the groove-binding P' helix. However, all these efforts failed to yield any groove-binding peptide ligands that could bind PCSK9 or PCSK9Δhelix.

In another approach to find a peptide that binds to the N-terminal groove of PCSK9, an extension peptide strategy was pursued based on the previously discovered Pep2-8, which binds to the LDLR binding site on PCSK9. Pep2-8 is a minimalist peptide ligand that mimics the interaction between EGF(A) domain and PCSK9 (Zhang et al. J. Biol. Chem. 289:942-55, 2014). The N-terminal groove on PCSK9 is right next to the EGF(A) binding site. The C-terminus of Pep2-8 points in the direction of the N-terminal groove and the distance between the C-terminus of Pep2-8 and the N-terminus of the PCSK9 catalytic domain (S153) is ~9 Å. Pep2-8 was used to find peptide extensions into the groove using a fully randomized phage peptide library that was fused to the C-terminus of Pep2-8 by an amino acid linker. The optimal linker between Pep2-8 and the peptide library was found to be a three-residue stretch of "GSG" (data not shown).

Figure 13:
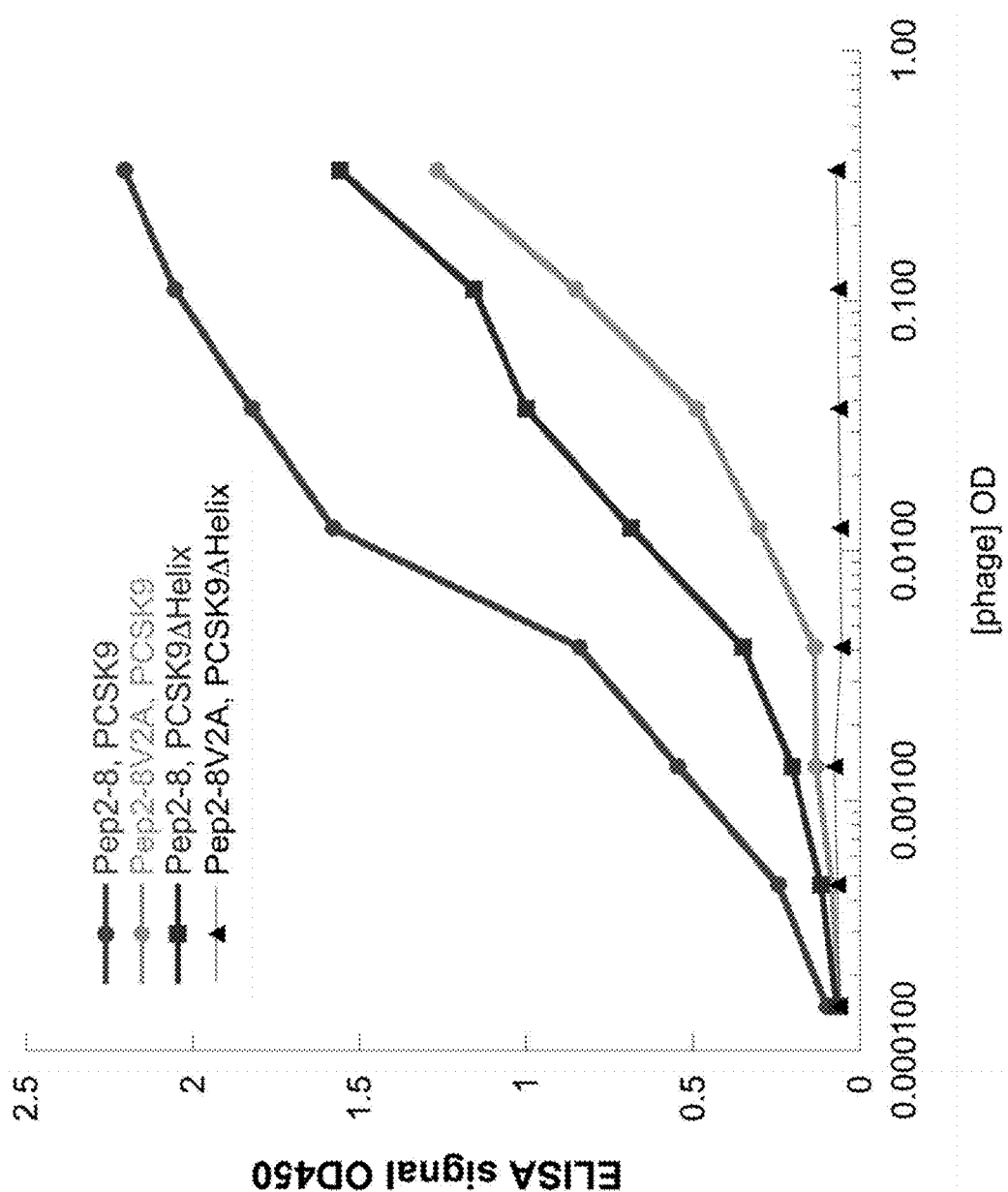
FIG. 13 shows the binding of phage displaying Pep2-8 or Pep2-8(V2A) to PCSK9 and to PCSK9Δhelix. The single mutation of Valine2 to an Alanine reduced binding affinity to both PCSK9 constructs. The reduced but still detectable binding of Pep2-8(V2A) to PCSK9 was suitable for its use as an anchor peptide to C-terminally attach peptide extension libraries via a GSG linker.

Pep2-8 binds to PCSK9 with a $K_d$ of 0.7 μM (Zhang et al. J. Biol. Chem. 289:942-55, 2014). Phage-displayed Pep2-8 (on p8) bound very tightly to both PCSK9 and PCSK9Δhelix, leaving no margin for affinity improvement with the extended library. In order to weaken the interaction, a single Valine2 to Alanine mutation was introduced in Pep2-8 (Pep2-8V2A), which was previously found to reduce the affinity by about 10-fold (Zhang et al. J. Biol. Chem. 289:942-55, 2014). In agreement, phage-displayed Pep2-8V2 Å bound to PCSK9 with reduced affinity, leaving enough margin to detect an affinity improvement (FIG. 13). This phage did however not bind to PCSK9Δhelix (FIG. 13). Therefore Pep2-8V2 Å was used as the anchor sequence for the phage library. The phage library was a fully randomized peptide library with lengths ranging from 8-16 amino acids fused to the C-terminus of Pep2-8V2 Å via a "GSG" linker (TAFTSWEEYLDWV-GSG-(NNK)$_{8-16}$ (SEQ ID NO: 289)).

The phage library was panned against both PCSK9 and PCSK9Δhelix for 4 rounds following the standard protocol for solution sorting (Zhang et al. J. Biol. Chem. 289:942-55, 2014). Hundreds of binders were found with improved affinity compared to Pep2-8V2 Å alone. These peptides could be grouped into several categories based on sequence motif conservation (FIGS. 14 and 15). One motif category was highly homologous to N13 (FIG. 14).

More than 100 of the phage fusion binders were reformatted by deleting the anchor sequence (Pep2-8V2A) plus the first Gly in the linker and they were displayed on the M13 phage major coat protein p8. Most of these phage clones lost binding signal to both PCSK9 and PCSK9Δhelix. 17 phage derived peptides retained weak binding to both PCSK9 and PCSK9Δhelix (FIG. 16). These peptides were further affinity matured using the previously described soft randomization strategy. The soft randomized libraries for all 17 peptides were pooled and panned against both PCSK9 and PCSK9Δhelix following the standard protocol (Tonikian et al. Nat Protoc. 2007; 2(6):1368-86). After four rounds of panning, a 5-fold enrichment was observed and 10 positive clones with strong binding signals could be identified by spot phage ELISA screening (FIG. 17). Seven of these ten peptides contain the PWNLXRIX motif (SEQ ID NO: 290), homologous to the core sequence of N13, suggesting that the improved binding affinities of these fusion peptides were indeed due to newly created groove interactions by the extension peptides. Also, seven of the ten hits contained disulfide bonds.

Figure 18:
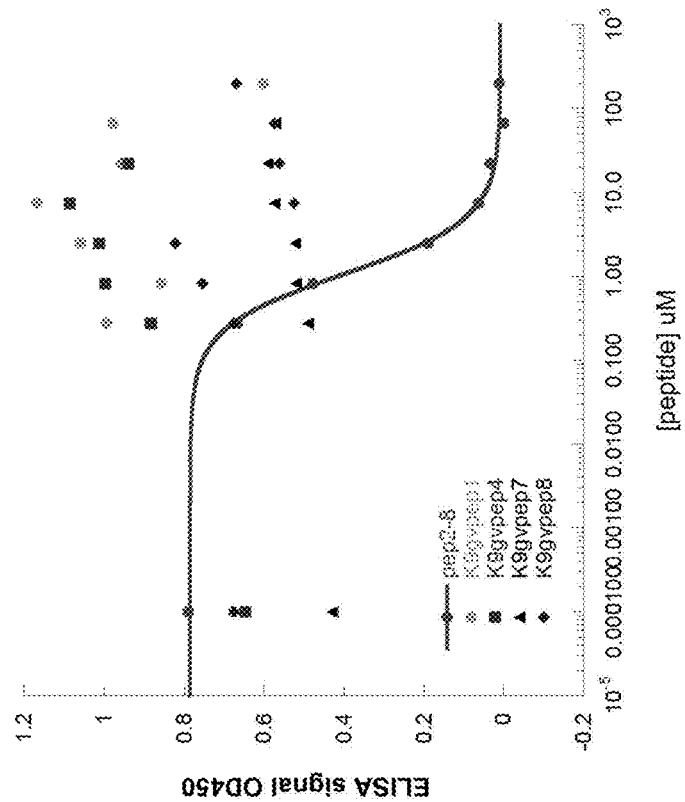
FIG. 18 shows the results of a standard phage competition ELISA with six synthesized peptides (SEQ ID NOS 393-398, respectively, in order of appearance) from the list in FIG. 17. Four peptides competed with phage-displayed peptides for binding to PCSK9 and to PCSK9Δhelix with $IC_{50}$ values in the sub-micromolar or low micromolar range. However, none of these four synthetic peptides competed with phage-displayed Pep2-8 binding (graph), indicating that they do not bind to the Pep2-8 binding site on PCSK9. As a positive control synthetic Pep2-8 was used, which inhibited phage-displayed Pep2-8 binding to PCSK9 in a concentration dependent manner. n.d.=no inhibition detectable.

Six of these peptides (K9gvpep1, 4, 5, 6, 7, and 8 in FIG. 18) were synthesized and tested in a standard phage competition ELISA. Four peptides with the conserved PWN-LXRIX motif (SEQ ID NO: 290) were able compete with their phage counterpart at IC$_{50}$s in the low μM or submicromolar range against both PCSK9 and PCSK9Δhelix (FIG. 18). Consistent with their predicted binding to the N-terminal groove, these four peptides (K9gvpep1, K9gvpep4, K9gvpep7, K9gvpep8) did not compete with binding of phage-displayed Pep2-8 to PCSK9 (FIG. 18).

Two of the phage-derived peptides were synthesized as 30 residue fusion peptides with the N-terminal Pep2-8 plus GSG linker. Both of these peptides (Pep2-8_K9gvpep4 and Pep2-8_K9gvpep7) potently inhibited PCSK9 binding of phage displaying extension peptide K9gvpep4, as well as of phage displaying Pep2-8, the $IC_{50}$ values being in the low nanomolar range (FIG. 19). This is consistent with the determined low nM and sub-nM $K_d$ values of these two synthetic peptides (Compound 19=Pep2-8_K9gvpep4; Compound 20=Pep2-8_K9gvpep7) in surface plasmon resonance experiments (Example 4, Table 7). These two fusion peptides were also able to potently rescue LDLR in HepG2 cell assays (Example 5, FIGS. 29 and 30). The crystal structure of one of these peptides, Compound 20, is shown in Example 3, FIG. 21.

Methods

Construction, Expression and Purification of PCSK9ΔHelix

Human PCSK9 construct M1-Q692 with an engineered TEV site (residue deletion Y166, R167; insertion ENLYFQS sequence (SEQ ID NO: 291) between R165 and A168, DNA 750364) was cloned into a mammalian expression vector (pRK5). 10 liters of CHO media containing expressed protein was concentrated using a Millipore tangential flow concentrator with a 10,000 molecular weight cutoff membrane. The concentrate was di-filtered using 2× one liter of PBS. The final volume was 0.8 L. PCSK9 (250 mL×4) was purified by using a 5 mL Ni column (GE Healthcare) equilibrated in 300 mM NaCl, 50 mM Tris pH 7.5, 50 mM imidazole, 10% glycerol and eluted with 0.3 M imidazole, 300 mM NaCl, 50 mM Tris pH 7.5. The PCSK9 was further purified by size exclusion chromatography using a Superdex 200 16/60 column in 0.15 M NaCl, 25 mM Tris pH 8.0, 10% glycerol. (4 separated runs) The fractions were assayed using SDS-PAGE.

PCSK9 was then treated with TEV protease (100 µL at 2.5 mg/mL per 10 mg of protein) for 24 hours at 4° C. using dialysis (Slidelyzer 10K (Thermo Scientific)) versus 1 M NaCl, 50 mM Tris pH 8.0, 10% glycerol and 3 mM reduced glutathione/0.3 mM oxidized glutathione. The TEV protease-cleaved PCSK9 was concentrated to 2 mL and passed through the Superdex 200 16/60 column in 250 mM NaCl, 25 mM Tris pH 8.0, 10% glycerol. The fractions corresponding to PCSK9Δhelix were pooled and characterized using mass spectrometry and SDS PAGE. The protein was homogenous and had the expected mass, consistent with the loss of the N-terminal sequence $^{153}$SIPWNLERITPPR$^{165}$ENLYFQ (SEQ ID NO: 292) (ENLYFQ (SEQ ID NO: 293) is TEV cleavage sequence). The new N-terminus of the PCSK9 catalytic domain was $S^{168}$A (the Serine is from the TEV cleavage sequence), which was confirmed by MS. Therefore, the PCSK9Δhelix construct was missing the first 15 residues of its native N-terminal sequence ($^{153}$SIPWNLER-ITPPRYR$^{167}$ (SEQ ID NO: 294)) and had an exposed "open" N-terminal groove.

Library Construction

The phage displayed peptide library was constructed using the standard Kunkel mutagenesis method (Kunkel et al., Methods Enzymol 154, 367-82). The fusion peptide libraries were constructed by fusing randomized peptides to the C-terminus of the anchor peptide Pep2-8V2A plus a GSG linker (TAFTSWEEYLDWVGSG (SEQ ID NO: 295)). The fusion peptide libraries were displayed on the N-terminus of M13 major coat protein following the standard protocol for making phage displayed libraries (Tonikian et al. Nat Protoc. 2007; 2(6):1368-86). The extension pool consisted of random peptides with 8, 10, 12, 14, 16 amino acids in length encoded by consecutive degenerate codons (NNK, where N=A/C/G/T and K=G/T). The libraries with different length were constructed individually and pooled together with the same concentration for each. The final diversity of the library was $1.3 \times 10^{10}$.

The soft randomized library was constructed using degenerate oligonucleotides synthesized with 70-10-10-10 mixtures of nucleotide bases, in which the wild type base was in excess. This results in the wild type amino acids occurring at approximately 50% frequency at the targeted position.

Selection of Fusion Ligands for PCSK9 and Affinity Maturation of Selected Peptide Library Clones Phage pools of the fusion library were cycled through rounds of binding selections with biotinylated PCSK9 and biotinylated PCSK9Δhelix in solution as described before (Zhang et al. J. Biol. Chem. 289:942-55, 2014). The panning of the soft-randomization library was carried out the same way, except for using 10 nM, 5 nM and 2 nM biotinylated PCSK9 and biotinylated PCSK9Δhelix for rounds 2, 3 and 4, respectively.

After four rounds of binding selection, individual phage clones were analyzed in a high-throughput spot phage ELISA using plate-immobilized PCSK9 as the target (Tonikian et al. Nat Protoc. 2007; 2(6): 1368-86). The binding signal of the same phage particle to NeutrAvidin was detected as non-specific binding noise. Clones with phage binding signal to target over 0.5 and signal/noise ratio >5 were considered to be positive clones and were subjected to DNA sequence analysis.

$IC_{50}$ Analysis of PCSK9 Peptide Ligands by Phage Competition ELISA

The sequences of selected clones were fused to the N-terminus of M13 major coat protein (p8) using Kunkel mutagenesis method (Kunkel et al., Methods Enzymol 154, 367-82). The resulting construct was transformed to E. Coli. XL1 blue, single colony was grown in 1 mL 2YT supplemented with 50 µg/mL carbenicillin, 10 µg/mL Tetracycline and M13 KO7 helper phage at 37° C. for 2 h, Kanamycin was added to final concentration of 25 µg/mL, growth was continued at 37° C. for 6 h. The culture was transferred to 30 mL 2YT supplemented with 50 µg/mL carbenicillin and 25 µg/mL kanamycin and grown at 37° C. overnight. The next day, the phage was harvested and purified using the standard protocol (Tonikian et al. Nat Protoc. 2007; 2(6): 1368-86). The serially diluted phage solution was applied to the biotinylated PCSK9 and biotinylated PCSK9Δhelix that had been immobilized for 15 min on a 384-well MaxiSorp ImmunoPlate previously coated with 5 µg/mL NeutrAvidin and blocked with Block buffer. The plate was incubated at 4° C. for 1 h, washed 10 times with PT buffer (PBS, 0.05% Tween® 20). The bound phage was detected with anti-M13-HRP and the ELISA signal was read at OD450 nm. The background was ELISA signal that the phage directly bound to NeutrAvidin-coated plate. The data was plotted and the curve fitted with KaleidaGraph. Sub-saturating phage concentration that gave 80% of maximum binding signal was determined by the binding curve.

$IC_{50}$ measurements were performed by mixing a fixed sub-saturating concentration of peptide-displaying phage with a serial dilution of synthetic peptides in PBT buffer. The mixture was added to plates coated with PCSK9 and PCSK9Δhelix and incubated for 1 h at room temperature. The plates were then washed 10 times with PBT buffer and the bound phage was detected by anti-M13-HRP. The data was plotted, curve fitted and $IC_{50}$ derived by use of KaleidaGraph. All measurements were repeated 3 times independently.

Example 3: Crystal Structures of Groove-Binding Peptides

For the purpose of applying X-ray crystallography to the study of PCSK9 N-terminal groove-binding peptides, it was necessary to select crystal systems known to provide sufficient room in the crystal lattice for such peptides to occupy the "N-terminal groove". Crystals of PCSK9ΔCRDΔhelix/Pep2-8 in space group P3$_2$21 were chosen. Such crystals are relatively easy to produce, they diffract to relatively high resolution, and offer a substantial volume otherwise occupied only by bulk solvent immediately adjacent to the "N-terminal groove". Thus, it was anticipated that the crystal packing of PCSK9ΔCRDΔhelix:Pep2-8 complexes in such crystals could accommodate groove-binding peptides.

Figure 20:
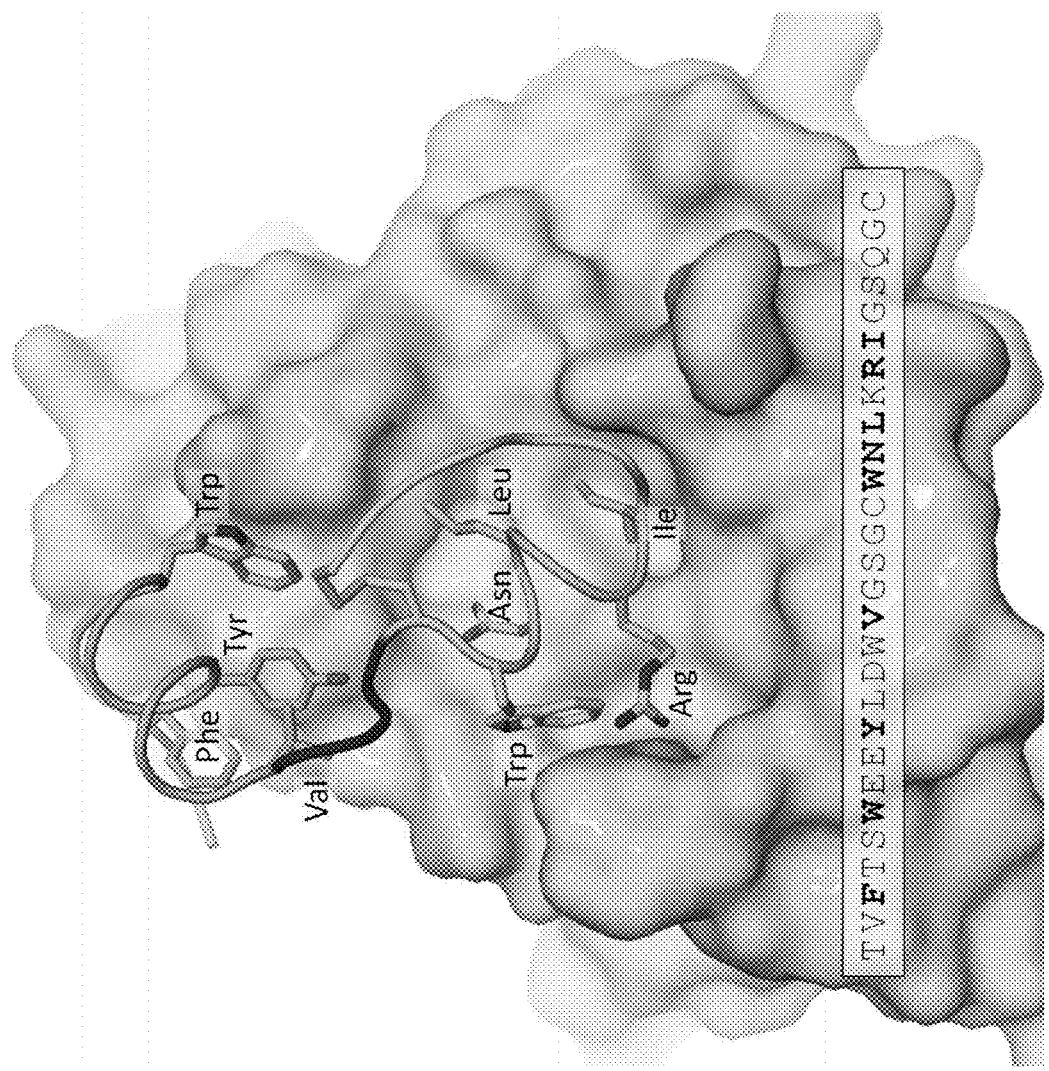
FIG. 20 shows the crystal structure of PCSK9ΔCRDΔhelix with bound fusion peptide Compound 2, consisting of Pep2-8 linked to the extension peptide CWNLKRIGSQGC (SEQ ID NO: 6) via a GSG linker. Figure discloses SEQ ID NO: 400.

A total of 9 crystal structures of peptides in complex with PCSK9ΔCRDΔhelix were determined, with good resolutions between 1.9 and 2.9 Å. They comprise three fusion peptides (FIGS. 20-22) and five groove-binding peptides co-crystallized with Pep2-8 (FIGS. 23, and 25-28). In addition, a structure of a groove-binding peptide co-crystallized with a modified Pep2-8 bearing fluoro-W6 (Compound 3) was solved (FIG. 24). The X-ray structure results are shown in Tables 3-5.

The structure obtained for Compound 2 (FIG. 20) clearly shows the binding mode of a fusion peptide. The Pep2-8 portion of the fusion peptide occupies the same location on the PCSK9 surface as in the previously reported structure of the Pep2-8:PCSK9 complex (Zhang et al., J Biol Chem. 2014 Jan. 10; 289(2):942-55; PDB Accession Number 4NMX). In particular: the peptide backbone of F3 forms two hydrogen bond interactions with the backbone of PCSK9 F379; the side chain of peptide V2 forms non-bonded contacts to the side chains of PCSK9 C378 and V380; the side chain of peptide W6 forms non-bonded contacts to the side chains of PCSK9 D238, A239 and F379 while the side chain of peptide Y9 forms non-bonded contacts to the side chains of PCSK9 I369. When the protein coordinates of the structure shown in FIG. 20 were overlaid with the protein coordinates of 4NMX, the backbone atoms of the peptide portions corresponding to Pep2-8 had a root mean squared change in coordinate positions of 0.36 Å.

Turning to the C-terminal fusion portion of Compound 2, the G14-S15-G16 linker is largely extended and forms no specific contacts with PCSK9ΔCRDΔhelix. The two cysteine residues (C17 and C28) are clearly disulfide bonded and although forming no contacts to PCSK9ΔCRDΔhelix, are involved in van der Waals packing against the Pep2-8 portion of the peptide (W6 and Y9). Residues W18-I23 of Compound 2 adopt a helical conformation that allows the side chains of these residues to form hydrogen bond interactions (W18 NεlH and N19 side chain CONH$_2$), ionic interactions (R22 guanidine) and van der Waals contacts (W18, N19, L20, and I23) to PCSK9ΔCRDΔhelix. This portion of the fusion peptide clearly occupies the same site that the N-terminal peptide ordinarily occupies in the wild-type PCSK9 structure. This newly-formed pocket is lined by the following portions of PCSK9ΔCRDΔhelix: A239-V241, T339-D343, P364-I368, H391 and V441-L444. The specific interactions of the fusion peptide to this pocket are listed in Table 6. The backbone dihedral angles of Gly24 (including a positive phi angle) direct the peptide portion from G24 to C28 back towards C17. This region is largely extended and makes no contacts with PCSK9ΔCRDΔhelix. Thus, the C-terminal portion of the fusion peptide, including the disulfide bond, appears to act as a tether to limit the conformational flexibility and promote specific contacts of the intervening section (W18-I23) with PCSK9ΔCRDΔhelix.

Figure 22:
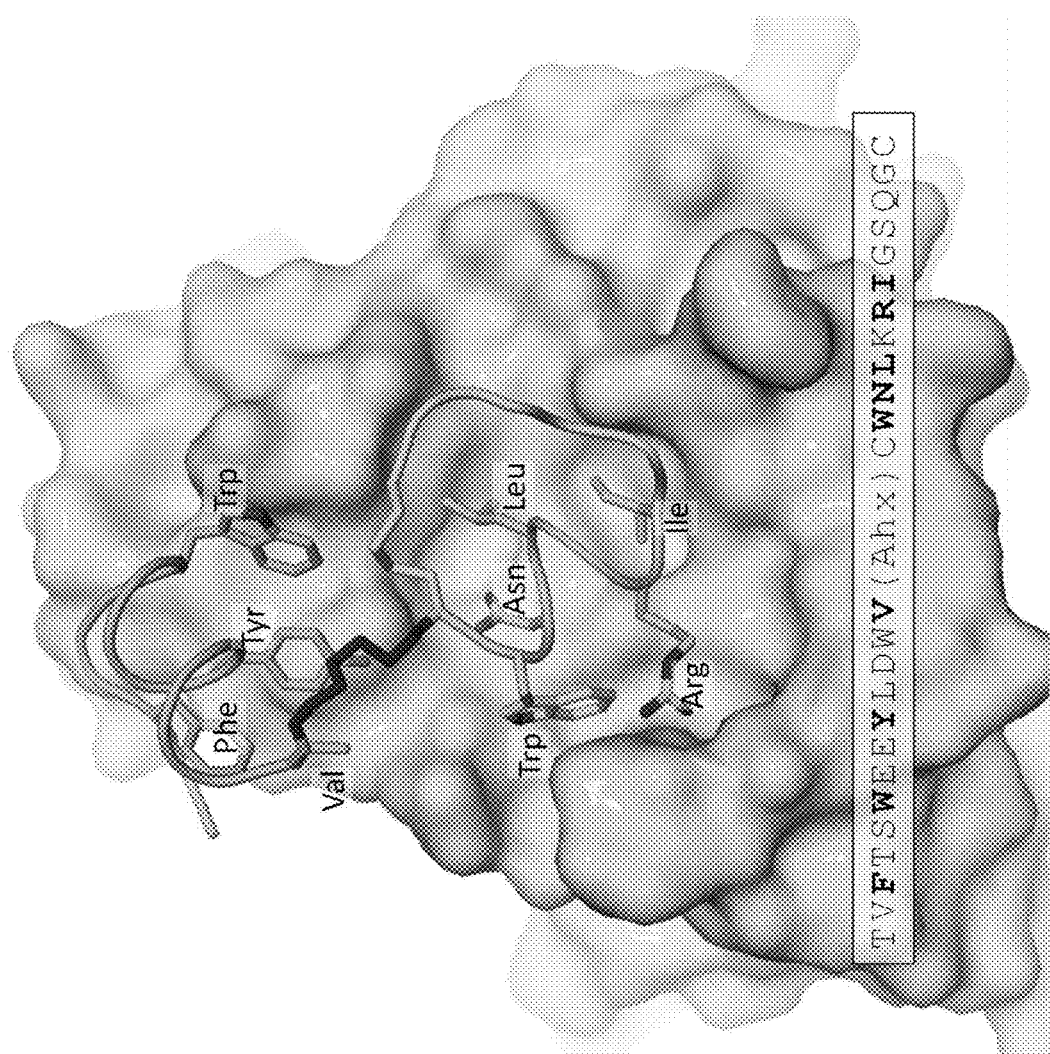
FIG. 22 shows the crystal structure of PCSK9ΔCRDΔhelix with the bound fusion peptide Compound 17, consisting of Pep2-8 linked to the extension peptide CWNLKRIGSQGC (SEQ ID NO: 6) via an aminohexanoic acid (Ahx) linker. Figure discloses SEQ ID NO: 44.

A structure was also obtained for the complex between PCSK9ΔCRDΔhelix Compound 17 (FIG. 22). This peptide has the "GSG" linker of Compound 2 replaced by 6-amino-hexanoic acid. The interactions of the Pep2-8 and the extension portion of this fusion with PCSK9ΔCRDΔhelix are exactly the same as for Compound 2. In this case also, the 6-aminohexanoic acid linker does not make any direct contact with the protein.

Figure 21:
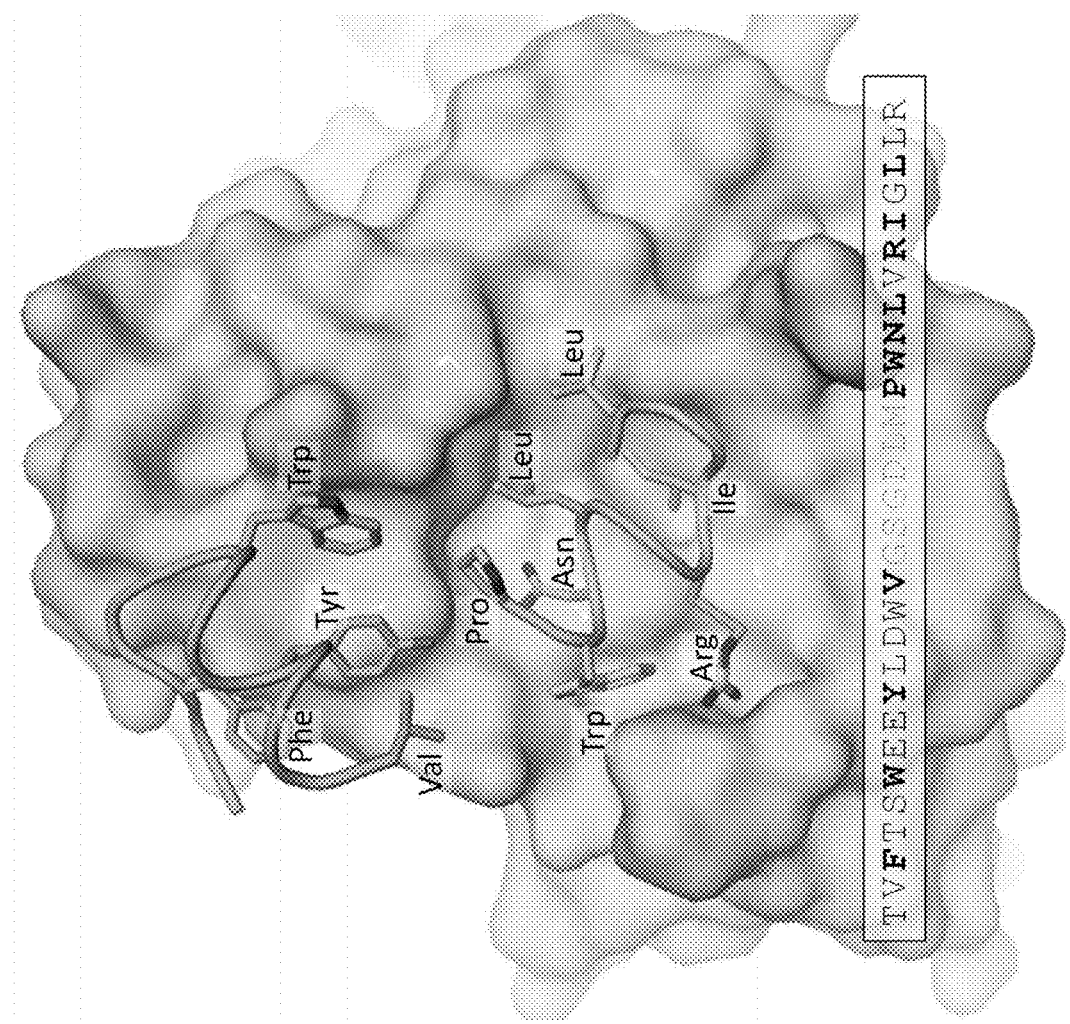
FIG. 21 shows the crystal structure of PCSK9ΔCRDΔhelix with the bound fusion peptide Compound 20, consisting of Pep2-8 linked to the extension peptide DLMPWNLVRIGLLR (SEQ ID NO: 7) via a GSG linker (not resolved). Figure discloses SEQ ID NO: 299.

Compound 20 was also amenable to the co-crystallization with PCSK9ΔCRDΔhelix (FIG. 21). The electron density for this peptide clearly defined the N-terminal portion (corresponding to Pep2-8) and the C-terminal extension M19-R29, although there was no clear electron density for the linker residues G14, S15, G16, D17 and L18. The key interactions with the N-terminal groove site of PCSK9 occur with residues W21, N22, L23, R25 and 116 in the peptide extension. The non-bonded contacts to these residues are ostensibly the same as with Compound 2 (Table 6). Additional van der Waals interactions are observed between peptide residue P20 and the side chain of 1369 of PCSK9 and peptide residue L28 and the side chain of L444 of PCSK9. Although this peptide does not contain a disulfide bond, there is a group of hydrophobic residues (M19, V24 and L29) that cluster together on the top surface of the peptide (away from PCSK9) and may be responsible for nucleating or stabilizing the fold of the C-terminal extension peptide, thereby improving binding affinity of the peptide for PCSK9.

The sequence motifs and interactions utilized by the extension peptides are reminiscent of the native interactions of the P' helix with the N-terminal groove. For example, in Compound 20, the extension peptide residues P20, W21, N22, L23, R25 and 126 correspond directly to P155, W156, N157, L158, R160 and I161 of the native PCSK9 P' helix. When the coordinates of PCSK9ΔCRDΔhelix in complex with Compound 20 are superimposed with those of wild type PCSK9, the backbone atoms corresponding to these 6 amino acids have a root mean squared change in coordinate positions of 0.18 Å. This points to the importance of the "PWNxLRI" motif for interacting with the N-terminal groove of PCSK9, either via the native P' helix or other exogenous ligands that occupy this site. For the peptides, a C-terminal glycine residue is an important addition to this motif so as to allow the peptide chain to be directed back towards the N-terminus (either to form the disulfide bond or the hydrophobic cluster listed above for Compound 20); a positive value of the backbone phi angle required for this geometry is energetically unfavorable for non-glycine residues.

The crystal lattice formed by PCSK9ΔCRDΔhelix in complex with Pep2-8 also afforded the possibility of forming crystals with additional peptides occupying the N-terminal groove site. One such example of this is Compound 21 (FIG. 25); this 12-residue peptide corresponds to the C-terminal portion of Compound 2 and Compound 17. Even in the absence of a covalent tether to the Pep2-8 peptide, Compound 21 was able to make the same non-bonded contacts with the N-terminal groove site. Indeed, when the coordinates of PCSK9 were overlaid between the Compound 21 and Compound 2 co-crystal structure, the location of the peptide residues contacting PCSK9 differed by less than 0.3 Å and the backbone root-mean-square deviation of the these residues was 0.07 Å. Some atoms of the non-contact residues (e.g. S9, Q10 and G11) of Compound 21 shifted by as much as 2 Å compared to the equivalent atoms of Compound 2 reinforcing that the non-contact residues form a flexible linker to restrain the peptide conformation. Although there is no covalent bond between Compound 21 and Pep2-8 there were van der Waals contacts from the cysteine residues of the former to W6 and Y9 of the latter.

Further, a hydrogen bond was observed from the N-terminal amine of Compound 21 to the phenolic hydroxyl group of Y9 in Pep2-8.

Figure 23:
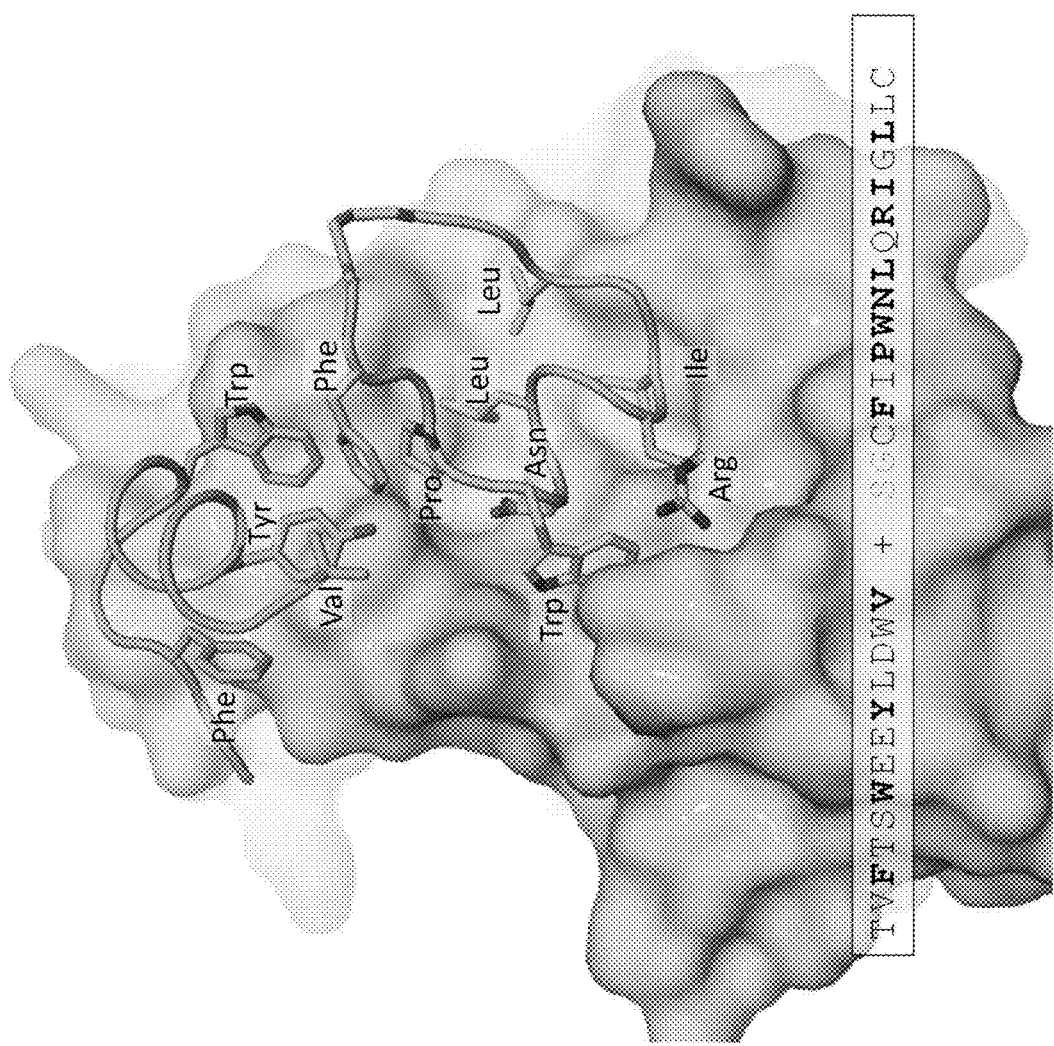
FIG. 23 shows the crystal structure of PCSK9ΔCRDΔhelix with the bound extension peptide Compound 26 co-crystallized with Pep2-8 (SEQ ID NOS 3 and 383, respectively, in order of appearance).
Figure 24:
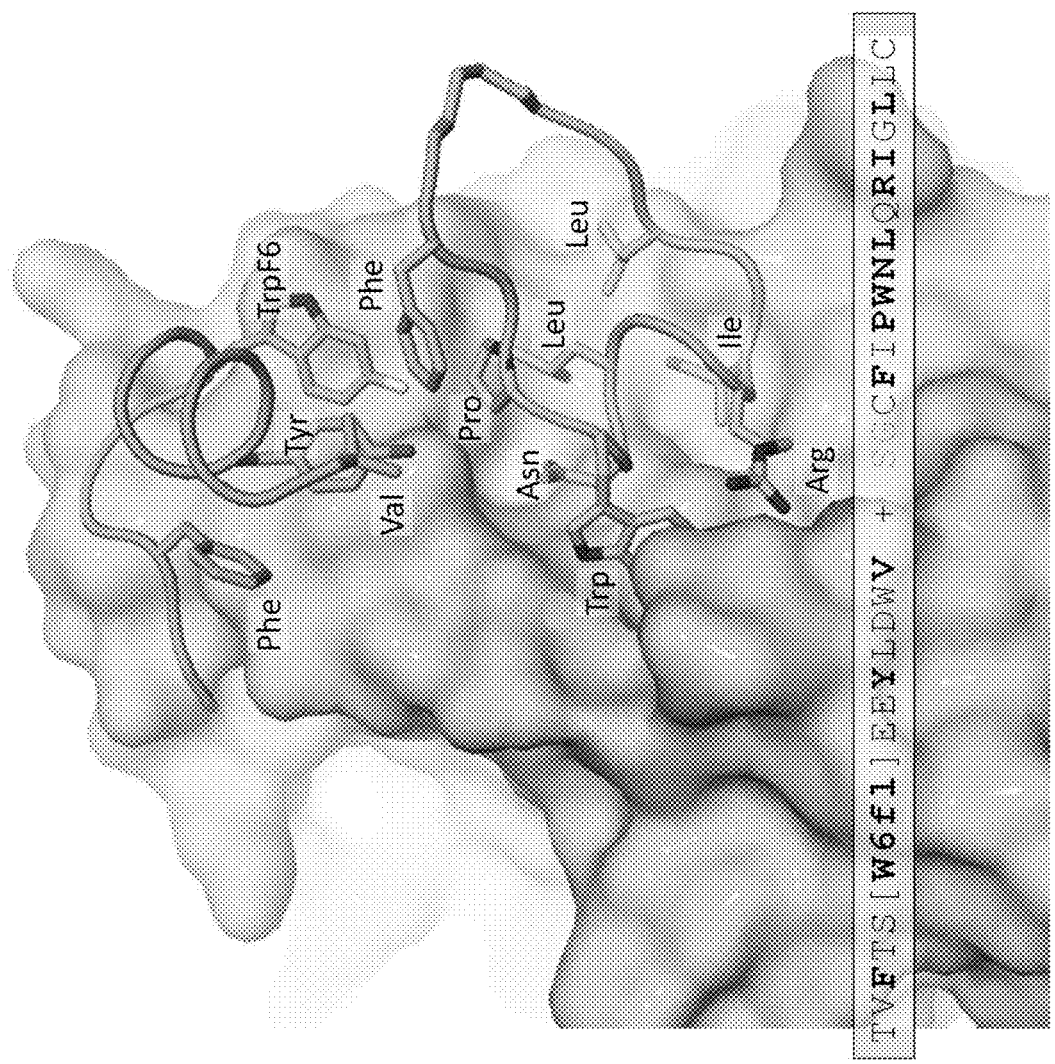
FIG. 24 shows the crystal structure of PCSK9ΔCRDΔhelix with the bound extension peptide Compound 26 co-crystallized with Pep2-8(W6fl) (Compound 3) (SEQ ID NOS 30 and 383, respectively, in order of appearance).
Figure 25:
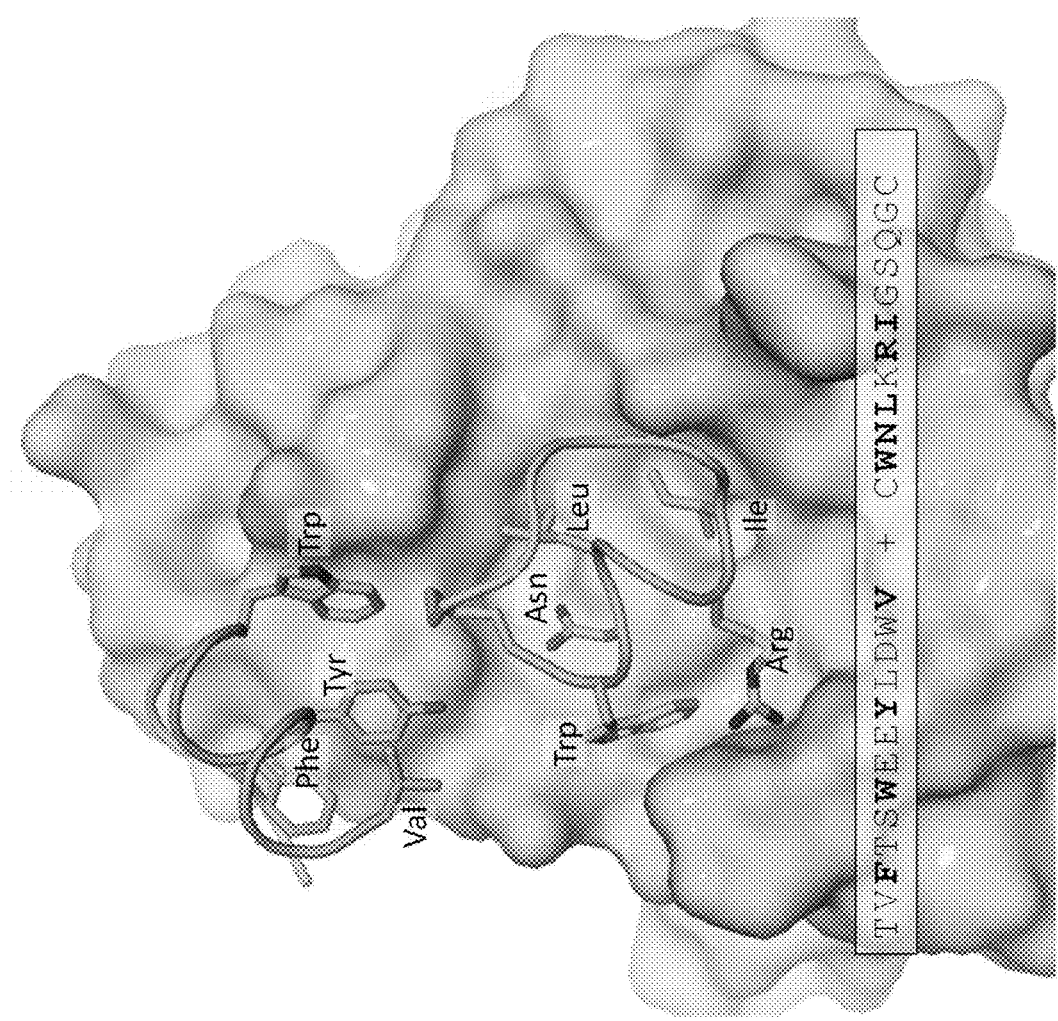
FIG. 25 shows the crystal structure of PCSK9ΔCRDΔhelix with the bound extension peptide Compound 21 co-crystallized with Pep2-8 (SEQ ID NOS 3 and 6, respectively, in order of appearance).
Figure 26:
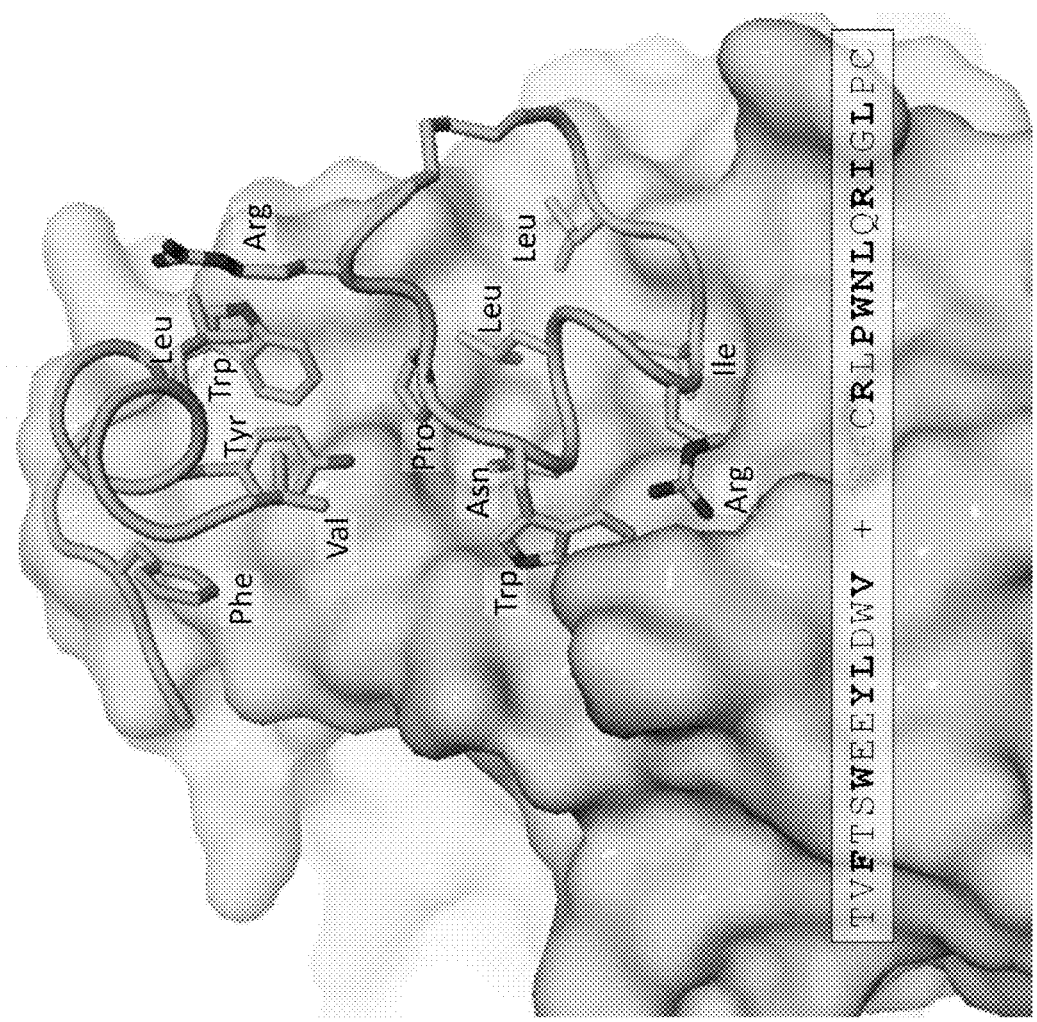
FIG. 26 shows the crystal structure of PCSK9ΔCRDΔhelix with the bound extension peptide Compound 30 co-crystallized with Pep2-8 (SEQ ID NOS 3 and 386, respectively, in order of appearance).
Figure 27:
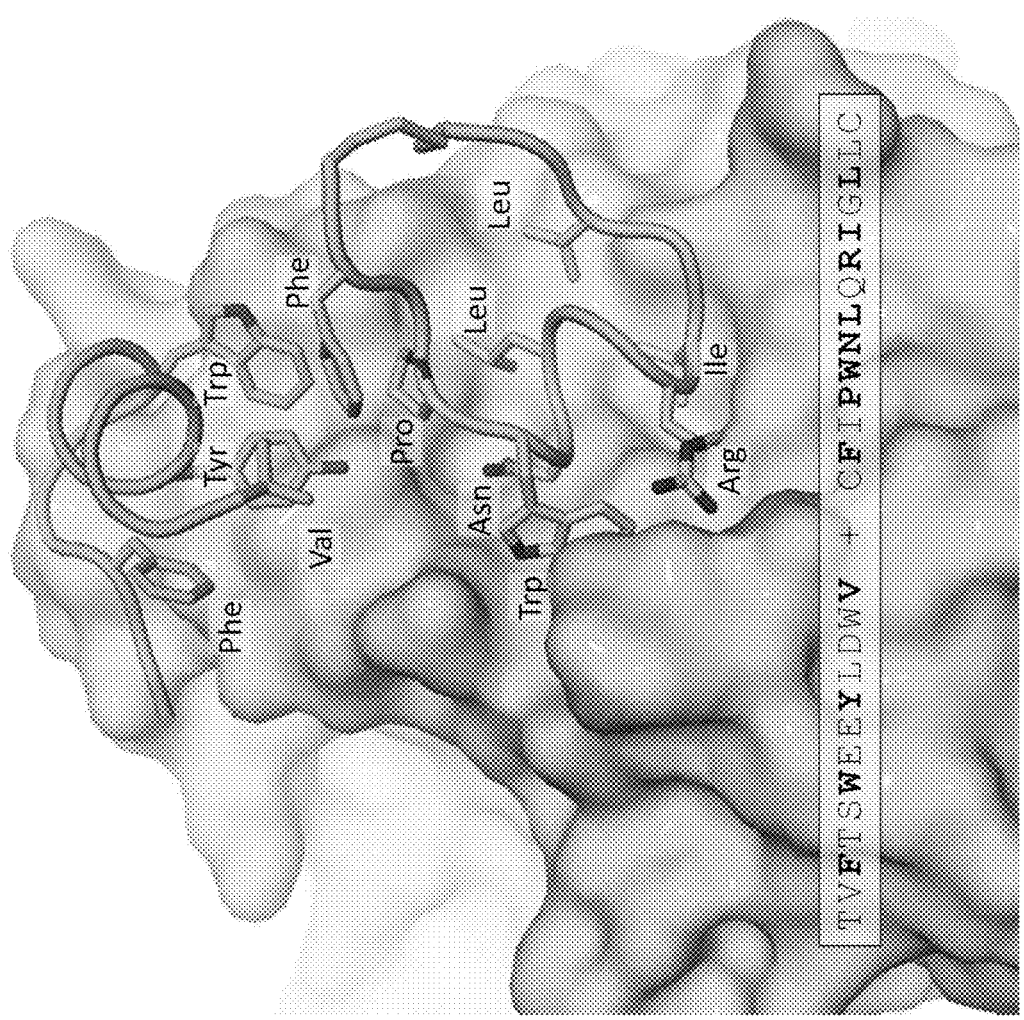
FIG. 27 shows the crystal structure of PCSK9ΔCRDΔhelix with the bound extension peptide Compound 31 co-crystallized with Pep2-8 (SEQ ID NOS 3 and 53, respectively, in order of appearance).
Figure 28:
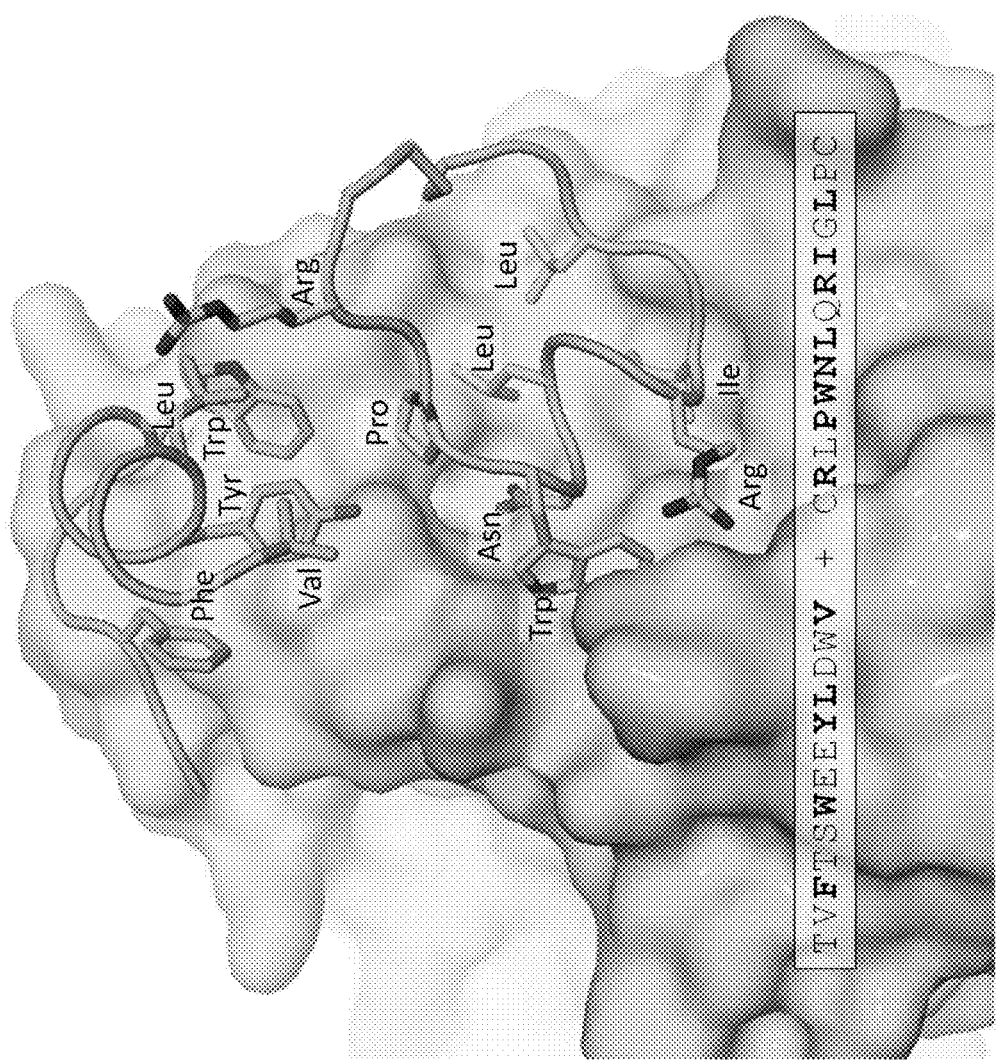
FIG. 28 shows the crystal structure of PCSK9ΔCRDΔhelix with the bound extension peptide Compound 32 co-crystallized with Pep2-8 (SEQ ID NOS 3 and 54, respectively, in order of appearance).

One further set of peptides that have been shown by crystallography to bind to the N-terminal groove site contain a disulfide-constrained macrocycle within which is the PWNLxRIG motif (SEQ ID NO: 296) flanked by two N-terminal and two C-terminal residues (e.g. Compound 26, FIG. 23; Compound 30, FIG. 26; Compound 31, FIG. 27, and Compound 32, FIG. 28). The hydrophobic residues corresponding to L7 of Compound 31 were involved in van der Waals contacts with other residues of the peptide and thus may have helped to stabilize the binding conformation. The leucine residues corresponding to L12 of Compound 31 were involved in hydrophobic contacts with PCSK9 (V241 and L444). The residues corresponding to L13 of Compound 31 did not make specific contacts to PCSK9; the varied conformations observed for this residue and both cysteine residues suggests a role as linker to restrain the conformation of the PWNLxRIG motif (SEQ ID NO: 296).

Compound 26 is identical to Compound 31 except for replacing the N-terminal acetyl group with "SG". The same interactions found between Compound 31 and PCSK9ΔCRDΔhelix, were also observed between Compound 26 and PCSK9 when Compound 26 was co-crystallized with PCSK9ΔCRDΔhelix and Compound 3, a modified version of Pep2-8 in which W6 was replaced by a 6-fluorotryptophan residue (FIG. 24). The addition of the fluorine improved the binding of Compound 3 to PCSK9 relative to Pep2-8 by about 3-fold (Table 7), most likely due to additional hydrophobic contacts between the fluorine and A239, I369 and P155 of PCSK9.

Methods

Expression, Purification and Crystallization of PCSK9ΔCRDΔHelix

Recombinant baculovirus bearing human PCSK9 construct R29-G452 with an engineered TEV site (residue deletion Y166,R167; insertion ENLYFQS (SEQ ID NO: 291) sequence between R165 and A168, DNA 766281, PCSK9ACRDTEV7) was generated using the Baculo-Gold™ system as described by the manufacturer (BD Biosciences). Expression was performed in Sf9 cells in baculovirus media in a 10 liter Wave® bioreactor for 72 hours. The medium containing expressed protein was treated with 1 mM nickel chloride, 2 mM calcium chloride and adjusted to pH 7.5 using sodium hydroxide. The resulting precipitate was removed by low speed centrifugation. The supernatant was concentrated using Millipore tangential flow over a 10 kDa membrane and buffer exchanged into PBS with 10% glycerol to a final volume of 1 liter. The PCSK9ACRDTEV7 was purified using a 5 mL HisTrap HP column (GE Healthcare) on an AKTA Explorer equilibrated in PBS with 10% glycerol. The PCSK9ΔCRDTEV7 was eluted with 10 mL 0.3 M imidazole/PBS/10% glycerol, which was directly loaded onto a Superdex 75 16/60 column (GE Healthcare) equilibrated in 0.25 M NaCl, 50 mM Tris pH 8, 10% glycerol.

The PCSK9ΔCRDTEV7 was then treated with TEV protease (100 μL at 2.5 mg/mL per 10 mg of protein) for 24 hours at 4° C. using dialysis (Slidelyzer 10K (Thermo Scientific)) versus 0.15 M NaCl, 50 mM Tris pH 8.0, 10% glycerol and 3 mM reduced glutathione/0.3 mM oxidized glutathione. The resulting PCSK9ΔCRDΔhelix PCSK9 was concentrated to 2 mL and passed through a Superdex 75 16/60 column in 1 M NaCl, 25 mM Tris pH 8.0. The protein was assayed using mass spectrometry and SDS PAGE. The final pool was then buffer exchanged (NAPS, GE Healthcare) into 0.2 M NaCl, 40 mM Tris pH 8.0, 5% glycerol and concentrated for crystallization trials to 10 mg/mL using a 10 kDa cutoff spin concentrator.

Co-crystallization trials using PCSK9ΔCRDΔhelix and one or two peptides were initiated by incubating the stock PCSK9ΔCRDΔhelix protein with a 2-fold molar excess of peptide(s) overnight at 4° C. Crystallization trails employed commercially available sparse matrix screens and a Mosquito liquid handler (Labtech). The best crystals grew as thin hexagonal plates in sitting drops at 18° C. using 0.2 M calcium acetate, 0.1 M Tris pH 8.0 and 20% (w/v) PEG 6000. Harvested crystals were treated with crystallization reservoir augmented with 30% (v/v) glycerol and suddenly immersed in liquid nitrogen prior to data collection.

Structure Determination of PCSK9ΔCRDΔHelix in Complex with Peptides

All peptide complexes of truncated PCSK9ΔCRDΔhelix crystallized in space group P3$_2$21. In each case, diffraction data were collected from a single cryo-preserved crystal at 110 K using X-rays of about 1 Å wavelength (Tables 3-5) and reduced using either HKL2000 (Otwinowski and Minor, Methods in Enzymol, 1997. 276: p. 307-326) or XDS (Kabsch, Acta Crystallogr D Biol Crystallogr, 2010. 66(Pt 2): p. 125-32; Vonrhein et al., Acta. Crystallogr., 2011. D67: p. 293-302) and elements of the CCP4 suit (Winn et al., Acta Crystallogr D Biol Crystallogr, 2011. 67(Pt 4): p. 235-242). The first structure was solved using molecular replacement with the short-form PCSK9 (PCSK9ΔCRD) in PDB accession code 4NMX as search probe. A single set of reflections sequestered from refinement for calculation of RFREE was used for all structures. Refinement (Murshudov et al., Acta Crystallogr D Biol Crystallogr, 2011. 67: p. 355-367; Adams et al., Acta Crystallogr D Biol Crystallogr, 2010. 66(Pt 2): p. 213-21; Bricogne et al., BUSTER version 2.11.2. 2011, Global Phasing Ltd.: Cambridge, United Kingdom) included automated water placements for higher resolution structures and TLS treatment of displacement factors. Model building and inspection of electron density maps was performed using Coot (Emsley et al., Acta Crystallogr D Biol Crystallogr, 2010. 66(Pt 4): p. 486-501).

TABLE 3

| | Compounds | | |
|---|---|---|---|
| | Compound 2 | Compound 20 | Compound 17 |
| Data | | | |
| X-ray source | ALS 5.0.1 | ALS 5.0.1 | ALS 5.0.2 |
| Wavelength (Å) | 0.9774 | 0.9774 | 1.0000 |
| Res. range (Å) | 26.27-2.15 (2.223-2.15) | 50.01-2.4 (2.48-2.40) | 50.01-2.05 (2.12-2.05) |
| Space group | P 32 2 1 | P 32 2 1 | P 32 2 1 |
| cell a = b = c (Å) | 70.285 70.285 156.026 | 70.267 70.267 157.254 | 70.473 70.473 163.269 |
| cell α, β, γ (°) | 90 90 120 | 90 90 120 | 90 90 120 |

TABLE 3-continued

| | Compounds | | |
|---|---|---|---|
| | Compound 2 | Compound 20 | Compound 17 |
| Total refs | 163523 | 128197 | 209443 |
| Unique refs | 23699 | 16868 | 30354 |
| Multiplicity | 6.9 (7.0) | 7.6 (7.8) | 6.9 (5.6) |
| Complete (%) | 94.7 (100) | 92.1 (100) | 99.9 (99.9) |
| Mean I/sigma(I) | 22.3 (3.2) | 22.3 (5.4) | 12.8 (2.7) |
| Wilson B ($Å^2$) | 35.4 | 34.6 | 25.9 |
| R-symm | 0.082 (0.709) | 0.085 (0.401) | 0.124 (0.664) |
| Refinement | | | |
| Refs for R-free | 932 | 707 | 1228 |
| R-work | 0.177 | 0.210 | 0.189 |
| R-free | 0.203 | 0.268 | 0.235 |
| No. non-H atoms | 3034 | 3030 | 3257 |
| macromolecules | 2905 | 2890 | 2938 |
| water | 122 | 138 | 301 |
| Protein residues | 383 | 379 | 381 |
| RMS (bonds) (Å) | 0.008 | 0.009 | 0.008 |
| RMS (angles) (°) | 1.26 | 1.06 | 1.23 |
| Rama. fav. (%) | 96 | 97 | 97 |
| Ave B-factor ($Å^2$) | 35.0 | 36.1 | 28.5 |
| macromolecules | 35.0 | 35.9 | 27.7 |
| water | 35.3 | 38.9 | 36.6 |

TABLE 4

| | Compounds | | |
|---|---|---|---|
| | Pep2-8 and Compound 26 | Compound 3 and Compound 26 | Pep2-8 and Compound 21 |
| Data | | | |
| X-ray source | ALS 5.0.2 | ALS 5.0.2 | ALS 5.0.2 |
| Wavelength (Å) | 0.9786 | 1.0000 | 1.0000 |
| Res. range (Å) | 48.29-1.9 (1.97-1.90) | 35.35-2.60 (2.69-2.60) | 48.68-2.60 (2.70-2.60) |
| Space group | P 32 2 1 | P 32 2 1 | P 32 2 1 |
| cell a = b = c (Å) | 70.404 70.404 158.193 | 70.7 70.7 160.637 | 70.647 70.647 160.736 |
| cell α, β, γ (°) | 90 90 120 | 90 90 120 | 90 90 120 |
| Total refs | 329913 | 102844 | 82275 |
| Unique refs | 36657 | 14692 | 27489 |
| Multiplicity | 9.0 (91.) | 7.0 (6.7) | 5..6 (4.8) |
| Complete (%) | 100 (100) | 98.5 (99.7) | 100 (100) |
| Mean I/sigma(I) | 21.0 (4.4) | 10.6 (2.2) | 10.1 (2.8) |
| Wilson B ($Å^2$) | 30.6 | 64.9 | 41.0 |
| R-symm | 0.085 (0.554) | 0.148 (0.743) | 0.166 (0.685) |
| Refinement | | | |
| Refs for R-free | 1462 | 608 | 614 |
| R-work | 0.165 | 0.242 | 0.187 |
| R-free | 0.186 | 0.289 | 0.262 |
| No. non-H atoms | 3182 | 2926 | 2998 |
| macromolecules | 2937 | 2925 | 2891 |
| water | 240 | 0 | 93 |
| Protein residues | 383 | 375 | 383 |
| RMS (bonds) (Å) | 0.007 | 0.008 | 0.01 |
| RMS (angles) (°) | 1.16 | 1.03 | 1.16 |
| Rama. fav. (%) | 98 | 95 | 97 |
| Ave B-factor ($Å^2$) | 36.6 | 53.7 | 42.7 |
| macromolecules | 36.1 | 53.7 | 42.5 |
| water | 43.2 | — | 45.7 |

TABLE 5

| | Compounds | | |
|---|---|---|---|
| | Pep2-8 and Compound 30 | Pep2-8 and Compound 31 | Pep2-8 and Compound 32 |
| Data | | | |
| X-ray source | APS 22-ID | APS 22-ID | APS 22-ID |
| Wavelength (Å) | 1.0000 | 1.0000 | 1.0000 |

TABLE 5-continued

| | Compounds | | |
|---|---|---|---|
| | Pep2-8 and Compound 30 | Pep2-8 and Compound 31 | Pep2-8 and Compound 32 |
| Res. range (Å) | 29.43-2.74 (2.84-2.74) | 29.34-2.37 (2.46-2.37) | 30.08-2.86 (2.97-2.86) |
| Space group | P 32 2 1 | P 32 2 1 | P 32 2 1 |
| cell a = b = c (Å) | 70.803 70.803 158.799 | 70.566 70.566 158.487 | 70.748 70.748 158.784 |
| cell α, β, γ (°) | 90 90 120 | 90 90 120 | 90 90 120 |
| Total refs | 44939 | 66073 | 75341 |
| Unique refs | 12483 | 17515 | 10763 |
| Multiplicity | 3.6 (3.5) | 3.8 (3.5) | 7.0 (7.0) |
| Complete (%) | 98.5 (99.5) | 91.2 (94.5) | 97.2 (84.7) |
| Mean I/sigma(I) | 8.8 (2.1) | 13.6 (2.1) | 10.7 (2.2) |
| Wilson B (Å$^2$) | 57.4 | 42.0 | 64.0 |
| R-symm | 0.153 (0.867) | 0.074 (0.677) | 0.149 (0.641) |
| Refinement | | | |
| Refs for R-free | 508 | 726 | 442 |
| R-work | 0.189 | 0.184 | 0.188 |
| R-free | 0.239 | 0.243 | 0.259 |
| No. non-H atoms | 2947 | 3013 | 2918 |
| macromolecules | 2914 | 2914 | 2913 |
| water | 28 | 94 | 0 |
| Protein residues | 384 | 384 | 384 |
| RMS (bonds) (Å) | 0.009 | 0.009 | 0.01 |
| RMS (angles) (°) | 1.08 | 1.1 | 1.15 |
| Rama. fav. (%) | 96 | 96 | 94 |
| Ave B-factor (Å$^2$) | 57.1 | 46.2 | 70.9 |
| macromolecules | 57.1 | 46.2 | 70.8 |
| water | 54.6 | 47.9 | — |

TABLE 6

| Compound 2 | Residues on PCSK9ΔCRDΔhelix | | |
|---|---|---|---|
| Peptide Residue | Van der Waals | Hydrogen bond | Ionic |
| W18 | T339, N340, A341, P364, D367, I368 | E366CO | |
| N19 | P364, I368, H391 | I369NH, D367CO, G370CO and A239CO via buried water molecules | |
| L20 | A239, G240, V241 | | |
| R22 | | A341CO | D343 |
| I23 | P364, A442, A443, L444 | L444NH | |

Example 4: Binding Affinities of Groove-Binding Peptides Determined by Surface Plasmon Resonance (SPR)

Results

The Pep2-8-groove-binding fusion peptides, Compound 2, Compound 17, Compound 19, and Compound 20 bound with high affinity to both PCSK9 and PCSK9Δhelix (Table 7). The high affinity, reaching $K_d$ values in the sub-nanomolar range for PCSK9Δhelix binding (Compound 17, Compound 19, and Compound 20; Table 7) is consistent with structural results showing that both the Pep2-8 and the groove-binding peptide of the fusion peptides make interactions with PCSK9 (Compound 2 in FIG. 20; Compound 17 in FIG. 22; Compound 20 in FIG. 21).

The groove-binding peptides depicted in Table 7 all bound to PCSK9Δhelix with $K_d$ values in the M or sub-μM range. The two peptides with the highest affinity for PCSK9Δhelix were Compound 32 ($K_d$ 0.21 μM) and Compound 73 ($K_d$ 0.167 μM). In general, the binding affinities to PCSK9Δhelix were stronger as compared to PCSK9, which is due to absence of the P' helix in the PCSK9Δhelix constructs enabling direct groove access by the peptides without any competition with the P' helix in PCSK9. In addition, the replacement of W6 to fluoro-W6 in Pep2-8 (Compound 3 in Table 7) resulted in a several fold increased binding affinity to PCSK9 and to PCSK9Δhelix.

The results demonstrate that the groove-binding peptides are able to bind to both PCSK9 and to PCSK9Δhelix with binding affinities in the μM and sub-μM range.

TABLE 7

| SEQ ID NO: | Compound No. | Peptide | Target | $K_d$ (nM) |
|---|---|---|---|---|
| 286 | Pep2-8 | Ac-TVFTSWEEYLDWV-NH$_2$ | PCSK9Δhelix | 11760 |
| | | | PCSK9 | 4533 |
| 29 | 2 | Ac-TVFTSWEEYLDWV-GSG-CWNLKRIGSQGC-NH$_2$ | PCSK9Δhelix | 1.871 |
| | | | PCSK9 | 30.300 |
| 30 | 3 | Ac-TVFTS(W6fl)EEYLDWV-NH$_2$ | PCSK9Δhelix | 2580 |
| | | | PCSK9 | 1400 |

TABLE 7-continued

| SEQ ID NO: | Compound No. | Peptide | Target | $K_d$ (nM) |
|---|---|---|---|---|
| 44 | 17 | Ac-TVFTSWEEYLDWV-(Ahx)-CWNLKRIGSQGC-NH$_2$ | PCSK9Δhelix<br>PCSK9 | 0.123<br>2.238 |
| 46 | 19 | Ac-TVFTSWEEYLDWV-GSG-CRLPWNLQRIGLPC-NH$_2$ | PCSK9Δhelix<br>PCSK9 | 0.0989<br>2.068 |
| 47 | 20 | Ac-TVFTSWEEYLDWV-GSG-DLMPWNLVRIGLLR-NH$_2$ | PCSK9Δhelix<br>PCSK9 | 0.3661<br>5.562 |
| 50 | 23 | Ac-SPCRVGYTPC-NH$_2$ | PCSK9Δhelix<br>PCSK9 | 754.100<br>5736.000 |
| 53 | 26 | SG-CFIPWNLQRIGLLC-NH$_2$ | PCSK9Δhelix<br>PCSK9 | 802.5<br>29040 |
| 55 | 28 | SG-DLMPWNLVRIGLLR | PCSK9Δhelix<br>58PCSK9 | 856<br>46100 |
| 58 | 31 | Ac-CFIPWNLQRIGLLC-NH$_2$ | PCSK9Δhelix<br>PCSK9 | 3010<br>5830 |
| 59 | 32 | Ac-CRLPWNLQRIGLPC-NH$_2$ | PCSK9Δhelix<br>PCSK9 | 210<br>1300 |
| 60 | 33 | FAM-SGSG-CFIPWNLQRIGLLC-NH$_2$ | PCSK9Δhelix<br>PCSK9 | 10000<br>6010 |
| 61 | 34 | FAM-SGSG-CRLPWNLQRIGLPC-NH$_2$ | PCSK9Δhelix<br>PCSK9 | 5280<br>4470 |
| 72 | 45 | Ac-ALMPWNLVRIGLLR-NH$_2$ | PCSK9Δhelix<br>PCSK9 | 8200<br>117000 |
| 77 | 50 | Ac-LMPWNLVRIGLLR-NH$_2$ | PCSK9Δhelix<br>PCSK9 | 1600<br>16100 |
| 78 | 51 | Ac-MPWNLVRIGLLR-NH$_2$ | PCSK9Δhelix<br>PCSK9 | 2700<br>26200 |
| 79 | 52 | Ac-PWNLVRIGLLR-NH$_2$ | PCSK9Δhelix<br>PCSK9 | 2600<br>17900 |
| 80 | 53 | Ac-WNLVRIGLLR-NH$_2$ | PCSK9Δhelix<br>PCSK9 | 33800<br>223000 |
| 82 | 55 | Ac-DLMPWNLVRIGLAR-NH$_2$ | PCSK9Δhelix<br>PCSK9 | 2800<br>96500 |
| 100 | 73 | Ac-CRLPWNLARIGLPC-NH$_2$ | PCSK9Δhelix<br>PCSK9 | 167<br>11000 |
| 109 | 82 | Ac-CRL(Ach)WNLQRIGLPC-NH$_2$ | PCSK9Δhelix<br>PCSK9 | 6400<br>117600 |
| 123 | 96 | Ac-FCLWNLKRIGAQCWF-NH$_2$ | PCSK9Δhelix<br>PCSK9 | 2500<br>46400 |
| 124 | 97 | Ac-GSG-CWNL(Dpr)RIGSQGC-NH | PCSK9Δhelix<br>PCSK9 | 89200<br>522000 |

Methods

Biosensor-Based Affinity Analysis

All assays were conducted at an analysis temperature of 20° C. Samples were held at 10° C. in the sample rack to prevent denaturation of PCSK9 proteins. A biacore T100 from GE HealthCare and a SensiQ Pioneer FE were employed. All reagents were obtained from Sigma-Aldrich unless otherwise stated. The full set of peptides was analyzed using three closely related biosensor protocols that were expected to report equivalent affinity/kinetic parameters. The need for multiple protocols was related to the aggregation potential of some peptides. The buffer composition was largely conserved other than the addition of solubilizers such as dimethylsulfoxide (DMSO), 10 kDa polyvinylpyrrolidone (PVP) and 10 kDa carboxymethylated dextran (CM dextran).

Method 1

Pep2-8, and Compounds 19, 20, 26, and 28 were analyzed using Method 1. A Series S NTA sensor chip was docked in the Biacore T100 biosensor system. The system was primed into running buffer (i.e. 50 mM HEPES, 0.15 M NaCl, 0.005% T20, pH 7.5). Hexahistidine-tagged proteins ("hexahistidine" disclosed as SEQ ID NO: 297) (i.e. PCSK9 or PCSK9Δhelix) were affinity captured onto separate sensing channels where at least one sensing surface remained uncoated in order to be applied as a referencing sensing surface. Compound samples were prepared in running buffer and injected. All affinity bound complexes were then removed before reloading each protein in order to test the next sample. Each sample cycle therefore consisted of five sequential injections that were repeated for each test sample as follows.

Injection 1

0.25 M ethylenediaminetetraacetic acid (EDTA) was injected for three minutes at a flow rate of 30 µL/minute over all sensing channels. This exposure removes all affinity complexes that are bound via a chelate linkage between poly-histidine and the Ni-NTA complexes and also removes any contaminating metal ions.

Injection 2

A nickel solution (1 mM Ni in deionized ultrapure water) was injected for 30 seconds at a flow rate of 30 µL/minute over all sensing channels. Ni ions form complexes with nitrilotriacetic acid that is pre-bound within the hydrogel-based sensing surface. When charged with Ni the resulting metal-NTA complexes enable high affinity binding to poly-histidine tagged proteins.

Injection 3

Prepared PCSK9Δhelix protein at 3 µg/mL in running buffer was injected for 80 seconds at a flow rate of 30 µL/minute over a single Ni-NTA activated sensing channel.

Injection 4

Prepared PCSK9 at 5 µg/mL in running buffer was injected for 20 seconds at a flow rate of 30 µL/minute over a single Ni-NTA activated sensing channel. The baseline was allowed stabilize for five minutes before injecting sample.

Injection 5

Injected sample using high quality injection mode. Compound 19 and Compound 20 were prepared as six serial doubling dilutions and each was injected at a flow rate of 50 µL/minute for 100 seconds with 900 seconds dissociation over all sensing channels. Pep2-8, Compound 26, and Compound 28 were prepared as eight serial doubling dilutions and each injected at a flow rate of 50 µL/minute for 100 seconds with 900 seconds dissociation over all sensing channels. For these compounds the entire sample cycle consisting of five serial injections was repeated for each dilution. This sample cycle was a repeated sequence that is executed for each sample in the sample table.

Method 2

Compound 2, Compound 23, and Compound 17 were analyzed using Method 2. This method was identical to method 1 except an alternative injection mode designated as single cycle kinetics (named by the manufacturer) was employed allowing a full dilution series to be completed during each sample cycle by replacing a single compound dilution injection with five sequential injections of increasing concentration. The resulting sensorgram (i.e. response curve) contained five binding-dissociation phases each associated with each injected compound dilution. The activation, capture and regeneration injections remained unchanged. Compounds were diluted to make five serial doubling dilutions from 100 nM for Compound 17 and 100 µM for all other compounds. Also CM dextran (Sigma-Aldrich product number 86524) was added to all buffers in the assay to a final concentration of 2 mg/mL in order to further lower non-specific binding to the surface. However Compound 17 was analyzed using the same single cycle kinetic, and an identical protocol, with the exception of omission of CM dextran, which was not required as non-specific binding was absent for this peptide. All recorded binding curves were automatically double referenced and fitted with a 1:1 model using BIAevaluation analysis software from GE HealthCare.

Method 3

Compound 31, Compound 32, Compound 33, Compound 34, Compound 3, Compound 73, Compound 50, Compound 52, Compound 51, Compound 55, Compound 82, Compound 45, Compound 96, Compound 53, and Compound 97 were analyzed using Method 3. Given the tendency of some peptides to aggregate it was decided that peptide analysis would be improved further by employing an alternative biosensor technology marketed as SensiQ Pioneer FE. This instrument is analogous to Biacore AB biosensors in terms of surface chemistry, flow injection analysis and methodologies that can be employed except that it also provides a method to titrate compounds over the sensing surfaces. The titration is formed using a capillary (Quinn, Analytical Biochemistry 421: 391, 2012; Quinn, Analytical Biochemistry 421: 401, 2012) and like conventional surface plasmon resonance-based biosensors, it produces binding response curves that report binding kinetics and affinity but unlike other technologies it reports a descriptor of compound aggregation owing to the dependence of the compounds gradient profile on molecular weight.

In this case both the PCSK9 and PCSK9Δhelix were immobilized by standard direct amine coupling according to the manufacturers recommendations onto a COOHV sensor chip yielding in excess of 2000RU of each covalently bound to separate sensing channels. The running buffer was reformulated to further reduce both aggregation and non-specific binding to the sensing surface and contained 50 mM HEPES, pH 7.2, containing 0.15 M NaCl, 3 mg/mL PVP, 1 mM EDTA, 0.005% Tween® 20, 1 mg/mL CM dextran and 5% DMSO. Each compound was prepared in running buffer at 20 µM, sonicated for 15 min, and a 5 µM sample of each was then prepared with attention to matching the concentration of dimethylsulfoxide of the final sample to that of the running buffer. Both 20 µM and 5 µM dilutions of each compound were analyzed by gradient injection. The injection was performed using the OneStep injection mode at a flow rate of 100 µL/min with a 200 second dissociation time. All binding curves exhibited rapid kinetics implying that the binding curves represented steady-state responses. Therefore all recorded binding curves were double referenced and fitted with a 1:1 affinity model using Qdat data analysis software from SensiQ Pioneer Inc.

Example 5: Groove-Binding Peptides Rescue LDLR on HepG2 Cells

Results

Figure 29:
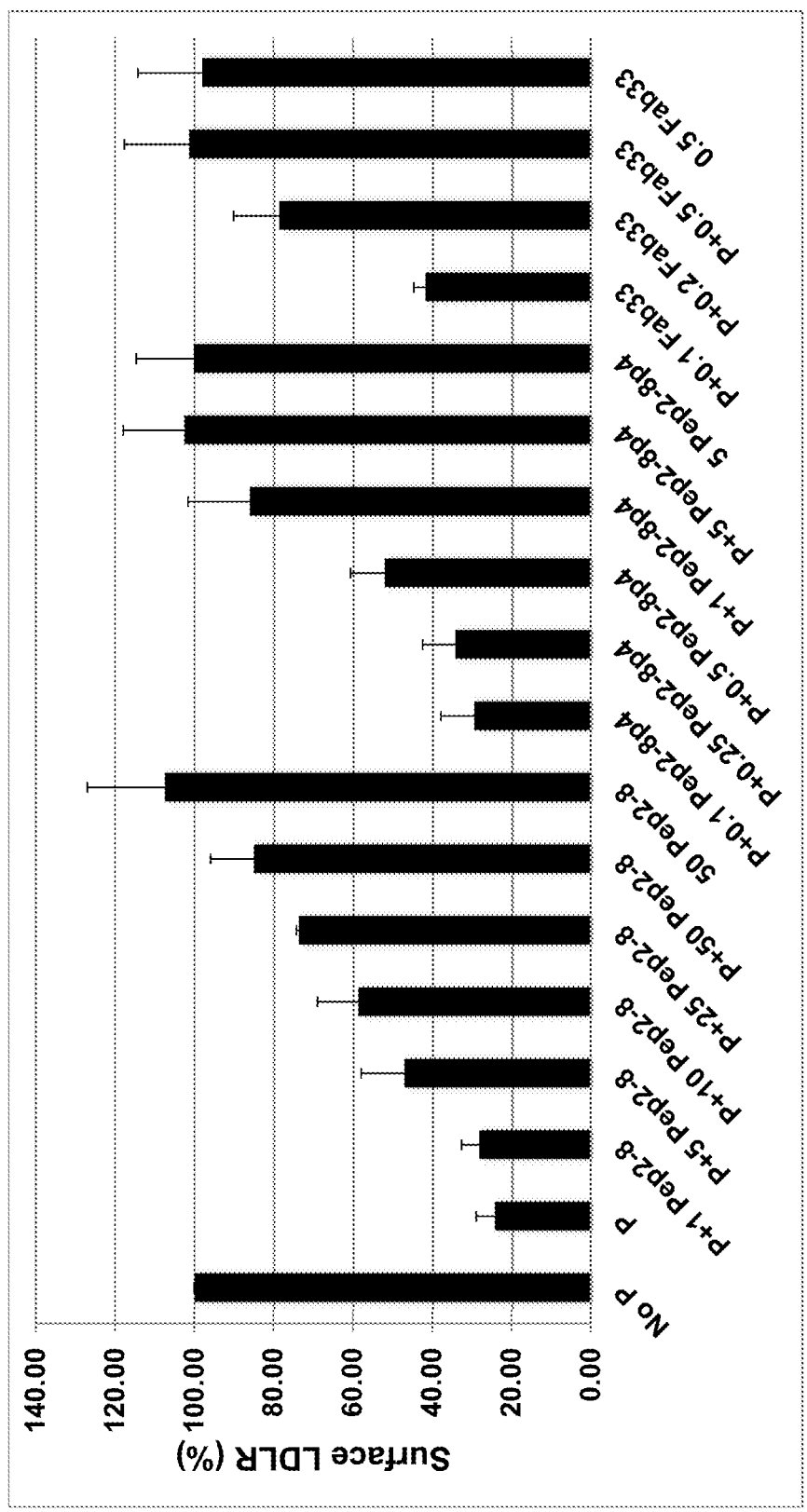
FIG. 29 shows the effects of fusion peptide Compound 19 (Pep2-8p4) on LDLR restoration on HepG2 cells. Exposure of HepG2 cells to recombinant PCSK9 (P) reduced the levels of surface exposed LDLR by about 75% as measured by FACS. Addition of Compound 19 (0.1-5.0 μM) restored LDLR levels to 100% in a concentration-dependent fashion, with an $EC_{50}$ value of about 0.5 μM. The experiment included the control peptide Pep2-8 (1.0-50 μM) and Fab33 (0.1-0.5 μM).
Figure 30:
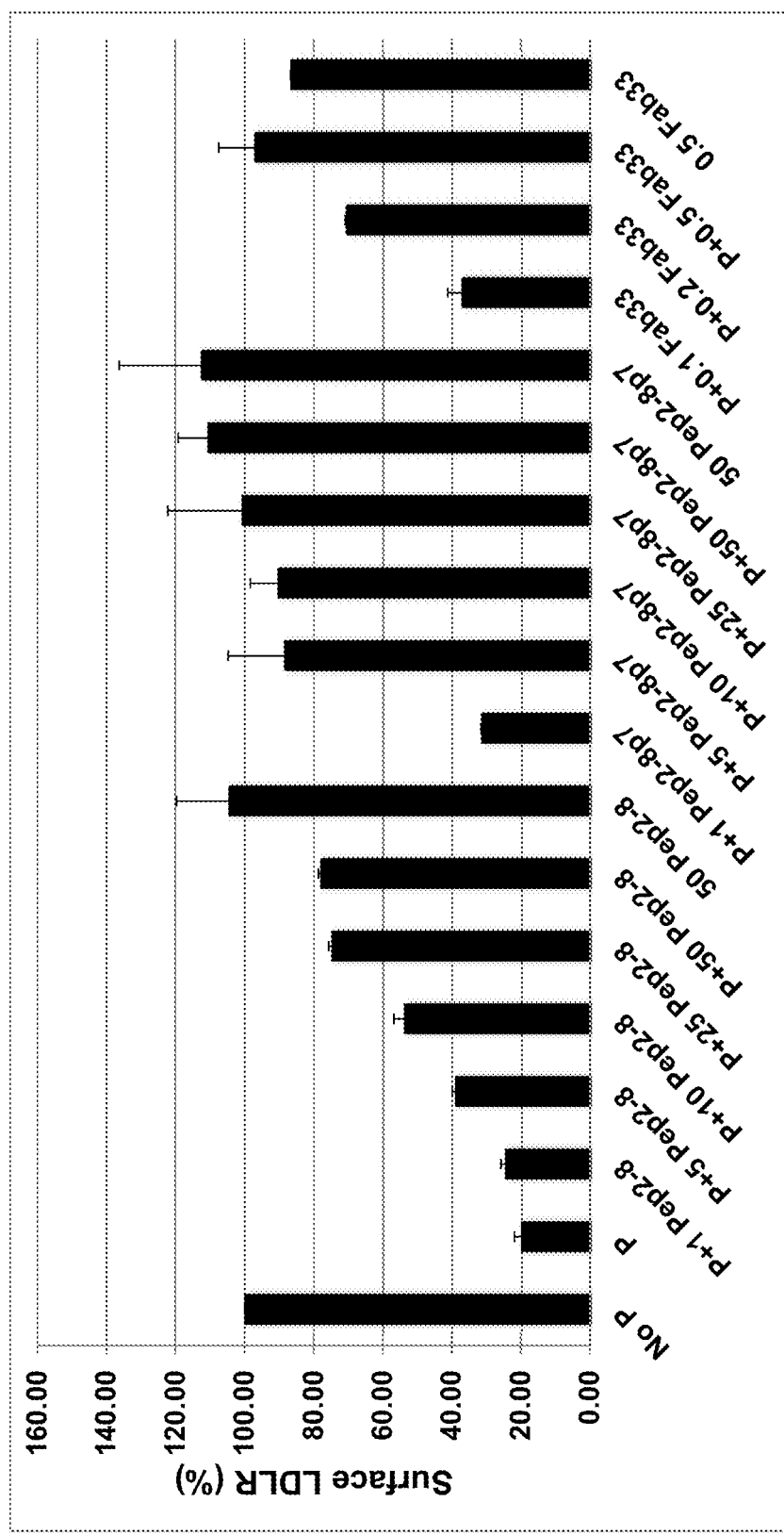
FIG. 30 shows the effects of fusion peptide Compound 20 (Pep2-8p7) on LDLR restoration on HepG2 cells. Exposure of HepG2 cells to recombinant PCSK9 (P) reduced the levels of surface exposed LDLR by about 80% as measured by FACS. Addition of Compound 20 (1.0-50 μM) restored LDLR levels to 100% in a concentration-dependent fashion, with an $EC_{50}$ value of about 1-5 μM. Both experiments included the control peptide Pep2-8 (1.0-50 μM) and the Fab33 (0.1-0.5 μM).

Treatment of HepG2 cells with rec.PCSK9 reduced LDLR surface levels by about 75% (FIGS. 29 and 30). Pep2-8 by itself was able to restore LDLR levels to 50% at a concentration of about 5-10 µM. The Fab33 was more potent, achieving 50% LDLR restoration at concentrations between 0.1-0.2 µM. The two groove-binding peptides Pep2-8p4 (Compound 19: Ac-T V F T S W E E Y L D W V G S G C R L P W N L Q R I G L P C-NH$_2$ (SEQ ID NO: 298)) and Pep2-8p7 (Compound 20: Ac-T V F T S W E E Y L D W V G S G D L M P W N L V R I G L L R—NH$_2$ (SEQ ID NO: 299)) and were much more potent than Pep2-8, restoring LDLR levels to 50% at concentrations of about 0.5 µM and 1-5 µM, respectively (FIGS. 29 and 30).

Methods

Cell Surface LDLR Assay with HepG2 Cells

HepG2 cells (ATCC; Manassas, Va.) were seeded into 48 well plates (Corning; Corning, N.Y.) at 1×10$^5$ cells per well in high glucose medium (DMEM, Gibco; Carlsbad, Calif.) containing 2 mM glutamine (Sigma), penicillin/streptomycin (Gibco) and 10% FBS (Sigma; St. Louis, Mo.) and incubated overnight. Then the medium was changed to DMEM containing 10% lipoprotein deficient serum (LPDS, Sigma). After 24 h, 15 μg/mL PCSK9 was incubated with peptides or Fab33 for 30 min, added to the cells and incubated at 37° C. for 4 h. Cells were rinsed with PBS and detached using Cell Dissociation Buffer in PBS (Gibco). After centrifugation, the resuspended cells were incubated with 1:20 anti LDLR antibody (Progen Biotechnik; Heidelberg, Germany) on ice for 10 min. The samples were then washed with PBS and incubated with 1:200 diluted goat anti mouse IgG (H+L) Alexa Fluor 488 (Invitrogen; Carlsbad, Calif.) on ice for 5 min. After two PBS washes, cells were re suspended in PBS containing 2.5 μg/mL of propidium iodide and analyzed on a dual laser flow cytometer (FACScan, Becton Dickinson; Franklin Lakes, N.J.). Relative fluorescence units (RFUs) were used to quantify LDLR expression levels on the HepG2 cell surface. Cell surface LDLR levels were expressed as percent of LDLR levels measured in the absence of PCSK9 (=control).

Figure 31:
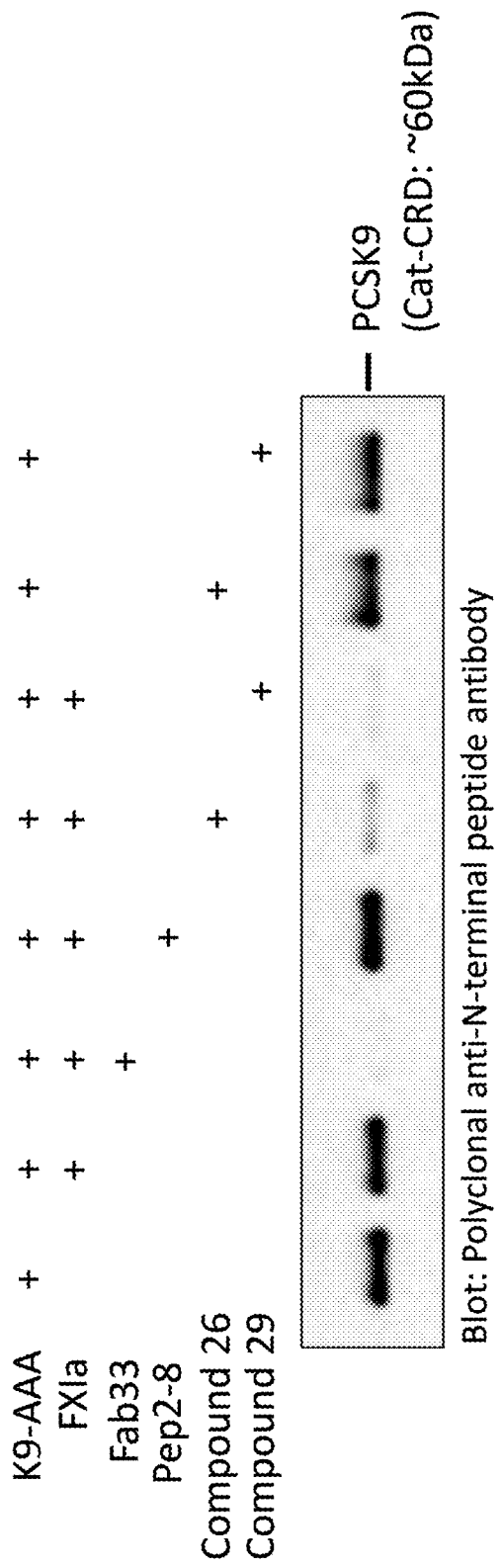
FIG. 31 shows the effects of the two groove-binding peptides, Compound 26 and Compound 29, on FXIa-mediated cleavage of PCSK9-R167A:R215A:R218A (K9-AAA).

Example 6: Groove-Binding Peptides Increase FXIa-Mediated Proteolysis of P' Helix Results The groove-binding peptides Compound 26 and Compound 29 only differ by having a free N-terminus (Compound 26) or an acetylated N-terminus (Compound 29). The determined crystal structure of Compound 26 (Example 3) shows that the peptide binds to the N-terminal groove of PCSK9 (FIG. 23). This peptide bound to PCSK9 with a $K_d$ value of 29 μM as determined in SPR experiments (Example 4, Table 7). The results in FIG. 31 demonstrate that similar to Fab33, both groove binding peptides accelerated the cleavage reaction, leading to almost complete cleavage of the P' helix. In the absence of FXIa, the two peptides had no effect (FIG. 31).

In another experiment, the linear peptides Compound 112 (n-BuC(O)-WNLVRIGLTR-NH$_2$ (SEQ ID NO: 139)) and its derivative Compound 118 (n-BuC(O)-WNLV(homoR)IGLTR-NH$_2$ (SEQ ID NO: 145)), which has a homo-arginine instead of the arginine, were used. The homo-arginine was introduced to prevent cleavage by FXIa, because the S1 pocket of FXIa is unable to accommodate modified or unnatural Arginine residues. Indeed, a time course of FXIa cleavage showed that the homo-arginine-containing peptide Compound 118 remained intact over a 6 h time course, as determined by LC-MS (FIG. 32). In contrast, the Arginine-containing peptide Compound 112 was cleaved in a time-dependent manner: 34% was cleaved after 1 h and 76% after 6 h as quantified by LC-MS (FIG. 33). FIG. 34 shows that incubation of K9-AAA with the uncleavable peptide Compound 118 resulted in a higher degree of P' helix cleavage by FXIa as compared to the peptide Compound 112.

The results demonstrate that the tested peptides Compound 26, Compound 29, Compound 112 and Compound 118 were able to increase the FXIa-mediated cleavage of the P' helix at R160-I161 in a similar fashion as shown for Fab33. The crystal structure of one of these peptides (Compound 26; FIG. 23) shows the peptide to occupy the N-terminal groove site that normally harbors the P' helix. Therefore, similar to Fab33 these peptides keep the P' helix in the ejected "out" conformation, which becomes susceptible to FXIa cleavage. This is consistent with the mechanism depicted in FIG. 12.

Methods

FXIa Cleavage Assay

PCSK9-R167 Å:R215 Å:R218 Å (PCSK9-AAA) at 2.6 μM was incubated in Tris buffer with 50 nM FXIa and either 50 μM of Compound 26, 50 μM of Compound 29, 50 μM Compound 112, or 50 μM Compound 118. Fab33 (2 μM) or Pep2-8 (4 μM) were used as controls. After 20 h (Compound 26 and Compound 29) or 6 h (Compound 112 and Compound 118) incubation at room temperature the samples were analyzed by SDS-PAGE and transferred to a nitrocellulose membrane using iBlot (Invitrogen). Proteins were then probed with a polyclonal rabbit antibody (1:3000) raised against the PCSK9 N-terminal peptide ($^{153}$SIPWN-LERITPPRYRA$^{168}$ (SEQ ID NO: 5)), followed with HRP-conjugated donkey anti-rabbit antibody (1:5000, GE Healthcare) using iBind (Invitrogen). PCSK9 signals were detected by ECL (GE Healthcare) and visualized by autoradiography. Liquid Chromatography-Mass Spectrometry (LC-MS) to Determine Cleavage of Groove-Binding Peptides To determine FXIa-mediated cleavage after Arginine in peptide Compound 112 or after homo-arginine in peptide Compound 118, 10 μl of reaction samples from FXIa cleavage assays (see above) were taken at 0 h, 1 h, 6 h and analyzed by analytical LC-MS on an Agilent 1260 infinity system equipped with a PLRP-S reversed phase column. Peptide cleavage was determined by using the calculated molecular weights and by measuring the area under the curves.

Example 7: Synthesis of Groove-Binding Peptides and Activity in TR-FRET-Based Assays Results Assays were established to measure the binding of molecules to the LDLR-binding site and also to the N-terminal binding groove. The former was based on a TF-FRET assay to measure the association of the EGF(A) domain of the LDLR to PCSK9 ("PCSK9/EGF(A) binding assay") whilst the latter was based on a TR-FRET assay to measure binding of Ab20 to PCSK9Δhelix ("PCSK9Δhelix/Ab20 binding assay"). Molecules were also tested for non-specific binding effects in a counter screen assay using EGF(A) protein with a His-tag at the N-terminus and an Fc domain at the C-terminus ("His-EGF(A)-Fc Counterscreen"); true inhibitors of binding to PCSK9 should not show any reduction in TR-FRET in the counter screen.

Peptides were first synthesized to recapitulate the phage-derived peptide sequences containing the anchor peptide, a linker and the C-terminal extension peptide. The series exemplified by Compound 1 (Table 8A) has comparable activity to Pep2-8 in the PCSK9/EGF(A) binding assay but superior activity in the PCSK9Δhelix/Ab20 binding assay indicating that the C-terminal extension is occupying the N-terminal groove site. Truncations of this peptide (Compounds 4-7) incrementally reduced the potency in the PCSK9Δhelix/Ab20 binding assay indicating weaker interactions with the N-terminal groove. A variety of peptide and non-peptide linkers were used to connect the anchor and extension peptides while maintaining the potency in the PCSK9Δhelix/Ab20 binding assay.

The peptide Compound 20 exemplifies a different sequence identified by phage display. In this case, inhibition in the PCSK9/EGF(A) binding assay is significantly improved relative to Pep2-8 and inhibition in the PCSK9Δhelix/Ab20 binding assay occurred at low nanomolar concentrations.

Anchor peptides with disulfide-linked C-terminal extensions were also assayed (Table 8B). Peptides with the 2 residues between the N-terminal cysteine and the "PWNLxRIG" motif (SEQ ID NO: 296) (Compound 19, Compound 25 and Compound 38) were all potent inhibitors in the PCSK9Δhelix/Ab20 binding assay indicating that the interactions with the N-terminal groove site described in Example 3 are contributing to the binding of these peptides. Compound 19 is also a potent inhibitor of the PCSK9/EGF (A) binding assay. Peptides with the "WNLxRIG" motif (SEQ ID NO: 300) immediately succeeding the N-terminal cysteine residue are also described in Table 8B. Examples with a 4-amino acid linker (Compound 13 and Compound 14) were potent inhibitors in the PCSK9/EGF(A) and PCSK9Δhelix/Ab20 assay formats. Non-peptidic linkers maintained potency in both assays (Compound 15, Compound 17 and Compound 24). Removal of the disulfide bond facilitated the creation of C-terminal truncations in this series; this reduced activity in the PCSK9/EGF(A) assay but activity in the PCSK9Δhelix/Ab20 assay was maintained until truncation beyond the isoleucine of the WNLxRIG motif (SEQ ID NO: 300).

The C-terminal extension peptides were also synthesized without the Pep2-8 anchor component and also tested in the biochemical assays. The linear extension peptides are listed in Table 8C. The 14-residue peptide Compound 35 is the progenitor of this series and does not exhibit any inhibition in the PCSK9/EGF(A) assay binding up to 50 μM but does inhibit in the PCSK9Δhelix/Ab20 assay with an $IC_{50}$ of 4.8 μM. Replacement of individual amino acids with alanine in this peptide emphasized the importance of the WNLxRIG motif (SEQ ID NO: 300)-all of these alanine substitutions abolished inhibition. Similarly, truncations from either the N- or C-terminus of this peptide dramatically reduced the level of inhibition once the truncations approached the WNLxRIG motif. Inhibition could be improved in the N-terminal truncations by replacing the capping acetyl with a valeric acid moiety. Thus, the 10 residue peptides Compound 111 and Compound 112 both inhibit in the PCSK9Δhelix/Ab20 with $IC_{50}$ values less than 10 μM. Replacement of the arginine side chain in the WNLxRIG motif (SEQ ID NO: 300) with a homo-arginine increased the inhibition by 5-fold (Compound 118; PCSK9Δhelix/Ab20 $IC_{50}$ of 1.4 μM).

The disulfide-cyclized extension peptides also showed measurable inhibition in the PCSK9Δhelix/Ab20 binding assay (Table 8D). Thus, Compound 32 (an example of the extension peptide series with 3 residues between the N-terminal cysteine and the WNLxRIG motif (SEQ ID NO: 300)), had an $IC_{50}$ of ~1 μM in the PCSK9Δhelix/Ab20 assay. An alanine-replacement scan performed on this series also indicated the importance of residues in the WNLxRIG motif (SEQ ID NO: 300) for maintaining potent inhibition. Substitution with amino acids of D-stereochemistry within the WNLxRIG motif (SEQ ID NO: 300) also lead to a loss of inhibition. A lysine residue is tolerated at the "x" position of the WNLxRIG motif (SEQ ID NO: 300) (Compound 67; PCSK9Δhelix/Ab20 $IC_{50}$ 0.7 μM), and replacement of the "R" of the motif with homo-arginine also leads to an improvement of inhibition (Compound 117; PCSK9Δhelix/Ab20 $IC_{50}$ 0.33 μM). Replacement of the 4 residues preceding the C-terminal cysteine with an organic linker removes inhibition (Compound 83, Compound 84, Compound 85 and Compound 86) whereas replacing the 3 residues preceding the C-terminal cysteine with an organic linker gives weak but detectable inhibition in the PCSK9Δhelix/Ab20 assay (Compound 116, Compound 121).

A series of disulfide-cyclized peptides with a single residue between the N-terminal cysteine and the WNLxRIG motif (SEQ ID NO: 300) were also found to inhibit in the PCSK9Δhelix/Ab20 assay with $IC_{50}$ values in the low micromolar range, e.g. see Compound 63. With the appropriate exocyclic substitutions, compounds from this series also weakly inhibit in the PCSK9/EGF(A) assay (e.g. Compound 88; PCSK9/EGF(A) assay $IC_{50}$ 17.9 μM), although these compounds also show some weak response in the His-EGF(A)-Fc counter screening assay, suggesting that there may be some element of non-specific binding to their effect.

Finally, in the series of disulfide-cyclized peptides with no residues intervening between the N-terminal cysteine and the WNLxRIG motif (SEQ ID NO: 300), inhibition in the PCSK9Δhelix/Ab20 assay is observed with the appropriate N-terminal substitutions (e.g. Compound 98; PCSK9Δhelix/Ab20 assay $IC_{50}$ 3.6 μM).

TABLE 8A

| SEQ ID NO: | Compound No. | Peptide | PCSK9/EGF(A) $IC_{50}$ (μM) | PCSK9Δhelix/Ab20 $IC_{50}$ (μM) | His-EGF(A)-Fc $IC_{50}$ (μM) |
|---|---|---|---|---|---|
| 286 | Pep2-8 | Ac-TVFTSWEEYLDWV-NH$_2$ | 0.650 | 35.000 | >50 |
| 28 | 1 | Ac-TVFTSWEEYLDWV-GSG-KLWNLGRV-NH$_2$ | 0.388 | 0.021 | >50 |
| 31 | 4 | Ac-TVFTSWEEYLDWV-GSG-KLWNLGR-NH$_2$ | 0.490 | 1.520 | >50 |
| 32 | 5 | Ac-TVFTSWEEYLDWV-GSG-KLWNLG-NH$_2$ | 0.720 | 11.120 | >50 |
| 33 | 6 | Ac-TVFTSWEEYLDWV-GSG-KLWNL-NH$_2$ | 0.740 | 10.020 | >50 |
| 34 | 7 | Ac-TVFTSWEEYLDWV-GSG-KLWN-NH$_2$ | 0.500 | 18.580 | >50 |
| 35 | 8 | Ac-TVFTSWEEYLDWV-GGSG-KLWNLGRV-NH$_2$ | 1.030 | 0.049 | >50 |

TABLE 8A-continued

| SEQ ID NO: | Compound No. | Peptide | PCSK9/ EGF(A) IC$_{50}$ (µM) | PCSK9Δhelix/ Ab20 IC$_{50}$ (µM) | His-EGF(A)-Fc IC$_{50}$ (µM) |
|---|---|---|---|---|---|
| 36 | 9 | Ac-TVFTSWEEYLDWV-GSGG-KLWNLGRV-NH$_2$ | 0.390 | 0.065 | >50 |
| 37 | 10 | Ac-TVFTSWEEYLDWV-(Aoc)-KLWNLGRV-NH$_2$ | 0.630 | 0.630 | >50 |
| 43 | 16 | Ac-TVFTSWEEYLDWV-(Ahp)-KLWNLGRV-NH$_2$ | 0.370 | 0.028 | >50 |
| 45 | 18 | Ac-TVFTSWEEYLDWV-(Ahx)-KLWNLGRV-NH$_2$ | 0.420 | 0.040 | >50 |
| 47 | 20 | Ac-TVFTSWEEYLDWV-GSG-DLMPWNLVRIGLLR-NH$_2$ | 0.037 | 0.001 | >50 |

TABLE 8B

| SEQ ID NO: | Compound No. | Peptide | PCSK9/ EGF(A) IC$_{50}$ (µM) | PCSK9Δhelix/ Ab20 IC$_{50}$ (µM) | His-EGF(A)-Fc IC$_{50}$ (µM) |
|---|---|---|---|---|---|
| 46 | 19 | Ac-TVFTSWEEYLDWV-GSG-CRLPWNLQRIGLPC-NH$_2$ | 0.009 | 0.002 | >50 |
| 52 | 25 | Ac-TVFTSWEEYLDWV-GSGG-CRLPWNLQRIGLPC-NH$_2$ | 0.781 | 0.083 | >50 |
| 65 | 38 | Ac-TVFTSWEEYLDWV-GSGG-CFLPWNLQRIGLLC-NH$_2$ | 0.471 | 0.003 | >50 |
| 29 | 2 | Ac-TVFTSWEEYLDWV-GSG-CWNLKRIGSQGC-NH$_2$ | 0.110 | 0.004 | >50 |
| 38 | 11 | Ac-TVFTSWEEYLDWV-GSG-CWNLGRIGSQGC-NH$_2$ | 0.340 | nd | >50 |
| 39 | 12 | Ac-TVFTSWEEYLDWV-GSG-CWNLKRVGSQGC-NH$_2$ | 0.190 | nd | >50 |
| 40 | 13 | Ac-TVFTSWEEYLDWV-GGSG-CWNLKRIGSQGC-NH$_2$ | 0.010 | 0.001 | >50 |
| 41 | 14 | Ac-TVFTSWEEYLDWV-GSGG-CWNLKRIGSQGC-NH$_2$ | 0.009 | 0.001 | >50 |
| 42 | 15 | Ac-TVFTSWEEYLDWV-(Aoc)-CWNLKRIGSQGC-NH$_2$ | 0.051 | 0.002 | >50 |
| 44 | 17 | Ac-TVFTSWEEYLDWV-(Ahx)-CWNLKRIGSQGC-NH$_2$ | 0.009 | 0.001 | >50 |
| 51 | 24 | Ac-TVFTSWEEYLDWV-(Ahp)-CWNLKRIGSQGC-NH$_2$ | 0.023 | 0.001 | >50 |
| 118 | 91 | Ac-TVFTSWEEYLDWV-(Ahx)-AWNLKRIGS-NH$_2$ | 0.216 | 0.010 | >50 |
| 119 | 92 | Ac-TVFTSWEEYLDWV-(Ahx)-AWNLKRIG-NH$_2$ | 0.209 | 0.013 | >50 |
| 120 | 93 | Ac-TVFTSWEEYLDWV-(Ahx)-AWNLKRI-NH$_2$ | 0.261 | 0.016 | >50 |
| 121 | 94 | Ac-TVFTSWEEYLDWV-(Ahx)-AWNLKR-NH$_2$ | 0.439 | 1.412 | >50 |

TABLE 8C

| SEQ ID NO: | Compound No. | Peptide | PCSK9/EGF(A) IC$_{50}$ (μM) | PCSK9Δhelix/Ab20 IC$_{50}$ (μM) | His-EGF(A)-Fc IC$_{50}$ (μM) |
|---|---|---|---|---|---|
| 62 | 35 | Ac-DLMPWNLVRIGLLR-NH$_2$ | >50 | 4.800 | >50 |
| 81 | 54 | Ac-DLMPWNLVRIGLLA-NH$_2$ | >50 | 15.400 | >50 |
| 82 | 55 | Ac-DLMPWNLVRIGLAR-NH$_2$ | >50 | 9.700 | >50 |
| 83 | 56 | Ac-DLMPWNLVRIGALR-NH$_2$ | >50 | 17.100 | >50 |
| 84 | 57 | Ac-DLMPWNLVRIALLR-NH$_2$ | >50 | 49.500 | >50 |
| 85 | 58 | Ac-DLMPWNLVRAGLLR-NH$_2$ | >50 | 49.500 | >50 |
| 86 | 59 | Ac-DLMPWNLVAIGLLR-NH$_2$ | >50 | 49.500 | >50 |
| 87 | 60 | Ac-DLMPWNLARIGLLR-NH$_2$ | >50 | 19.200 | >50 |
| 88 | 61 | Ac-DLMPWNAVRIGLLR-NH$_2$ | >50 | 49.500 | >50 |
| 89 | 62 | Ac-DLMPWALVRIGLLR-NH$_2$ | >50 | 49.500 | >50 |
| 68 | 41 | Ac-DLMPANLVRIGLLR-NH$_2$ | >50 | 49.500 | >50 |
| 69 | 42 | Ac-DLMAWNLVRIGLLR-NH$_2$ | >50 | 28.480 | >50 |
| 70 | 43 | Ac-DLAPWNLVRIGLLR-NH$_2$ | >50 | 8.190 | >50 |
| 71 | 44 | Ac-DAMPWNLVRIGLLR-NH$_2$ | >50 | 6.900 | >50 |
| 72 | 45 | Ac-ALMPWNLVRIGLLR-NH$_2$ | >50 | 2.020 | >50 |
| 73 | 46 | Ac-DLMPWNLVRIGLL-NH$_2$ | >50 | 14.040 | >50 |
| 74 | 47 | Ac-DLMPWNLVRIGL-NH$_2$ | >50 | 12.640 | >50 |
| 75 | 48 | Ac-DLMPWNLVRIG-NH$_2$ | >50 | 49.500 | >50 |
| 76 | 49 | Ac-DLMPWNLVRI-NH$_2$ | >50 | 49.500 | >50 |
| 77 | 50 | Ac-LMPWNLVRIGLLR-NH$_2$ | >50 | 2.660 | >50 |
| 78 | 51 | Ac-MPWNLVRIGLLR-NH$_2$ | >50 | 4.690 | >50 |
| 79 | 52 | Ac-PWNLVRIGLLR-NH$_2$ | >50 | 10.200 | >50 |
| 80 | 53 | Ac-WNLVRIGLLR-NH$_2$ | >50 | 33.130 | >50 |
| 146 | 119 | Ac-PWNLVRIGL-NH$_2$ | >50 | 49.500 | >50 |
| 147 | 120 | Ac-WNLVRIGL-NH$_2$ | >50 | 49.500 | >50 |
| 138 | 111 | n-BuC(O)-WNLVRIGLLR-NH$_2$ | >50 | 4.900 | >50 |
| 139 | 112 | n-BuC(O)-WNLVRIGLTR-NH$_2$ | >50 | 7.500 | >50 |
| 140 | 113 | n-BuC(O)-WNLVRIGTTR-NH$_2$ | >50 | >50 | >50 |
| 141 | 114 | n-BuC(O)-WNLVRIGTLR-NH$_2$ | >50 | >50 | >50 |
| 145 | 118 | n-BuC(O)-WNLV(homoR)IGLTR-NH$_2$ | >50 | 1.400 | >50 |

TABLE 8D

| SEQ ID NO: | Compound No. | Peptide | PCSK9/EGF(A) IC$_{50}$ (μM) | PCSK9Δhelix/Ab20 IC$_{50}$ (μM) | His-EGF(A)-Fc IC$_{50}$ (μM) |
|---|---|---|---|---|---|
| 56 | 29 | Ac-SG-CFIPWNLQRIGLLC-NH$_2$ | >50 | 1.900 | >50 |
| 57 | 30 | Ac-SG-CRLPWNLQRIGLPC-NH$_2$ | >50 | 0.950 | >50 |
| 58 | 31 | Ac-CFIPWNLQRIGLLC-NH$_2$ | >50 | 2.400 | >50 |

TABLE 8D-continued

| SEQ ID NO: | Compound No. | Peptide | PCSK9/EGF(A) IC$_{50}$ (μM) | PCSK9Δhelix/Ab20 IC$_{50}$ (μM) | His-EGF(A)-Fc IC$_{50}$ (μM) |
|---|---|---|---|---|---|
| 59 | 32 | Ac-CRLPWNLQRIGLPC-NH$_2$ | >50 | 0.970 | >50 |
| 95 | 68 | Ac-CRLPWNLQRIGLAC-NH$_2$ | >50 | 0.939 | >50 |
| 96 | 69 | Ac-CRLPWNLQRIGAPC-NH$_2$ | >50 | 6.640 | >50 |
| 97 | 70 | Ac-CRLPWNLQRIALPC-NH$_2$ | >50 | 7.260 | >50 |
| 98 | 71 | Ac-CRLPWNLQRAGLPC-NH$_2$ | >50 | 49.500 | >50 |
| 99 | 72 | Ac-CRLPWNLQAIGLPC-NH$_2$ | >50 | 39.600 | >50 |
| 100 | 73 | Ac-CRLPWNLARIGLPC-NH$_2$ | >50 | 0.915 | >50 |
| 101 | 74 | Ac-CRLPWNAQRIGLPC-NH$_2$ | >50 | 49.500 | >50 |
| 102 | 75 | Ac-CRLPWALQRIGLPC-NH$_2$ | >50 | 49.500 | >50 |
| 103 | 76 | Ac-CRLPANLQRIGLPC-NH$_2$ | >50 | 49.500 | >50 |
| 104 | 77 | Ac-CRLAWNLQRIGLPC-NH$_2$ | >50 | 6.020 | >50 |
| 105 | 78 | Ac-CRAPWNLQRIGLPC-NH$_2$ | >50 | 5.560 | >50 |
| 106 | 79 | Ac-CALPWNLQRIGLPC-NH$_2$ | >50 | 1.530 | >50 |
| 126 | 99 | Ac-CRLPWNLQRIGLpC-NH$_2$ | >50 | 1.300 | >50 |
| 127 | 100 | Ac-CRLPWNLQRIGlPC-NH$_2$ | >50 | >50 | >50 |
| 128 | 101 | Ac-CRLPWNLQRiGLPC-NH$_2$ | >50 | >50 | >50 |
| 129 | 102 | Ac-CRLPWNLQrIGLPC-NH$_2$ | >50 | >50 | >50 |
| 130 | 103 | Ac-CRLPWNLqRIGLPC-NH$_2$ | >50 | >50 | >50 |
| 131 | 104 | Ac-CRLPWNlQRIGLPC-NH$_2$ | >50 | >50 | >50 |
| 132 | 105 | Ac-CRLPWnLQRIGLPC-NH$_2$ | >50 | >50 | >50 |
| 133 | 106 | Ac-CRLPwNLQRIGLPC-NH$_2$ | >50 | >50 | >50 |
| 134 | 107 | Ac-CRLpWNLQRIGLPC-NH$_2$ | >50 | >50 | >50 |
| 135 | 108 | Ac-CRlPWNLQRIGLPC-NH$_2$ | >50 | 28.200 | >50 |
| 136 | 109 | Ac-CrLPWNLQRIGLPC-NH$_2$ | >50 | 1.670 | >50 |
| 137 | 110 | Ac-cRLPWNLQRIGLPC-NH$_2$ | >50 | 1.780 | >50 |
| 94 | 67 | Ac-CRLPWNLKRIGLPC-NH$_2$ | >50 | 0.699 | >50 |
| 144 | 117 | Ac-CRLPWNLQ(homoR)IGLPC-NH$_2$ | >50 | 0.334 | >50 |
| 107 | 80 | Ac-CRLPWNLQRIGLGC-NH$_2$ | >50 | 0.650 | >50 |
| 108 | 81 | Ac-CRLPWNLQRIGGGC-NH$_2$ | >50 | 28.800 | >50 |
| 110 | 83 | Ac-CRLPWNLQR-(Aun)-C-NH$_2$ | >50 | >50 | >50 |
| 111 | 84 | Ac-CRLPWNLQR-(Ade)-C-NH$_2$ | >50 | >50 | >50 |
| 112 | 85 | Ac-CRLPWNLQR-(Ano)-C-NH$_2$ | >50 | >50 | >50 |
| 113 | 86 | Ac-CRLPWNLQR-(Aoc)-C-NH$_2$ | >50 | >50 | >50 |
| 142 | 115 | Ac-CRLPWNLQRI-(Ape)-C-NH$_2$ | >50 | >50 | >50 |
| 143 | 116 | Ac-CRLPWNLQRI-(Ahx)-C-NH$_2$ | >50 | 31.600 | >50 |
| 148 | 121 | Ac-CRLPWNLQRI-(Ahp)-C-NH$_2$ | >50 | 40.300 | >50 |
| 63 | 36 | Ac-SG-CFIPWNLQ(Cit)IGLPC- | >50 | >50 | >50 |

TABLE 8D-continued

| SEQ ID NO: | Compound No. | Peptide | PCSK9/EGF(A) IC$_{50}$ (μM) | PCSK9Δhelix/Ab20 IC$_{50}$ (μM) | His-EGF(A)-Fc IC$_{50}$ (μM) |
|---|---|---|---|---|---|
| 64 | 37 | Ac-SG-CRL(Hyp)WNLQRIGLPC-NH$_2$ | >50 | 11.100 | >50 |
| 90 | 63 | Ac-MCLWNLKRIGSQCEY-NH$_2$ | 14.600 | 6.000 | 41.000 |
| 91 | 64 | Ac-DCLWNLKRIGSQCEY-NH$_2$ | >50 | >50 | >50 |
| 92 | 65 | Ac-WCLWNLKRIGSQCEY-NH$_2$ | >50 | 7.100 | >50 |
| 122 | 95 | Ac-FCLWNLKRIGSQCEY-NH$_2$ | >50 | 12.700 | >50 |
| 114 | 87 | Ac-GCLWNLKRIGSQCWF-NH$_2$ | >50 | 9.530 | >50 |
| 115 | 88 | Ac-FCLWNLARIGSQCWF-NH$_2$ | 17.900 | 7.460 | >50* |
| 116 | 89 | WCLWNLKRIGSQCWF-NH$_2$ | 6.900 | 2.980 | 38.4 |
| 117 | 90 | Ac-WCLWNLKRIGSQCWF | 29.200 | 7.380 | 49.5 |
| 93 | 66 | WCLWNLKRIGSQCWF | 31.300 | 12.000 | 49.5 |
| 48 | 21 | Ac-CWNLKRIGSQGC-NH$_2$ | >50 | >50 | >50 |
| 49 | 22 | Ac-GSG-CWNLKRIGSQGC-NH$_2$ | 42/>50 | 14/>50 | >50 |
| 67 | 40 | Ac-GSG-CWNLKRIGSQGCW-NH$_2$ | 5.960 | 2.410 | >50* |
| 66 | 39 | Ac-CWNLKRIGSQGCW-NH$_2$ | >50 | 37.500 | >50 |
| 125 | 98 | Fmoc-GSG-CWNLKRIGSQGC-NH$_2$ | 37.600 | 3.600 | >50 |

*Some inhibition seen at highest concentrations although not sufficient to allow fitting of an IC$_{50}$.

Additional compounds were prepared and tested as shown in Table 8E.

TABLE 8E

| SEQ ID NO: | Compound No. | Peptide | PCSK9/EGF(A) IC$_{50}$ (μM) | PCSK9Δhelix/Ab20 IC$_{50}$ (μM) | His-EGF(A)-Fc IC$_{50}$ (μM) |
|---|---|---|---|---|---|
| 162 | 122 | Ac-SG-DLMPWNLVRIGLLR-NH$_2$ | 50.00 | 5.60 | 50.00 |
| 163 | 123 | n-PrC(O)-WNLVRIGLLR-NH$_2$ | 50.00 | 18.00 | 50.00 |
| 164 | 124 | Ac-G-LMPWNLVRIGLLR-NH$_2$ | 50.00 | 3.90 | 50.00 |
| 165 | 125 | Ac-GG-MPWNLVRIGLLR-NH$_2$ | 50.00 | 7.00 | 50.00 |
| 166 | 126 | (1,1-dioxothiomorpholine)-CH$_2$CH$_2$-C(O)-WNLVRIGLLR-NH$_2$ | 50.00 | 19.00 | 50.00 |
| 167 | 127 | (1-methylpyrazol-4-yl)-cyclopropyl-C(O)-WNLVRIGLLR-NH$_2$ | 50.00 | 29.00 | 50.00 |

TABLE 8E-continued
| SEQ ID NO: | Compound No. | Peptide | PCSK9/ EGF(A) IC$_{50}$ (μM) | PCSK9Δhelix/ Ab20 IC$_{50}$ (μM) | His-EGF(A)-Fc IC$_{50}$ (μM) |
|---|---|---|---|---|---|
| 168 | 128 | 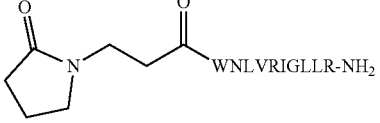 WNLVRIGLLR-NH$_2$ | 50.00 | 7.50 | 50.00 |
| 169 | 129 | 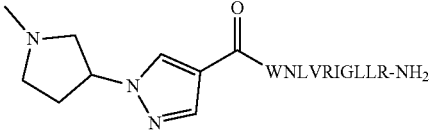 WNLVRIGLLR-NH$_2$ | 50.00 | 23.00 | 50.00 |
| 170 | 130 | 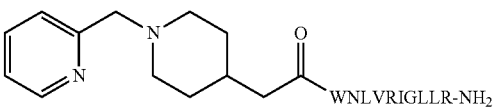 WNLVRIGLLR-NH$_2$ | 50.00 | 8.60 | 50.00 |
| 171 | 131 | 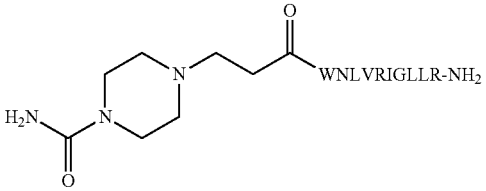 WNLVRIGLLR-NH$_2$ | 50.00 | 6.70 | 50.00 |
| 172 | 132 | 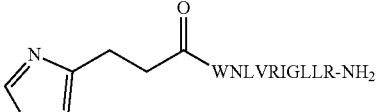 WNLVRIGLLR-NH$_2$ | 50.00 | 9.00 | 50.00 |
| 173 | 133 | 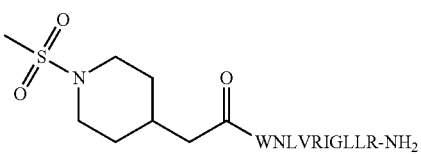 WNLVRIGLLR-NH$_2$ | 50.00 | 17.00 | 50.00 |
| 174 | 134 | 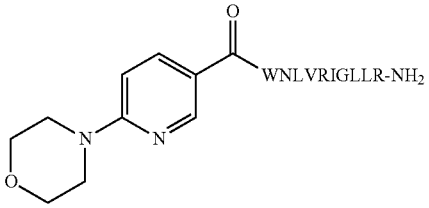 WNLVRIGLLR-NH$_2$ | 50.00 | 4.20 | 50.00 |
| 175 | 135 | 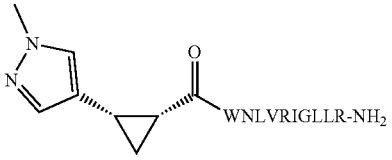 WNLVRIGLLR-NH$_2$ | 50.00 | 10.00 | 50.00 |
| 176 | 136 | 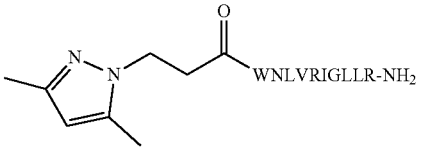 WNLVRIGLLR-NH$_2$ | 50.00 | 9.00 | 50.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His- EGF(A)-Fc IC$_{50}$ (μM) |
|---|---|---|---|---|---|
| 177 | 137 | morpholine-CH$_2$CH$_2$-C(O)-WNLVRIGLLR-NH$_2$ | 50.00 | 6.70 | 50.00 |
| 178 | 138 | pyridin-3-yl-CH$_2$CH$_2$-C(O)-WNLVRIGLLR-NH$_2$ | 48.00 | 4.90 | 50.00 |
| 179 | 139 | (1,1-dioxo-tetrahydrothiophen-3-yl)-CH$_2$-C(O)-WNLVRIGLLR-NH$_2$ | 50.00 | 19.00 | 50.00 |
| 180 | 140 | 4-methylpiperazin-1-yl-CH$_2$CH$_2$-C(O)-WNLVRIGLLR-NH$_2$ | 50.00 | 26.00 | 50.00 |
| 181 | 141 | H$_2$N-C(O)-NH-CH$_2$CH$_2$-C(O)-WNLVRIGLLR-NH$_2$ | 50.00 | 36.00 | 50.00 |
| 182 | 142 | 1,2,4-triazol-1-yl-CH$_2$CH$_2$-C(O)-WNLVRIGLLR-NH$_2$ | 50.00 | 15.00 | 50.00 |
| 183 | 143 | uracil-1-yl-CH$_2$-C(O)-WNLVRIGLLR-NH$_2$ | 50.00 | 23.00 | 50.00 |
| 184 | 144 | 3-benzylcyclobutyl-C(O)-WNLVRIGLLR-NH$_2$ | 9.70 | 4.00 | 24.00 |
| 185 | 145 | biphenyl-4-yl-C(O)-WNLVRIGLLR-NH$_2$ | 7.30 | 2.20 | 32.00 |
| 186 | 146 | phenyl-CH$_2$CH$_2$CH$_2$CH$_2$-C(O)-WNLVRIGLLR-NH$_2$ | 11.00 | 1.70 | 26.00 |

TABLE 8E-continued

| SEQ ID NO: | Compound No. | Peptide | PCSK9/ EGF(A) IC$_{50}$ (µM) | PCSK9Δhelix/ Ab20 IC$_{50}$ (µM) | His-EGF(A)-Fc IC$_{50}$ (µM) |
|---|---|---|---|---|---|
| 187 | 147 | 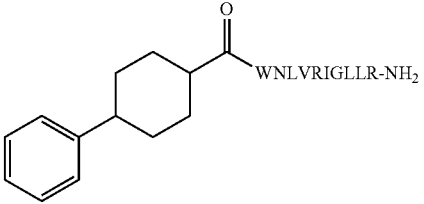WNLVRIGLLR-NH$_2$ | 2.60 | 0.41 | 23.00 |
| 188 | 148 | 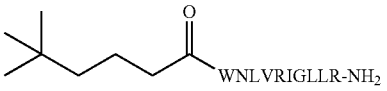WNLVRIGLLR-NH$_2$ | 19.00 | 11.00 | 34.00 |
| 189 | 149 | 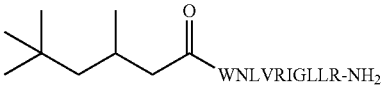WNLVRIGLLR-NH$_2$ | 11.00 | 8.90 | 27.00 |
| 190 | 150 | 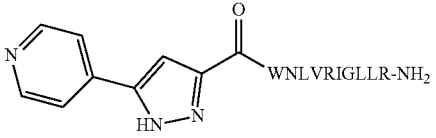WNLVRIGLLR-NH$_2$ | 22.00 | 8.20 | 40.00 |
| 191 | 151 | 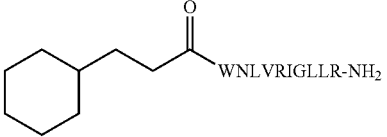WNLVRIGLLR-NH$_2$ | 6.90 | 2.50 | 20.00 |
| 192 | 152 | n-BuC(O)-WNLVRIGLLR | 43.00 | 14.00 | 50.00 |
| 193 | 153 | Ac-MDSFPGWNLVRIGLLR-NH$_2$ | 12.00 | 50.00 | >50 |
| 194 | 154 | Ac-SFAFPGWNLVRIGLLR-NH$_2$ | 11.00 | 50.00 | >50 |
| 195 | 155 | Ac-DSYPGWNLVRIGLLR-NH$_2$ | 11.00 | 50.00 | >50 |
| 196 | 156 | Ac-ESYPGWNLVRIGLLR-NH$_2$ | 11.00 | 50.00 | >50 |
| 197 | 157 | Ac-ESFPGWNLVRIGLLR-NH$_2$ | no data | no data | no data |
| 198 | 158 | Ac-DLMPWNLKRIGLLR-NH$_2$ | 50.00 | 12.00 | 50.00 |
| 199 | 159 | n-BuC(O)-WNLKRIGLLR-NH$_2$ | 50.00 | 6.60 | 50.00 |
| 200 | 160 | Ac-DLMPWNLVRIGLPR-NH$_2$ | 50.00 | 19.00 | 50.00 |
| 201 | 161 | 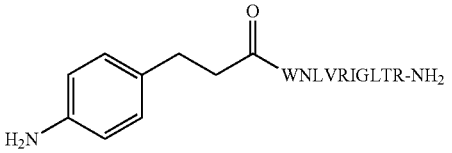WNLVRIGLTR-NH$_2$ | 50.00 | 5.00 | 50.00 |
| 202 | 162 | 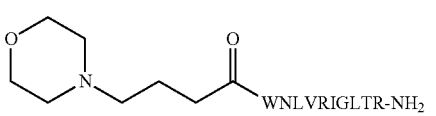WNLVRIGLTR-NH$_2$ | 50.00 | 37.00 | 50.00 |
| 203 | 163 | 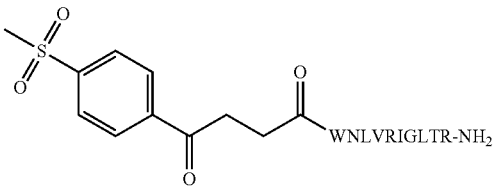WNLVRIGLTR-NH$_2$ | 50.00 | 37.00 | 50.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His- EGF(A)-Fc IC$_{50}$ (μM) |
|---|---|---|---|---|---|
| 204 | 164 | H$_2$N-(3-aminophenyl)-CH$_2$CH$_2$-C(O)-WNLVRIGLTR-NH$_2$ | 50.00 | 12.00 | 50.00 |
| 205 | 165 | 4-methylphenyl-C(O)-CH$_2$CH$_2$-C(O)-WNLVRIGLTR-NH$_2$ | 50.00 | 18.00 | 50.00 |
| 206 | 166 | 4-methoxyphenyl-CH$_2$CH$_2$-C(O)-WNLVRIGLTR-NH$_2$ | 50.00 | 5.90 | 50.00 |
| 207 | 167 | morpholinyl-C(O)-CH$_2$CH$_2$-C(O)-WNLVRIGLTR-NH$_2$ | 50.00 | 43.00 | 50.00 |
| 208 | 168 | 3-hydroxyphenyl-CH$_2$CH$_2$-C(O)-WNLVRIGLTR-NH$_2$ | 50.00 | 7.80 | 50.00 |
| 209 | 169 | benzyl-O-C(O)-NH-CH$_2$CH$_2$CH$_2$-C(O)-WNLVRIGLTR-NH$_2$ | 50.00 | 6.80 | 50.00 |
| 210 | 170 | 4-hydroxyphenyl-CH$_2$CH$_2$-C(O)-WNLVRIGLTR-NH$_2$ | 50.00 | 3.10 | 50.00 |
| 211 | 171 | 6-amino-pyridin-3-yl-CH$_2$CH$_2$-C(O)-WNLVRIGLTR-NH$_2$ | 50.00 | 7.70 | 50.00 |
| 212 | 172 | 6-morpholino-pyridin-3-yl-C(O)-WNLVRIGLTR-NH$_2$ | 50.00 | 8.50 | 50.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His- EGF(A)-Fc IC$_{50}$ (μM) |
| --- | --- | --- | --- | --- | --- |
| 213 | 173 | [pyridin-3-yl-propanoyl]-WNLVRIGLTR-NH$_2$ | 50.00 | 9.80 | 50.00 |
| 214 | 174 | n-BuC(O)-(W6fl)NLVRIGLTR-NH$_2$ | 50.00 | 6.20 | 50.00 |
| 215 | 175 | n-BuC(O)-(W6me)NLVRIGLTR-NH$_2$ | 50.00 | 39.00 | 50.00 |
| 216 | 176 | n-BuC(O)-WNLVRIGLTR | 50.00 | 18.00 | 50.00 |
| 217 | 177 | n-BuC(O)-WNLVRIGLER-NH$_2$ | 50.00 | 35.00 | 50.00 |
| 218 | 178 | n-BuC(O)-WNLVRIGLDR-NH$_2$ | 50.00 | 18.00 | 50.00 |
| 219 | 179 | n-BuC(O)-WNLVRIGLGR-NH$_2$ | 50.00 | 11.00 | 50.00 |
| 220 | 180 | n-BuC(O)-WNLVRIGLAR-NH$_2$ | 50.00 | 12.00 | 50.00 |
| 221 | 181 | n-BuC(O)-WNLVRIGLSR-NH$_2$ | 50.00 | 8.90 | 50.00 |
| 222 | 182 | [4-(4-bromophenoxy)butanoyl]-WNLVRIGLTR-NH$_2$ | 14.00 | 4.00 | 35.00 |
| 223 | 183 | [4-(4-acetylphenoxy)butanoyl]-WNLVRIGLTR-NH$_2$ | 18.00 | 2.50 | 41.00 |
| 224 | 184 | [3-benzylcyclobutanecarbonyl]-WNLVRIGLTR-NH$_2$ | 19.00 | 12.00 | 29.00 |
| 225 | 185 | [4-phenylcyclohexanecarbonyl]-WNLVRIGLTR-NH$_2$ | 5.70 | 0.39 | 30.00 |
| 226 | 186 | n-BuC(O)-(W6cl)NLVRIGLTR-NH$_2$ | 31.00 | 11.00 | 46.00 |
| 227 | 187 | n-BuC(O)-(W6br)NLVRIGLTR-NH$_2$ | 26.00 | 36.00 | 38.00 |
| 228 | 188 | [3-(pyridin-4-yl)-1H-pyrazole-5-carbonyl]-WNLVRIGLTR-NH$_2$ | 22.00 | 7.60 | 47.00 |
| 229 | 189 | [3-(1H-indol-3-yl)propanoyl]-WNLVRIGLTR-NH$_2$ | 38.00 | 12.00 | 50.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His-EGF(A)-Fc IC$_{50}$ (μM) |
|---|---|---|---|---|---|
| 230 | 190 | 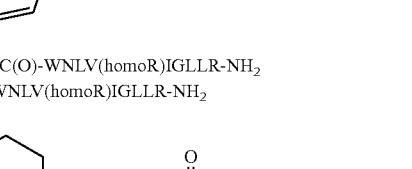WNLVRIGLTR-NH$_2$ | 30.00 | 7.00 | 50.00 |
| 231 | 191 | n-BuC(O)-WNLV(homoR)IGLLR-NH$_2$ | 50.00 | 1.30 | 50.00 |
| 232 | 192 | Ac-WNLV(homoR)IGLLR-NH$_2$ | 50.00 | 5.30 | 50.00 |
| 233 | 193 | 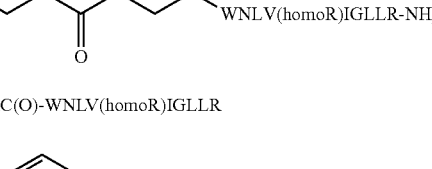WNLV(homoR)IGLLR-NH$_2$ | 50.00 | 1.50 | 50.00 |
| 234 | 194 | 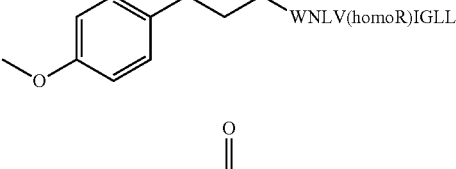WNLV(homoR)IGLLR-NH$_2$ | 50.00 | 1.90 | 50.00 |
| 235 | 195 | n-BuC(O)-WNLV(homoR)IGLLR | 22.00 | 1.70 | 45.00 |
| 236 | 196 | 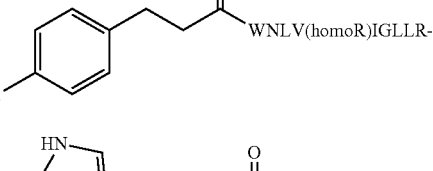WNLV(homoR)IGLLR-NH$_2$ | 7.30 | 1.40 | 22.00 |
| 237 | 197 | 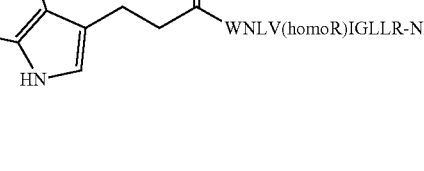WNLV(homoR)IGLLR-NH$_2$ | 0.97 | 0.09 | 38.00 |
| 238 | 198 | WNLV(homoR)IGLLR-NH$_2$ | 1.70 | 0.25 | 26.00 |
| 239 | 199 | WNLV(homoR)IGLLR-NH$_2$ | 0.98 | 0.20 | 21.00 |
| 240 | 200 | WNLV(homoR)IGLLR-NH$_2$ | 3.20 | 0.67 | 24.00 |
| 241 | 201 | WNLV(homoR)IGLLR-NH$_2$ | 3.90 | 1.00 | 28.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His- EGF(A)-Fc IC$_{50}$ (μM) |
|---|---|---|---|---|---|
| 242 | 202 | (3-methoxyphenyl propanoyl)-WNLV(homoR)IGLLR-NH$_2$ | 2.60 | 0.34 | 38.00 |
| 243 | 203 | (4-methoxyphenoxy propanoyl)-WNLV(homoR)IGLLR-NH$_2$ | 21.00 | 1.60 | 46.00 |
| 244 | 204 | (3-methoxy-4-(hydroxymethyl)phenoxy butanoyl)-WNLV(homoR)IGLLR-NH$_2$ | 3.60 | 0.87 | 23.00 |
| 245 | 205 | (4-acetylphenoxy propanoyl)-WNLV(homoR)IGLLR-NH$_2$ | 2.80 | 0.64 | 22.00 |
| 246 | 206 | (4-bromophenoxy butanoyl)-WNLV(homoR)IGLLR-NH$_2$ | 1.80 | 0.87 | 20.00 |
| 247 | 207 | (4-methylphenoxy butanoyl)-WNLV(homoR)IGLLR-NH$_2$ | 1.30 | 0.32 | 26.00 |
| 248 | 208 | (4-phenylcyclohexanecarbonyl)-WNLV(homoR)IGLLR-NH$_2$ | 0.45 | 0.10 | 18.00 |
| 249 | 209 | (phenoxy butanoyl)-WNLV(homoR)IGLLR-NH$_2$ | 2.90 | 0.45 | 41.00 |
| 250 | 210 | (4-ethylphenoxy butanoyl)-WNLV(homoR)IGLLR-NH$_2$ | 3.00 | 0.84 | 21.00 |

TABLE 8E-continued
| SEQ ID NO: | Compound No. | Peptide | PCSK9/ EGF(A) IC$_{50}$ (μM) | PCSK9Δhelix/ Ab20 IC$_{50}$ (μM) | His- EGF(A)-Fc IC$_{50}$ (μM) |
|---|---|---|---|---|---|
| 251 | 211 | 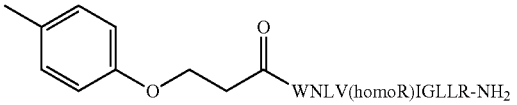 WNLV(homoR)IGLLR-NH$_2$ | 14.00 | 3.80 | 31.00 |
| 252 | 212 | 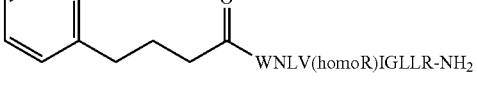 WNLV(homoR)IGLLR-NH$_2$ | 15.00 | 1.60 | 35.00 |
| 253 | 213 | 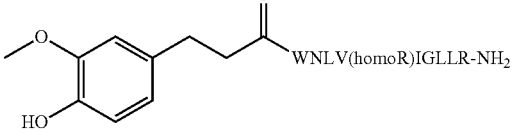 WNLV(homoR)IGLLR-NH$_2$ | 3.80 | 0.20 | 50.00 |
| 254 | 214 | 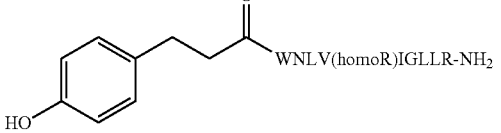 WNLV(homoR)IGLLR-NH$_2$ | 3.00 | 0.21 | 50.00 |
| 255 | 215 | 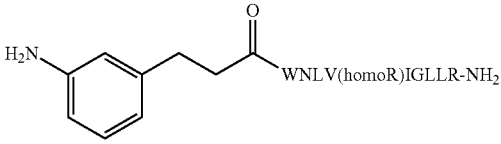 WNLV(homoR)IGLLR-NH$_2$ | 7.00 | 0.48 | 50.00 |
| 256 | 216 | 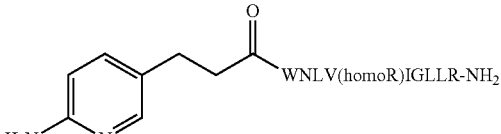 WNLV(homoR)IGLLR-NH$_2$ | 6.00 | 0.30 | 50.00 |
| 257 | 217 | 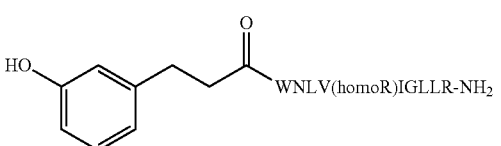 WNLV(homoR)IGLLR-NH$_2$ | 4.10 | 0.39 | 50.00 |
| 258 | 218 | 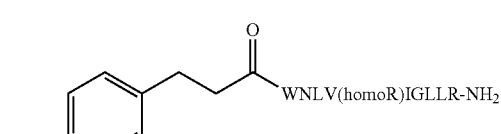 WNLV(homoR)IGLLR-NH$_2$ | 5.00 | 0.26 | 50.00 |
| 259 | 219 | 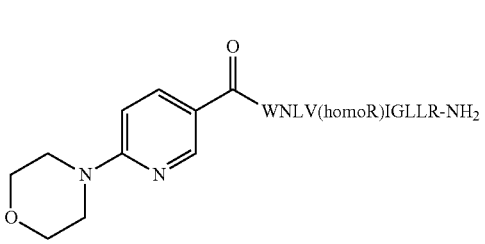 WNLV(homoR)IGLLR-NH$_2$ | 9.90 | 0.68 | 50.00 |

TABLE 8E-continued

| SEQ ID NO: | Compound No. | Peptide | PCSK9/ EGF(A) IC$_{50}$ (μM) | PCSK9Δhelix/ Ab20 IC$_{50}$ (μM) | His-EGF(A)-Fc IC$_{50}$ (μM) |
|---|---|---|---|---|---|
| 260 | 220 | 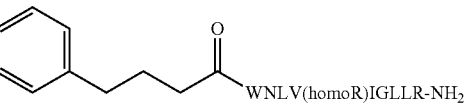 WNLV(homoR)IGLLR-NH$_2$ | 37.00 | 0.91 | 50.00 |
| 261 | 221 | 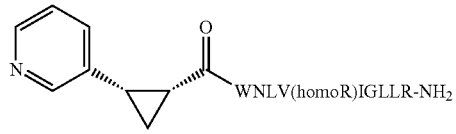 WNLV(homoR)IGLLR-NH$_2$ | 9.50 | 0.65 | 50.00 |
| 262 | 222 | 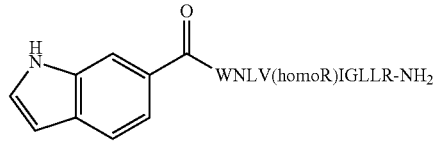 WNLV(homoR)IGLLR-NH$_2$ | 21.00 | 1.40 | 50.00 |
| 263 | 223 | 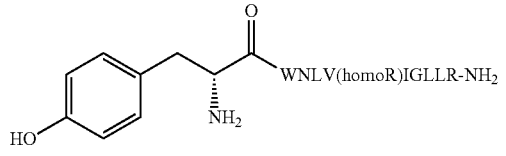 WNLV(homoR)IGLLR-NH$_2$ | 21.00 | 1.40 | 50.00 |
| 264 | 224 | 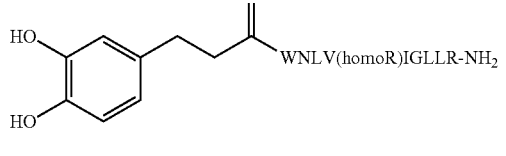 WNLV(homoR)IGLLR-NH$_2$ | 7.00 | 0.53 | 50.00 |
| 265 | 225 | 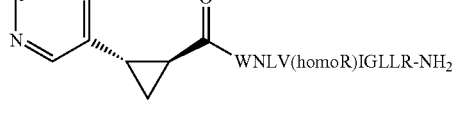 WNLV(homoR)IGLLR-NH$_2$ | 27.00 | 1.80 | 50.00 |
| 266 | 226 | 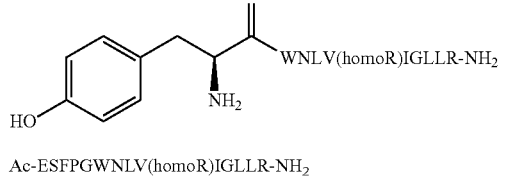 WNLV(homoR)IGLLR-NH$_2$ | 6.20 | 0.35 | 50.00 |
| 267 | 227 | Ac-ESFPGWNLV(homoR)IGLLR-NH$_2$ | 2.50 | 24.00 | 50.00 |
| 268 | 228 | Ac-SFAFPGWNLV(homoR)IGLLR-NH$_2$ | 1.30 | 13.00 | 50.00 |
| 269 | 229 | Ac-MESFPGWNLV(homoR)IGLLR-NH$_2$ | 0.81 | 8.10 | 50.00 |
| 270 | 230 | Ac-DSYPGWNLV(homoR)IGLLR-NH$_2$ | 2.30 | 24.00 | 50.00 |
| 271 | 231 | Ac-ESYPGWNLV(homoR)IGLLR-NH$_2$ | 1.60 | 17.00 | 50.00 |
| 272 | 232 | Ac-SFAFPGWNLK(homoR)IGLLR-NH$_2$ | 0.93 | 13.00 | 50.00 |
| 273 | 233 | Ac-MESFPGWNLK(homoR)IGLLR-NH$_2$ | 3.10 | 50.00 | 50.00 |
| 274 | 234 | n-BuC(O)-WNLV(homoR)IGLTR-NH$_2$ | 50.00 | 1.40 | 50.00 |
| 275 | 235 | n-BuC(O)-WNLV(homoR)IGLTR | 50.00 | 2.70 | 50.00 |
| 276 | 236 | WNLV(homoR)IG-NH$_2$ | 50.00 | 22.00 | 50.00 |
| 277 | 237 | WNLV(homoR)IGLLQ-NH$_2$ | 8.80 | 0.33 | 46.00 |
| 278 | 238 | 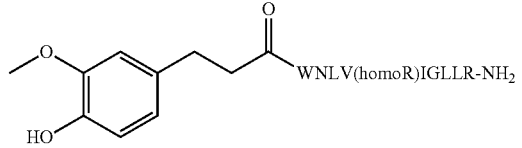 WNLV(homoR)IGLLR-NH$_2$ | 7.70 | 0.33 | 50.00 |

TABLE 8E-continued

| SEQ ID NO: | Compound No. | Peptide | PCSK9/ EGF(A) IC$_{50}$ (µM) | PCSK9Δhelix/ Ab20 IC$_{50}$ (µM) | His-EGF(A)-Fc IC$_{50}$ (µM) |
|---|---|---|---|---|---|
| 279 | 239 | 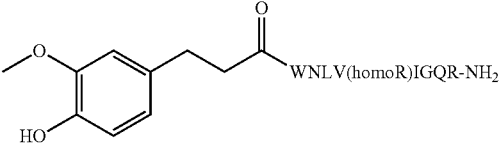 WNLV(homoR)IGQR-NH$_2$ | 32.00 | 1.20 | 50.00 |
| 280 | 240 | 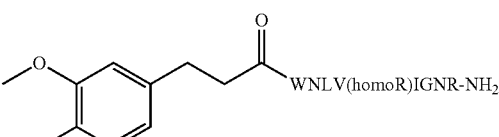 WNLV(homoR)IGNR-NH$_2$ | 31.00 | 0.92 | 50.00 |
| 281 | 241 | Ac-TVFTS(W6fl)EEYLDWV-GSG-CRLPWNLQRIGLPC-NH$_2$ | 1.60 | 0.10 | 50.00 |
| 282 | 242 | Ac-SG-CFI(Hyp)WNLQRIGLLC-NH$_2$ | 50.00 | 31.00 | 50.00 |

Methods

Peptide Synthesis Methods

Peptides were synthesized and purified using standard fluorenylmethoxycarbonyl (Fmoc)/tert-butyl (tBu) solid-phase methods known to those practiced in the arts (Chan, W. C., White, P. D., Eds. Fmoc Solid Phase Peptide Synthesis: A Practical Approach; Oxford University Press: New York, 2000; Albericio, Fernando; Tulla-Puche, Judit; Kates, Steven A. Amino Acids, Peptides and Proteins in Organic Chemistry Volume 3, Pages 349-369, 2011).

PCSK9 TR-FRET Binding Assay Methods

The ability of compounds to inhibit binding to PCSK9 was evaluated with a panel of time-resolved fluorescence resonance energy transfer (TR-FRET) binding assays. The PCSK9/EGF(A)-Fc binding assay assessed the ability of compounds to compete with EGF(A)-Fc for binding to His-tagged, full-length PCSK9. The PCSK9Δhelix/Ab20 binding assay evaluated the ability of compounds to compete with Ab20 for binding to the N-terminal groove region in a His-tagged, PCSK9Δhelix construct. Ab20 is the low affinity precursor antibody YW508.20 of the affinity-matured Ab YW508.20.33 (Wu et al., U.S. Pat. No. 9,266,961). The His-EGF(A)-Fc binding assay served as a counterscreen to identify compounds that interfere with the assay detection system. Signal generation in the PCSK9 binding assays was dependent upon the binding interaction to bring into close proximity the His-tag on the PCSK9 and the Fc-tag on the ligand. Anti-His-APC was bound to the His-tag, and anti-Fc-europium was bound to the Fc-tag. When these two antibodies were in close proximity and were irradiated with light at 340 nm, the europium was excited and emitted energy at 615 nm. This energy was taken up by the APC and was emitted as light at 665 nm. Compounds that competed with the ligand reduced the energy transfer and thus the emission at 665 nm. In the His-EGFA-Fc molecule in the counterscreen, the two tags were always in close proximity, thus any reduction in emission at 665 nm was due to interference with the detection system.

Compounds were solubilized and dilutions were prepared in DMSO. Forty nanoliters of test compound, reference compound, or DMSO control were added to the wells of a 1536-well black COC assay plate (Aurora Microplates, Whitefish, Mont.) followed by 2 µL test protein (PCSK9, PCSK9Δhelix, or His-EGF(A)-Fc) plus 40 nM anti-His-APC (PerkinElmer, Waltham, Mass.) in assay buffer (50 mM Tris-HCl pH 7.5, 150 mM NaCl, 2 mM CaCl$_2$, 0.01% Tween-20, 0.1% bovine gamma globulins, and protease inhibitor cocktail). The plate was centrifuged to mix the well contents and allowed to incubate for 30 min. Then 2 µL ligand (EGF(A)-Fc or Ab20 in assay buffer or buffer alone for counterscreen) with 4 nM anti-Fc-europium (PerkinElmer) were added, and the plate was incubated for 2 h following a brief centrifugation to mix the well contents. The TR-FRET signal was read on a ViewLux reader (PerkinElmer) with excitation at 340 nm and emission at 615 and 665 nm with a 50-µs time delay between excitation and measurement of emission. The TR-FRET ratio was calculated as the fluorescence emission at 665 nm divided by the fluorescence emission at 615 nm. The normalized TR-FRET ratios were plotted as a function of the compound concentrations, and the IC$_{50}$ values were determined using a 4-parameter logistic regression. Certain assay parameters are summarized in Table 9.

TABLE 9

| | Assay | | |
|---|---|---|---|
| | PCSK9/ EGF(A) Binding | PCSK9Δhelix/ Ab20 Binding | His-EGF(A)-Fc Counterscreen |
| Target Protein | His-PCSK9 | His-PCSK9Δhelix | His-EGF(A)-Fc |
| Concentration (nM) | 10 | 1.25 | 2 |
| Ligand | EGF(A)-Fc | Ab20 | — |
| Concentration (nM) | 12 | 0.75 | — |

Example 8: Converting Groove-Binding Peptides into PCSK9 Antagonists

Deletion of the first three residues of Compound 35 (Asp/Leu/Met) had very little impact on binding to PCSK9Δhelix as determined in the Ab20 assay and by SPR (Table 10, Compounds 50-52), consistent with the disordered state of Asp/Leu in the crystal structure of Compound 20 (FIG. 21).

TABLE 10

| SEQ ID NO: | Compound No. | Peptide | Ab20 IC$_{50}$ (µM) | SPR K$_d$ (µM) |
|---|---|---|---|---|
| 62 | 35 | Ac-DLMPWNLVRIGLLR-NH$_2$ | 7.9 ± 0.1 | 1.38 |
| 77 | 50 | Ac-LMPWNLVRIGLLR-NH$_2$ | 3.6 ± 0.2 | 0.47 |
| 78 | 51 | Ac-MPWNLVRIGLLR-NH$_2$ | 6.6 ± 0.3 | 1.40 |
| 79 | 52 | Ac-PWNLVRIGLLR-NH$_2$ | 15.9 ± 1.1 | 2.10 |
| 80 | 53 | Ac-WNLVRIGLLR-NH$_2$ | 52.4 ± 3.4 | 14.00 |
| 232 | 192 | Ac-WNLV(homoR)IGLLR-NH$_2$ | 5.6 ± 0.36 | 1.00 |

The additional elimination of the important EGF(A)-stabilizing residue Pro4 resulted in a 10-residue peptide with a 10-fold reduced binding affinity (Table 10, Compound 53). Homo-arginine substitution improved binding affinity by 14-fold (Table 10, Compound 192). A crystal structure of Compound 192 bound to PCSK9ΔCRDΔhelix at 2.20 Å resolution explained the affinity improvement by homo-Arg (FIG. 35). Compared to the natural Arg residue in Compound 20 and the native P'-helix, the homo-Arg side chain was flipped and the guanidinium group was now optimally positioned to engage in a salt bridge with PCSK9 residue Asp343.

A phage library having 3-6 amino acid extensions from the N-terminal Trp of Compound 53 was constructed. In order to avoid the emergence of an EGF(A)-stabilizing Pro residue preceding the N-terminal Trp and to provide maximal flexibility for the extension sequences, this first position preceding the Trp residue was fixed as a Gly or Ser residue. Peptide-displaying phage were panned against PCSK9Δhelix and several affinity-improved binders with five and six extension residues were identified. They all shared the three amino acid motif Phe/Tyr-Pro-Gly. Five peptides were synthesized with the homo-Arg substitution and their inhibitory potencies determined (Table 11).

LDLR levels to maximally 70% (FIG. 37). The incomplete activity was likely due to solubility limitations of the compound. In comparison to the parent peptide (Compound 192), the MESFPG extension (SEQ ID NO: 160) (Compound 229) improved the affinity to PCSK9Δhelix by more than 6-fold (Table 11), an increase that could be due to additional interactions with PCSK9Δhelix or due to stabilization of the helical conformation of the WNLV(hR)IGLLR peptide portion (SEQ ID NO: 301), which would reduce the entropic penalty to binding. To test this hypothesis the conformational preferences of both Compounds 192 and 229 in solution were studied using nuclear magnetic resonance (NMR) spectroscopy. Although Compound 229 did not adopt a preferred conformation in solution, it appeared to have a propensity to form an α-helical structure in the region spanning residues 7WNLV(hR)IGL14 (SEQ ID NO: 302). The detection of a few, weak medium-range NOE contacts, dNα(i,i+3) and dαβ(i,i+3), characteristic of α-helical structures, suggested that only a small population of Compound 229 tended to form an α-helix in this region of the sequence, thus contributing to the detection of weak medium-range NOEs (FIG. 38). A similar NOE pattern was also observed for Compound 192 (FIG. 38), suggesting that even without the MESFPG extension (SEQ ID NO: 160) Compound 192

TABLE 11

| SEQ ID NO: | Compound No. | Peptide | EGF(A) IC$_{50}$ (µM) | LDLR IC$_{50}$ (µM) | Ab20 IC$_{50}$ (µM) |
|---|---|---|---|---|---|
| 232 | 192 | Ac-WNLV(homoR)IGLLR-NH$_2$ | >50 | >50 | 5.55 ± 0.36 |
| 267 | 227 | Ac-ESFPGWNLV(homoR)IGLLR-NH$_2$ | 23.2 ± 0.3 | >50 | 2.51 ± 0.11 |
| 268 | 228 | Ac-SFAFPGWNLV(homoR)IGLLR-NH$_2$ | 13.2 ± 0.8 | 30.4 ± 1.1 | 1.37 ± 0.12 |
| 269 | 229 | Ac-MESFPGWNLV(homoR)IGLLR-NH$_2$ | 8.3 ± 0.1 | 25.0 ± 0.8 | 0.84 ± 0.08 |
| 270 | 230 | Ac-DSYPGWNLV(homoR)IGLLR-NH$_2$ | 24.2 ± 0.8 | >50 | 2.42 ± 0.20 |
| 271 | 231 | Ac-ESYPGWNLV(homoR)IGLLR-NH$_2$ | 15.8 ± 0.1 | >50 | 1.49 ± 0.10 |

Compared to Compound 192, Compounds 227-231 had improved binding affinities, based on the Ab20 assay results, and inhibitory activities towards EGF(A)-Fc (Table 11). Compounds 228 and 229 were the most potent and inhibited EGF(A)-Fc as well as LDLR-Fc binding (FIG. 36, Table 11). The better potency of Compound 229 was consistent with its stronger binding affinity to PCSK9 determined in SPR experiments (KD 0.94±0.01 µM vs KD 2.8±0.05 µM for Compounds 229 and 228, respectively). In HepG2 cells Compound 229 inhibited PCSK9-mediated LDLR degradation in a concentration-dependent manner, restoring surface retains its propensity to form an α-helical structure and that the affinity improvement observed for Compound 229 was likely derived from additional contacts between MESFPG (SEQ ID NO: 160) and PCSK9Δhelix.

To understand the role of the MESFPG extension (SEQ ID NO: 160) for the affinity increase, as well as its antagonistic property, the crystal structure of the bound peptide was obtained by using an alternative crystallization system with PCSK9Δhelix and a CRD-binding Fab7G7 (FIGS. 39-41). Crystals grown in this system did not have any Pep2-8 present and there were no intermolecular contacts interfering with peptide binding to the groove site. The 2.90 Å structure showed that, rather than extending towards the EGF(A) binding site in a "straight line" fashion, the six N-terminal residues MESFPG (SEQ ID NO: 160) adopted a type I α-turn for the three residues of the identified "FPG" motif and the subsequent Trp of the core peptide. There were two new H-bonds with PCSK9, from the main chain carbonyl oxygen atom of the Met1 residue to Gln342 and from the Ser3 side chain to Asp367 (FIG. 39). In addition, the N-terminal part of Compound 229 included a collection of intra-peptide hydrophobic contacts provided by side chains from Met1, Phe4, Trp7, Val10 and hArg11, which may have stabilized the bound conformation (FIG. 40) and all of which were well-indicated by electron-density (FIG. 42). The dual role of Met1 (H-bonding, hydrophobic core) may explain the approximately 3-fold lower inhibitory activity of the shorter Compound 227, in which the N-terminal Met residue is absent (Table 11). The antagonism of the peptide originates with the Pro residue, which is predicted to sterically clash with EGF(A) residues Leu298, Asp299 and Asn300 based on a modeling exercise (FIG. 41). The presence of the FPG or YPG motif in four additional antagonistic peptides indicated that they all adopted a similar α-turn conformation and antagonized EGF(A) binding to PCSK9 by the same mechanism as described for the MESPFG peptide (SEQ ID NO: 160).

Methods

Construction of Phage-Displayed Fusion Peptide Libraries and Binding Selection

The libraries were constructed using the standard Kunkel mutagenesis method (Kunkel et al., Methods Enzymol 154, 367-82 (1987)). The WNLVRIGLLR fusion peptide (SEQ ID NO: 80) library was constructed by fusing randomized peptides ranging from 2-5 residues to the N-terminus of peptide (G/S)WNLVRLGLLR (SEQ ID NO: 303). The randomized peptides were encoded by consecutive degenerate codon NNK, Gly/Ser by RGT (R=A/G). The final diversity of the library was $2.5 \times 10^{10}$. Phage pools of the WNLVRIGLLR (SEQ ID NO: 80) N-terminal extension library were panned against biotinylated PCSK9Δhelix. After four rounds of binding selection, individual phage clones were analyzed in a high-throughput spot phage ELISA using plate-immobilized PCSK9 or PCSK9Δhelix as the target (Tonikian et. al., Nat Protoc 2, 1368-86 (2007)). The binding signal of the same phage particle to NeutrAvidin was considered as non-specific binding ("noise"). Phage clones with binding signals to PCSK9 or PCSK9Δhelix over 0.4 and signal:noise ratios >2 were considered positive and were subjected to DNA sequence analysis.

Other Protein Reagents

LDLR-Fc and EGF(A)-Fc fusion proteins were prepared as described in Zhang, et al., J Biol Chem 289, 942-55 (2014), and Zhang et al., J Mol Biol 422, 685-96 (2012).

HepG2 Assay for Measuring Cell Surface LDL Receptor.

The effect of Compound 229 on PCSK9-mediated LDL receptor degradation was measured in a HepG2 cell assay as previously described (Zhang et al., J Biol Chem. 2014 Jan. 10; 289(2):942-55). Peptides at various concentrations were preincubated with 15 μg/mL PCSK9 in the presence of 0.5% DMSO for 30 min prior to the addition to cells. After a 4 h incubation, the cells were processed for measurements of LDL receptor surface levels by flow cytometry as described (Zhang et al., J Biol Chem. 2014 Jan. 10; 289(2):942-55) (FIG. 37).

Time-Resolved Fluorescence Resonance Energy Transfer (TR-FRET) Assays.

In black 1536-well assay plates (MaKO, Aurora® Microplates, Whitefish, Mont.), 40 nL of peptide in DMSO were preincubated with 2 μL His-tagged PCSK9 plus anti-His-allophycocyanin in assay buffer (50 mM Tris-HCl, pH 7.5, 150 mM NaCl, 2 mM $CaCl_2$, 0.01% Tween®-20, 0.1% bovine gamma globulins, and protease inhibitor cocktail) for 30 min. Then 2 μL of Fc-tagged ligand and anti-Fc-europium in assay buffer were added and allowed to incubate for 2 h. The PCSK9 and ligand conditions for each assay are as follows: 10 nM C-terminal (His)s-tagged PCSK9 ("(His)s" disclosed as SEQ ID NO: 304) and 12 nM EGF(A)-Fc for the EGF(A) assay, 10 nM C-terminal (His)s-tagged PCSK9 ("(His)s" disclosed as SEQ ID NO: 304) and 2.5 nM LDLR-Fc for the LDLR assay, 1.25 nM C-terminal (His)s-tagged PCSK9Δhelix ("(His)s" disclosed as SEQ ID NO: 304) and 0.75 nM Ab20 for the Ab20 assay, and 2 nM His-EGF(A)-Fc alone for the counterscreen. In all assays, anti-His-allophycocyanin and anti-Fc-europium were used at 20 nM and 2 nM, respectively. Fluorescence was measured with excitation at 340 nm and emission at 671 nm and 618 nm. The TR-FRET ratio was calculated as fluorescence at 671 nm/fluorescence at 618 nm. The ratios were normalized to controls and plotted against peptide concentration to determine $IC_{50}$ values (Screener Analyzer, Genedata, Basel, CH). The peptides were evaluated in three separate experiments per assay with 10-point titrations and n=2 per concentration. The values presented are the average±S.D. of three independent experiments.

Structure Determination for PCSK9ΔHelix/Fab7G7

The Fab7G7 was prepared from antibody 7G7 (Lipari et al., J Biol Chem 287, 43482-91 (2012)) by papain cleavage using standard techniques and purified using Protein G Sepharose® affinity chromatography. Fab7G7 and PCSK9Δhelix were mixed at equimolar concentrations and the complex isolated using Superdex™ 200 size exclusion chromatography. The concentrated PCSK9Δhelix/Fab7G7 complex (5 mg/mL) was subjected to high-throughput crystallization screens. Crystals were observed growing from a high salt condition containing 2.8 M NaOAc, 0.1 M Tris, pH 7.0. Optimized conditions in sitting drops at 18° C. used 2 μL complex to 2 μL of 4 M ammonium acetate, 0.1 M Tris pH 8.5 and 3% (v/v) 1.8 diaminooctane. Crystals of PCSK9Δhelix/Fab7G7 were then soaked in reservoir solution saturated with Compound 229 for 5 days. A crystal was swiped through a solution of 3.4 M sodium malonate pH 7.0 and preserved for data collection by sudden immersion in liquid nitrogen. Diffraction data were collected at 110 K using 1.0000 Å X-rays at ALS beamline 5.0.2 and reduced to 2.90 Å by standard methods (Table 12).

TABLE 12

|  | Compound 192 + PCSK9ΔCRDΔhelix | Compound 229 + Fab7G7 + PCSK9Δhelix |
|---|---|---|
| Data collection* |  |  |
| Space group | P3$_2$21 | I222 |
| Cell dimensions |  |  |
| a, b, c (Å) | 70.39, 70.39, 156.98 | 110.86, 142.17, 239.36 |
| α, β, γ (°) | 90 90 120 | 90 90 90 |
| Resolution (Å)* | 35.19-2.20 (2.28-2.20) | 70.60-2.90 (3.00-2.90) |
| Rsym | 0.111 (0.863) | 0.153 (0.781) |
| I/σ(I) | 16.1 (2.5) | 10.8 (2.5) |
| Completeness (%) | 100 (97.2) | 99.9 (99.9) |
| Redundancy | 9.9 (9.3) | 5.9 (6.1) |

TABLE 12-continued

|  | Compound 192 + PCSK9ΔCRDΔhelix | Compound 229 + Fab7G7 + PCSK9Δhelix |
|---|---|---|
| Refinement |  |  |
| Resolution (Å) | 35.19-2.20 | 70.60-2.90 |
| No. reflections | 22615 | 42267 |
| Rwork/Rfree | 0.195/0.237 | 0.171/0.209 |
| No. atoms | 3096 | 7814 |
| Protein | 2894 | 7803 |
| Ligand/ion | 1 | 2 |
| Water | 213 | 6 |
| R.m.s. deviations |  |  |
| Bond lengths (Å) | 0.008 | 0.009 |
| Bond angles (°) | 1.26 | 1.2 |

The structure was solved in space group I222 by molecular replacement (McCoy et al., J. Appl. Crystallogr. 40, 658-674 (2007)) using PCSK9 (PDB accession 2QTW) and a mouse Fab from the PDB (accession code 5EOQ) and contained a single complex in the asymmetric unit. Fab7G7 variable domain sequences, extending a few codons into the constant regions, were determined using DNA sequence derived from hybridoma cells. This sequence and electron density indications permitted assignment of antibody 7G7 as IgG2b/VK. Fab7G7 binds PCSK9Δhelix in the C-terminal cysteine-rich domain (CRD). Clear electron density permitted addition of the peptide and refinement (Bricogne, G. et al. BUSTER version 2.11.2. (Global Phasing Ltd., Cambridge, United Kingdom, 2011)) (Table 12). The final refined model had 96% of main chain torsion angles in most-favored Ramachandran space.

Structure Determination for Peptide Complexes with PCSK9ΔCRDΔHelix.

A TEV protease cleavage site was engineered into the previously described baculovirus construct PCSK9 Q31-G452 (PCSK9ΔCRD) (Zhang et al., J Biol Chem. 2014 Jan. 10; 289(2):942-55) as described above for PCSK9Δhelix. This construct was expressed and purified essentially as described (Zhang et al., J Biol Chem. 2014 Jan. 10; 289(2): 942-55) and then processed by TEV protease as described above for PCSK9Δhelix to produce PCSK9ΔCRDΔhelix, which lacked the P'-helix. Co-crystallization trials using PCSK9ΔCRDΔhelix (10 mg/mL in 0.2 M NaCl, 40 mM Tris, pH 8.0, 5% glycerol) and peptides (2-fold molar excess) were carried out with commercially available sparse matrix screens. The best crystals grew as thin hexagonal plates in sitting drops at 18° C. using 0.2 M calcium acetate, 0.1 M Tris, pH 8.0 and 20% (w/v) PEG 6000. Harvested crystals were preserved for data collection by treatment with crystallization reservoir augmented with 30% (v/v) glycerol and sudden immersion in liquid nitrogen.

Diffraction data were collected from single cryo-preserved crystals at 110 K using 0.97946 Å X-rays at beamline SSRL 12-2 for the complex with Compound 192 (Table 12) and reduced using either HKL2000 (Otwinowski et al., Methods in Enzymol 276, 307-326 (1997)) or XDS (Kabsch, Acta Crystallogr D Biol Crystallogr 66, 125-32 (2010); Vonrhein et al., Acta. Crystallogr. D67, 293-302 (2011)) and elements of the CCP4 suite (Winn et al., Acta Crystallogr D Biol Crystallogr, 2011. 67(Pt 4): p. 235-242). The structure was solved using molecular replacement (McCoy et al., J. Appl. Crystallogr. 40, 658-674 (2007)) with PCSK9ΔCRD in PDB accession code 4NMX as search probe. A single set of reflections sequestered from refinement for calculation of RFREE was used. Refinement (Murshudov et al., Acta Crystallogr D Biol Crystallogr 67, 355-367 (2011); Bricogne et al., BUSTER version 2.11.2. (Global Phasing Ltd., Cambridge, United Kingdom, 2011); Delaglio et al., J Biomol NMR 6, 277-93 (1995)) included automated water placements and TLS treatment of displacement factors. The final refined model had 97% of main chain torsion angles in most-favored Ramachandran space. Model building and inspection of electron density maps was performed using Coot (Emsley et al., Acta Crystallogr D Biol Crystallogr 66, 486-501 (2010)).

Affinity Measurements of Peptide Binding to PCSK9 and to PCSK9ΔHelix by Surface Plasmon Resonance (SPR).

A Biacore™ T100 or Biacore™ 8K was adjusted to 20° C. The system was primed into assay buffer which consisted of 25 mM HEPES, pH 7.5, 0.15 M NaCl, 0.005% (v/v) Tween® 20, 0.2 mM tris(2-carboxyethyl)phosphine and optionally contained 0.1% (w/v) carboxymethylated dextran (average MW 10 kDa) and 0.2% (w/v) PEG (average MW 3450 Da) in order to reduce potential non-specific binding. Peptides were assayed by capturing fresh PCSK9 or PCSK9Δhelix after each binding regeneration cycle by exploiting a histidine tag and an NTA-sensor chip. The surface was charged with (His)$_8$-tagged PCSK9 (approximately 800 RU captured). With the exception of Compound 19 and Compound 20, five serial three-fold dilutions of peptide were prepared in assay buffer from 100 µM for less potent peptides and 25 µM for potent peptides. Compound 19 and Compound 20 were assayed in six serial two-fold dilutions from 100 nM to 3.1 nM. All peptides were analyzed in duplicate by serial injection (50 µL/min for 1 min) of peptide dilution from low to high concentration. The surface was then stripped of target by injecting 0.5 M EDTA, pH 8.0. This sequence was repeated for each peptide binding cycle and blank control cycles.

Irreversible capture using an SA-sensor chip (pre-coated with streptavidin by manufacturer) proved more robust when testing intact PCSK9 (chemically biotinylated form) for all peptides except for Compound 19 and Compound 20. All SPR data was recorded in duplicate for five, or more serial dilutions, except for the two fusion peptides, which produced extremely low fitting error. Multicycle data (i.e. separate curves for each concentration) and single cycle data (i.e. single curve with serial injection of each concentration) were double referenced and fitted to an interaction model using BIAevaluation software. Peptide binding to PCSK9 produced deviations from a simple 1:1 binding interaction model that required application of a two-state model for determination of $K_d$ while interactions with PCSK9Δhelix conformed well to simple 1:1 binding. Kinetic curvature was poorly defined for rapidly dissociating peptides and in these cases $K_d$ was estimated from a steady-state dose response plot. $K_d$ values were reported with associated standard error, a measure of confidence in that parameter value.

Peptide Synthesis.

Peptides were synthesized using standard fluorenylmethoxycarbonyl (Fmoc)/tert-butyl (tBu) solid-phase methods. For disulfide-containing peptides, the crude linear peptides were cyclized in the presence of iodine and acetic acid. Treatment of the solution with zinc powder removed the excess iodine. The solution was diluted with water and lyophilized to give crude cyclic peptide. The crude peptides were purified by preparative HPLC on a C18 column using trifluoroacetic acid as the counter ion to a purity >85% as determined by analytical LC-MS.

NMR Spectroscopy.

Nuclear magnetic resonance experiments were carried out on a Bruker DRX-600 equipped with a triple-resonance cryoprobe. Samples for NMR studies were prepared by dissolving Compounds 192 and 229 in H$_2$O/CD$_3$CN (70:30), to final concentrations of 0.52 and 1.5 mM, respectively. All of the NMR spectra were collected at 284 K and internally referenced to DSS (4,4-dimethyl-4-silapentane-1-sulfonic acid). Assignment of the proton resonances was achieved using a combination of 2D TOCSY, 2D DQF-COSY and 2D NOESY experiments. The mixing times for the TOCSY and NOESY spectra were 60 and 250 ms, respectively. The NMR data were processed using TOPSPIN and the NMRPipe/NMRDraw package (Delaglio et al., J Biomol NMR 6, 277-93 (1995)) and analyzed with NMR-ViewJ (Johnson et al., J Biomol NMR 4, 603-14 (1994)).

Those skilled in the art will recognize that various modifications, additions, substitutions, and variations to the illustrative examples set forth herein can be made without departing from the spirit of the invention and are, therefore, considered within the scope of the invention.

What is claimed is:

1. A PCSK9 inhibitor that binds an epitope of SEQ ID NO:1, wherein the epitope comprises at least one residue selected from the group consisting of V241, T339, D343, P364, A442, A443, and L444 of SEQ ID NO: 1 selected from compounds of Formula I:

Formula I
(SEQ ID NO: 2)
$R^1-X^1-X^2-X^3-Trp-Asn-Leu-X^4-X^5-Ile-Gly-X^6-R^2$, and pharmaceutically acceptable salts thereof; wherein,
$R^1$ is $C_1-C_4$ acyl; or $R^1$ is absent;
$X^1$ is an amino acid sequence selected from: TVFTSWEEYLDWV (SEQ ID NO:3) and TAFTSWEEYLDWV (SEQ ID NO: 4); or $X^1$ is absent;
$X^2$ is an amino acid sequence comprising 1 to 4 amino acid residues selected from: glycine and serine; or $X^2$ is an amino acid residue selected from: 5-aminopentanoic acid, 6-aminohexanoic acid, 7-aminoheptanoic acid, 8-aminooctanoic acid, 9-aminononoanoic acid, 10-aminodecanoic acid, and 11-aminoundecanoic acid; or $X^2$ is absent;
$X^3$ is an amino acid sequence comprising 1 to 4 amino acid residues selected from: alanine, 2-aminocyclohexane-1-carboxylic acid, arginine, aspartic acid, cysteine, glycine, 3-hydroxyproline, isoleucine, leucine, methionine, phenylalanine, proline, and tryptophan;
$X^4$ is an amino acid residue selected from: alanine, 2,3-diaminopropionic acid, glutamine, glycine, lysine, and valine;
$X^5$ is an amino acid residue selected from: arginine and homo-arginine;
$X^6$ is an amino acid sequence comprising 1 to 5 amino acid residues selected from:
alanine, arginine, cysteine, glutamic acid, glutamine, glycine, leucine, lysine, phenylalanine, proline, serine, threonine, and tryptophan; or $X^6$ is absent; and
$R^2$ is amino; or $R^2$ is absent.

2. The PCSK9 inhibitor of claim 1, wherein $R^1$ is $C_1-C_4$ acyl.

3. The PCSK9 inhibitor of claim 2, wherein $R^1$ is acetyl.

4. The PCSK9 inhibitor of claim 2, wherein $R^1$ is valeryl.

5. The PCSK9 inhibitor of claim 1, wherein $R^1$ is absent.

6. The PCSK9 inhibitor of claim 1, wherein $X^1$ is an amino acid sequence selected from: TVFTSWEEYLDWV (SEQ ID NO: 3) and TAFTSWEEYLDWV (SEQ ID NO: 4).

7. The PCSK9 inhibitor of claim 6, wherein $X^1$ is the amino acid sequence TVFTSWEEYLDWV (SEQ ID NO: 3).

8. The PCSK9 inhibitor of claim 6, wherein $X^1$ is the amino acid sequence TAFTSWEEYLDWV (SEQ ID NO: 4).

9. The PCSK9 inhibitor of claim 1, wherein $X^1$ is absent.

10. The PCSK9 inhibitor of claim 1, wherein $X^2$ is an amino acid sequence comprising 1 to 4 amino acid residues selected from: glycine and serine.

11. The PCSK9 inhibitor of claim 10, wherein $X^2$ is an amino acid sequence selected from: SG, GSG, GGSG (SEQ ID NO: 11), GSGG (SEQ ID NO: 12), and SGSG (SEQ ID NO: 13).

12. The PCSK9 inhibitor of claim 1, wherein $X^2$ is an amino acid residue selected from: 5-aminopentanoic acid, 6-aminohexanoic acid, 7-aminoheptanoic acid, 8-aminooctanoic acid, 9-aminononoanoic acid, 10-aminodecanoic acid, and 11-aminoundecanoic acid.

13. The PCSK9 inhibitor of claim 12, wherein $X^2$ is the amino acid residue 6-aminohexanoic acid.

14. The PCSK9 inhibitor of claim 12, wherein $X^2$ is the amino acid residue 7-aminoheptanoic acid.

15. The PCSK9 inhibitor of claim 12, wherein $X^2$ is the amino acid residue 8-aminooctanoic acid.

16. The PCSK9 inhibitor of claim 1, wherein $X^2$ is absent.

17. The PCSK9 inhibitor of claim 1, wherein $X^3$ is an amino acid sequence selected from: P, MP, LMP, ALMP (SEQ ID NO: 14), CALP (SEQ ID NO: 15), CFIP (SEQ ID NO: 16), CFLP (SEQ ID NO: 17), CRAP (SEQ ID NO: 18), CRL(Hyp) (SEQ ID NO: 19), CRLP (SEQ ID NO: 20), DAMP (SEQ ID NO: 21), DLAP (SEQ ID NO: 22), and DLMP (SEQ ID NO: 23).

18. The PCSK9 inhibitor of claim 1, wherein $X^4$ is the amino acid residue alanine.

19. The PCSK9 inhibitor of claim 1, wherein $X^4$ is the amino acid residue 2,3-diaminopropionic acid.

20. The PCSK9 inhibitor of claim 1, wherein $X^4$ is the amino acid residue glutamine.

21. The PCSK9 inhibitor of claim 1, wherein $X^4$ is the amino acid residue glycine.

22. The PCSK9 inhibitor of claim 1, wherein $X^4$ is the amino acid residue lysine.

23. The PCSK9 inhibitor of claim 1, wherein $X^4$ is the amino acid residue valine.

24. The PCSK9 inhibitor of claim 1, wherein $X^5$ is the amino acid residue arginine.

25. The PCSK9 inhibitor of claim 1, wherein $X^5$ is the amino acid residue homo-arginine.

26. The PCSK9 inhibitor of claim 1, wherein $X^6$ is an amino acid sequence selected from: L, S, LL, LAR, LGC, LLA, LLC, LLR, LPC, LTR, SQGC (SEQ ID NO: 24), SQCWF (SEQ ID NO: 26), and SQGCW (SEQ ID NO: 27).

27. The PCSK9 inhibitor of claim 1, wherein $X^6$ is absent.

28. The PCSK9 inhibitor of claim 1, wherein $R^2$ is amino.

29. The PCSK9 inhibitor of claim 1, wherein $R^2$ is absent.

30. The PCSK9 inhibitor of claim 1, selected from the following compounds and pharmaceutically acceptable salts thereof:

```
                                         (SEQ ID NO: 29)
Ac-TVFTSWEEYLDWV-GSG-CWNLKRIGSQGC-NH2;

(SEQ ID NO: 38)
Ac-TVFTSWEEYLDWV-GSG-CWNLGRIGSQGC-NH2;

(SEQ ID NO: 40)
Ac-TVFTSWEEYLDWV-GGSG-CWNLKRIGSQGC-NH2;

(SEQ ID NO: 41)
Ac-TVFTSWEEYLDWV-GSGG-CWNLKRIGSQGC-NH2;

(SEQ ID NO: 42)
Ac-TVFTSWEEYLDWV-(Aoc)-CWNLKRIGSQGC-NH2;

(SEQ ID NO: 44)
Ac-TVFTSWEEYLDWV-(Ahx)-CWNLKRIGSQGC-NH2;

(SEQ ID NO: 46)
Ac-TVFTSWEEYLDWV-GSG-CRLPWNLQRIGLPC-NH2;

(SEQ ID NO: 47)
Ac-TVFTSWEEYLDWV-GSG-DLMPWNLVRIGLLR-NH2;

(SEQ ID NO: 48)
Ac-CWNLKRIGSQGC-NH2;

(SEQ ID NO: 49)
Ac-GSG-CWNLKRIGSQGC-NH2;

(SEQ ID NO: 51)
Ac-TVFTSWEEYLDWV-(Ahp)-CWNLKRIGSQGC-NH2;

(SEQ ID NO: 149)
Ac-TVFTSWEEYLDWV-SGG-CRLPWNLQRIGLPC-NH2;

(SEQ ID NO: 52)
Ac-TVFTSWEEYLDWV-GSGG-CRLPWNLQRIGLPC-NH2;

(SEQ ID NO: 53)
SG-CFIPWNLQRIGLLC-NH2;

(SEQ ID NO: 54)
SG-CRLPWNLQRIGLPC-NH2;

(SEQ ID NO: 55)
SG-DLMPWNLVRIGLLR (SEQ ID NO: 56)
Ac-SG-CFIPWNLQRIGLLC-NH2;

(SEQ ID NO: 57)
Ac-SG-CRLPWNLQRIGLPC-NH2;

(SEQ ID NO: 58)
Ac-CFIPWNLQRIGLLC-NH2;

(SEQ ID NO: 59)
Ac-CRLPWNLQRIGLPC-NH2;

(SEQ ID NO: 62)
Ac-DLMPWNLVRIGLLR-NH2;

(SEQ ID NO: 64)
Ac-SG-CRL(Hyp)WNLQRIGLPC-NH2;

(SEQ ID NO: 65)
Ac-TVFTSWEEYLDWV-GSGG-CFLPWNLQRIGLLC-NH2;

(SEQ ID NO: 66)
Ac-CWNLKRIGSQGCW-NH2;

(SEQ ID NO: 67)
Ac-GSG-CWNLKRIGSQGCW-NH2;

(SEQ ID NO: 69)
Ac-DLMAWNLVRIGLLR-NH2;

(SEQ ID NO: 70)
Ac-DLAPWNLVRIGLLR-NH2;

(SEQ ID NO: 71)
Ac-DAMPWNLVRIGLLR-NH2;

(SEQ ID NO: 72)
Ac-ALMPWNLVRIGLLR-NH2;

(SEQ ID NO: 73)
Ac-DLMPWNLVRIGLL-NH2;

(SEQ ID NO: 74)
Ac-DLMPWNLVRIGL-NH2;

(SEQ ID NO: 75)
Ac-DLMPWNLVRIG-NH2;

(SEQ ID NO: 77)
Ac-LMPWNLVRIGLLR-NH2;

(SEQ ID NO: 78)
Ac-MPWNLVRIGLLR-NH2;

(SEQ ID NO: 79)
Ac-PWNLVRIGLLR-NH2;

(SEQ ID NO: 81)
Ac-DLMPWNLVRIGLLA-NH2;

(SEQ ID NO: 82)
Ac-DLMPWNLVRIGLAR-NH2;

(SEQ ID NO: 83)
Ac-DLMPWNLVRIGALR-NH2;

(SEQ ID NO: 87)
Ac-DLMPWNLARIGLLR-NH2;

(SEQ ID NO: 150)
GCLWNLKRIGSQCWF (SEQ ID NO: 94)
Ac-CRLPWNLKRIGLPC-NH2;
```

| | |
|---|---|
| Ac-CRLPWNLQRIGLAc-NH2; | (SEQ ID NO: 95) |
| Ac-CRLPWNLQRIGAPC-NH2; | (SEQ ID NO: 96) |
| Ac-CRLPWNLARIGLPC-NH2; | (SEQ ID NO: 100) |
| Ac-CRLAWNLQRIGLPC-NH2; | (SEQ ID NO: 104) |
| Ac-CRAPWNLQRIGLPC-NH2; | (SEQ ID NO: 105) |
| Ac-CALPWNLQRIGLPC-NH2; | (SEQ ID NO: 106) |
| Ac-CRLPWNLQRIGLGC-NH2; | (SEQ ID NO: 107) |
| Ac-CRLPWNLQRIGGGC-NH2; | (SEQ ID NO: 108) |
| Ac-CRL(Ach)WNLQRIGLPC-NH2; | (SEQ ID NO: 109) |
| Ac-GCLWNLKRIGSQCWF-NH2; | (SEQ ID NO: 114) |
| Ac-GCLWNLARIGSQCWF-NH2; | (SEQ ID NO: 151) |
| Ac-FCLWNLARIGSQCWF-NH2; | (SEQ ID NO: 115) |
| GCLWNLKRIGSQCWF-NH2; | (SEQ ID NO: 152) |
| WCLWNLKRIGSQCWF-NH2; | (SEQ ID NO: 116) |
| Ac-GCLWNLKRIGSQCWF | (SEQ ID NO: 153) |
| Ac-WCLWNLKRIGSQCWF | (SEQ ID NO: 117) |
| Ac-TVFTSWEEYLDWV-(Ahx)-AWNLKRIGS-NH2; | (SEQ ID NO: 118) |
| Ac-TVFTSWEEYLDWV-(Ahx)-AWNLKRIG-NH2; | (SEQ ID NO: 119) |
| Ac-FCLWNLKRIGAQCWF-NH2; | (SEQ ID NO: 123) |
| Ac-GSG-CWNL(Dpr)RIGSQGC-NH2; | (SEQ ID NO: 124) |
| Ac-CRLPWNLQRIGLpC-NH2; | (SEQ ID NO: 126) |
| Ac-CRLPWNLQRIGIPC-NH2; | (SEQ ID NO: 127) |
| Ac-CRLPWNLqRIGLPC-NH2; | (SEQ ID NO: 130) |
| Ac-CRLpWNLQRIGLPC-NH2; | (SEQ ID NO: 134) |
| Ac-CR1PWNLQRIGLPC-NH2; | (SEQ ID NO: 135) |
| Ac-CrLPWNLQRIGLPC-NH2; | (SEQ ID NO: 136) |
| Ac-cRLPWNLQRIGLPC-NH2; | (SEQ ID NO: 137) |
| Ac-CRLPWNLQ(homoR)IGLPC-NH2; and | (SEQ ID NO: 144) |
| Ac-PWNLVRIGL-NH2. | (SEQ ID NO: 146) |

31. A PCSK9 inhibitor that binds an epitope of SEQ ID NO:1, wherein the epitope comprises at least one residue selected from the group consisting of V241, T339, D343, P364, A442, A443, and L444 of SEQ ID NO: 1 selected from compounds of Formula II:

Formula II
(SEQ ID NO: 154)
$R^1-X^1-X^2-X^3-X^7$-Asn-Leu-$X^4$-$X^5$-Ile-Gly-X6-$R^2$, and pharmaceutically acceptable salts thereof;
wherein,
$R^1$ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:
$C_1$-$C_4$ alkyl;
amino;
aryl, optionally substituted with one or two substituents each independently selected from: $C_1$-$C_4$ alkoxy, amino, halo, and hydroxy;
aryl-$C_1$-$C_4$ alkyl;
arylcarbonyl, optionally substituted with one substituent selected from: $C_1$-$C_4$ alkyl and $C_1$-$C_4$ alkylsulfonyl;
aryloxy, optionally substituted with one or two substituents each independently selected from: $C_1$-$C_4$ acyl, $C_1$-$C_4$ alkoxy, $C_1$-$C_4$ alkyl, halo, and hydroxy-$C_1$-$C_4$ alkyl;
carboxyamino, optionally substituted with one substituent selected from: aryl-$C_1$-$C_4$ alkyl;
$C_3$-$C_7$ cycloalkyl;
heteroaryl, optionally substituted with one or two substituents each independently selected from: $C_1$-$C_4$ alkyl and amino;
heterocyclyl, optionally substituted with one or two substituents each independently selected from: $C_1$-$C_4$ alkyl, $C_1$-$C_4$ alkylsulfonyl, carboxamide, heteroaryl-$C_1$-$C_4$ alkyl, and oxo;
heterocyclylcarbonyl; and
ureido;
or $R^1$ is absent;
$X^1$ is an amino acid sequence selected from: TVFTS-WEEYLDWV (SEQ ID NO: 3), TVFTS(W6fl)EEY-LDWV (SEQ ID NO: 30), and TAFTSWEEY-LDWV (SEQ ID NO: 4); or $X^1$ is absent;
$X^2$ is an amino acid sequence comprising 1 to 4 amino acid residues selected from: glycine and serine; or $X^2$ is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid; or $X^2$ is absent;
$X^3$ is an amino acid sequence comprising 1 to 6 amino acid residues selected from: alanine, 2-aminocyclohexane-1-carboxylic acid, arginine, aspartic acid, cysteine, glutamic acid, glycine, 3-hydroxyproline, isoleucine, leucine, methionine, phenylalanine, proline, serine, tryptophan, and tyrosine;

X⁴ is an amino acid residue selected from: alanine, 2,3-diaminopropionic acid, glutamine, glycine, lysine, and valine;

X⁵ is an amino acid residue selected from: arginine and homo-arginine;

X⁶ is an amino acid sequence comprising 1 to 5 amino acid residues selected from: alanine, arginine, aspartic acid, cysteine, glutamic acid, glutamine, glycine, leucine, lysine, phenylalanine, proline, serine, threonine, and tryptophan; or X⁶ is absent;

X⁷ is an amino acid residue selected from: tryptophan, 6-fluorotryptophan, 6-chlorotryptophan, 6-bromotryptophan, and 6-methyltryptophan; and R² is amino; or R² is absent.

32. The PCSK9 inhibitor of claim 31, wherein R¹ is $C_1$-$C_4$ acyl.

33. The PCSK9 inhibitor of claim 32, wherein R¹ is acetyl.

34. The PCSK9 inhibitor of claim 32, wherein R¹ is valeryl.

35. The PCSK9 inhibitor of claim 31, wherein R¹ is absent.

36. The PCSK9 inhibitor of claim 31, wherein R¹ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:
$C_1$-$C_4$ alkyl;
amino;
aryl, optionally substituted with one or two substituents each independently selected from: methoxy, amino, fluoro, chloro, and hydroxy;
aryl-$C_1$-$C_4$ alkyl;
arylcarbonyl, optionally substituted with one substituent selected from: methyl and methylsulfonyl;
aryloxy, optionally substituted with one or two substituents each independently selected from: acetyl, methoxy, methyl, ethyl, bromo, and hydroxymethyl;
carboxyamino, optionally substituted with one substituent selected from: phenylmethyl;
$C_3$-$C_7$ cycloalkyl;
heteroaryl, optionally substituted with one or two substituents each independently selected from: methyl and amino;
heterocyclyl, optionally substituted with one or two substituents each independently selected from: methyl, methylsulfonyl, carboxamide, pyridinylmethyl, and oxo;
heterocyclylcarbonyl; and
ureido.

37. The PCSK9 inhibitor of claim 31, wherein R¹ is selected from: $C_1$-$C_4$ acyl, arylcarbonyl, $C_3$-$C_7$ cycloalkylcarbonyl, and heteroarylcarbonyl; each optionally substituted with one or two substituents each independently selected from:
$C_1$-$C_4$ alkyl selected from: methyl and t-butyl;
amino;
phenyl, optionally substituted with one or two substituents each independently selected from: methoxy, amino, fluoro, chloro, and hydroxy;
phenylmethyl;
benzoyl, optionally substituted with one substituent selected from: methyl and methylsulfonyl;
phenoxy, optionally substituted with one or two substituents each independently selected from: acetyl, methoxy, methyl, ethyl, bromo, and hydroxymethyl;
carboxyamino, optionally substituted with one substituent selected from: phenylmethyl;
cyclohexyl;
heteroaryl selected from: imidazolyl, indolyl, pyrazolyl, pyridinyl, and triazolyl, each optionally substituted with one or two substituents each independently selected from: methyl and amino;
heterocyclyl selected from: morpholinyl, piperidinyl, piperazinyl, pyrrolidinyl, tetrahydrothiophenyl, tetrahydropyrimidinyl, thiomorpholinyl, each optionally substituted with one or two substituents each independently selected from: methyl, methylsulfonyl, carboxamide, pyridinylmethyl, and oxo;
morpholinylcarbonyl; and
ureido.

38. The PCSK9 inhibitor of claim 31, wherein R¹ is selected from: acetyl, n-propionyl, n-butanoyl, isovaleryl, valeryl, benzoyl, cyclopropylcarbonyl, cyclobutylcarbonyl, cyclohexylcarbonyl, indolylcarbonyl, pyrazolylcarbonyl, and pyridinylcarbonyl; each optionally substituted with one or two substituents each independently selected from:
$C_1$-$C_4$ alkyl selected from: methyl and t-butyl;
amino;
phenyl, optionally substituted with one or two substituents each independently selected from: methoxy, amino, fluoro, chloro, and hydroxy;
phenylmethyl;
benzoyl, optionally substituted with one substituent selected from: methyl and methylsulfonyl;
phenoxy, optionally substituted with one or two substituents each independently selected from: acetyl, methoxy, methyl, ethyl, bromo, and hydroxymethyl;
carboxyamino, optionally substituted with one substituent selected from: phenylmethyl;
cyclohexyl;
heteroaryl selected from: imidazolyl, indolyl, pyrazolyl, pyridinyl, and triazolyl, each optionally substituted with one or two substituents each independently selected from: methyl and amino;
heterocyclyl selected from: morpholinyl, piperidinyl, piperazinyl, pyrrolidinyl, tetrahydrothiophenyl, tetrahydropyrimidinyl, thiomorpholinyl, each optionally substituted with one or two substituents each independently selected from: methyl, methylsulfonyl, carboxamide, pyridinylmethyl, and oxo;
morpholinylcarbonyl; and
ureido.

39. The PCSK9 inhibitor of claim 31, wherein R¹ is selected from: acetyl, n-butanoyl, dioxidothiomorpholino) propanoyl, 2-(1-methyl-1H-pyrazol-4-yl)cyclopropane-1-carbonyl, 3-(2-oxopyrrolidin-1-yl)propanoyl, 1-(1-methylpyrrolidin-3-yl)-1H-pyrazole-4-carbonyl, 2-(1-(pyridin-2-ylmethyl)piperidin-4-yl)acetyl, 3-(4-carbamoylpiperazin-1-yl)propanoyl, 3-(1H-imidazol-4-yl)propanoyl, 2-(1-(methylsulfonyl)piperidin-4-yl)acetyl, 6-morpholinonicotinoyl, 3-(3,5-dimethyl-1H-pyrazol-1-yl)propanoyl, 3-morpholinopropanoyl, 3-(pyridin-3-yl)propanoyl, 2-(1,1-dioxidotetrahydrothiophen-3-yl)acetyl, 3-(4-methylpiperazin-1-yl)propanoyl, 3-ureidopropanoyl, 3-(1H-1,2,4-triazol-1-yl)propanoyl, 2-(2,4-dioxo-3,4-dihydropyrimidin-1(2H)-yl)acetyl, 3-benzylcyclobutane-1-carbonyl, [1,1'-biphenyl]-4-carbonyl, 5-phenylpentanoyl, 4-phenylcyclohexane-1-carbonyl, 5,5-dimethylhexanoyl, 3,5,5-trimethylhexanoyl, 5-(pyridin-4-yl)-1H-pyrazole-3-carbonyl, 3-cyclohexylpropanoyl, 3-(4-aminophenyl)propanoyl, 4-morpholinobutanoyl, 4-(4-(methylsulfonyl)phenyl)-4-oxobutanoyl, 3-(3-aminophenyl)propanoyl, 4-oxo-4-

(p-tolyl)butanoyl, 3-(4-methoxyphenyl)propanoyl, 4-morpholino-4-oxobutanoyl, 3-(3-hydroxyphenyl)propanoyl, 4-(((benzyloxy)carbonyl)amino)butanoyl, 3-(4-hydroxyphenyl)propanoyl, 3-(6-aminopyridin-3-yl)propanoyl, 4-(4-bromophenoxy)butanoyl, 4-(4-acetylphenoxy)butanoyl, 3-(pyridin-4-yl)-1H-pyrazole-5-carbonyl, 3-(1H-indol-3-yl)propanoyl, 4-(1H-indol-3-yl)butanoyl, 4-(4-fluorophenyl)butanoyl, 3-(4-fluorophenyl)propanoyl, 3-(4-chlorophenyl)propanoyl, 3-(3-methoxyphenyl)propanoyl, 3-(4-methoxyphenoxy)propanoyl, 4-(4-(hydroxymethyl)-3-methoxyphenoxy)butanoyl, 3-(4-acetylphenoxy)propanoyl, 4-(p-tolyloxy)butanoyl, 4-phenoxybutanoyl, 4-(4-ethylphenoxy)butanoyl, 3-(p-tolyloxy)propanoyl, 4-phenylbutanoyl, 3-(4-hydroxy-3-methoxyphenyl)propanoyl, 4-(4-hydroxyphenyl)butanoyl, 2-(pyridin-3-yl)cyclopropane-1-carbonyl, 1H-indole-6-carbonyl, 2-amino-3-(4-hydroxyphenyl)propanoyl, and 3-(3,4-dihydroxyphenyl)propanoyl.

40. The PCSK9 inhibitor claim 31, wherein $X^1$ is an amino acid sequence selected from: TVFTSWEEYLDWV (SEQ ID NO: 3), TVFTS(W6fl)EEYLDWV (SEQ ID NO: 30), and TAFTSWEEYLDWV (SEQ ID NO: 4).

41. The PCSK9 inhibitor of claim 40, wherein $X^1$ is the amino acid sequence TVFTSWEEYLDWV (SEQ ID NO: 3).

42. The PCSK9 inhibitor of claim 40, wherein $X^1$ is the amino acid sequence TVFTS(W6fl)EEYLDWV (SEQ ID NO: 30).

43. The PCSK9 inhibitor of claim 40, wherein $X^1$ is the amino acid sequence TAFTSWEEYLDWV (SEQ ID NO: 4).

44. The PCSK9 inhibitor of claim 31, wherein $X^1$ is absent.

45. The PCSK9 inhibitor of claim 31, wherein $X^2$ is an amino acid sequence comprising 1 to 4 amino acid residues selected from: glycine and serine.

46. The PCSK9 inhibitor of claim 45, wherein $X^2$ is an amino acid sequence selected from: G, GG, SG, GSG, GGSG (SEQ ID NO: 11), GSGG (SEQ ID NO: 12), and SGSG (SEQ ID NO: 13).

47. The PCSK9 inhibitor of claim 31, wherein $X^2$ is an amino acid residue selected from: 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid.

48. The PCSK9 inhibitor of claim 47, wherein $X^2$ is the amino acid residue 6-aminohexanoic acid.

49. The PCSK9 inhibitor of claim 47, wherein $X^2$ is the amino acid residue 7-aminoheptanoic acid.

50. The PCSK9 inhibitor of claim 47, wherein $X^2$ is the amino acid residue 8-aminooctanoic acid.

51. The PCSK9 inhibitor of claim 31, wherein $X^2$ is absent.

52. The PCSK9 inhibitor of claim 31, wherein $X^3$ is an amino acid sequence selected from: P, MP, LMP, ALMP (SEQ ID NO: 14), CALP (SEQ ID NO: 15), CFI(Hyp) (SEQ ID NO: 155), CFIP (SEQ ID NO: 16), CFLP (SEQ ID NO: 17), CRAP (SEQ ID NO: 18), CRL(Hyp) (SEQ ID NO: 19), CRLP (SEQ ID NO: 20), DAMP (SEQ ID NO: 21), DLAP (SEQ ID NO: 22), DLMP (SEQ ID NO: 23), DSYPG (SEQ ID NO: 156), ESFPG (SEQ ID NO: 157), ESYPG (SEQ ID NO: 158), MDSFPG (SEQ ID NO: 159), MESFPG (SEQ ID NO: 160), and SFAFPG (SEQ ID NO: 161).

53. The PCSK9 inhibitor of claim 31, wherein $X^4$ is the amino acid residue alanine.

54. The PCSK9 inhibitor of claim 31, wherein $X^4$ is the amino acid residue 2,3-diaminopropionic acid.

55. The PCSK9 inhibitor of claim 31, wherein $X^4$ is the amino acid residue glutamine.

56. The PCSK9 inhibitor of claim 31, wherein $X^4$ is the amino acid residue glycine.

57. The PCSK9 inhibitor of claim 31, wherein $X^4$ is the amino acid residue lysine.

58. The PCSK9 inhibitor of claim 31, wherein $X^4$ is the amino acid residue valine.

59. The PCSK9 inhibitor of claim 31, wherein $X^5$ is the amino acid residue arginine.

60. The PCSK9 inhibitor of claim 31, wherein $X^5$ is the amino acid residue homo-arginine.

61. The PCSK9 inhibitor of claim 31, wherein $X^6$ is an amino acid sequence selected from: L, S, LL, LAR, LDR, LER, LGC, LGR, LLA, LLC, LLQ, LLR, LPC, LPR, LSR, LTR, SQGC (SEQ ID NO: 24), SQCEY (SEQ ID NO: 25), SQCWF (SEQ ID NO: 26), and SQGCW (SEQ ID NO: 27).

62. The PCSK9 inhibitor of claim 31, wherein $X^6$ is absent.

63. The PCSK9 inhibitor of claim 31, wherein $X^7$ is tryptophan.

64. The PCSK9 inhibitor of claim 31, wherein $X^7$ is 6-fluorotryptophan.

65. The PCSK9 inhibitor of claim 31, wherein $X^7$ is 6-chlorotryptophan.

66. The PCSK9 inhibitor of claim 31, wherein $X^7$ is 6-bromotryptophan.

67. The PCSK9 inhibitor of claim 31, wherein $X^7$ is 6-methyltryptophan.

68. The PCSK9 inhibitor of claim 31, wherein $R^2$ is amino.

69. The PCSK9 inhibitor of claim 31, wherein $R^2$ is absent.

70. The PCSK9 inhibitor of claim 31, selected from the following compounds and pharmaceutically acceptable salts thereof:

```
                                          (SEQ ID NO: 29)
Ac-TVFTSWEEYLDWV-GSG-CWNLKRIGSQGC-NH2;

(SEQ ID NO: 38)
Ac-TVFTSWEEYLDWV-GSG-CWNLGRIGSQGC-NH2;

(SEQ ID NO: 40)
Ac-TVFTSWEEYLDWV-GGSG-CWNLKRIGSQGC-NH2;

(SEQ ID NO: 41)
Ac-TVFTSWEEYLDWV-GSGG-CWNLKRIGSQGC-NH2;

(SEQ ID NO: 42)
Ac-TVFTSWEEYLDWV-(Aoc)-CWNLKRIGSQGC-NH2;

(SEQ ID NO: 44)
Ac-TVFTSWEEYLDWV-(Ahx)-CWNLKRIGSQGC-NH2

(SEQ ID NO: 46)
Ac-TVFTSWEEYLDWV-GSG-CRLPWNLQRIGLPC-NH2;

(SEQ ID NO: 47)
Ac-TVFTSWEEYLDWV-GSG-DLMPWNLVRIGLLR-NH2;

(SEQ ID NO: 48)
Ac-CWNLKRIGSQGC-NH2;

(SEQ ID NO: 49)
Ac-GSG-CWNLKRIGSQGC-NH2;

(SEQ ID NO: 51)
Ac-TVFTSWEEYLDWV-(Ahp)-CWNLKRIGSQGC-NH2;

(SEQ ID NO: 149)
Ac-TVFTSWEEYLDWV-SGG-CRLPWNLQRIGLPC-NH2;
```

-continued

```
                                      (SEQ ID NO: 52)
Ac-TVFTSWEEYLDWV-GSGG-CRLPWNLQRIGLPC-NH2;

(SEQ ID NO: 53)
SG-CFIPWNLQRIGLLC-NH2;

(SEQ ID NO: 54)
SG-CRLPWNLQRIGLPC-NH2;

(SEQ ID NO: 55)
SG-DLMPWNLVRIGLLR;

(SEQ ID NO: 56)
Ac-SG-CFIPWNLQRIGLLC-NH2;

(SEQ ID NO: 57)
Ac-SG-CRLPWNLQRIGLPC-NH2;

(SEQ ID NO: 58)
Ac-CFIPWNLQRIGLLC-NH2;

(SEQ ID NO: 59)
Ac-CRLPWNLQRIGLPC-NH2;

(SEQ ID NO: 62)
Ac-DLMPWNLVRIGLLR-NH2;

(SEQ ID NO: 64)
Ac-SG-CRL(Hyp)WNLQRIGLPC-NH2;

(SEQ ID NO: 65)
Ac-TVFTSWEEYLDWV-GSGG-CFLPWNLQRIGLLC-NH2;

(SEQ ID NO: 66)
Ac-CWNLKRIGSQGCW-NH2;

(SEQ ID NO: 67)
Ac-GSG-CWNLKRIGSQGCW-NH2;

(SEQ ID NO: 69)
Ac-DLMAWNLVRIGLLR-NH2;

(SEQ ID NO: 70)
Ac-DLAPWNLVRIGLLR-NH2;

(SEQ ID NO: 71)
Ac-DAMPWNLVRIGLLR-NH2;

(SEQ ID NO: 72)
Ac-ALMPWNLVRIGLLR-NH2;

(SEQ ID NO: 73)
Ac-DLMPWNLVRIGLL-NH2;

(SEQ ID NO: 74)
Ac-DLMPWNLVRIGL-NH2;

(SEQ ID NO: 75)
Ac-DLMPWNLVRIG-NH2;

(SEQ ID NO: 77)
Ac-LMPWNLVRIGLLR-NH2;

(SEQ ID NO: 78)
Ac-MPWNLVRIGLLR-NH2;

(SEQ ID NO: 79)
Ac-PWNLVRIGLLR-NH2;

(SEQ ID NO: 81)
Ac-DLMPWNLVRIGLLA-NH2;

(SEQ ID NO: 82)
Ac-DLMPWNLVRIGLAR-NH2;

(SEQ ID NO: 83)
Ac-DLMPWNLVRIGALR-NH2;

(SEQ ID NO: 87)
Ac-DLMPWNLARIGLLR-NH2;
```

-continued

```
                                      (SEQ ID NO: 150)
GCLWNLKRIGSQCWF;

(SEQ ID NO: 94)
Ac-CRLPWNLKRIGLPC-NH2;

(SEQ ID NO: 95)
Ac-CRLPWNLQRIGLAC-NH2;

(SEQ ID NO: 96)
Ac-CRLPWNLQRIGAPC-NH2;

(SEQ ID NO: 100)
Ac-CRLPWNLARIGLPC-NH2;

(SEQ ID NO: 101)
Ac-CRLAWNLQRIGLPC-NH2;

(SEQ ID NO: 102)
Ac-CRAPWNLQRIGLPC-NH2;

(SEQ ID NO: 103)
Ac-CALPWNLQRIGLPC-NH2;

(SEQ ID NO: 107)
Ac-CRLPWNLQRIGLGC-NH2;

(SEQ ID NO: 108)
Ac-CRLPWNLQRIGGGC-NH2;

(SEQ ID NO: 109)
Ac-CRL(Ach)WNLQRIGLPC-NH2;

(SEQ ID NO: 114)
Ac-GCLWNLKRIGSQCWF-NH2;

(SEQ ID NO: 151)
Ac-GCLWNLARIGSQCWF-NH2;

(SEQ ID NO: 115)
Ac-FCLWNLARIGSQCWF-NH2;

(SEQ ID NO: 152)
GCLWNLKRIGSQCWF-NH2;

(SEQ ID NO: 116)
WCLWNLKRIGSQCWF-NH2;

(SEQ ID NO: 153)
Ac-GCLWNLKRIGSQCWF;

(SEQ ID NO: 117)
Ac-WCLWNLKRIGSQCWF;

(SEQ ID NO: 118)
Ac-TVFTSWEEYLDWV-(Ahx)-AWNLKRIGS-NH2;

(SEQ ID NO: 119)
Ac-TVFTSWEEYLDWV-(Ahx)-AWNLKRIG-NH2;

(SEQ ID NO: 123)
Ac-FCLWNLKRIGAQCWF-NH2;

(SEQ ID NO: 124)
Ac-GSG-CWNL(Dpr)RIGSQGC-NH2;

(SEQ ID NO: 126)
Ac-CRLPWNLQRIGLpC-NH2;

(SEQ ID NO: 127)
Ac-CRLPWNLQRIGIPC-NH2;

(SEQ ID NO: 128)
Ac-CRLPWNLQRiGLPC-NH2;

(SEQ ID NO: 129)
Ac-CRLPWNLQrIGLPC-NH2;

(SEQ ID NO: 130)
Ac-CRLPWNLqRIGLPC-NH2;
```

```
Ac-CRLPWNIQRIGLPC-NH2;                  (SEQ ID NO: 131)
Ac-CRLPWnLQRIGLPC-NH2;                  (SEQ ID NO: 132)
Ac-CRLPRwNLQRIGLPC-NH2;                 (SEQ ID NO: 133)
Ac-CRLpWNLQRIGLPC-NH2;                  (SEQ ID NO: 134)
Ac-CRlPWNLQRIGLPC-NH2;                  (SEQ ID NO: 135)
Ac-CrLPWNLQRIGLPC-NH2;                  (SEQ ID NO: 136)
Ac-cRLPWNLQRIGLPC-NH2;                  (SEQ ID NO: 137)
Ac-CRLPWNLQ(homoR)IGLPC-NH2;            (SEQ ID NO: 144)
Ac-PWNLVRIGL-NH2;                       (SEQ ID NO: 146)
Ac-SG-DLMPWNLVRIGLLR-NH2;               (SEQ ID NO: 162)
n-PrC(O)-WNLVRIGLLR-NH2;                (SEQ ID NO: 163)
Ac-G-LMPWNLVRIGLLR-NH2;                 (SEQ ID NO: 164)
Ac-GG-MPWNLVRIGLLR-NH2;                 (SEQ ID NO: 165)
Ac-MDSFPGWNLVRIGLLR-NH2;                (SEQ ID NO: 193)
Ac-SFAFPGWNLVRIGLLR-NH2;                (SEQ ID NO: 194)
Ac-DSYPGWNLVRIGLLR-NH2;                 (SEQ ID NO: 195)
Ac-ESYPGWNLVRIGLLR-NH2;                 (SEQ ID NO: 196)
Ac-ESFPGWNLVRIGLLR-NH2;                 (SEQ ID NO: 197)
Ac-DLMPWNLKRIGLLR-NH2;                  (SEQ ID NO: 198)
Ac-DLMPWNLVRIGLPR-NH2;                  (SEQ ID NO: 200)
Ac-ESFPGWNLV(homoR)IGLLR-NH2;           (SEQ ID NO: 267)
Ac-SFAFPGWNLV(homoR)IGLLR-NH2;          (SEQ ID NO: 268)
Ac-MESFPGWNLV(homoR)IGLLR-NH2;          (SEQ ID NO: 269)
Ac-DSYPGWNLV(homoR)IGLLR-NH2;           (SEQ ID NO: 270)
Ac-ESYPGWNLV(homoR)IGLLR-NH2;           (SEQ ID NO: 271)
Ac-SFAFPGWNLK(homoR)IGLLR-NH2;          (SEQ ID NO: 272)
Ac-MESFPGWNLK(homoR)IGLLR-NH2;          (SEQ ID NO: 273)
Ac-TVFTS(W6fl)EEYLDWV-GSG-CRLPWNLQRIGLPC-NH2;   (SEQ ID NO: 281)
and
Ac-SG-CFI(Hyp)WNLQRIGLLC-NH2.           (SEQ ID NO: 282)
```

71. An inhibited PCSK9 comprising a PCSK9 inhibitor of claim 1 bound to PCSK9.

72. A pharmaceutical composition comprising a PCSK9 inhibitor of claim 1 and a pharmaceutically acceptable carrier.

73. A PCSK9 inhibitor, or pharmaceutically acceptable salts thereof selected from the group consisting of:

```
Ac-TVFTSWEEYLDWV-(Ahp)-KLWNLGRV-NH2;    (SEQ ID NO: 43)
Ac-WNLVRIGLLR-NH2;                      (SEQ ID NO: 80)
n-BuC(O)-WNLVRIGLLR-NH2;                (SEQ ID NO: 138)
n-BuC(O)-WNLVRIGLTR-NH2;                (SEQ ID NO: 139)
n-BuC(O)-WNLVRIGTTR-NH2;                (SEQ ID NO: 140)
n-BuC(O)-WNLVRIGTTR-NH2;                (SEQ ID NO: 141)
n-BuC(O)-WNL(homoR)IGLTR-NH2;           (SEQ ID NO: 145)
```

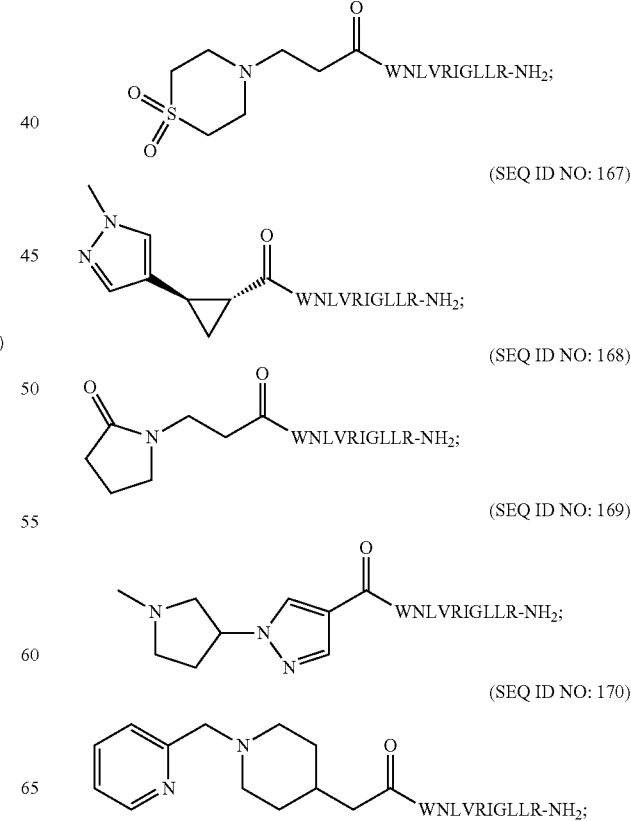

(SEQ ID NO: 171)
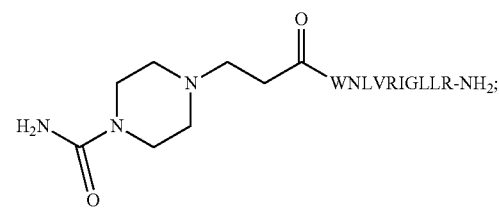
(SEQ ID NO: 172)
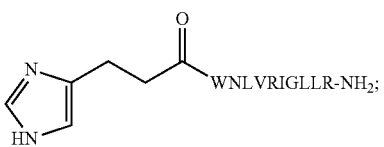
(SEQ ID NO: 173)
(SEQ ID NO: 174)
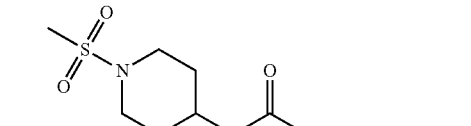
(SEQ ID NO: 175)
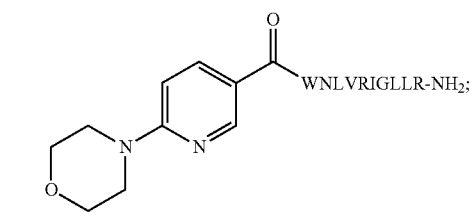
(SEQ ID NO: 176)
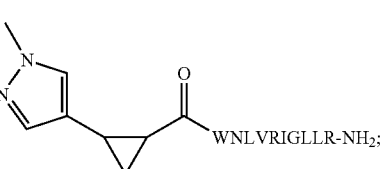
(SEQ ID NO: 177)
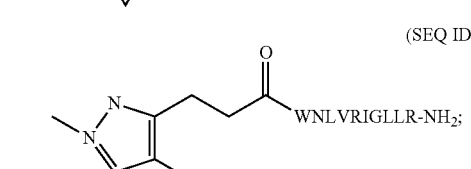
(SEQ ID NO: 178)
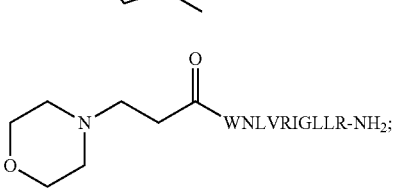
(SEQ ID NO: 179)
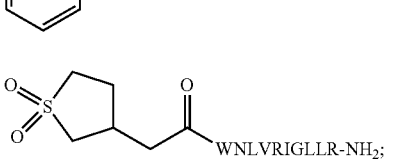
(SEQ ID NO: 180)
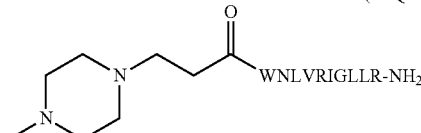
(SEQ ID NO: 181)
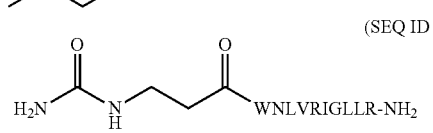
(SEQ ID NO: 182)
(SEQ ID NO: 183)
(SEQ ID NO: 184)
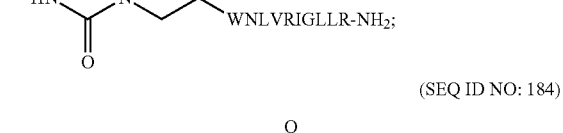
(SEQ ID NO: 185)
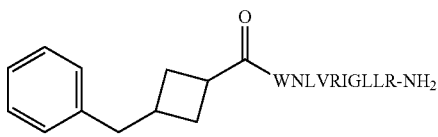
(SEQ ID NO: 186)
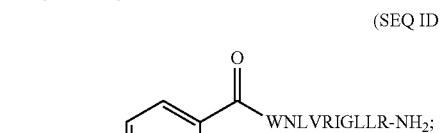
(SEQ ID NO: 187)
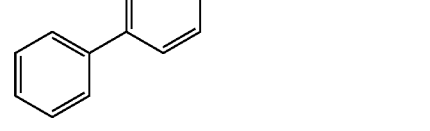
(SEQ ID NO: 188)
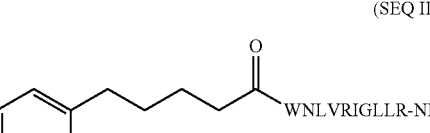
(SEQ ID NO: 189)
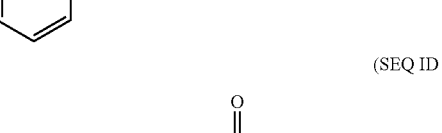

(SEQ ID NO: 190)
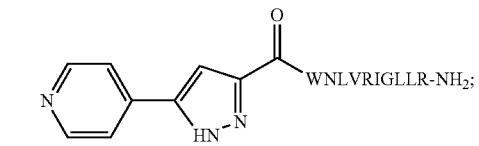
WNLVRIGLLR-NH₂;

(SEQ ID NO: 191)
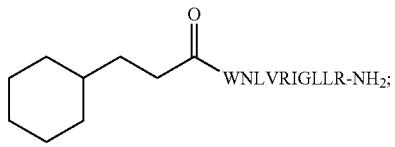
WNLVRIGLLR-NH₂;

(SEQ ID NO: 192)
n-Buc(O)-WNLVRIGLLR;

(SEQ ID NO: 199)
n-BuC(O)-WNLKRIGLLR-NH2;

(SEQ ID NO: 201)
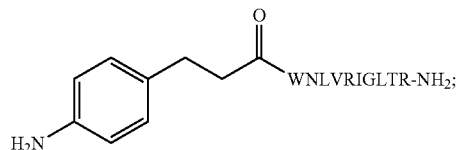
WNLVRIGLTR-NH₂;

(SEQ ID NO: 202)
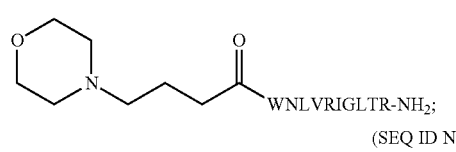
WNLVRIGLTR-NH₂;

(SEQ ID NO: 203)
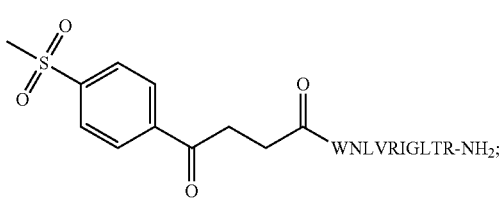
WNLVRIGLTR-NH₂;

(SEQ ID NO: 204)
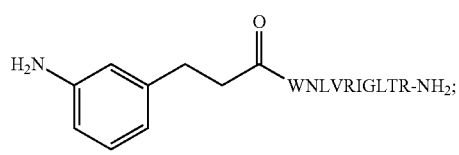
WNLVRIGLTR-NH₂;

(SEQ ID NO: 205)
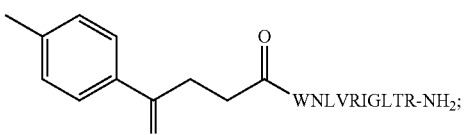
WNLVRIGLTR-NH₂;

(SEQ ID NO: 206)
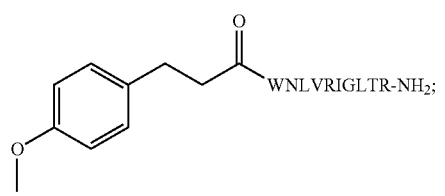
WNLVRIGLTR-NH₂;

(SEQ ID NO: 207)
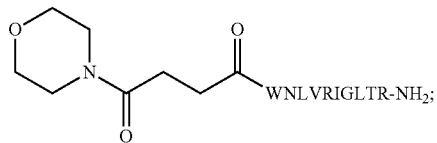
WNLVRIGLTR-NH₂;

(SEQ ID NO: 208)
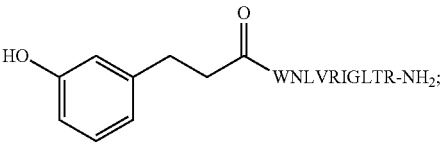
WNLVRIGLTR-NH₂;

(SEQ ID NO: 209)
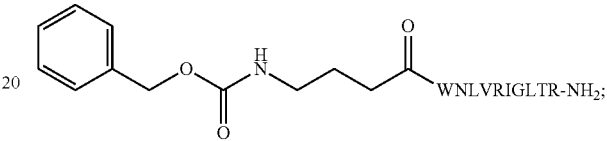
WNLVRIGLTR-NH₂;

(SEQ ID NO: 210)
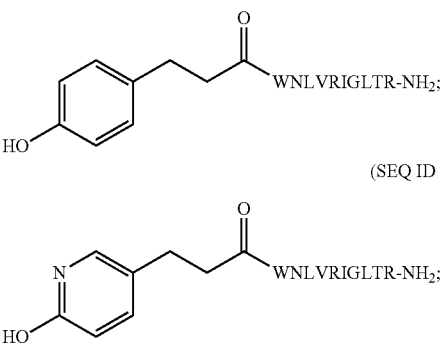
WNLVRIGLTR-NH₂;

(SEQ ID NO: 211)
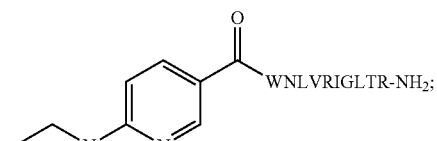
WNLVRIGLTR-NH₂;

(SEQ ID NO: 212)
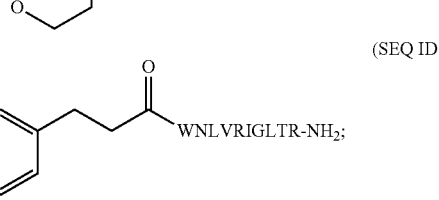
WNLVRIGLTR-NH₂;

(SEQ ID NO: 213)
WNLVRIGLTR-NH₂;

(SEQ ID NO: 214)
n-BuC(O)-(W6fl)NLVRIGLTR-NH2;

(SEQ ID NO: 215)
n-BuC(O)-(W6me)NLVRIGLTR-NH2;

(SEQ ID NO: 216)
n-BuC(O)-WNLVRIGLTR;

(SEQ ID NO: 217)
n-BuC(O)-WNLVRIGLER-NH2;

(SEQ ID NO: 218)
n-BuC(O)-WNLVRIGLDR-NH2;

(SEQ ID NO: 219)
n-BuC(O)-WNLVRIGLGR-NH2;

(SEQ ID NO: 220)
n-BuC(O)-WNLVRIGLAR-NH2;

n-BuC(O)-WNLVRIGLSR-NH2; (SEQ ID NO: 221)
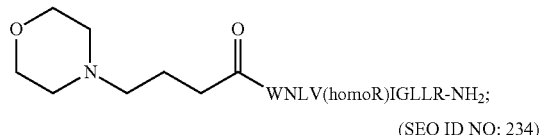 (SEQ ID NO: 222)
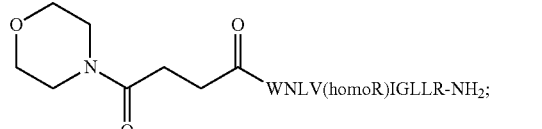 (SEQ ID NO: 223)
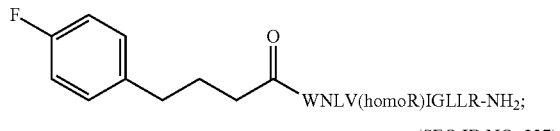 (SEQ ID NO: 224)
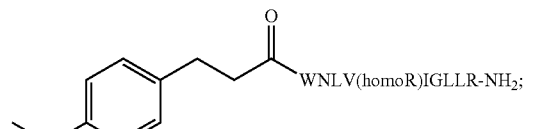 (SEQ ID NO: 225)
n-BuC(O)-(W6cl)NLVRIGLTR-NH2; (SEQ ID NO: 226)
n-BuC(O)-(W6br)NLVRIGLTR-NH2; (SEQ ID NO: 227)
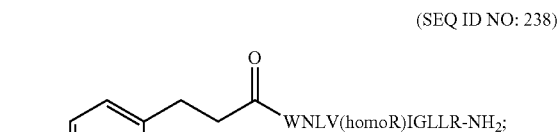 (SEQ ID NO: 228)
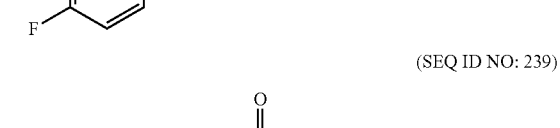 (SEQ ID NO: 229)
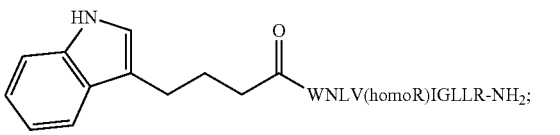 (SEQ ID NO: 230)
n-BuC(O)-WNLV(homoR)IGLLR-NH2; (SEQ ID NO: 231)
Ac-WNLV(homoR)IGLLR-NH2; (SEQ ID NO: 232)
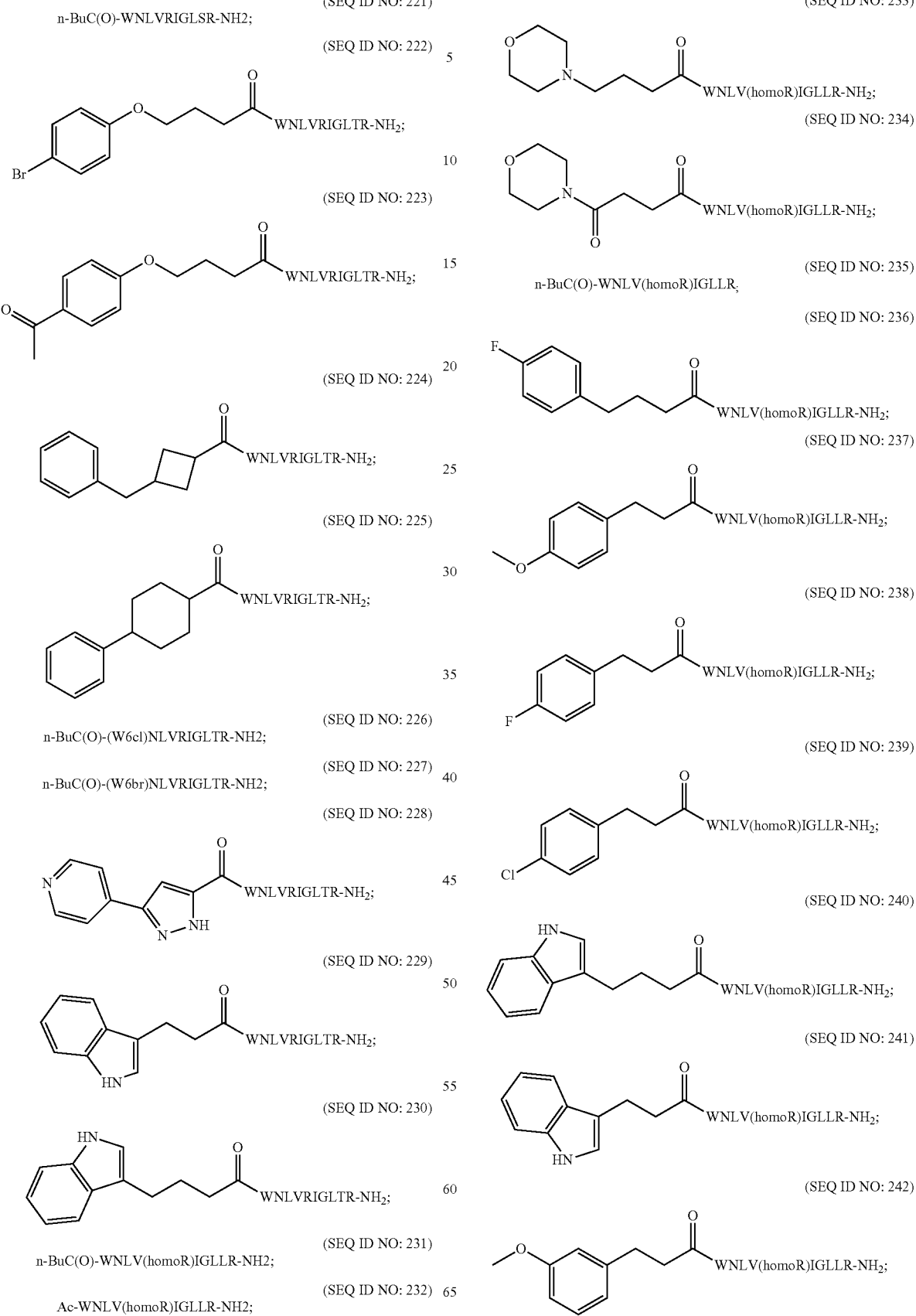
(SEQ ID NO: 233)
(SEQ ID NO: 234)
n-BuC(O)-WNLV(homoR)IGLLR; (SEQ ID NO: 235)
(SEQ ID NO: 236)
(SEQ ID NO: 237)
(SEQ ID NO: 238)
(SEQ ID NO: 239)
(SEQ ID NO: 240)
(SEQ ID NO: 241)
(SEQ ID NO: 242)

(SEQ ID NO: 243)
4-methoxyphenyl-O-CH2CH2-C(O)-WNLV(homoR)IGLLR-NH2;

(SEQ ID NO: 244)
[3-methoxy-4-(hydroxymethyl)phenyl]-O-CH2CH2CH2-C(O)-WNLV(homoR)IGLLR-NH2;

(SEQ ID NO: 245)
4-acetylphenyl-O-CH2CH2-C(O)-WNLV(homoR)IGLLR-NH2;

(SEQ ID NO: 246)
4-bromophenyl-O-CH2CH2CH2-C(O)-WNLV(homoR)IGLLR-NH2;

(SEQ ID NO:247)
4-methylphenyl-O-CH2CH2CH2-C(O)-WNLV(homoR)IGLLR-NH2;

(SEQ ID NO: 248)
trans-4-phenylcyclohexyl-C(O)-WNLV(homoR)IGLLR-NH2;

(SEQ ID NO: 249)
phenyl-O-CH2CH2CH2-C(O)-WNLV(homoR)IGLLR-NH2;

(SEQ ID NO: 250)
4-ethylphenyl-O-CH2CH2CH2-C(O)-WNLV(homoR)IGLLR-NH2;

(SEQ ID NO: 251)
4-methylphenyl-O-CH2CH2-C(O)-WNLV(homoR)IGLLR-NH2;

(SEQ ID NO: 252)
phenyl-CH2CH2CH2-C(O)-WNLV(homoR)IGLLR-NH2;

(SEQ ID NO: 253)
(3-methoxy-4-hydroxyphenyl)-CH2CH2-C(O)-WNLV(homoR)IGLLR-NH2;

(SEQ ID NO: 254)
4-hydroxyphenyl-CH2CH2-C(O)-WNLV(homoR)IGLLR-NH2;

(SEQ ID NO: 255)
3-aminophenyl-CH2CH2-C(O)-WNLV(homoR)IGLLR-NH2;

(SEQ ID NO: 256)
(6-aminopyridin-3-yl)-CH2CH2-C(O)-WNLV(homoR)IGLLR-NH2;

(SEQ ID NO: 257)
3-hydroxyphenyl-CH2CH2-C(O)-WNLV(homoR)IGLLR-NH2;

(SEQ ID NO: 258)
4-aminophenyl-CH2CH2-C(O)-WNLV(homoR)IGLLR-NH2;

(SEQ ID NO: 259)
(6-morpholinopyridin-3-yl)-C(O)-WNLV(homoR)IGLLR-NH2;

(SEQ ID NO: 260)
4-hydroxyphenyl-CH2CH2CH2-C(O)-WNLV(homoR)IGLLR-NH2;

(SEQ ID NO: 261)

[3-pyridyl-cyclopropanecarbonyl]-WNLV(homoR)IGLLR-NH₂;

(SEQ ID NO: 262)

[1H-indol-6-yl-carbonyl]-WNLV(homoR)IGLLR-NH₂;

(SEQ ID NO: 263)

[Tyr]-WNLV(homoR)IGLLR-NH₂;

(SEQ ID NO: 264)

[3,4-dihydroxyphenylpropanoyl]-WNLV(homoR)IGLLR-NH₂;

(SEQ ID NO: 265)

[3-pyridyl-cyclopropanecarbonyl]-WNLV(homoR)IGLLR-NH₂;

(SEQ ID NO: 266)

[Tyr]-WNLV(homoR)IGLLR-NH₂;

(SEQ ID NO: 274)
n-BuC(O)-WNLV(homoR)IGLTR-NH2;

(SEQ ID NO: 275)
n-Buc(O)-WNLV(homoR)IGLTR;

(SEQ ID NO: 276)
WNLV(homoR)IG-NH2;

(SEQ ID NO: 277)
WNLV(homoR)IGLLQ-NH2

(SEQ ID NO: 278)

[3-methoxy-4-hydroxyphenylpropanoyl]-WNLV(homoR)IGLLN-NH₂

(SEQ ID NO: 279)

[3-methoxy-4-hydroxyphenylpropanoyl]-WNLV(homoR)IGQR-NH₂; and (SEQ ID NO: 280)

[3-methoxy-4-hydroxyphenylpropanoyl]-WNLV(homoR)IGNR-NH₂.

\* \* \* \* \*